US008236792B2

(12) United States Patent
Carruthers et al.

(10) Patent No.: US 8,236,792 B2
(45) Date of Patent: Aug. 7, 2012

(54) SUBSTITUTED PYRROLIDINE AMIDES AS MODULATORS OF THE HISTAMINE H$_3$ RECEPTOR

(75) Inventors: Nicholas I Carruthers, Poway, CA (US); Michael A. Letavic, San Diego, CA (US); Kiev S. Ly, San Diego, CA (US); Neelakandha S. Mani, San Diego, CA (US); Daniel J. Pippel, Del Mar, CA (US); Chandravadan R. Shah, San Diego, CA (US); Akinola Soyode-Johnson, San Diego, CA (US); Emily M. Stocking, Encinitas, CA (US); Lana Young, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 451 days.

(21) Appl. No.: 12/468,632

(22) Filed: May 19, 2009

(65) Prior Publication Data
US 2009/0291903 A1   Nov. 26, 2009

Related U.S. Application Data

(60) Provisional application No. 61/055,538, filed on May 23, 2008.

(51) Int. Cl.
| | |
|---|---|
| A61K 31/55 | (2006.01) |
| A61K 31/497 | (2006.01) |
| A61K 31/445 | (2006.01) |
| A61K 31/40 | (2006.01) |
| C07D 243/08 | (2006.01) |
| C07D 403/00 | (2006.01) |
| C07D 401/00 | (2006.01) |
| C07D 205/00 | (2006.01) |

(52) U.S. Cl. .................... 514/218; 514/254.01; 514/326; 514/422; 540/575; 544/372; 546/208; 548/953

(58) Field of Classification Search ......................... None
See application file for complete search history.

(56) References Cited

U.S. PATENT DOCUMENTS

| | | | | |
|---|---|---|---|---|
| 7,067,507 | B2 * | 6/2006 | Pulley et al. ................... | 514/183 |
| 2002/0055469 | A1 | 5/2002 | Pastor et al. | |
| 2004/0106655 | A1 | 6/2004 | Kitajima et al. | |
| 2007/0270440 | A1 | 11/2007 | Cole et al. | |

FOREIGN PATENT DOCUMENTS

| | | | |
|---|---|---|---|
| EP | 518558 | * | 12/1992 |
| EP | 551993 | * | 7/1993 |
| WO | WO 03 004480 A2 | | 1/2003 |
| WO | WO 2005 040144 A1 | | 5/2005 |
| WO | WO 2006 040192 A1 | | 4/2006 |

OTHER PUBLICATIONS

Jantzen and Robinson. Modern Phamaceutics, 1996, p. 596.*
"Metabolite-Encyclopedia.com", http://www.encyclopedia.com/doc/1E1-metabolit.html, 2007.*
Berlin. Expert Opinion on Therapeutic Patents, 2007, 17(6), 675-687.*
Stark et al "Recent Advances in Histamine H3/H4 Receptor Ligands" Expert Opinion Ther Patents 2003 vol. 13(6) pp. 851-865.
International Search Report for Corresponding International Application No. PCT/US2009/044518 Mailed Sep. 22, 2009, 4 Pgs.
Arrang, J.-M. et al. "Auto-Inhibition of Brain Histamine Release Mediated by a Novel Class (H3) of Histamine Receptor" 1983, Nature, 302, pp. 832-837.
Barbier et al. "Acute Wake-Promoting Actions of JNJ-5207852, A Novel, Diamine-Based H$_3$ Antagonist" 2004, Br J Pharmacol, 143(5), pp. 649-661.
Barnes J.C. et al. "The Selective Histamine H3 Receptor Antagonist Thioperamide Improves Cognition and Enhances Hippocampal Acetylcholine Release In Vivo." 1993, Soc. Neurosci. Abstr., 19, p. 1813.
Berge, et al., "Pharmaceutical Salts", 1977, J Pharm Sci., 66, pp. 1-19.
Bonaventure et al. "Histamine H-3 Receptor Antagonists: From Target Identification to Drug Leads" 2007, Biochemical Pharmacology, 73(8), pp. 1084-1096.
Boros et al. "Synthesis of Aminomethylazetidines Regioselective Reactions of Mesyloxymethylazetidinones With Nucleophiles II" 2006, Journal of Heterocyclic Chemistry, 43(2), pp. 371-388.
Bundgaard Design of Prodrugs Elsevier 1985.
Chen et al. "Effect of Histamine H3-Receptor Antagonist Clobenpropit on Spatial Memory of Radial Maze Performance in Rats" 2000, Acta Pharmacologica Sinic, 21(10), pp. 905-910.
Chiba et al "Synthesis, Biological Evaluation, and Pharmacokinetic Study of Prolyl-1-Piperazinylacetic Acid and Prolyl-4-Piperidinylacetic Acid Derivatives As VLA-4 Antagonists" 2006 Bioorganic & Medicinal Chemistry, 14(8), pp. 2725-2746.
Croce et al. "Stereoselective Synthesis of (1R,4R)-N-Acyl-2-OXA-5-Azabicyclo[2.2.1]Heptan-3-Ones Via Mesoionic Compounds. An Improved Synthesis of cis-4-Hydroxy-D-Proline" 2002, Tetrahedron: Asymmetry, 13 (2), pp. 197-201.
Del Valle et al. "Asymmetric Hydrogenations for the Synthesis of Boc-Protected 4-Alkylprolinols and Prolines" 2003, Journal of Organic Chemisry, 68(10), pp. 3923-3931.
Fox et al. "Effects of Histamine H3 Receptor Ligands GT-2331 and Ciproxifan in a Repeated Acquisition Avoidance Response in the Spontaneously Hypertensive Rat Pup" 2002, Behavioural Brain Research,131(1-2), pp. 151-161.
Ganellin et al. "Inhibitors of Tripeptidyl Peptidase II. 3. Derivation of Butabindide by Successive Structure Optimizations Leading to a Potential General Approach to Designing Exopeptidase Inhibitors" 2005, Journal of Medicinal Chemistry, 48(23), pp. 7333-7342.
Kawabata et al "Asymmetric Cyclization Via Memory of Chirality: A Concise Access to Cyclic Amino Acids With a Quaternary Stereocenter" 2003, Journal of the American Chemical Society. 125(43), pp. 13012-13013.
Kawabata et al "Stereochemical Diversity in Asymmetric Cyclization Via Memory of Chirality" 2006, Journal of the American Chemical Society, 128(48), pp. 15394-15395.
Krause et al. "In the Histamine H3 Receptor—A Target for New Drugs, Chapter: Medicinal Chemistry of Histamine H3 Receptor Agonists" 1998, Elsevier, Leurs, R.; Timmerman, H., Eds. pp. 175-196.
Lamberti et al "Antidepressant-Like Effects of Endogenous Histamine and of Two Histamine H1 Receptor Agonists in the Mouse Forced Swim Test" 1998, British Journal of Pharmacology, 123(7), pp. 1331-1336.

(Continued)

Primary Examiner — Noble Jarrell
(74) Attorney, Agent, or Firm — Michael J. Atkins

(57) ABSTRACT

Certain substituted pyrrolidine amide compounds are histamine H$_3$ receptor modulators useful in the treatment of histamine H$_3$ receptor-mediated diseases.

40 Claims, No Drawings

OTHER PUBLICATIONS

Letavic et al. "Recent Medicinal Chemistry of the Histamine H3 Receptor" 1996, Progress in Medicinal Chemistry, 44, pp. 181-206.

Leurs et al. The Medicinal Chemistry and Therapeutic Potentials of Ligands of the Histamine H3 Receptor 1995, *Progress in Drug Research*, 45, pp. 107-165.

Lintunen et al "Increased Brain Histamine in an Alcohol-Preferring Rat Line and Modulation of Ethanol Consumption by H3 Receptor Mechanisms" 2001, FASEB Journal, 15(6), pp. 1074-1076.

Lovenberg, T.W. et al. "Cloning of Rat Histamine $H_3$ Receptor Reveals Distinct Species Pharmacological Profiles" 2000, *J. Pharmacol, Exp. Ther.*, 293(3), pp. 771-778.

Machidori et al. "Zucker Obese Rats: Defect in Brain Histamine Control of Feeding" 1992, *Brain Research*, 590(1-2), pp. 180-186.

Miyazaki et al "Effects of Thioperamide, a Histamine H-3-Receptor Antagonist, on a Scopolamine-Induced Learning Deficit Using an Elevated Plus-Maze Test in Mice" 1995, *Life Sciences*, 57(23), pp. 2137-2144.

Miyazaki et al "Effects of Thioperamide on the Cholinergic System and the Step-Through Passive Avoidance Test in Mice" 1995, *Methods & Findings in Experimental & Clinical Pharmacology*, 17(10), pp. 653-658.

Morisset, S. et al. "High Constitutive Activity of Native $H_3$ Receptors Regulates Histamine Neurons in Brain" 2000, *Nature* (London), 408(6814), pp. 860-864.

Orsetti et al "Histamine H(3)-Receptor Antagonism Improves Memory Retention and Reverses the Cognitive Deficit Induced by Scopolamine in a Two-Trial Place Recognition Task" 2001, *Behavioural Brain Research*, 124(2), pp. 235-242.

Panula, P. et al. "Significant Changes in the Human Brain Histaminergic System in Alzheimer's Disease" 1995, *Society for Neuroscience Abstracts*, 21(1-3), p. 1977.

Perez-Garcia et al. "Effects of Histamine H3 Receptor Ligands in Experimental Models of Anxiety and Depression" 1999, Psychopharmacology, 142(2), pp. 215-220.

Phillips et al. "In the Histamine H3 Receptor—A Target for New Drugs, Chapter: Medicinal Chemistry of Histamine H3 Receptor Agonists" 1998, Elsevier, Leurs, R.; Timmerman, H., Eds. pp. 197-222.

Schlicker et al. "The Moderate Affinity of Clozapine at H-3 Receptors is Not Shared by Its Two Major Metabolites and by Structurally Related and Unrelated Atypical Neuroleptics" 1996, Naunyn-Schmiedeberg's Archives of Pharmacology, 353(3), pp. 290-294.

Stahl et al. "Handbook of Pharmaceutical Salts, Properties, Selection, and Use" 2002, Eds Wiley-VCH and VHCA Zurich.

Stark et al. "Developments of Histamine H-3-Receptor Antagonists" 1996, *Drugs of the Future*, 21(5), pp. 507-520.

Yokoyama et al. "Effect of Thioperamide, A Histamine H-3 Receptor Antagonist, on Electrically Induced Convulsions in Mice" 1993, *European Journal of Pharmacology*, 234(1), pp. 129-133.

Zhang et al. "Efficient and Stereoselective Synthesis of Novel cis-4-Substituted Proline Analogues" 2003, *Tetrahedron Letters*, 44(7), pp. 1413-1415.

* cited by examiner

SUBSTITUTED PYRROLIDINE AMIDES AS MODULATORS OF THE HISTAMINE $H_3$ RECEPTOR

This application claims the benefit of U.S. provisional patent application Ser. No. 61/055,538, filed May 23, 2008, which is hereby incorporated by reference.

FIELD OF THE INVENTION

The present invention relates to certain substituted pyrrolidine amide compounds, pharmaceutical compositions containing them, and methods of using them for the treatment of disease states, disorders, and conditions mediated by the histamine $H_3$ receptor.

BACKGROUND OF THE INVENTION

The histamine $H_3$ receptor was first described as a presynaptic autoreceptor in the central nervous system (CNS) (Arrang, J.-M. et al. *Nature* 1983, 302, 832-837) controlling the synthesis and release of histamine. The histamine $H_3$ receptor is primarily expressed in the mammalian central nervous system (CNS), with some minimal expression in peripheral tissues such as vascular smooth muscle.

Thus, several indications for histamine $H_3$ antagonists and inverse agonists have been proposed based on animal pharmacology and other experiments with known histamine $H_3$ antagonists (e.g. thioperamide). (See: Krause et al. and Phillips et al. in "The Histamine $H_3$ Receptor-A Target for New Drugs", Leurs, R. and Timmerman, H., (Eds.), Elsevier, 1998, pp. 175-196 and 197-222; Morisset, S. et al. *Nature* 2000, 408, 860-864.) These include conditions such as cognitive disorders, sleep disorders, psychiatric disorders, and other disorders.

For example, histamine $H_3$ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. For reviews, see: Bonaventure, P. et al. *Biochem. Pharm.* 2007, 73, 1084-1096; Letavic, M. A. et al. *Prog. Med. Chem.* 1996, 44, 181-206. There remains a need for potent histamine $H_3$ receptor modulators with desirable pharmaceutical properties.

N-Benzoyl and N-benzylpyrrolidin-3-ylamines were disclosed as histamine $H_3$ antagonists by Cole and co-workers (U.S. Pat. Appl. Publ. US 2007/0270440, Nov. 22, 2007). Certain amidine compounds were described as serine protease inhibitors in U.S. Pat. Appl. Publ. US 2002/0055469 (May 9, 2002). Certain prolyl-1-piperazinylacetic acid and prolyl-4-piperidinylacetic acid derivatives were described as VLA-4 antagonists for inflammatory conditions (Chiba et al. *Bioorg. Med. Chem.* 2006, 14, 2725-2746). Aminomethylazetidines were prepared by Boros et al. (*J. Het. Chem.* 2006, 43(2), 371-388). Proline derivatives were shown as DPP-IV modulators in U.S. Pat. Appl. Publ. US 2004/0106655 (Jun. 3, 2004).

SUMMARY OF THE INVENTION

Certain substituted pyrrolidine derivatives have now been found to have histamine $H_3$ receptor modulating activity. Thus, the invention is directed to the general and preferred embodiments defined, respectively, by the independent and dependent claims appended hereto, which are incorporated by reference herein.

In one general aspect the invention relates to a compound of the following Formula (I):

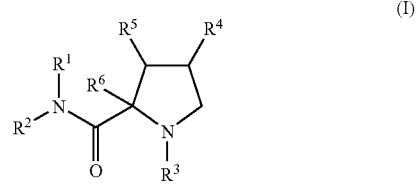

wherein
$R^1$ and $R^2$ taken together with the nitrogen to which they are attached form

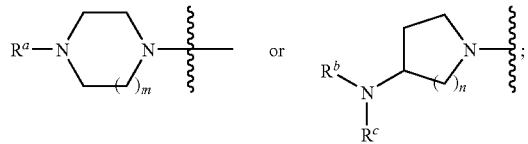

where m is 1 or 2;
n is 1 or 2;
$R^a$ is H, $C_{1-6}$alkyl, cycloalkyl, heterocycloalkyl, or benzyl; and
$R^b$ and $R^c$ are each independently H or $C_{1-4}$alkyl; or
$R^b$ and $R^c$ taken together with the nitrogen to which they are attached form a heterocycloalkyl ring;
$R^3$ is H; $C_{1-6}$alkyl; $C_{2-6}$alkyl substituted with OH, —$OC_{1-4}$alkyl, fluoro, or cycloalkyl; cycloalkyl; heterocycloalkyl; —$COC_{1-6}$alkyl; —CO-(cycloalkyl); benzoyl; —$CO_2C_{1-4}$alkyl; —$CO_2$-benzyl; —$SO_2C_{1-4}$alkyl; —$SO_2$-(cycloalkyl); or —$SO_2$-phenyl;
$R^4$, $R^5$, and $R^6$ are defined as one of a), b) or c);
a) $R^4$ is -X-$R^d$ and $R^5$ and $R^6$ are each H;
b) $R^5$ is -X-$R^d$ and $R^4$ and $R^6$ are each H;
c) $R^6$ is —$CH_2$—$R^e$ and $R^4$ and $R^5$ are each H;
X is O, S, or $CH_2$;
$R^d$ is H or $C_{1-6}$alkyl, or a phenyl, benzyl, cycloalkyl, heterocycloalkyl, or monocyclic heteroaryl group, each group unsubstituted or substituted with one or two $R^f$ substituents;
where each $R^f$ substituent is independently selected from the group consisting of: halo; —$C_{1-4}$alkyl; —$C_{2-4}$alkyl substituted with OH, F, or —$OC_{1-4}$alkyl; —$CHF_2$; —$CF_3$; —OH; —$OC_{1-4}$alkyl; —$SC_{1-4}$alkyl; —$SO_2C_{1-4}$alkyl; —CN; —$CONR^gR^h$; and —$NO_2$; or two $R^f$ substituents together form —$O(CH_2)_{1-2}$—O—;
where $R^g$ and $R^h$ are each independently —H or —$C_{1-4}$alkyl;
and
$R^e$ is phenyl or monocyclic heteroaryl, each unsubstituted or substituted with one or two $R^f$ substituents;
or a pharmaceutically acceptable salt, a pharmaceutically acceptable prodrug,
or a pharmaceutically active metabolite thereof.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by histamine $H_3$ receptor activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me), ethyl (Et), n-propyl, isopropyl (iPr), butyl (Bu or n-Bu), isobutyl (iBu), sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic carbocycle having from 3 to 10 ring atoms per carbocycle. Illustrative examples of cycloalkyl groups include the following entities, in the form of properly bonded moieties:

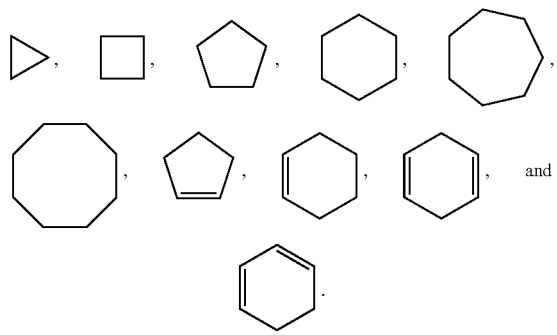

A "heterocycloalkyl" refers to a monocyclic ring structure that is saturated or partially saturated and has from 4 to 7 ring atoms per ring structure selected from carbon atoms and one or two heteroatoms selected from nitrogen, oxygen, and sulfur. The ring structure may optionally contain up to two oxo groups on carbon or sulfur ring members. Illustrative entities, in the form of properly bonded moieties, include:

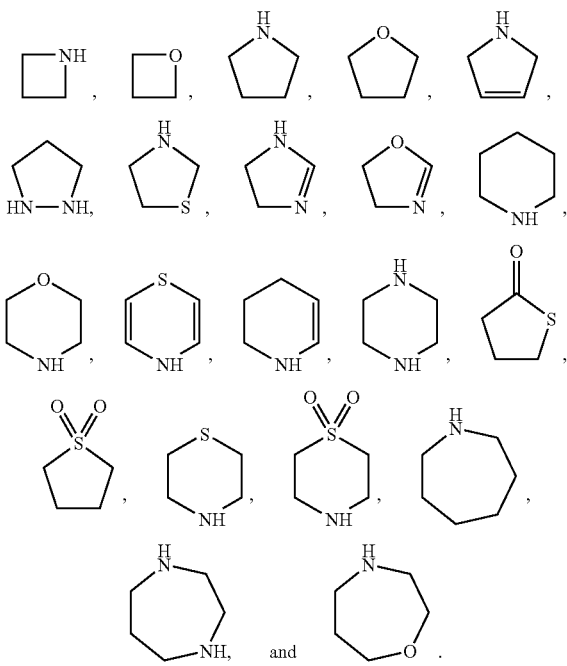

The term "heteroaryl" refers to a monocyclic, fused bicyclic, or fused polycyclic aromatic heterocycle (ring structure having ring atoms selected from carbon atoms and one, two, three, or four heteroatoms selected from nitrogen, oxygen, and sulfur) having from 3 to 12 ring atoms per heterocycle. Illustrative examples of heteroaryl groups include the following entities, in the form of properly bonded moieties:

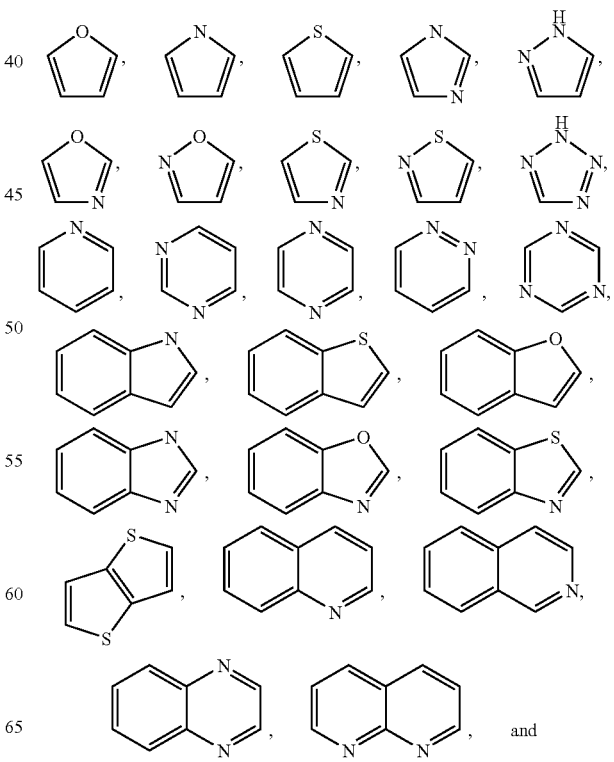

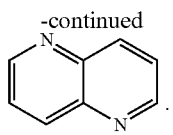

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In some embodiments of Formula (I), $R^1$ and $R^2$ are taken together with the nitrogen to which they are attached to form:

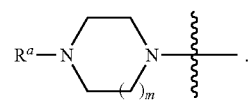

In some embodiments, m is 1. In other embodiments, m is 2. In still other embodiments, n is 1.

In some embodiments, $R^a$ is H, methyl, isopropyl, isobutyl, cyclopropyl, cyclobutyl, cyclopentyl, tetrahydropyranyl, or benzyl. In other embodiments, $R^a$ is cyclopropyl or cyclobutyl. In still other embodiments, $R^a$ is cyclobutyl.

In some embodiments, $R^b$ is H. In other embodiments, $R^c$ is dimethylamino. In other embodiments, $R^b$ and $R^c$ are taken together with the nitrogen to which they are attached to form pyrrolidinyl.

In some embodiments, $R^3$ is H, methyl, ethyl, isopropyl, hydroxyethyl, fluoroethyl, cyclopropylmethyl, cyclopropyl, cyclobutyl, tetrahydrofuranyl, tetrahydropyranyl, acetyl, propionyl, isobutyryl, 3,3-dimethylbutyryl, cyclopropanecarbonyl, benzoyl, methoxycarbonyl, ethoxycarbonyl, tert-butoxycarbonyl, benzyloxycarbonyl, or methylsulfonyl. In other embodiments, $R^3$ is —$COC_{1-6}$alkyl, —CO-(cycloalkyl), or —$SO_2C_{1-4}$alkyl. In still other embodiments, $R^3$ is acetyl or methanesulfonyl.

In some embodiments, $R^4$ is -X-$R^d$ and $R^5$ and $R^6$ are each H. In other embodiments, $R^5$ is -X-$R^d$ and $R^4$ and $R^6$ are each H. In still other embodiments, $R^6$ is —$CH_2$—$R^e$ and $R^4$ and $R^5$ are each H.

In some embodiments, X is O. In other embodiments, X is S. In still other embodiments, X is $CH_2$.

In some embodiments, $R^d$ is H. In other embodiments, $R^d$ is isopropyl. In other embodiments, $R^d$ is cyclopropyl, cyclobutyl, tetrahydrofuranyl, or tetrahydropyranyl. In still other embodiments, $R^d$ is phenyl, unsubstituted or substituted with one or two $R^f$ substituents. In still other embodiments, $R^d$ is benzyl, 3-fluorobenzyl, 4-fluorobenzyl, or 4-cyanobenzyl. In still other embodiments, $R^d$ is phenyl, unsubstituted or substituted with one or two $R^f$ substituents. In still other embodiments, $R^d$ is phenyl, 4-fluorophenyl, 3-fluorophenyl, 3-chlorophenyl, 4-chlorophenyl, 3-cyanophenyl, 4-methanesulfanyl-phenyl, 4-chloro-3-methylphenyl, 4-methanesulfonylphenyl, 3-methoxyphenyl, 3-methylphenyl, 3-trifluoromethylphenyl, 4-methylphenyl, 2-methylphenyl, 4-cyanophenyl, 3,4-dichlorophenyl, or 2,3-dihydro-benzo[1,4]dioxin-6-yl. In still other embodiments, $R^d$ is pyridin-2-yl, pyridin-4-yl, 2-fluoro-5-methyl-pyridin-4-yl, 4-iodo-5-methyl-pyridin-2-yl, pyridin-3-yl, pyrimidin-2-yl, pyrazin-2-yl, thiophen-3-yl, thiophen-2-yl, thiazol-4-yl, thiazol-5-yl, 5-methyl-isoxazol-4-yl, or 3,5-dimethyl-isoxazol-4-yl.

In some embodiments, each $R^f$ substituent is independently selected from the group consisting of: fluoro, chloro, bromo, iodo, methyl, ethyl, isopropyl, trifluoromethyl, hydroxy, methoxy, ethoxy, isopropoxy, methanesulfanyl, methanesulfonyl, cyano, dimethylcarbamoyl, and nitro; or two $R^f$ substituents together form —O(CH$_2$)$_2$—O—.

In some embodiments, $R^e$ is phenyl unsubstituted or substituted with one or two $R^f$ substituents. In other embodiments, $R^e$ is phenyl, 3-fluorophenyl, 4-fluorophenyl, 4-trifluoromethylphenyl, 3-cyanophenyl, 4-cyanophenyl, 2-fluorophenyl, or 2-chlorophenyl.

In some embodiments, the -X-$R^d$ substituent is in the S configuration. In some embodiments, the —CO$_2$N(R$^1$)R$^2$ substituent is in the R configuration.

In some embodiments, compounds of Formula (I) are compounds of Formula (II):

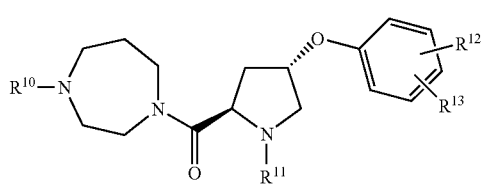

(II)

wherein $R^{10}$ is isopropyl, cyclopropyl, or cyclobutyl;

$R^{10}$ is isopropyl, cyclopropyl, or cyclobutyl;

$R^{11}$ is —C(O)C$_{1-4}$alkyl or —SO$_2$C$_{1-4}$alkyl;

$R^{12}$ is —H; halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^s$R$^t$; and —NO$_2$; and $R^{13}$ is halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^s$R$^t$; and —NO$_2$;

or adjacent $R^{12}$ and $R^{13}$ substituents together form —O(CH$_2$)$_{1-2}$—O—;

where $R^5$ and $R^t$ are each independently —H or —C$_{1-4}$alkyl;

or pharmaceutically acceptable salts thereof.

In certain preferred embodiments, the compound of Formula (I) is selected from the group consisting of:

| Ex. | Chemical Name |
|---|---|
| 1 | (2S,4R)-2-(4-Cyclobutyl-[1,4]diazepane-1-carbonyl)-4-hydroxy-pyrrolidine-1-carboxylic acid tert-butyl ester; |
| 2 | (2S,4R)-2-(4-Cyclobutyl-piperazine-1-carbonyl)-4-hydroxy-pyrrolidine-1-carboxylic acid tert-butyl ester; |
| 3 | (2S,3S)-2-(4-Cyclobutyl-[1,4]diazepane-1-carbonyl)-3-hydroxy-pyrrolidine-1-carboxylic acid tert-butyl ester; |
| 4 | (2R,4S)-2-(4-Cyclobutyl-[1,4]diazepane-1-carbonyl)-4-hydroxy-pyrrolidine-1-carboxylic acid tert-butyl ester; |
| 5 | (2R,4R)-2-(4-Cyclopropyl-[1,4]diazepane-1-carbonyl)-4-hydroxy-pyrrolidine-1-carboxylic acid tert-butyl ester; |
| 6 | (2R,4R)-2-(4-Cyclopentyl-piperazine-1-carbonyl)-4-hydroxy-pyrrolidine-1-carboxylic acid tert-butyl ester; |
| 7 | (2R,4R)-2-(4-Cyclopentyl-[1,4]diazepane-1-carbonyl)-4-hydroxy-pyrrolidine-1-carboxylic acid tert-butyl ester; |
| 8 | (2R,4R)-2-(4-Cyclobutyl-[1,4]diazepane-1-carbonyl)-4-hydroxy-pyrrolidine-1-carboxylic acid tert-butyl ester; |
| 9 | (2R,4R)-2-(4-Cyclobutyl-[1,4]diazepane-1-carbonyl)-4-hydroxy-pyrrolidine-1-carboxylic acid benzyl ester; |
| 10 | (2R,4S)-1-[2-(4-Cyclobutyl-[1,4]diazepane-1-carbonyl)-4-hydroxy-pyrrolidin-1-yl]-ethanone; |
| 11 | (2S,4S)-2-(4-Cyclobutyl-[1,4]diazepane-1-carbonyl)-4-(4-fluoro-phenoxy)-pyrrolidine-1-carboxylic acid tert-butyl ester; |
| 12 | (2S,4S)-2-(4-Cyclobutyl-piperazine-1-carbonyl)-4-(4-fluoro-phenoxy)-pyrrolidine-1-carboxylic acid tert-butyl ester; |
| 13 | (2S,4S)-2-(4-Cyclobutyl-[1,4]diazepane-1-carbonyl)-4-(3-fluoro-phenoxy)-pyrrolidine-1-carboxylic acid tert-butyl ester; |
| 14 | (2S,4S)-2-(4-Cyclobutyl-[1,4]diazepane-1-carbonyl)-4-phenoxy-pyrrolidine-1-carboxylic acid tert-butyl ester; |
| 15 | (2S,4R)-2-(4-Cyclobutyl-[1,4]diazepane-1-carbonyl)-4-(4-fluoro-phenoxy)-pyrrolidine-1-carboxylic acid tert-butyl ester; |
| 16 | (2R,4S)-4-(4-Cyano-phenoxy)-2-(4-cyclobutyl-[1,4]diazepane-1-carbonyl)-pyrrolidine-1-carboxylic acid tert-butyl ester; |
| 17 | (2R,4S)-2-(4-Cyclobutyl-[1,4]diazepane-1-carbonyl)-4-(3-fluoro-phenoxy)-pyrrolidine-1-carboxylic acid tert-butyl ester; |
| 18 | (2R,4S)-2-(4-Cyclobutyl-[1,4]diazepane-1-carbonyl)-4-(4-fluoro-phenoxy)-pyrrolidine-1-carboxylic acid tert-butyl ester; |
| 19 | (2R,4S)-2-(4-Cyclobutyl-[1,4]diazepane-1-carbonyl)-4-phenoxy-pyrrolidine-1-carboxylic acid tert-butyl ester; |
| 20 | (2R,4S)-4-(3-Chloro-phenoxy)-2-(4-cyclobutyl-[1,4]diazepane-1-carbonyl)-pyrrolidine-1-carboxylic acid tert-butyl ester; |
| 21 | (2R,4S)-4-(4-Chloro-phenoxy)-2-(4-cyclobutyl-[1,4]diazepane-1-carbonyl)-pyrrolidine-1-carboxylic acid tert-butyl ester; |
| 22 | (2R,4S)-4-(3-Cyano-phenoxy)-2-(4-cyclobutyl-[1,4]diazepane-1-carbonyl)-pyrrolidine-1-carboxylic acid tert-butyl ester; |
| 23 | (2R,4S)-2-(4-Cyclobutyl-[1,4]diazepane-1-carbonyl)-4-(4-methylsulfanyl-phenoxy)-pyrrolidine-1-carboxylic acid tert-butyl ester; |

| Ex. | Chemical Name |
|---|---|
| 24 | (2R,4S)-4-(4-Chloro-3-methyl-phenoxy)-2-(4-cyclobutyl-[1,4]diazepane-1-carbonyl)-pyrrolidine-1-carboxylic acid tert-butyl ester; |
| 25 | (2R,4S)-2-(4-Cyclobutyl-[1,4]diazepane-1-carbonyl)-4-(4-methanesulfonyl-phenoxy)-pyrrolidine-1-carboxylic acid tert-butyl ester; |
| 26 | (2R,4S)-2-(4-Cyclobutyl-[1,4]diazepane-1-carbonyl)-4-(3-methoxy-phenoxy)-pyrrolidine-1-carboxylic acid tert-butyl ester; |
| 27 | (2R,4S)-2-(4-Cyclobutyl-[1,4]diazepane-1-carbonyl)-4-m-tolyloxy-pyrrolidine-1-carboxylic acid tert-butyl ester; |
| 28 | (2R,4S)-2-(4-Cyclobutyl-[1,4]diazepane-1-carbonyl)-4-(4-trifluoromethyl-phenoxy)-pyrrolidine-1-carboxylic acid tert-butyl ester; |
| 29 | (2R,4S)-2-(4-Cyclobutyl-[1,4]diazepane-1-carbonyl)-4-p-tolyloxy-pyrrolidine-1-carboxylic acid tert-butyl ester; |
| 30 | (2R,4S)-2-(4-Cyclobutyl-[1,4]diazepane-1-carbonyl)-4-o-tolyloxy-pyrrolidine-1-carboxylic acid tert-butyl ester; |
| 31 | (2R,4S)-2-(4-Cyclopropyl-[1,4]diazepane-1-carbonyl)-4-(4-fluoro-phenoxy)-pyrrolidine-1-carboxylic acid tert-butyl ester; |
| 32 | (2R,4S)-4-(4-Cyano-phenoxy)-2-(4-cyclopropyl-[1,4]diazepane-1-carbonyl)-pyrrolidine-1-carboxylic acid tert-butyl ester; |
| 33 | (2R,4S)-2-(4-Cyclopentyl-piperazine-1-carbonyl)-4-(4-fluoro-phenoxy)-pyrrolidine-1-carboxylic acid tert-butyl ester; |
| 34 | (2R,4S)-4-(4-Cyano-phenoxy)-2-(4-cyclopentyl-piperazine-1-carbonyl)-pyrrolidine-1-carboxylic acid tert-butyl ester; |
| 35 | (2R,4S)-2-(4-Cyclopentyl-[1,4]diazepane-1-carbonyl)-4-(4-fluoro-phenoxy)-pyrrolidine-1-carboxylic acid tert-butyl ester; |
| 36 | (2R,4S)-4-(4-Cyano-phenoxy)-2-(4-cyclopentyl-[1,4]diazepane-1-carbonyl)-pyrrolidine-1-carboxylic acid tert-butyl ester; |
| 37 | (2R,4S)-2-((3R)-3-Dimethylamino-pyrrolidine-1-carbonyl)-4-(3-fluoro-phenoxy)-pyrrolidine-1-carboxylic acid tert-butyl ester; |
| 38 | (2R,4S)-2-((3S)-3-Dimethylamino-pyrrolidine-1-carbonyl)-4-(3-fluoro-phenoxy)-pyrrolidine-1-carboxylic acid tert-butyl ester; |
| 39 | (2R,4S)-2-([1,3']Bipyrrolidinyl-1'-carbonyl)-4-(3-fluoro-phenoxy)-pyrrolidine-1-carboxylic acid tert-butyl ester; |
| 40 | (2R,4S)-2-(4-Dimethylamino-piperidine-1-carbonyl)-4-(4-fluoro-phenoxy)-pyrrolidine-1-carboxylic acid tert-butyl ester; |
| 41 | (2S)-2-(4-Cyclobutyl-[1,4]diazepane-1-carbonyl)-4-(3-fluoro-phenoxy)-pyrrolidine-1-carboxylic acid tert-butyl ester; |
| 42 | (2S)-4-(3-Chloro-phenoxy)-2-(4-cyclobutyl-[1,4]diazepane-1-carbonyl)-pyrrolidine-1-carboxylic acid tert-butyl ester; |
| 43 | (2S)-4-(4-Chloro-phenoxy)-2-(4-cyclobutyl-[1,4]diazepane-1-carbonyl)-pyrrolidine-1-carboxylic acid tert-butyl ester; |
| 44 | (2S)-2-(4-Cyclobutyl-[1,4]diazepane-1-carbonyl)-4-(3,4-dichloro-phenoxy)-pyrrolidine-1-carboxylic acid tert-butyl ester; |
| 45 | (2S)-4-(4-Cyano-phenoxy)-2-(4-cyclobutyl-[1,4]diazepane-1-carbonyl)-pyrrolidine-1-carboxylic acid tert-butyl ester; |
| 46 | (2S)-2-(4-Cyclobutyl-[1,4]diazepane-1-carbonyl)-4-(4-methylsulfanyl-phenoxy)-pyrrolidine-1-carboxylic acid tert-butyl ester; |
| 47 | (2S)-2-(4-Cyclobutyl-[1,4]diazepane-1-carbonyl)-4-phenoxy-pyrrolidine-1-carboxylic acid tert-butyl ester; |
| 48 | (2S,4R)-2-(4-Cyclobutyl-[1,4]diazepane-1-carbonyl)-4-phenoxy-pyrrolidine-1-carboxylic acid tert-butyl ester; |
| 49 | (2S,4R)-2-(4-Cyclobutyl-[1,4]diazepane-1-carbonyl)-4-(3-fluoro-phenoxy)-pyrrolidine-1-carboxylic acid tert-butyl ester; |
| 50 | (2S,4R)-2-(4-Cyclobutyl-[1,4]diazepane-1-carbonyl)-4-(pyridin-2-yloxy)-pyrrolidine-1-carboxylic acid tert-butyl ester; |
| 51 | (2S,4R)-2-(4-Cyclobutyl-[1,4]diazepane-1-carbonyl)-4-(2-fluoro-5-methyl-pyridin-4-yloxy)-pyrrolidine-1-carboxylic acid tert-butyl ester; |
| 52 | (2R,4S)-2-(4-Cyclobutyl-[1,4]diazepane-1-carbonyl)-4-(4-iodo-5-methyl-pyridin-2-yloxy)-pyrrolidine-1-carboxylic acid tert-butyl ester; |
| 53 | (2R,4S)-2-(4-Cyclobutyl-[1,4]diazepane-1-carbonyl)-4-(pyridin-3-yloxy)-pyrrolidine-1-carboxylic acid tert-butyl ester; |
| 54 | (2R,4S)-2-(4-Cyclobutyl-[1,4]diazepane-1-carbonyl)-4-(thiophen-3-yloxy)-pyrrolidine-1-carboxylic acid tert-butyl ester; |
| 55 | (2R,4R)-2-(4-Cyclobutyl-[1,4]diazepane-1-carbonyl)-4-(3-fluoro-phenoxy)-pyrrolidine-1-carboxylic acid tert-butyl ester; |
| 56 | (2R,4R)-2-(4-Cyclobutyl-[1,4]diazepane-1-carbonyl)-4-(4-fluoro-phenoxy)-pyrrolidine-1-carboxylic acid tert-butyl ester; |
| 57 | (2R,4R)-4-(4-Chloro-phenoxy)-2-(4-cyclobutyl-[1,4]diazepane-1-carbonyl)-pyrrolidine-1-carboxylic acid tert-butyl ester; |
| 58 | (2R,4R)-2-(4-Cyclobutyl-[1,4]diazepane-1-carbonyl)-4-phenoxy-pyrrolidine-1-carboxylic acid tert-butyl ester; |
| 59 | (2S,4R)-2-(4-Cyclobutyl-[1,4]diazepane-1-carbonyl)-4-isopropoxy-pyrrolidine-1-carboxylic acid tert-butyl ester; |
| 60 | (2R,4R)-4-(4-Cyano-phenoxy)-2-(4-cyclobutyl-[1,4]diazepane-1-carbonyl)-pyrrolidine-1-carboxylic acid tert-butyl ester; |
| 61 | (2R,4S)-2-(4-Cyclobutyl-[1,4]diazepane-1-carbonyl)-4-(4-fluoro-phenylsulfanyl)-pyrrolidine-1-carboxylic acid tert-butyl ester; |
| 62 | (2S,4S)-2-(4-Cyclobutyl-[1,4]diazepane-1-carbonyl)-4-(4-fluoro-phenoxy)-pyrrolidine; |

-continued

| Ex. | Chemical Name |
|---|---|
| 63 | (2S,4S)-2-(4-Cyclobutyl-piperazine-1-carbonyl)-4-(4-fluoro-phenoxy)-pyrrolidine; |
| 64 | (3S,5R)-4-[5-(4-Cyclobutyl-[1,4]diazepane-1-carbonyl)-pyrrolidin-3-yloxy]-benzonitrile; |
| 65 | (2R,4S)-4-(3-Fluoro-phenoxy)-2-(4-cyclobutyl-[1,4]diazepane-1-carbonyl)-pyrrolidine; |
| 66 | (2R,4S)-4-(4-Fluoro-phenoxy)-2-(4-cyclobutyl-[1,4]diazepane-1-carbonyl)-pyrrolidine; |
| 67 | (2R,4S)-4-Phenoxy-2-(4-cyclobutyl-[1,4]diazepane-1-carbonyl)-pyrrolidine; |
| 68 | (2R,4S)-4-(3-chloro-phenoxy)-2-(4-cyclobutyl-[1,4]diazepane-1-carbonyl)-pyrrolidine; |
| 69 | (2R,4S)-4-(4-Chloro-phenoxy)-2-(4-cyclobutyl-[1,4]diazepane-1-carbonyl)-pyrrolidine; |
| 70 | (2R,4S)-4-(3-Cyano-phenoxy)-2-(4-cyclobutyl-[1,4]diazepane-1-carbonyl)-pyrrolidine; |
| 71 | (2R,4S)-4-(4-Methylsulfanyl-phenoxy)-2-(4-cyclobutyl-[1,4]diazepane-1-carbonyl)-pyrrolidine; |
| 72 | (2R,4S)-4-(4-Chloro-3-methyl-phenoxy)-2-(4-cyclobutyl-[1,4]diazepane-1-carbonyl)-pyrrolidine; |
| 73 | (2R,4S)-4-(3-Methoxy-phenoxy)-2-(4-cyclobutyl-[1,4]diazepane-1-carbonyl)-pyrrolidine; |
| 74 | (2R,4S)-4-(4-m-Tolyloxy)-2-(4-cyclobutyl-[1,4]diazepane-1-carbonyl)-pyrrolidine; |
| 75 | (2R,4S)-4-(4-Trifluoromethyl-phenoxy)-2-(4-cyclobutyl-[1,4]diazepane-1-carbonyl)-pyrrolidine; |
| 76 | (2R,4S)-4-(4-p-Tolyloxy)-2-(4-cyclobutyl-[1,4]diazepane-1-carbonyl)-pyrrolidine; |
| 77 | (2R,4S)-4-(4-o-Tolyloxy)-2-(4-cyclobutyl-[1,4]diazepane-1-carbonyl)-pyrrolidine; |
| 78 | (2R,4S)-2-(4-Cyclopropyl-[1,4]diazepane-1-carbonyl)-4-(4-fluoro-phenoxy)-pyrrolidine; |
| 79 | (2R,4S)-4-(4-Cyano-phenoxy)-2-(4-cyclopropyl-[1,4]diazepane-1-carbonyl)-pyrrolidine; |
| 80 | (2R,4S)-2-(4-Cyclopentyl-piperazine-1-carbonyl)-4-(4-fluoro-phenoxy)-pyrrolidine; |
| 81 | (2R,4S)-4-(4-Cyano-phenoxy)-2-(4-cyclopentyl-piperazine-1-carbonyl)-pyrrolidine; |
| 82 | (2R,4S)-2-(4-Cyclopentyl-[1,4]diazepane-1-carbonyl)-4-(4-fluoro-phenoxy)-pyrrolidine; |
| 83 | (2R,4S)-4-(4-Cyano-phenoxy)-2-(4-cyclopentyl-[1,4]diazepane-1-carbonyl)-pyrrolidine; |
| 84 | (2R,4S)-2-((3R)-3-Dimethylamino-pyrrolidine-1-carbonyl)-4-(3-fluoro-phenoxy)-pyrrolidine; |
| 85 | (2R,4S)-2-((3S-3-Dimethylamino-pyrrolidine-1-carbonyl)-4-(3-fluoro-phenoxy)-pyrrolidine; |
| 86 | (2S,4R)-2-(4-Cyclobutyl-[1,4]diazepane-1-carbonyl)-4-(4-fluoro-phenoxy)-pyrrolidine; |
| 87 | (2S,4R)-2-(4-Cyclobutyl-[1,4]diazepane-1-carbonyl)-4-(3-fluoro-phenoxy)-pyrrolidine; |
| 88 | (2S,4R)-4-(3-Chloro-phenoxy)-2-(4-cyclobutyl-[1,4]diazepane-1-carbonyl)-pyrrolidine; |
| 89 | (2S,4S)-4-(3-Chloro-phenoxy)-2-(4-cyclobutyl-[1,4]diazepane-1-carbonyl)-pyrrolidine; |
| 90 | (2S,4R)-4-(4-Chloro-phenoxy)-2-(4-cyclobutyl-[1,4]diazepane-1-carbonyl)-pyrrolidine; |
| 91 | (2S,4S)-4-(4-Chloro-phenoxy)-2-(4-cyclobutyl-[1,4]diazepane-1-carbonyl)-pyrrolidine; |
| 92 | (2S,4R)-2-(4-Cyclobutyl-[1,4]diazepane-1-carbonyl)-4-(3,4-dichloro-phenoxy)-pyrrolidine; |
| 93 | (2S,4S)-2-(4-Cyclobutyl-[1,4]diazepane-1-carbonyl)-4-(3,4-dichloro-phenoxy)-pyrrolidine; |
| 94 | (2S,4R)-4-(4-Cyano-phenoxy)-2-(4-cyclobutyl-[1,4]diazepane-1-carbonyl)-pyrrolidine; |
| 95 | (2S,4S)-4-(4-Cyano-phenoxy)-2-(4-cyclobutyl-[1,4]diazepane-1-carbonyl)-pyrrolidine; |
| 96 | (2S,4R)-2-(4-Cyclobutyl-[1,4]diazepane-1-carbonyl)-4-(4-methylsulfanyl-phenoxy)-pyrrolidine; |
| 97 | (2S,4S)-2-(4-Cyclobutyl-[1,4]diazepane-1-carbonyl)-4-(4-methylsulfanyl-phenoxy)-pyrrolidine; |
| 98 | (2R,4S)-2-(4-Cyclobutyl-[1,4]diazepane-1-carbonyl)-4-(pyridin-2-yloxy)-pyrrolidine; |
| 99 | (2R,4S)-2-(4-Cyclobutyl-[1,4]diazepane-1-carbonyl)-4-(2-fluoro-5-methyl-pyridin-4-yloxy)-pyrrolidine; |
| 100 | (2R,4S)-2-(4-Cyclobutyl-[1,4]diazepane-1-carbonyl)-4-(4-iodo-5-methyl-pyridin-2-yloxy)-pyrrolidine; |
| 101 | (2R,4S)-2-(4-Cyclobutyl-[1,4]diazepane-1-carbonyl)-4-(pyridin-3-yloxy)-pyrrolidine; |

| Ex. | Chemical Name |
|---|---|
| 102 | (2R,4S)-2-(4-Cyclobutyl-[1,4]diazepane-1-carbonyl)-4-(thiophen-3-yloxy)-pyrrolidine; |
| 103 | (2R,4R)-4-(3-fluoro-phenoxy)-2-(4-cyclobutyl-[1,4]diazepane-1-carbonyl)-pyrrolidine; |
| 104 | (2S,4R)-2-(4-Cyclobutyl-[1,4]diazepane-1-carbonyl)-4-isopropoxy-pyrrolidine; |
| 105 | (2R,4S)-4-(4-Cyano-phenoxy)-2-(4-cyclobutyl-[1,4]diazepane-1-carbonyl)-pyrrolidine; |
| 106 | (2S,4S)-1-Methyl-2-(4-cyclobutyl-[1,4]diazepane-1-carbonyl)-4-(4-fluoro-phenoxy)-pyrrolidine; |
| 107 | (2S,4S)-1-Methyl-2-(4-cyclobutyl-piperazine-1-carbonyl)-4-(4-fluoro-phenoxy)-pyrrolidine; |
| 108 | (2S,4S)-(4-Cyclobutyl-[1,4]diazepan-1-yl)-[4-(4-fluoro-phenoxy)-1-isopropyl-pyrrolidin-2-yl]-methanone; |
| 109 | (2S,4S)-(4-Cyclobutyl-[1,4]diazepan-1-yl)-[1-ethyl-4-(4-fluoro-phenoxy)-pyrrolidin-2-yl]-methanone; |
| 110 | (2R,4S)-1-Methyl-2-(4-cyclobutyl-[1,4]diazepane-1-carbonyl)-4-(4-fluoro-phenoxy)-pyrrolidine; |
| 111 | (2R,4S)-1-Cyclobutyl-2-(4-cyclobutyl-[1,4]diazepane-1-carbonyl)-4-(4-fluoro-phenoxy)-pyrrolidine; |
| 112 | (2R,4S)-1-Isopropyl-1-cyclobutyl-2-(4-cyclobutyl-[1,4]diazepane-1-carbonyl)-4-(4-fluoro-phenoxy)-pyrrolidine; |
| 113 | (2R,4S)-1-Cyclopropylmethyl-2-(4-cyclobutyl-[1,4]diazepane-1-carbonyl)-4-(4-fluoro-phenoxy)-pyrrolidine; |
| 114 | (2S,4S)-1-[2-(4-Cyclobutyl-[1,4]diazepane-1-carbonyl)-4-(4-fluoro-phenoxy)-pyrrolidin-1-yl]-ethanone; |
| 115 | (2S,4S)-1-[2-(4-Cyclobutyl-[1,4]diazepane-1-carbonyl)-4-(3-fluoro-phenoxy)-pyrrolidin-1-yl]-ethanone; |
| 116 | (2S,4S)-1-[2-(4-Cyclobutyl-[1,4]diazepane-1-carbonyl)-4-(4-fluoro-phenoxy)-pyrrolidin-1-yl]-propan-1-one; |
| 117 | (2S,4S)-1-[2-(4-Cyclobutyl-[1,4]diazepane-1-carbonyl)-4-(4-fluoro-phenoxy)pyrrolidin-1-yl]-2-methyl-propan-1-one; |
| 118 | (2S,4S)-1-[2-(4-Cyclobutyl-[1,4]diazepane-1-carbonyl)-4-(4-fluoro-phenoxy)-pyrrolidin-1-yl]-3,3-dimethyl-butan-1-one; |
| 119 | (2S,4S)-1-[2-(4-Cyclobutyl-piperazine-1-carbonyl)-4-(4-fluoro-phenoxy)-pyrrolidin-1-yl]-ethanone; |
| 120 | (2R,4S)-1-[2-(4-Cyclobutyl-[1,4]diazepane-1-carbonyl)-4-(4-fluoro-phenoxy)-pyrrolidin-1-yl]-ethanone; |
| 121 | (2R,4S)-1-[2-(4-Cyclobutyl-[1,4]diazepane-1-carbonyl)-4-(4-methylsulfanyl-phenoxy)-pyrrolidin-1-yl]-ethanone; |
| 122 | (2R,4S)-1-[4-(4-Chloro-3-methyl-phenoxy)-2-(4-cyclobutyl-[1,4]diazepane-1-carbonyl)-pyrrolidin-1-yl]-ethanone; |
| 123 | (2R,4S)-1-[2-(4-Cyclobutyl-[1,4]diazepane-1-carbonyl)-4-(3-fluoro-phenoxy)-pyrrolidin-1-yl]-2-methyl-propan-1-one; |
| 124 | (2R,4S)-1-Cyclopropanecarbonyl-2-(4-cyclobutyl-[1,4]diazepane-1-carbonyl)-4-(4-fluoro-phenoxy)-pyrrolidine; |
| 125 | (2R,4S)-1-[2-(4-Cyclobutyl-[1,4]diazepane-1-carbonyl)-4-(3-fluoro-phenoxy)-pyrrolidin-1-yl]-propan-1-one; |
| 126 | (2R,4S)-2-(4-Cyclobutyl-[1,4]diazepane-1-carbonyl)-4-(3-fluoro-phenoxy)-pyrrolidine-1-carboxylic acid methyl ester; |
| 127 | (2R,4S)-2-(4-Cyclobutyl-[1,4]diazepane-1-carbonyl)-4-(3-fluoro-phenoxy)pyrrolidine-1-carboxylic acid ethyl ester; |
| 128 | (2S,4R)-1-[2-(4-Cyclobutyl-[1,4]diazepane-1-carbonyl)-4-(4-fluoro-phenoxy)-pyrrolidin-1-yl]-ethanone; |
| 129 | (2S,4R)-1-[2-(4-Cyclobutyl-[1,4]diazepane-1-carbonyl)-4-(3-fluoro-phenoxy)-pyrrolidin-1-yl]-ethanone; |
| 130 | (2R,4R)-4-(3-Fluoro-phenoxy)-2-(4-cyclobutyl-[1,4]diazepane-1-carbonyl)-pyrrolidine; |
| 131 | (2R,4S)-1-[2-(4-Cyclobutyl-[1,4]diazepane-1-carbonyl)-4-(3-fluoro-phenoxy)-pyrrolidin-1-yl]-ethanone; |
| 132 | (2S,4S)-1-[2-(4-Cyclobutyl-[1,4]diazepane-1-carbonyl)-4-(pyridin-2-yloxy)-pyrrolidin-1-yl]-ethanone; |
| 133 | (2S,4S)-1-[2-(4-Cyclobutyl-[1,4]diazepane-1-carbonyl)-4-(pyridin-3-yloxy)-pyrrolidin-1-yl]-ethanone; |
| 134 | (2S,4S)-1-[2-(4-Cyclobutyl-[1,4]diazepane-1-carbonyl)-4-(thiophen-3-yloxy)-pyrrolidin-1-yl]-ethanone; |
| 135 | (2S,4S)-1-[2-(4-Cyclobutyl-[1,4]diazepane-1-carbonyl)-4-(thiophen-2-yloxy)-pyrrolidin-1-yl]-ethanone; |
| 136 | (2S,4S)-1-[2-(4-Cyclobutyl-[1,4]diazepane-1-carbonyl)-4-(2,3-dihydro-benzo[1,4]dioxin-6-yloxy)-pyrrolidin-1-yl]-ethanone; |
| 137 | (2S,4S)-1-Methanesulfonyl-2-(4-cyclobutyl-[1,4]diazepane-1-carbonyl)-4-(4-fluoro-phenoxy)-pyrrolidine; |
| 138 | (2S,4S)-2-(4-Cyclobutyl-piperazin-1-yl)-[4-(4-fluoro-phenoxy)-1-methanesulfonyl-pyrrolidin-2-yl]-methanone; |
| 139 | (2S,4S)-1-Methanesulfonyl-2-(4-cyclobutyl-[1,4]diazepane-1-carbonyl)-4-(4-fluoro-phenoxy)-pyrrolidine; |
| 140 | (2R,4S)-(4-Cyclobutyl-[1,4]diazepan-1-yl)-[4-(4-fluoro-phenoxy)-1-methanesulfonyl-pyrrolidin-2-yl]-methanone; |

| Ex. | Chemical Name |
|---|---|
| 141 | (2S,4S)-2-(4-Cyclobutyl-[1,4]diazepan-1-yl)-[1-cyclopropyl-4-(4-fluoro-phenoxy)-pyrrolidin-2-yl]-methanone; |
| 142 | (2R,4S)-1-Cyclopropyl-2-(4-cyclobutyl-[1,4]diazepane-1-carbonyl)-4-(4-fluoro-phenoxy)-pyrrolidine; |
| 143 | (2S,3R)-2-(4-Cyclobutyl-[1,4]diazepane-1-carbonyl)-3-(3-fluoro-phenoxy)-pyrrolidine-1-carboxylic acid tert-butyl ester; |
| 144 | (2S,3R)-2-(4-Cyclobutyl-[1,4]diazepane-1-carbonyl)-3-(4-fluoro-phenoxy)-pyrrolidine-1-carboxylic acid tert-butyl ester; |
| 145 | (2S,3R)-3-(4-Cyano-phenoxy)-2-(4-cyclobutyl-[1,4]diazepane-1-carbonyl)-pyrrolidine-1-carboxylic acid tert-butyl ester; |
| 146 | (2S,3R)-2-(4-Cyclobutyl-[1,4]diazepane-1-carbonyl)-3-(4-methylsulfanyl-phenoxy)-pyrrolidine-1-carboxylic acid tert-butyl ester; |
| 147 | (2R,4S)-2-(4-Cyclobutyl-[1,4]diazepane-1-carbonyl)-4-(3-fluoro-benzyloxy)-pyrrolidine-1-carboxylic acid tert-butyl ester; |
| 148 | (2R,4S)-2-(4-Cyclobutyl-[1,4]diazepane-1-carbonyl)-4-(4-fluoro-benzyloxy)-pyrrolidine-1-carboxylic acid tert-butyl ester; |
| 149 | (2R,4S)-4-(4-Cyano-benzyloxy)-2-(4-cyclobutyl-[1,4]diazepane-1-carbonyl)-pyrrolidine-1-carboxylic acid tert-butyl ester; |
| 150 | (2R,4R)-2-(4-Cyclobutyl-[1,4]diazepane-1-carbonyl)-4-(3-fluoro-benzyloxy)-pyrrolidine-1-carboxylic acid tert-butyl ester; |
| 151 | (2R,4R)-2-(4-Cyclobutyl-[1,4]diazepane-1-carbonyl)-4-(4-fluoro-benzyloxy)-pyrrolidine-1-carboxylic acid tert-butyl ester; |
| 152 | (2R,4S)-2-(4-Cyclobutyl-[1,4]diazepane-1-carbonyl)-4-(3-fluoro-benzyloxy)-pyrrolidine; |
| 153 | (2R,4S)-2-(4-Cyclobutyl-[1,4]diazepane-1-carbonyl)-4-(4-fluoro-benzyloxy)-pyrrolidine; |
| 154 | (2R,4R)-2-(4-Cyclobutyl-[1,4]diazepane-1-carbonyl)-4-(3-fluoro-benzyloxy)-pyrrolidine; |
| 155 | (2R,4R)-2-(4-Cyclobutyl-[1,4]diazepane-1-carbonyl)-4-(4-fluoro-benzyloxy)-pyrrolidine; |
| 156 | (2R,4S)-4-[1-Acetyl-4-(3-fluoro-phenoxy)-pyrrolidine-2-carbonyl]-[1,4]diazepane; |
| 157 | (2R,4S)-1-[4-(3-Fluoro-phenoxy)-2-(4-isopropyl-[1,4]diazepane-1-carbonyl)-pyrrolidin-1-yl]-ethanone; |
| 158 | (2R,4S)-1-[2-(4-Cyclopentyl-[1,4]diazepane-1-carbonyl)-4-(3-fluoro-phenoxy)-pyrrolidin-1-yl]-ethanone; |
| 159 | (2R,4S)-1-[4-(3-Fluoro-phenoxy)-2-(4-isobutyl-[1,4]diazepane-1-carbonyl)-pyrrolidin-1-yl]-ethanone; |
| 160 | (2R,4S)-1-{4-(3-Fluoro-phenoxy)-2-[4-(tetrahydro-pyran-4-yl)-[1,4]diazepane-1-carbonyl]-pyrrolidin-1-yl}-ethanone; |
| 161 | (2R,4S)-1-[2-(4-Cyclopropyl-[1,4]diazepane-1-carbonyl)-4-(3-fluoro-phenoxy)-pyrrolidin-1-yl]-ethanone; |
| 162 | (2R,4S)-1-[2-(4-Benzyl-[1,4]diazepane-1-carbonyl)-4-(3-fluoro-phenoxy)-pyrrolidin-1-yl]-ethanone; |
| 163 | (2R,4S)-1-[4-(3-Fluoro-phenoxy)-2-(4-methyl-[1,4]diazepane-1-carbonyl)-pyrrolidin-1-yl]-ethanone; |
| 164 | (2S)-2-(4-Cyclobutyl-[1,4]diazepane-1-carbonyl)-2-(3-fluoro-benzyl)-pyrrolidine-1-carboxylic acid tert-butyl ester; |
| 165 | (2S)-2-(4-Cyclobutyl-[1,4]diazepane-1-carbonyl)-2-(4-fluoro-benzyl)-pyrrolidine-1-carboxylic acid tert-butyl ester; |
| 166 | (2S)-2-(4-Cyclobutyl-[1,4]diazepane-1-carbonyl)-2-(4-trifluoromethyl-benzyl)-pyrrolidine-1-carboxylic acid tert-butyl ester; |
| 167 | (2S)-2-Benzyl-2-(4-cyclobutyl-[1,4]diazepane-1-carbonyl)-pyrrolidine-1-carboxylic acid tert-butyl ester; |
| 168 | (2S)-2-(4-Cyclobutyl-[1,4]diazepane-1-carbonyl)-2-(3-fluoro-benzyl)-pyrrolidine; |
| 169 | (2S)-(4-Cyclobutyl-[1,4]diazepan-1-yl)-[2-(4-fluoro-benzyl)-pyrrolidin-2-yl]-methanone; |
| 170 | (2S)-(4-Cyclobutyl-[1,4]diazepan-1-yl)-[2-(4-trifluoromethyl-benzyl)-pyrrolidin-2-yl]-methanone; |
| 171 | (2S)-(2-Benzyl-pyrrolidin-2-yl)-(4-cyclobutyl-[1,4]diazepan-1-yl)-methanone; |
| 172 | (2S)-(1-[2-(4-Cyclobutyl-[1,4]diazepane-1-carbonyl)-2-(4-fluoro-benzyl)-pyrrolidin-1-yl]-ethanone; |
| 173 | (2S,4R)-4-Benzyl-2-(4-cyclobutyl-[1,4]diazepane-1-carbonyl)-pyrrolidine-1-carboxylic acid tert-butyl ester; |
| 174 | (2S,4R)-2-(4-Cyclobutyl-[1,4]diazepane-1-carbonyl)-4-(4-fluoro-benzyl)pyrrolidine-1-carboxylic acid tert-butyl ester; |
| 175 | (2S,4R)-2-(4-Cyclobutyl-[1,4]diazepane-1-carbonyl)-4-(3-fluoro-benzyl)-pyrrolidine-1-carboxylic acid tert-butyl ester; |
| 176 | (2S,4R)-2-(4-Cyclobutyl-[1,4]diazepane-1-carbonyl)-4-thiophen-3-ylmethyl-pyrrolidine-1-carboxylic acid tert-butyl ester; |
| 177 | (2S,4R)-(4-Benzyl-pyrrolidin-2-yl)-(4-cyclobutyl-[1,4]diazepan-1-yl)-methanone; |
| 178 | (2S,4R)-(4-Cyclobutyl-[1,4]diazepan-1-yl)-[4-(4-fluoro-benzyl)-pyrrolidin-2-yl]-methanone; |
| 179 | (2S,4R)-(4-Cyclobutyl-[1,4]diazepan-1-yl)-[4-(3-fluoro-benzyl)-pyrrolidin-2-yl]-methanone; |

| Ex. | Chemical Name |
|---|---|
| 180 | (2S,4R)-(4-Cyclobutyl-[1,4]diazepan-1-yl)-(4-thiophen-3-ylmethyl-pyrrolidin-2-yl)-methanone; |
| 181 | (2S,4R)-(1-[2-(4-Cyclobutyl-[1,4]diazepane-1-carbonyl)-4-(4-fluoro-benzyl)-pyrrolidin-1-yl]-ethanone; |
| 182 | (2S,4R)-(1-[2-(4-Cyclobutyl-[1,4]diazepane-1-carbonyl)-4-(3-fluoro-benzyl)-pyrrolidin-1-yl]-ethanone; |
| 183 | (2S,4R)-(1-[2-(4-Cyclobutyl-[1,4]diazepane-1-carbonyl)-4-thiophen-3-ylmethyl-pyrrolidin-1-yl]-ethanone; |
| 184 | (2R,4S)-(4-Cyclobutyl-[1,4]diazepan-1-yl)-[4-(3-fluoro-phenoxy)-1-(2-hydroxy-ethyl)-pyrrolidin-2-yl]-methanone; |
| 185 | (2R,4S)-(4-Cyclobutyl-[1,4]diazepan-1-yl)-[1-(2-fluoro-ethyl)-4-(3-fluoro-phenoxy)-pyrrolidin-2-yl]-methanone; |
| 186 | (2R,4S)-(4-Cyclobutyl-[1,4]diazepan-1-yl)-[4-(3-fluoro-phenoxy)-1-(tetrahydro-pyran-4-yl)-pyrrolidin-2-yl]-methanone; |
| 187 | (2R,4S)-[2-(4-Cyclobutyl-[1,4]diazepane-1-carbonyl)-4-(3-fluoro-phenoxy)-pyrrolidin-1-yl]-phenyl-methanone; |
| 188 | (2R,4S)-1-[4-Cyclobutoxy-2-(4-cyclobutyl-[1,4]diazepane-1-carbonyl)-pyrrolidin-1-yl]-ethanone; |
| 189 | (2R,4S)-1-[2-(4-Cyclobutyl-[1,4]diazepane-1-carbonyl)-4-(tetrahydro-furan-3-yloxy)-pyrrolidin-1-yl]-ethanone; |
| 190 | (2R,4S)-1-[2-(4-Cyclobutyl-[1,4]diazepane-1-carbonyl)-4-(tetrahydro-pyran-4-yloxy)-pyrrolidin-1-yl]-ethanone; |
| 191 | (2R,4S)-1-[2-(4-Cyclobutyl-[1,4]diazepane-1-carbonyl)-4-(pyridin-4-yloxy)-pyrrolidin-1-yl]-ethanone; |
| 192 | (2R,4S)-1-[2-(4-Cyclobutyl-[1,4]diazepane-1-carbonyl)-4-(pyrimidin-5-yloxy)-pyrrolidin-1-yl]-ethanone; |
| 193 | (2R,4S)-1-[2-(4-Cyclobutyl-[1,4]diazepane-1-carbonyl)-4-(pyrazin-2-yloxy)-pyrrolidin-1-yl]-ethanone; |
| 194 | (2R,4S)-1-[2-(4-Cyclobutyl-[1,4]diazepane-1-carbonyl)-4-(thiazol-4-yloxy)-pyrrolidin-1-yl]-ethanone; |
| 195 | (2R,4S)-1-[2-(4-Cyclobutyl-[1,4]diazepane-1-carbonyl)-4-(thiazol-5-yloxy)-pyrrolidin-1-yl]-ethanone; |
| 196 | (2R,4S)-1-[2-(4-Cyclobutyl-[1,4]diazepane-1-carbonyl)-4-(5-methyl-isoxazol-4-yloxy)-pyrrolidin-1-yl]-ethanone; |
| 197 | (2R,4S)-1-[2-(4-Cyclobutyl-[1,4]diazepane-1-carbonyl)-4-(3,5-dimethyl-isoxazol-4-yloxy)-pyrrolidin-1-yl]-ethanone; |
| 198 | (2R,4S)-(4-Cyclobutyl-[1,4]diazepan-1-yl)-[4-(3-fluoro-phenoxy)-1-(tetrahydro-furan-3-yl)-pyrrolidin-2-yl]-methanone; |
| 199 | (2R,4S)-(4-Cyclobutyl-[1,4]diazepan-1-yl)-[4-(3-fluoro-phenoxy)-1-(tetrahydro-pyran-3-yl)-pyrrolidin-2-yl]-methanone; |
| 200 | 1-[2-Benzyl-2-(4-cyclobutyl-[1,4]diazepane-1-carbonyl)-pyrrolidin-1-yl]-ethanone; |
| 201 | 1-[2-(4-Cyclobutyl-[1,4]diazepane-1-carbonyl)-2-(3-fluoro-benzyl)-pyrrolidin-1-yl]-ethanone; |
| 202 | 1-[2-(4-Cyclobutyl-[1,4]diazepane-1-carbonyl)-2-(4-trifluoromethyl-benzyl)-pyrrolidin-1-yl]-ethanone; |
| 203 | 3-[1-Acetyl-2-(4-cyclobutyl-[1,4]diazepane-1-carbonyl)-pyrrolidin-2-ylmethyl]-benzonitrile; |
| 204 | 3-[2-(4-Cyclobutyl-[1,4]diazepane-1-carbonyl)-pyrrolidin-2-ylmethyl]-benzonitrile; |
| 205 | 4-[2-(4-Cyclobutyl-[1,4]diazepane-1-carbonyl)-pyrrolidin-2-ylmethyl]-benzonitrile; |
| 206 | 4-[1-Acetyl-2-(4-cyclobutyl-[1,4]diazepane-1-carbonyl)-pyrrolidin-2-ylmethyl]-benzonitrile; |
| 207 | 1-[2-(4-Cyclobutyl-[1,4]diazepane-1-carbonyl)-2-(2-fluoro-benzyl)-pyrrolidin-1-yl]-ethanone; |
| 208 | (4-Cyclobutyl-[1,4]diazepan-1-yl)-[2-(2-fluoro-benzyl)-pyrrolidin-2-yl]-methanone; |
| 209 | [2-(2-Chloro-benzyl)-pyrrolidin-2-yl]-(4-cyclobutyl-[1,4]diazepan-1-yl)-methanone; and |
| 210 | 1-[2-(2-Chloro-benzyl)-2-(4-cyclobutyl-[1,4]diazepane-1-carbonyl)-pyrrolidin-1-yl]-ethanone; | and pharmaceutically acceptable salts thereof.

The invention includes also pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art.

The compounds of Formula (I) and their pharmaceutically acceptable salts, pharmaceutically acceptable prodrugs, and pharmaceutically active metabolites of the present invention are useful as modulators of the histamine $H_3$ receptor in the methods of the invention. As such modulators, the compounds may act as antagonists, agonists, or inverse agonists. "Modulators" include both inhibitors and activators, where "inhibitors" refer to compounds that decrease, prevent, inactivate, desensitize or down-regulate histamine $H_3$ receptor expression or activity, and "activators" are compounds that increase, activate, facilitate, sensitize, or up-regulate histamine $H_3$ receptor expression or activity.

The term "treat" or "treating" as used herein is intended to refer to administration of an active agent or composition of the invention to a subject for the purpose of effecting a therapeutic or prophylactic benefit through modulation of histamine $H_3$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by histamine $H_3$ receptor activity, such as: cognitive disorders, sleep disorders, psychiatric disorders, and other disorders. Symptoms or disease states are intended to be included within the scope of "medical conditions, disorders, or diseases."

Cognitive disorders include, for example, dementia, Alzheimer's disease (Panula, P. et al., *Soc. Neurosci. Abstr.* 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., *Soc. Neurosci. Abstr.* 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag (phase delay), and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., *Naunyn-Schmiedeberg's Arch. Pharmacol.* 1996, 353, 290-294), including cognitive deficits and negative symptoms associated with schizophrenia, bipolar disorders, manic disorders, depression (Lamberti, C. et al. *Br. J. Pharmacol.* 1998, 123(7), 1331-1336; Perez-Garcia, C. et al. *Psychopharmacology* 1999, 142(2), 215-220) (Also see: Stark, H. et al., *Drugs Future* 1996, 21(5), 507-520; and Leurs, R. et al., *Prog. Drug Res.* 1995, 45, 107-165 and references cited therein.), including bipolar depression, obsessive-compulsive disorder, and post-traumatic stress disorder.

Other disorders include, for example, motion sickness, vertigo (e.g. vertigo or benign postural vertigo), tinitus, epilepsy (Yokoyama, H. et al., *Eur. J. Pharmacol.* 1993, 234, 129-133), migraine, neurogenic inflammation, neuropathic pain, Down Syndrome, seizures, eating disorders (Machidori, H. et al., *Brain Res.* 1992, 590, 180-186), obesity, substance abuse disorders, movement disorders (e.g. restless legs syndrome), eye-related disorders (e.g. macular degeneration and retinitis pigmentosis), and drug addiction (including alcoholism; See: Lintunen et al. *FASEB J.* 2001, 15, 1074-1076).

Particularly, as modulators of the histamine $H_3$ receptor, the compounds of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In treatment methods according to the invention, an effective amount of at least one compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.001 to 100 mg/kg/day, or about 0.001 to 35 mg/kg/day, in single or divided dosage units (e.g., BID, TID, QID). For a 70-kg human, an illustrative range for a suitable dosage amount is from about 0.05 to about 70 mg/day, or about 1 to about 30 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by histamine $H_3$ receptor activity or that are active against another target associated with the particular condition, disorder, or disease, such as $H_1$ receptor antagonists, $H_2$ receptor antagonists, $H_4$ receptor antagonists, topiramate, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, donepezil, rivastigmine, or galantamine), or modafinil. The combination may serve to increase efficacy (e.g., by including in the combination a compound potentiating the potency or effectiveness of a compound according to the invention), decrease one or more side effects, or decrease the required dose of the compound according to the invention.

More particularly, compounds of the invention in combination with modafinil are useful for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag. Preferably, the combination method employs doses of modafinil in the range of about 20 to 300 mg per dose.

In another embodiment, compounds of the invention in combination with topiramate are useful for the treatment of obesity. Preferably, the combination method employs doses of topiramate in the range of about 20 to 300 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.001 to about 100 mg/kg daily, or from about 0.001 to about 35 mg/kg daily, or from about 0.01 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent.

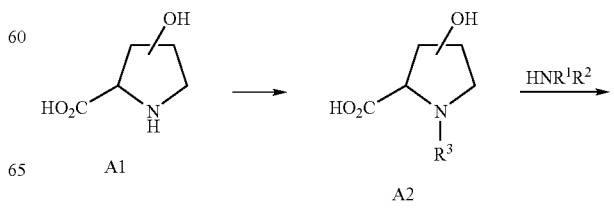

SCHEME A

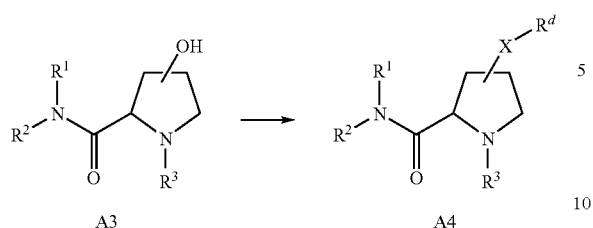

lp;1pSome embodiments of Formula (I), where X is O or S are prepared according to Scheme A. Hydroxy-prolines A1, which are commercially available, are converted to substituted prolines A2 using, for example, acylation, sulfonylation, alkylation, or reductive amination methods known in the art. Compounds A2 are coupled with amines $HNR^1R^2$ using standard amide coupling methods to form amides A3. Preferably, amide coupling is performed in the presence of 1-(3-dimethylaminopropyl)-3-ethylcarbodiimide (EDC), 1-hydroxybenzotriazole (HOBt), and a tertiary amine base such as triethylamine or N-methylmorpholine, and optional addition of 4-dimethylaminopyridine (DMAP), or in the presence of EDC and DMAP, in a solvent such as N,N-dimethylformamide (DMF), tetrahydrofuran (THF), $CH_2Cl_2$, or acetonitrile, or a mixture thereof. One skilled in the art will recognized compounds A3 as embodiments of Formula (I).

The -X-$R^d$ substituent is installed in one of several ways to provide compounds A4, which are embodiments of Formula (I). In one method, compounds A3 are reacted with reagents $R^d$—OH or $R^d$—SH (where $R^d$ is not H) under standard Mitsunobu conditions to generate compounds A4 with inversion of stereochemistry at the hydroxyl position. Preferably, Mitsunobu reactions are performed in the presence of a trialkyl- or triarylphosphine ligand, such as tri-butylphosphine or triphenylphosphine (optionally resin-bound), and diethyl-, dibutyl, or diisopropyl-azodicarboxylate (DEAD, DBAD or DIAD, respectively), in a solvent such as THF or $CH_2Cl_2$. In another method, reagents $R^d$-Hal1 (where $R^d$ is phenyl or monocyclic heteroaryl and Hal1 is iodide or bromide) are coupled with compounds A4 in the presence of a copper(I) catalyst, such as copper(I) iodide, an additive, such as 3,4,7,8-tetramethyl-1,10-phenanthroline, and a base, such as $Cs_2CO_3$, in a solvent such as toluene. Preferably, reactions are run at temperatures from about 70° C. to about 110° C. in a sealed tube. In another method, reagents $R^d$-Hal2 (where $R^d$ is $C_{1-6}$alkyl, an optionally substituted benzyl, cycloalkyl, or heterocycloalkyl group, or a phenyl group substituted with an electron-withdrawing group such as —$SO_2C_{1-4}$alkyl; —CN; —$CONR^gR^h$; or —$NO_2$; and Hal2 is iodide, bromide, or chloride) are reacted with compounds A3 under $S_N2$ or $S_NAr$ conditions, including a suitable base, such as NaH, in a solvent such as DMF. In another method, the hydroxy substituent in compounds A3 is converted to a suitable leaving group, such as methanesulfonate, p-toluenesulfonate, p-nitrophenylsulfonate, bromide, or chloride), and displaced with reagents $R^d$—OH or $R^d$—SH. Such displacement reactions are preferably accomplished in the presence of a suitable base, such as $K_2CO_3$, in a solvent such as DMF, and optionally with heating to a temperature from about 70° C. to about 100° C. in a sealed tube.

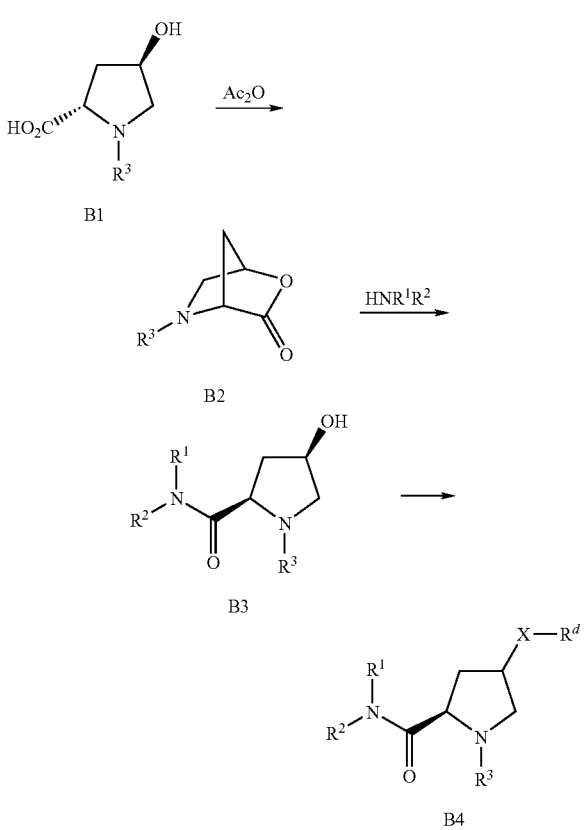

Compounds of Formula (I) are also prepared according to Scheme B. Trans-hydroxy prolines B1 (or their enantiomers) are reacted with acetic anhydride as described by Croce et al. (*Tetrahedron: Asymmetry* 2002, 13, 197-201) to give bicyclic compounds B2. Ring opening with amines $HNR^1R^2$ in a solvent such as isopropyl alcohol (IPA) or tert-amyl alcohol, at a temperature from about 50° C. to about 100° C. provides compounds B3. Further transformation as described in Scheme A gives compounds B4. One skilled in the art will recognize compounds B3 and B4 are embodiments of Formula (I).

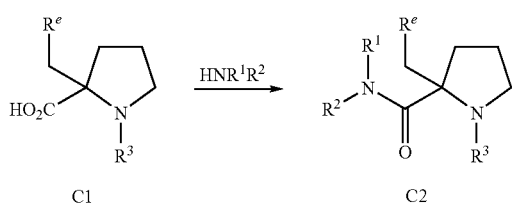

Some embodiments of Formula (I) are also available as shown in Scheme C. Compounds C1 are commercially available or are prepared according to the methods of Kawabata et al. (*J. Am. Chem. Soc.* 1993, 125(43), 13012-13013; *J. Am. Chem. Soc.* 1996, 128(48), 15394-15395). Amide coupling with amines $HNR^1R^2$ using standard amide coupling methods provides amides C2, which are embodiments of Formula (I).

SCHEME D

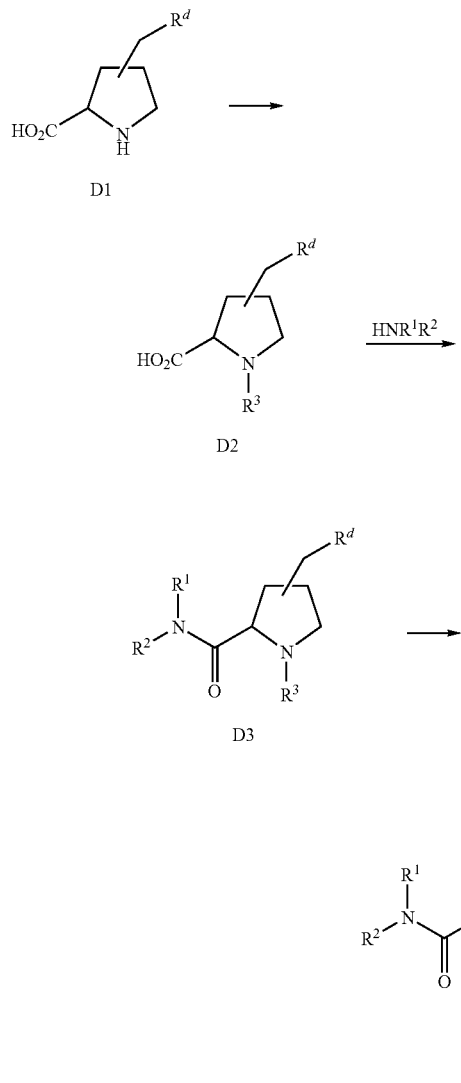

Some embodiments of Formula (I), where X is CH₂, are prepared as in Scheme D. Compounds D1, which are commercially available or are prepared according to literature methods (Ganellin et al. *J. Med. Chem.* 2005, 48, 7333-7342; Del Valle et al. *J. Org. Chem.* 2003, 68, 3923-3931; Zhang et al. *Tetrahedron Lett.* 2003, 44, 1413-1415), are processed as described in Scheme A to form compounds D4, which are embodiments of Formula (I).

The present invention is also directed to methods of making a compound of Formula (II) or a pharmaceutically acceptable salt thereof:

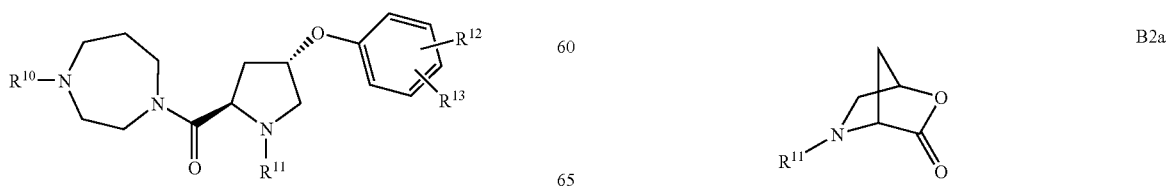

comprising
a) activating a compound of formula 10:

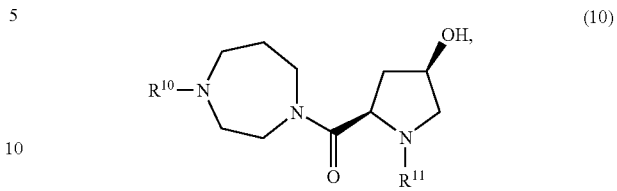

wherein said activating comprises:
1) reacting the compound of formula (10) under Mitsunobu conditions; or
2) reacting the compound of formula (10) with an activating agent selected from the group consisting of methanesulfonyl chloride, p-toluenesulfonyl chloride, and p-nitrophenylsulfonyl chloride;

to form an activated compound; and
b) reacting the activated compound with a phenol of formula 11:

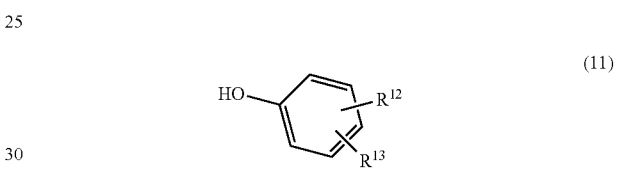

wherein
$R^{10}$ is isopropyl, cyclopropyl, or cyclobutyl;
$R^{11}$ is —C(O)C$_{1-4}$alkyl or —SO$_2$C$_{1-4}$alkyl;
$R^{12}$ is —H; halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^s$R$^t$; and —NO$_2$; and
$R^{13}$ is halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^s$R$^t$; and —NO$_2$;
or adjacent $R^{12}$ and $R^{13}$ substituents together form —O(CH$_2$)$_{1-2}$—O—;
where R$^s$ and R$^t$ are each independently —H or —C$_{1-4}$alkyl.

In some embodiments, Mitsunobu conditions employ a trialkyl- or triarylphosphine ligand, such as tri-butylphosphine or triphenylphosphine (optionally resin-bound), and diethyl-, dibutyl-, or diisopropyl-azodicarboxylate (DEAD, DBAD or DIAD, respectively), in a solvent such as THF or CH$_2$Cl$_2$.

The methods of the invention further comprise reacting a compound of formula B2a:

B2a with an amine of formula 12:

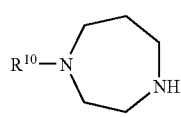

to form a compound of formula (10).

Alternatively, methods of the invention further comprise reacting a compound of formula B2a:

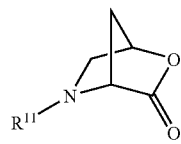

with [1,4]diazepane to form a compound of formula 13:

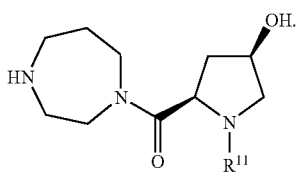

In some embodiments, the compound of formula 13 is produced in greater than 70% yield.

In each of the Schemes above, when $R^3$ is a tert-butoxycarbonyl (Boc) or benzyloxycarbonyl (Cbz) group, it may serve as a protecting group for the proline nitrogen. Such protecting groups are carried through the synthesis and removed at a latter stage to provide compounds where $R^3$ is H. The free amines are then optionally reacted through acylation, sulfonylation, alkylation, or reductive amination methods to prepare further $R^3$ analogs.

Those skilled in the art will recognize that several of the chemical transformations described above may be performed in a different order than that depicted in the above Schemes.

Compounds of Formula (I) may be converted to their corresponding salts using methods known to those skilled in the art. For example, amines of Formula (I) may be treated with trifluoroacetic acid (TFA), HCl, maleic acid, or citric acid in a solvent such as diethyl ether (Et$_2$O), CH$_2$Cl$_2$, THF, or methanol (MeOH) to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Normal-phase flash column chromatography (FCC) was performed on silica gel (SiO$_2$) using prepackaged cartridges, eluting with 2 M NH$_3$/MeOH in CH$_2$Cl$_2$ or 1% NH$_4$OH in MeOH/CH$_2$Cl$_2$ unless otherwise indicated.

Preparative reverse-phase high performance liquid chromatography (HPLC) was performed on a Gilson® HPLC with an Xterra Prep RP$_{18}$ (5 µm, 30×100 mm) column, and a gradient of 10 to 99% acetonitrile/water (20 mM NH$_4$OH) over 12 to 18 min, and a flow rate of 30 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Version 6.0.2 (CambridgeSoft, Cambridge, Mass.).

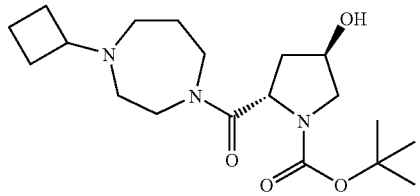

Example 1

(2S,4R)-2-(4-Cyclobutyl-[1,4]diazepane-1-carbonyl)-4-hydroxy-pyrrolidine-1-carboxylic acid tert-butyl Ester To a solution of N-Boc-trans-4-hydroxy-L-proline (1.0 g, 4.32 mmol), 1-cyclobutyl-[1,4]diazepane hydrochloride (981 mg, 4.32 mmol), EDC (869 mg, 4.54 mmol) and HOBt (583 mg, 4.32 mmol) in DMF (22 mL) was added Et$_3$N (1.2 mL, 8.64 mmol). The solution was allowed to stir overnight at room temperature (rt). The mixture was diluted with 5% aqueous (aq.) NaHCO$_3$ and extracted with CH$_2$Cl$_2$ (3×). The combined organic layers were dried and concentrated. Purification by FCC provided the desired product (897 mg, 56%). MS (ESI): mass calcd. for C$_{19}$H$_{33}$N$_3$O$_4$, 367.25; m/z found, 368.6 [M+H]⁺. ¹H NMR (CDCl₃): 4.81-4.67 (m, 1H), 4.59-4.48 (m, 1H), 3.79-3.42 (m, 6H), 2.92-2.80 (m, 1H), 2.63-2.30 (m, 4H), 2.26-2.07 (m, 2H), 2.07-1.97 (m, 3H), 1.91-1.75 (m, 4H), 1.73-1.54 (m, 2H), 1.48-1.39 (m, 9H).

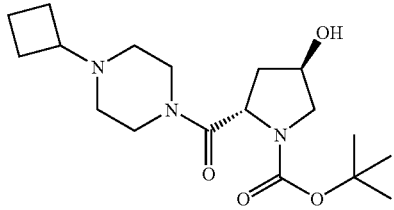

Example 2

(2S,4R)-2-(4-Cyclobutyl-piperazine-1-carbonyl)-4-hydroxy-pyrrolidine-1-carboxylic acid tert-butyl Ester The title compound was prepared using methods analogous to those described for Example 1. MS (ESI): mass calcd. for C₁₈H₃₁N₃O₄, 353.23; m/z found, 354.5 [M+H]⁺. ¹H NMR (CDCl₃): 4.87-4.69 (m, 1H), 4.57-4.47 (m, 1H), 3.77-3.44 (m, 6H), 2.77-2.67 (m, 1H), 2.50-2.32 (m, 2H), 2.30-2.17 (m, 3H), 2.16-1.97 (m, 4H), 1.93-1.61 (m, 4H), 1.49-1.38 (m, 9H).

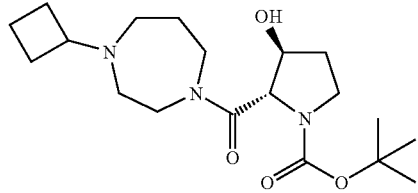

Example 3

(2S,3S)-2-(4-Cyclobutyl-[1,4]diazepane-1-carbonyl)-3-hydroxy-pyrrolidine-1-carboxylic acid tert-butyl Ester Step A. N-Boc-trans-3-hydroxy-L-proline. A mixture of 3-trans-hydroxy-L-proline (3.0 g, 22.9 mmol), di-tert-butyl dicarbonate (5.5 g, 25.2 mmol), and 1 M NaOH (23 mL) in 1,4-dioxane (0.5 M) and water (1 M) was stirred for 1.5 h at rt. The reaction mixture was acidified with 10% aq. KHSO₄ and extracted with ethyl acetate (EtOAc; 3×). The combined organic layers were dried and concentrated.

Step B. The title compound was prepared using the method outlined in Example 1. MS (ESI): mass calcd. for C₁₉H₃₃N₃O₄, 367.25; m/z found, 368.4 [M+H]⁺. ¹H NMR (CDCl₃): 4.54-4.24 (m, 2H), 4.06-3.20 (m, 7H), 2.89-2.78 (m, 1H), 2.73-2.53 (m, 1H), 2.52-2.09 (m, 4H), 2.05-1.71 (m, 7H), 1.70-1.52 (m, 2H), 1.41-1.35 (m, 9H).

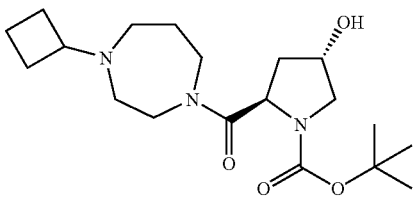

Example 4

(2R,4S)-2-(4-Cyclobutyl-[1,4]diazepane-1-carbonyl)-4-hydroxy-pyrrolidine-1-carboxylic acid tert-butyl Ester The title compound was prepared from 4-trans-hydroxy-D-proline as described for Example 3. MS (ESI): mass calcd. for C₁₉H₃₃N₃O₄, 367.25; m/z found, 368.3 [M+H]⁺. ¹H NMR (CDCl₃): 4.86-4.65 (m, 1H), 4.61-4.49 (m, 1H), 3.83-3.41 (m, 6H), 2.93-2.78 (m, 1H), 2.72-2.30 (m, 4H), 2.27-1.94 (m, 5H), 1.94-1.56 (m, 6H), 1.43 (d, J=13.0 Hz, 9H).

The compounds in Examples 5-8 were prepared from 4-cis-hydroxy-D-proline using methods analogous to those described for Example 3.

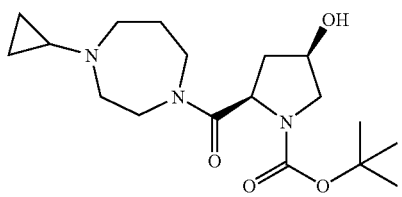

Example 5

(2R,4R)-2-(4-Cyclopropyl-[1,4]diazepane-1-carbonyl)-4-hydroxy-pyrrolidine-1-carboxylic acid tert-butyl Ester MS (ESI): mass calcd. for C₁₈H₃₁N₃O₄, 353.23; m/z found, 354.3 [M+H]⁺. ¹H NMR (CDCl₃): 6.01-5.14 (m, 1H), 4.85-4.62 (m, 1H), 4.39-4.28 (m, 1H), 4.04-3.29 (m, 6H), 3.12-2.68 (m, 4H), 2.38-2.21 (m, 1H), 2.05-1.75 (m, 4H), 1.51-1.39 (m, 9H), 0.57-0.33 (m, 4H).

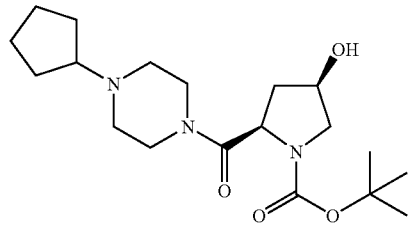

Example 6

(2R,4R)-2-(4-Cyclopentyl-piperazine-1-carbonyl)-4-hydroxy-pyrrolidine-1-carboxylic acid tert-butyl Ester MS (ESI): mass calcd. for C₁₉H₃₃N₃O₄, 367.25; m/z found, 368.3 [M+H]⁺. ¹H NMR (CDCl₃): 5.72-4.64 (m, 2H), 4.43-4.25 (m, 1H), 3.99-3.38 (m, 6H), 2.79-2.19 (m, 6H), 2.04-1.81 (m, 3H), 1.79-1.53 (m, 6H), 1.50-1.36 (m, 9H).

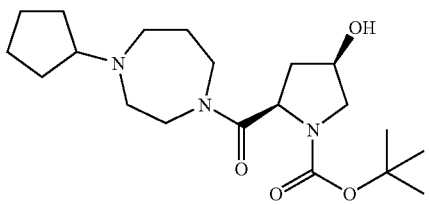

Example 7

(2R,4R)-2-(4-Cyclopentyl-[1,4]diazepane-1-carbonyl)-4-hydroxy-pyrrolidine-1-carboxylic acid tert-butyl Ester MS (ESI): mass calcd. for $C_{20}H_{35}N_3O_4$, 381.26; m/z found, 382.4 [M+H]$^+$. $^1$H NMR (CDCl$_3$): 6.02-5.23 (m, 1H), 4.86-4.62 (m, 1H), 4.39-4.28 (m, 1H), 4.07-3.63 (m, 4H), 3.60-3.29 (m, 3H), 3.01-2.16 (m, 6H), 2.08-1.23 (m, 19H).

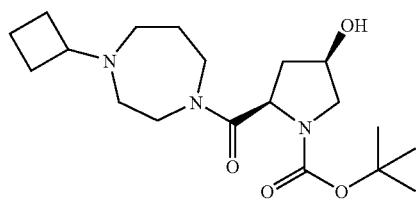

Example 8

(2R,4R)-2-(4-Cyclobutyl-[1,4]diazepane-1-carbonyl)-4-hydroxy-pyrrolidine-1-carboxylic acid tert-butyl Ester MS (ESI): mass calcd. for $C_{19}H_{33}N_3O_4$, 367.25; found 368.3 [M+H]$^+$. $^1$H NMR (CDCl$_3$) 5.98-5.08 (m, 1H), 4.76-4.58 (m, 1H), 4.35-4.21 (m, 1H), 3.99-3.85 (m, 1H), 3.84-3.58 (m, 2H), 3.57-3.28 (m, 2H), 2.92-2.76 (m, 1H), 2.75-2.14 (m, 5H), 2.06-1.87 (m, 3H), 1.85-1.68 (m, 3H), 1.68-1.49 (m, 2H), 1.46-1.27 (m, 9H).

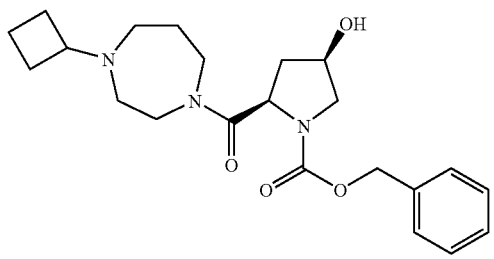

Example 9

(2R,4R)-2-(4-Cyclobutyl-[1,4]diazepane-1-carbonyl)-4-hydroxy-pyrrolidine-1-carboxylic Acid Benzyl Ester A solution of cis-D-hydroxyproline (221.1 mg, 1.687 mmol) in CH$_2$Cl$_2$ (15 mL) was treated with diisopropylethylamine (0.60 mL) and chlorotrimethylsilane (0.60 mL). The mixture was stirred for 2 hours, cooled to 0° C. and treated with benzyl chloroformate (0.250 mL). The reaction was stirred for 15 h at rt and then extracted with 1 N NaOH/Et$_2$O. The aqueous layer was acidified with 1 N HCl and extracted with EtOAc. The organic layer was dried and concentrated to give 4-hydroxy-pyrrolidine-1,2-dicarboxylic acid 1-benzyl ester (0.270 g), which was used directly in the next step. A solution of 4-hydroxy-pyrrolidine-1,2-dicarboxylic acid 1-benzyl ester (0.2377 g) in acetonitrile (20 mL) was treated with cyclobutyl-[1,4]diazepane dihydrochloride (0.2411 g), triethylamine (0.400 mL), and O-(7-azabenzotriazol-1-yl)-N,N,N',N'-tetramethyluronium hexafluorophosphate (0.4780 g). After 3 h, the reaction mixture was extracted with 1 N NaOH/CH$_2$Cl$_2$, and the organic layer was dried and concentrated. Purification by FCC provided the desired product (0.1628 g, 24% over two steps). MS (ESI): mass calcd. for $C_{22}H_{31}N_3O_4$, 401.50; m/z found, 402.3 [M+H]$^+$.

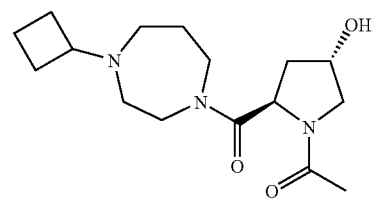

Example 10

(2R,4S)-1-[2-(4-Cyclobutyl-[1,4]diazepane-1-carbonyl)-4-hydroxy-pyrrolidin-1-yl]-ethanone Step A: (2R,4S)-1-Acetyl-4-hydroxy-pyrrolidine-2-carboxylic acid. A solution of 4-trans-hydroxy-D-proline (1.31 g, 10 mmol) in glacial acetic acid (10 mL) was heated to reflux. Acetic anhydride (945 µL, 10 mmol) was added dropwise with stirring. Upon complete addition, the reacton mixture was cooled, concentrated, and placed under high vacuum for 18 h to provide the desired compound (1.9 g). The crude product was carried forward without further purification. MS (ESI): mass calcd. for $C_7H_{11}NO_4$, 173.07; m/z found, 174.2 [M+H]$^+$.

Step B. The title compound was prepared using the method outlined in Example 1. MS (ESI): mass calcd. for $C_{16}H_{27}N_3O_3$, 309.21; m/z found, 310.3 [M+H]$^+$. $^1$H NMR (CDCl$_3$): 4.93 (ddd, J=7.3, 7.3, 4.3 Hz, 1H), 4.73-4.65 (m, 1H), 3.90 (dd, J=10.7, 4.8 Hz, 1H), 3.84-3.75 (m, 1H), 3.72-3.60 (m, 2H), 2.95-2.84 (m, 1H), 3.54-3.43 (m, 2H), 2.72-2.34 (m, 4H), 2.20-2.12 (m, 2H), 2.08 (s, 3H), 2.06-1.98 (m, 3H), 1.91-1.70 (m, 4H), 1.70-1.58 (m, 2H).

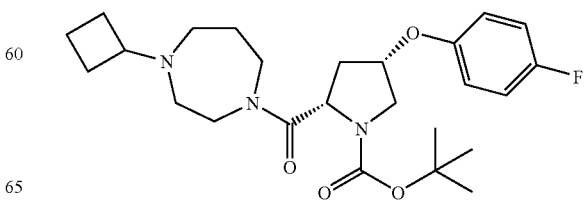

Example 11

(2S,4S)-2-(4-Cyclobutyl-[1,4]diazepane-1-carbonyl)-4-(4-fluoro-phenoxy)-pyrrolidine-1-carboxylic acid tert-butyl ester To a solution of (2S,4R)-2-(4-cyclobutyl-[1,4]diazepane-1-carbonyl)-4-hydroxy-pyrrolidine-1-carboxylic acid tert-butyl ester (1.74 g, 4.73 mmol) in THF (24 mL) was added 4-fluorophenol (795 mg, 7.10 mmol), triphenylphosphine (1.86 g, 7.10 mmol), and DEAD (1.12 mL, 7.10 mmol). After 48 h, the mixture was diluted with 1 M NaOH and extracted with $CH_2Cl_2$ (3×). The combined organic layers were dried and concentrated. Purification by FCC provided the desired product (969 mg, 44%). MS (ESI): mass calcd. for $C_{25}H_{36}FN_3O_4$, 461.27; m/z found, 462.6 $[M+H]^+$. $^1$H NMR ($CDCl_3$): 6.98-6.89 (m, 2H), 6.79 (dd, J=8.5, 4.1 Hz, 2H), 4.81-4.74 (m, 1H), 4.71-4.51 (m, 1H), 4.03-3.90 (m, 1H), 3.79-3.59 (m, 2H), 3.59-3.41 (m, 3H), 2.88-2.73 (m, 1H), 2.68-2.29 (m, 5H), 2.18-2.06 (m, 1H), 2.04-1.94 (m, 2H), 1.93-1.70 (m, 4H), 1.69-1.53 (m, 2H), 1.46-1.40 (m, 9H).

The compounds in Examples 12-15 were prepared using methods analogous to those described for Example 11, with exceptions where noted.

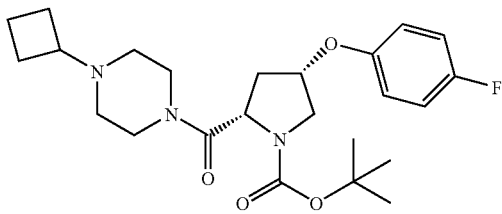

Example 12

(2S,4S)-2-(4-Cyclobutyl-piperazine-1-carbonyl)-4-(4-fluoro-phenoxy)-pyrrolidine-1-carboxylic acid tert-butyl ester MS (ESI): mass calcd. for $C_{24}H_{34}FN_3O_4$, 447.25; m/z found, 448.2 $[M+H]^+$. $^1$H NMR ($CDCl_3$): 6.95 (dd, J=15.7, 8.3 Hz, 2H), 6.83-6.76 (m, 2H), 4.85-4.74 (m, 1H), 4.74-4.54 (m, 1H), 4.03-3.89 (m, 1H), 3.76-3.35 (m, 5H), 2.73-2.46 (m, 2H), 2.45-2.34 (m, 1H), 2.33-2.21 (m, 2H), 2.16-1.95 (m, 4H), 1.92-1.77 (m, 2H), 1.77-1.65 (m, 2H), 1.50-1.38 (m, 9H).

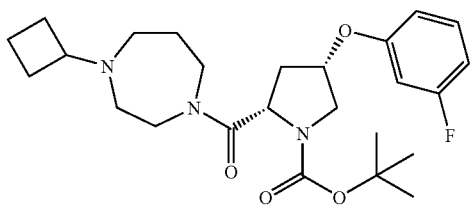

Example 13

(2S,4S)-2-(4-Cyclobutyl-[1,4]diazepane-1-carbonyl)-4-(3-fluoro-phenoxy)-pyrrolidine-1-carboxylic acid tert-butyl ester MS (ESI): mass calcd. for $C_{25}H_{36}FN_3O_4$, 461.27; m/z found 462.3 $[M+H]^+$. $^1$H NMR ($CDCl_3$): 7.26-7.16 (m, 1H), 6.72-6.62 (m, 2H), 6.62-6.55 (m, 1H), 4.90-4.79 (m, 1H), 4.76-4.55 (m, 1H), 4.12-3.94 (m, 1H), 3.81-3.42 (m, 5H), 2.91-2.75 (m, 1H), 2.73-1.54 (m, 14H), 1.53-1.37 (m, 9H).

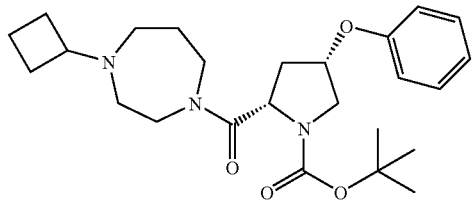

Example 14

(2S,4S)-2-(4-Cyclobutyl-[1,4]diazepane-1-carbonyl)-4-phenoxy-pyrrolidine-1-carboxylic acid tert-butyl ester The resulting mixture of cis and trans diastereomers (~8:1) was separated by reverse phase HPLC (5-99% 20 mM aq. $NH_4OH/CH_3CN$) to provide the title compound and the minor isomer (identical to Example 48 by chiral HPLC). MS (ESI): mass calcd. for $C_{25}H_{37}N_3O_4$, 443.3; m/z found, 444.4 $[M+H]^+$. $^1$H NMR ($CDCl_3$): 7.30-7.23 (m, 2H), 6.95 (dd, J=12.6, 6.8 Hz, 1H), 6.86 (d, J=7.8 Hz, 2H), 4.90-4.81 (m, 1H), 4.72-4.54 (m, 1H), 4.11-3.97 (m, 1H), 3.79-3.43 (m, 5H), 2.87-2.75 (m, 1H), 2.71-2.21 (m, 5H), 2.20-2.09 (m, 1H), 2.06-1.96 (m, 2H), 1.95-1.73 (m, 4H), 1.66-1.53 (m, 2H), 1.44 (d, J=16.8 Hz, 9H).

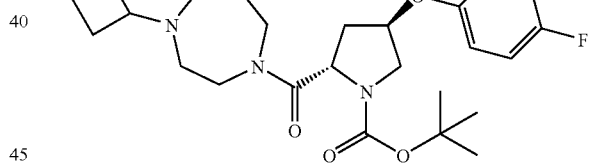

Example 15

(2S,4R)-2-(4-Cyclobutyl-[1,4]diazepane-1-carbonyl)-4-(4-fluoro-phenoxy)-pyrrolidine-1-carboxylic acid tert-butyl ester The title compound was prepared from N-Boc-cis-4-hydroxy-L-proline. MS (ESI): mass calcd. for $C_{25}H_{36}FN_3O_4$, 461.27; m/z found, 462.3 $[M+H]^+$. $^1$H NMR ($CDCl_3$): 6.93 (dd, J=16.1, 8.2 Hz, 2H), 6.79-6.74 (m, 2H), 4.94-4.67 (m, 2H), 3.80 (dd, J=11.8, 4.7 Hz, 1H), 3.77-3.40 (m, 5H), 2.88-2.77 (m, 1H), 2.58-2.35 (m, 4H), 2.35-2.15 (m, 2H), 2.03-1.95 (m, 2H), 1.86-1.71 (m, 4H), 1.67-1.50 (m, 2H), 1.39 (d, J=3.0 Hz, 9H).

The compounds in Examples 16-40 were prepared using methods analogous to those described for Example 11, with exceptions where noted.

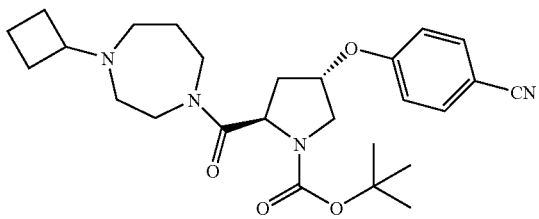

Example 16

(2R,4S)-4-(4-Cyano-phenoxy)-2-(4-cyclobutyl-[1,4]diazepane-1-carbonyl)-pyrrolidine-1-carboxylic acid tert-butyl ester MS (ESI): mass calcd. for $C_{26}H_{36}N_4O_4$, 468.27; m/z found 469.3 [M+H]$^+$. $^1$H NMR (CDCl$_3$): 7.67-7.55 (m, 2H), 6.99-6.88 (m, 2H), 5.18-4.97 (m, 1H), 4.94-4.72 (m, 1H), 3.99-3.91 (m, 1H), 3.86-3.44 (m, 5H), 2.96-2.82 (m, 1H), 2.72-2.27 (m, 6H), 2.12-1.55 (m, 8H), 1.48-1.40 (m, 9H).

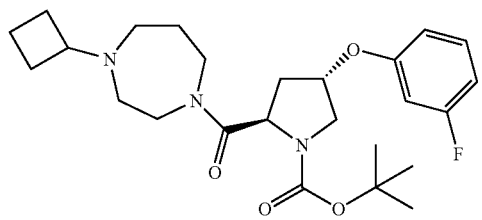

Example 17

(2R,4S)-2-(4-Cyclobutyl-[1,4]diazepane-1-carbonyl)-4-(3-fluoro-phenoxy)-pyrrolidine-1-carboxylic acid tert-butyl ester MS (ESI): mass calcd. for $C_{25}H_{36}FN_3O_4$, 461.27; m/z found, 462.3 [M+H]$^+$. $^1$H NMR (CDCl$_3$): 7.27-7.20 (m, 1H), 6.74-6.63 (m, 2H), 6.62-6.56 (m, 1H), 5.08-4.70 (m, 2H), 3.95-3.41 (m, 6H), 2.99-2.77 (m, 1H), 2.75-2.20 (m, 6H), 2.11-1.53 (m, 8H), 1.50-1.39 (m, 9H).

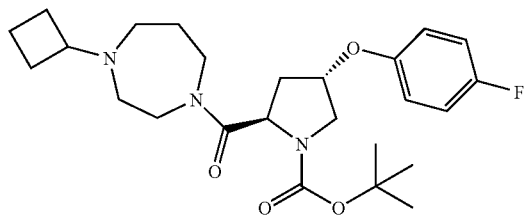

Example 18

(2R,4S)-2-(4-Cyclobutyl-[1,4]diazepane-1-carbonyl)-4-(4-fluoro-phenoxy)-pyrrolidine-1-carboxylic acid tert-butyl ester MS (ESI): mass calcd. for $C_{25}H_{36}FN_3O_4$, 461.27; m/z found, 462.3 [M+H]$^+$. $^1$H NMR (CDCl$_3$): 7.05-6.93 (m, 2H), 6.86-6.78 (m, 2H), 5.01-4.72 (m, 2H), 3.91-3.39 (m, 6H), 2.97-2.81 (m, 1H), 2.74-2.17 (m, 6H), 2.10-1.97 (m, 2H), 1.93-1.58 (m, 6H), 1.50-1.40 (m, 9H).

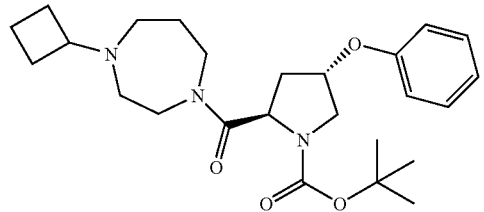

Example 19

(2R,4S)-2-(4-Cyclobutyl-[1,4]diazepane-1-carbonyl)-4-phenoxy-pyrrolidine-1-carboxylic acid tert-butyl ester MS (ESI): mass calcd. for $C_{25}H_{37}N_3O_4$, 443.28; m/z found, 444.3 [M+H]$^+$. $^1$H NMR (CDCl$_3$): 7.34-7.28 (m, 2H), 7.02-6.95 (m, 1H), 6.92-6.84 (m, 2H), 5.08-4.68 (m, 2H), 3.94-3.42 (m, 6H), 3.01-2.81 (m, 1H), 2.77-2.19 (m, 6H), 2.13-1.56 (m, 8H), 1.48-1.42 (m, 9H).

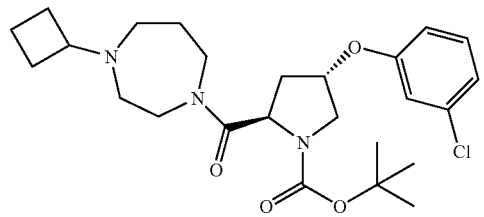

Example 20

(2R,4S)-4-(3-Chloro-phenoxy)-2-(4-cyclobutyl-[1,4]diazepane-1-carbonyl)-pyrrolidine-1-carboxylic acid tert-butyl ester MS (ESI): mass calcd. for $C_{25}H_{36}ClN_3O_4$, 477.24; m/z found, 478.3 [M+H]$^+$. $^1$H NMR (CDCl$_3$): 7.25-7.18 (m, 1H), 7.00-6.93 (m, 1H), 6.90-6.86 (m, 1H), 6.80-6.73 (m, 1H), 5.07-4.72 (m, 2H), 3.92-3.47 (m, 6H), 2.99-2.79 (m, 1H), 2.74-2.22 (m, 6H), 2.14-1.55 (m, 8H), 1.49-1.38 (m, 9H).

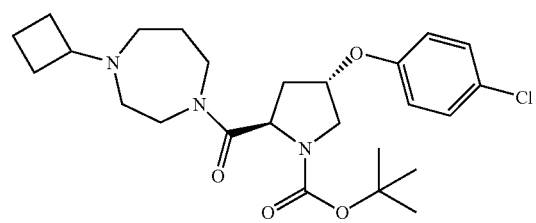

Example 21

(2R,4S)-4-(4-Chloro-phenoxy)-2-(4-cyclobutyl-[1,4]diazepane-1-carbonyl)-pyrrolidine-1-carboxylic acid tert-butyl ester MS (ESI): mass calcd. for $C_{25}H_{36}ClN_3O_4$, 477.24; m/z found, 478.3 [M+H]$^+$. $^1$H NMR (CDCl$_3$): 7.32-7.22 (m, 2H), 6.86-6.77 (m, 2H), 5.05-4.71 (m, 2H), 3.94-3.35 (m, 6H), 2.99-2.80 (m, 1H), 2.74-2.21 (m, 6H), 2.11-1.53 (m, 8H), 1.48-1.40 (m, 9H).

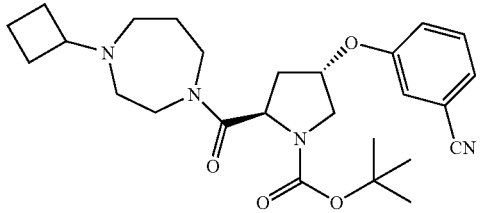

Example 22

(2R,4S)-4-(3-Cyano-phenoxy)-2-(4-cyclobutyl-[1,4]diazepane-1-carbonyl)-pyrrolidine-1-carboxylic acid tert-butyl ester MS (ESI): mass calcd. for $C_{26}H_{36}N_4O_4$, 468.27; m/z found, 469.3 [M+H]$^+$. $^1$H NMR (CDCl$_3$): 7.44-7.36 (m, 1H), 7.31-7.26 (m, 1H), 7.15-7.08 (m, 2H), 5.11-4.73 (m, 2H), 4.02-3.39 (m, 6H), 2.97-2.81 (m, 1H), 2.73-2.27 (m, 6H), 2.11-1.54 (m, 8H), 1.47-1.42 (m, 9H).

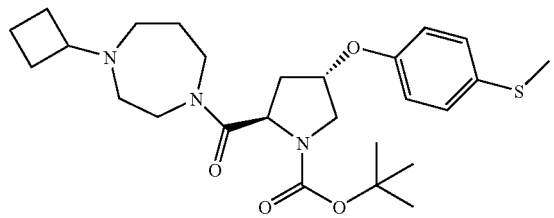

Example 23

(2R,4S)-2-(4-Cyclobutyl-[1,4]diazepane-1-carbonyl)-4-(4-methylsulfanyl-phenoxy)-pyrrolidine-1-carboxylic acid tert-butyl ester MS (ESI): mass calcd. for $C_{26}H_{39}N_3O_4S$, 489.26; m/z found, 490.3 [M+H]$^+$. $^1$H NMR (CDCl$_3$): 7.26 (dd, J=8.6, 3.9 Hz, 2H), 6.82 (dd, J=8.6, 4.6 Hz, 2H), 5.04-4.90 (m, 1H), 4.89-4.72 (m, 1H), 3.90-3.44 (m, 6H), 2.94-2.82 (m, 1H), 2.71-2.50 (m, 2H), 2.50-2.41 (m, 5H), 2.40-2.32 (m, 1H), 2.31-2.21 (m, 1H), 2.08-2.00 (m, 2H), 1.95-1.76 (m, 4H), 1.73-1.57 (m, 2H), 1.44 (d, J=4.2 Hz, 9H).

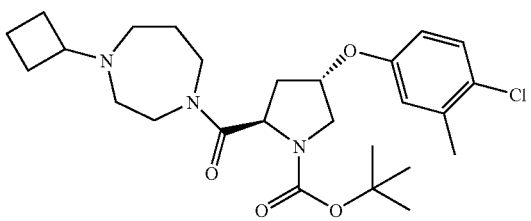

Example 24

(2R,4S)-4-(4-Chloro-3-methyl-phenoxy)-2-(4-cyclobutyl-[1,4]diazepane-1-carbonyl)-pyrrolidine-1-carboxylic acid tert-butyl ester.

MS (ESI): mass calcd. for $C_{26}H_{38}ClN_3O_4$, 491.26; m/z found, 492.3 [M+H]$^+$. $^1$H NMR (CDCl$_3$): 7.27-7.24 (m, 1H), 6.77-6.73 (m, 1H), 6.67-6.62 (m, 1H), 5.03-4.89 (m, 1H), 4.89-4.72 (m, 1H), 3.91-3.44 (m, 6H), 2.95-2.83 (m, 1H), 2.71-2.50 (m, 1H), 2.50-2.37 (m, 3H), 2.34 (d, J=6.0 Hz, 4H), 2.32-2.21 (m, 1H), 2.08-2.00 (m, 2H), 1.96-1.76 (m, 4H), 1.73-1.54 (m, 2H), 1.44 (d, J=5.3 Hz, 9H).

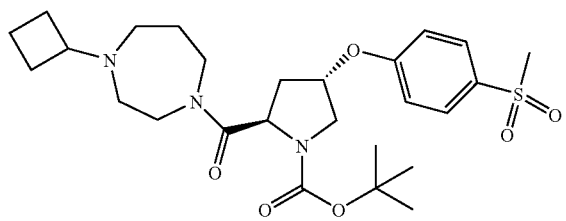

Example 25

(2R,4S)-2-(4-Cyclobutyl-[1,4]diazepane-1-carbonyl)-4-(4-methanesulfonyl-phenoxy)-pyrrolidine-1-carboxylic acid tert-butyl ester MS (ESI): mass calcd. for $C_2H_{39}N_3O_6S$, 521.26; m/z found, 522.3 [M+H]$^+$. $^1$H NMR (CDCl$_3$): 7.88-7.83 (m, 2H), 7.00-6.96 (m, 2H), 5.17-5.01 (m, 1H), 4.91-4.73 (m, 1H), 3.97-3.89 (m, 1H), 3.82-3.44 (m, 5H), 3.02 (d, J=4.1 Hz, 3H), 2.91-2.82 (m, 1H), 2.61-2.27 (m, 6H), 2.06-1.98 (m, 2H), 1.88-1.75 (m, 4H), 1.70-1.54 (m, 2H), 1.42 (d, J=5.0 Hz, 9H).

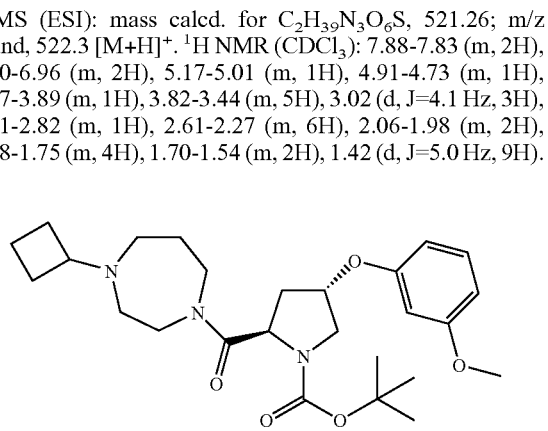

Example 26

(2R,4S)-2-(4-Cyclobutyl-[1,4]diazepane-1-carbonyl)-4-(3-methoxy-phenoxy)-pyrrolidine-1-carboxylic acid tert-butyl ester MS (ESI): mass calcd. for $C_{26}H_{39}N_3O_5$, 473.24; m/z found, 474.4 [M+H]$^+$. $^1$H NMR (CDCl$_3$): 7.02-7.13 (m, 1H), 6.52 (ddd, J=7.9, 5.9, 2.1 Hz, 1H), 6.47-6.40 (m, 2H), 5.02-4.89 (m, 1H), 4.88-4.70 (m, 1H), 3.88-3.79 (m, 2H), 3.77 (d, J=3.8 Hz, 3H), 3.76-3.48 (m, 4H), 2.93-2.80 (m, 1H), 2.61-2.19 (m, 6H), 2.06-1.97 (m, 2H), 1.90-1.73 (m, 4H), 1.71-1.53 (m, 2H), 1.42 (d, J=4.5 Hz, 9H).

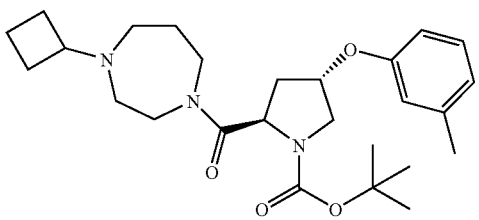

Example 27

(2R,4S)-2-(4-Cyclobutyl-[1,4]diazepane-1-carbonyl)-4-m-tolyloxy-pyrrolidine-1-carboxylic acid tert-butyl ester.

MS (ESI): mass calcd. for $C_{26}H_{39}N_3O_4$, 457.29; m/z found, 458.4 [M+H]+. 1H NMR (CDCl3): 7.13-7.06 (m, 1H), 6.74-6.68 (m, 1H), 6.71-6.64 (m, 2H), 5.04-4.90 (m, 1H), 4.89-4.72 (m, 1H), 3.90-3.42 (m, 6H), 2.93-2.82 (m, 1H), 2.61-2.20 (m, 9H), 2.07-1.74 (m, 6H), 1.72-1.54 (m, 2H), 1.43 (d, J=4.6 Hz, 9H).

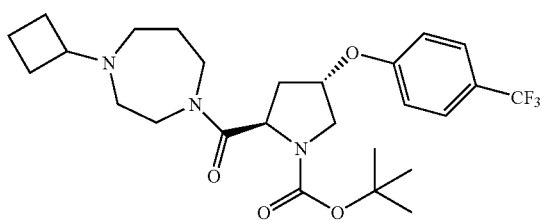

Example 28

(2R,4S)-2-(4-Cyclobutyl-[1,4]diazepane-1-carbonyl)-4-(4-trifluoromethyl-phenoxy)-pyrrolidine-1-carboxylic acid tert-butyl ester.

MS (ESI): mass calcd. for $C_{26}H_{36}F_3N_3O_4$, 511.27; m/z found, 512.3 [M+H]+. 1H NMR (CDCl3): 7.57-7.50 (m, 2H), 6.92 (dd, J=8.3, 4.0 Hz, 2H), 5.13-4.96 (m, 1H), 4.90-4.72 (m, 1H), 3.95-3.88 (m, 1H), 3.83-3.43 (m, 5H), 2.93-2.80 (m, 1H), 2.60-2.24 (m, 6H), 2.08-1.94 (m, 2H), 1.88-1.75 (m, 4H), 1.71-1.53 (m, 2H), 1.43 (d, J=2.1 Hz, 9H).

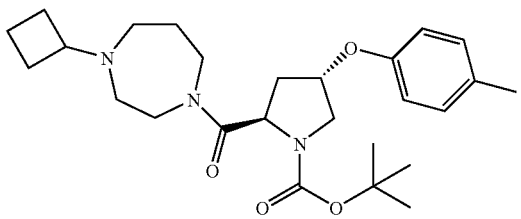

Example 29

(2R,4S)-2-(4-Cyclobutyl-[1,4]diazepane-1-carbonyl)-4-D-tolyloxy-pyrrolidine-1-carboxylic acid tert-butyl ester.

MS (ESI): mass calcd. for $C_{26}H_{39}N_3O_4$, 457.29; m/z found, 458.4 [M+H]+. 1H NMR (CDCl3): 7.10-7.03 (m, 2H), 6.75 (dd, J=8.5, 4.1 Hz, 2H), 5.00-4.87 (m, 1H), 4.86-4.70 (m, 1H), 3.87-3.44 (m, 6H), 2.91-2.78 (m, 1H), 2.59-2.31 (m, 5H), 2.27 (d, J=4.6 Hz, 3H), 2.25-2.17 (m, 1H), 2.12-1.96 (m, 3H), 1.88-1.73 (m, 3H), 1.72-1.54 (m, 2H), 1.42 (d, J=4.1 Hz, 9H).

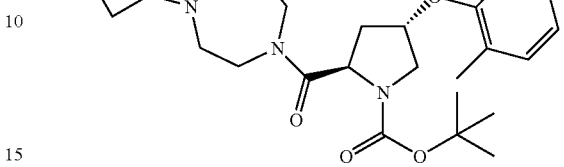

Example 30

(2R,4S)-2-(4-Cyclobutyl-[1,4]diazepane-1-carbonyl)-4-o-tolyloxy-pyrrolidine-1-carboxylic acid tert-butyl ester.

MS (ESI): mass calcd. for $C_{26}H_{39}N_3O_4$, 457.29; m/z found, 458.4 [M+H]+. 1H NMR (CDCl3): 7.17-7.07 (m, 2H), 6.91-6.83 (m, 1H), 6.80-6.73 (m, 1H), 5.04-4.91 (m, 1H), 4.90-4.71 (m, 1H), 3.89-3.43 (m, 6H), 2.92-2.79 (m, 1H), 2.61-2.20 (m, 6H), 2.18 (s, 3H), 2.07-1.95 (m, 3H), 1.89-1.73 (m, 3H), 1.72-1.54 (m, 2H), 1.42 (s, 9H).

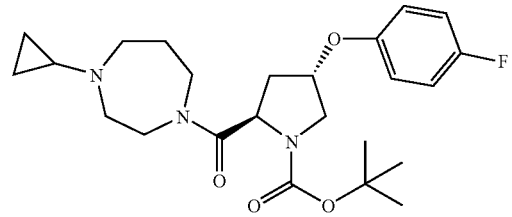

Example 31

(2R,4S)-2-(4-Cyclopropyl-[1,4]diazepane-1-carbonyl)-4-(4-fluoro-phenoxy)-pyrrolidine-1-carboxylic acid tert-butyl ester.

MS (ESI): mass calcd. for $C_{24}H_{34}FN_3O_4$, 447.25; m/z found, 448.3 [M+H]+. 1H NMR (CDCl3): 7.07-6.90 (m, 2H), 6.85-6.76 (m, 2H), 5.02-4.69 (m, 2H), 3.90-3.35 (m, 6H), 3.03-2.64 (m, 4H), 2.49-2.19 (m, 2H), 2.06-1.73 (m, 3H), 1.48-1.34 (m, 9H), 0.53-0.32 (m, 4H).

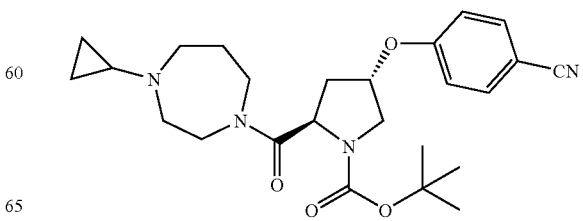

Example 32

(2R,4S)-4-(4-Cyano-phenoxy)-2-(4-cyclopropyl-[1,4]diazepane-1-carbonyl)-pyrrolidine-1-carboxylic acid tert-butyl ester.

MS (ESI): mass calcd. for $C_{25}H_{34}N_4O_4$, 454.26; m/z found, 455.3 [M+H]$^+$. $^1$H NMR (CDCl$_3$): 7.70-7.45 (m, 2H), 6.97-6.85 (m, 2H), 5.18-4.96 (m, 1H), 4.94-4.71 (m, 1H), 3.99-3.88 (m, 1H), 3.84-3.35 (m, 5H), 3.07-2.64 (m, 4H), 2.51-2.24 (m, 2H), 2.07-1.74 (m, 3H), 1.50-1.33 (m, 9H), 0.56-0.25 (m, 4H).

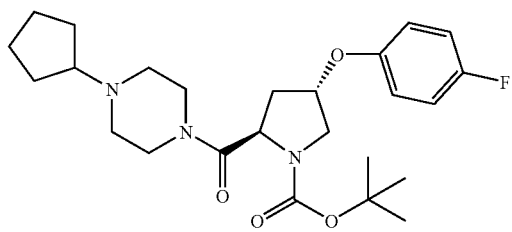

Example 33

(2R,4S)-2-(4-Cyclopentyl-piperazine-1-carbonyl)-4-(4-fluoro-phenoxy)-pyrrolidine-1-carboxylic acid tert-butyl ester.

MS (ESI): mass calcd. for $C_{25}H_{36}FN_3O_4$, 461.27; m/z found, 462.3 [M+H]$^+$. $^1$H NMR (CDCl$_3$): 7.04-6.91 (m, 2H), 6.85-6.74 (m, 2H), 4.99-4.71 (m, 2H), 3.90-3.44 (m, 6H), 2.69-2.31 (m, 6H), 2.27-2.13 (m, 1H), 1.94-1.78 (m, 2H), 1.76-1.48 (m, 6H), 1.47-1.22 (m, 9H).

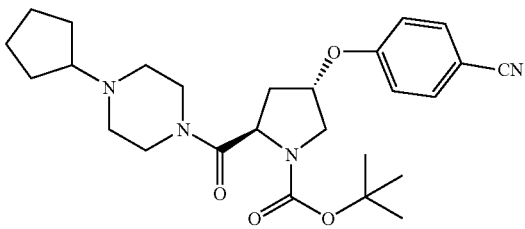

Example 34

(2R,4S)-4-(4-Cyano-phenoxy)-2-(4-cyclopentyl-piperazine-1-carbonyl)-pyrrolidine-1-carboxylic acid tert-butyl ester.

MS (ESI): mass calcd. for $C_{26}H_{36}N_4O_4$, 468.27; m/z found, 469.3 [M+H]$^+$. $^1$H NMR (CDCl$_3$): 7.64-7.53 (m, 2H), 6.96-6.86 (m, 2H), 5.18-4.71 (m, 2H), 3.96-3.85 (m, 1H), 3.83-3.45 (m, 5H), 2.67-2.21 (m, 7H), 1.92-1.79 (m, 2H), 1.77-1.63 (m, 2H), 1.63-1.50 (m, 4H), 1.47-1.35 (m, 9H).

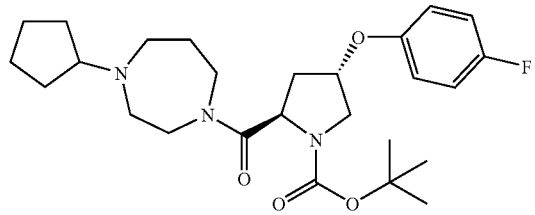

Example 35

(2R,4S)-2-(4-Cyclopentyl-[1,4]diazepane-1-carbonyl)-4-(4-fluoro-phenoxy)-pyrrolidine-1-carboxylic acid tert-butyl ester.

MS (ESI): mass calcd. for $C_{26}H_{38}FN_3O_4$, 475.28; m/z found, 476.4 [M+H]$^+$. $^1$H NMR (CDCl$_3$): 7.02-6.92 (m, 2H), 6.85-6.76 (m, 2H), 5.01-4.69 (m, 2H), 3.89-3.34 (m, 6H), 2.94-2.16 (m, 7H), 2.07-1.25 (m, 19H).

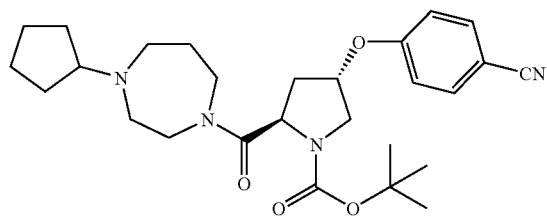

Example 36

(2R,4S)-4-(4-Cyano-phenoxy)-2-(4-cyclopentyl-[1,4]diazepane-1-carbonyl)-pyrrolidine-1-carboxylic acid tert-butyl ester.

MS (ESI): mass calcd. for $C_{27}H_{38}N_4O_4$, 482.29; m/z found, 483.4 [M+H]$^+$. $^1$H NMR (CDCl$_3$): 7.68-7.49 (m, 2H), 6.96-6.87 (m, 2H), 5.17-4.96 (m, 1H), 4.93-4.70 (m, 1H), 3.98-3.89 (m, 1H), 3.88-3.35 (m, 5H), 2.96-2.22 (m, 7H), 2.08-1.23 (m, 19H).

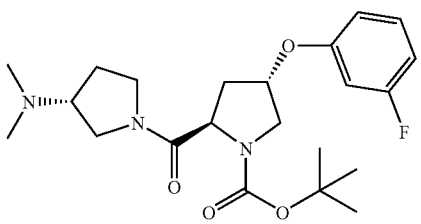

Example 37

(2R,4S)-2-((3R)-3-Dimethylamino-pyrrolidine-1-carbonyl)-4-(3-fluoro-phenoxy)-pyrrolidine-1-carboxylic acid tert-butyl ester.

MS (ESI): mass calcd. for $C_{22}H_{32}FN_3O_4$, 421.24; m/z found, 422.4 [M+H]$^+$. $^1$H NMR (CDCl$_3$): 7.28-7.17 (m, 1H), 6.73-6.63 (m, 2H), 6.63-6.57 (m, 1H), 5.08-4.91 (m, 1H), 4.74-4.52 (m, 1H), 4.20-3.60 (m, 4H), 3.52-3.11 (m, 2H), 2.91-2.55 (m, 1H), 2.50-2.04 (m, 9H), 2.00-1.65 (m, 1H), 1.50-1.37 (m, 9H).

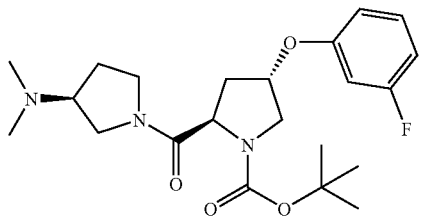

Example 38

(2R,4S)-2-((3S)-3-Dimethylamino-pyrrolidine-1-carbonyl)-4-(3-fluoro-phenoxy)-pyrrolidine-1-carboxylic acid tert-butyl ester.

MS (ESI): mass calcd. for $C_{22}H_{32}FN_3O_4$, 421.24; m/z found, 422.3 [M+H]$^+$. $^1$H NMR (CDCl$_3$): 7.29-7.19 (m, 1H), 6.73-6.55 (m, 3H), 5.06-4.89 (m, 1H), 4.72-4.50 (m, 1H), 4.02-3.07 (m, 6H), 2.90-2.53 (m, 1H), 2.51-2.01 (m, 9H), 1.97-1.52 (m, 1H), 1.48-1.37 (m, 9H).

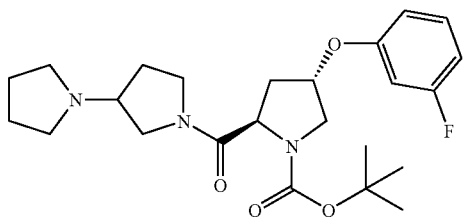

Example 39

(2R,4S)-2-([1,3']Bipyrrolidinyl-1'-carbonyl)-4-(3-fluoro-Phenoxy)-pyrrolidine-1-carboxylic acid tert-butyl ester.

MS (ESI): mass calcd. for $C_{24}H_{34}FN_3O_4$, 447.25; m/z found, 448.4 [M+H]$^+$. $^1$H NMR (CDCl$_3$): 7.31-7.13 (m, 1H), 6.74-6.63 (m, 2H), 6.63-6.56 (m, 1H), 5.09-4.88 (m, 1H), 4.73-4.48 (m, 1H), 3.96-3.19 (m, 6H), 2.95-1.90 (m, 9H), 1.88-1.54 (m, 4H), 1.48-1.40 (m, 9H).

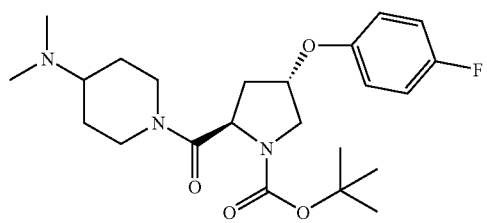

Example 40

(2R,4S)-2-(4-Dimethylamino-piperidine-1-carbonyl)-4-(4-fluoro-phenoxy)-pyrrolidine-1-carboxylic acid tert-butyl ester.

MS (ESI): mass calcd. for $C_{24}H_{33}FN_3O_4$, 435.25; m/z found, 436.4 [M+H]$^+$. $^1$H NMR (CDCl$_3$): 7.05-6.93 (m, 2H), 6.88-6.77 (m, 2H), 4.95-4.49 (m, 3H), 4.33-3.94 (m, 1H), 3.84-2.97 (m, 4H), 2.92-2.63 (m, 6H), 2.57-1.93 (m, 5H), 1.82-1.13 (m, 10H).

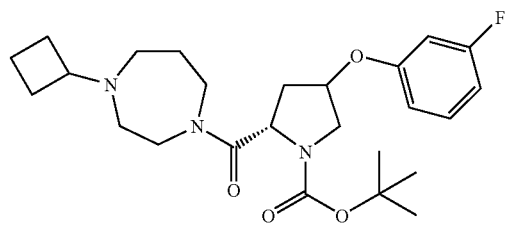

Example 41

(2S)-2-(4-Cyclobutyl-[1,4]diazepane-1-carbonyl)-4-(3-fluoro-phenoxy)-pyrrolidine-1-carboxylic acid tert-butyl ester.

Reaction of 3-fluorophenol and (2S,4R)-2-(4-cyclobutyl-[1,4]diazepane-1-carbonyl)-4-hydroxy-pyrrolidine-1-carboxylic acid tert-butyl ester was performed as described in Example 11, using resin bound triphenylphosphine and CH$_2$Cl$_2$ to give the title compound as a mixture of diastereomers (89:11), as determined by chiral SFC. MS (ESI): mass calcd. for $C_{25}H_{36}FN_3O_4$, 461.27; m/z found, 462.3 [M+H]$^+$. $^1$H NMR (CDCl$_3$): 7.25-7.16 (m, 1H), 6.69-6.53 (m, 3H), 5.01-4.69 (m, 2H), 3.89-3.42 (m, 6H), 2.92-2.79 (m, 1H), 2.69-2.20 (m, 6H), 2.06-1.72 (m, 6H), 1.71-1.53 (m, 2H), 1.44-1.39 (m, 9H).

The compounds in Examples 42-47 were prepared using methods analogous to those described for Example 41.

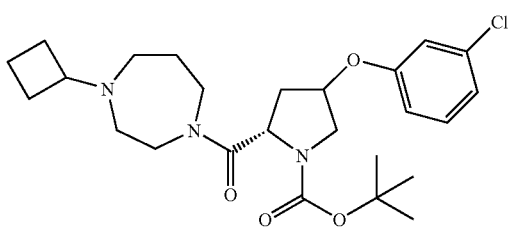

Example 42

(2S)-4-(3-Chloro-phenoxy)-2-(4-cyclobutyl-[1,4]diazepane-1-carbonyl)-pyrrolidine-1-carboxylic acid tert-butyl ester.

MS (ESI): mass calcd. for $C_{25}H_{36}ClN_3O_4$, 477.24; m/z found, 478.3 [M+H]$^+$. $^1$H NMR (CDCl$_3$): 7.15-7.05 (m, 1H), 6.89-6.83 (m, 1H), 6.79-6.75 (m, 1H), 6.69-6.63 (m, 1H), 4.94-4.46 (m, 2H), 3.98-3.76 (m, 1H), 3.74-3.35 (m, 5H), 2.82-2.66 (m, 1H), 2.61-1.93 (m, 8H), 1.89-1.46 (m, 6H), 1.39-1.32 (m, 9H).

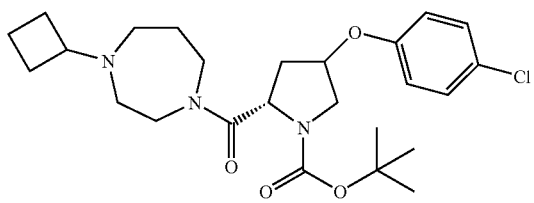

Example 43

(2S)-4-(4-Chloro-phenoxy)-2-(4-cyclobutyl-[1,4]diazepane-1-carbonyl)-pyrrolidine-1-carboxylic acid tert-butyl ester.

MS (ESI): mass calcd. for $C_{25}H_{36}ClN_3O_4$, 477.24; m/z found, 478.3 [M+H]$^+$. $^1$H NMR (CDCl$_3$): 7.23-7.15 (m, 2H), 6.80-6.73 (m, 2H), 4.99-4.51 (m, 2H), 4.21-3.40 (m, 6H), 2.89-2.70 (m, 1H), 2.67-1.88 (m, 9H), 1.86-1.50 (m, 5H), 1.47-1.35 (m, 9H).

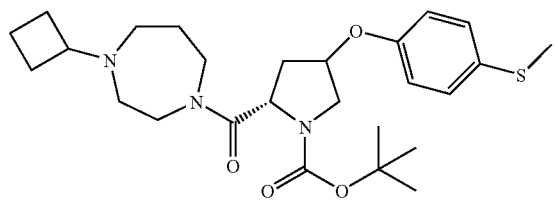

Example 46

(2S)-2-(4-Cyclobutyl-[1,4]diazepane-1-carbonyl)-4-(4-methylsulfanyl-phenoxy)-pyrrolidine-1-carboxylic acid tert-butyl ester.

MS (ESI): mass calcd. for $C_{26}H_{39}N_3O_4S$, 489.27; m/z found, 490.3 [M+H]$^+$. $^1$H NMR (CDCl$_3$): 7.25-7.17 (m, 2H), 6.83-6.75 (m, 2H), 5.00-4.52 (m, 2H), 4.22-3.91 (m, 1H), 3.87-3.40 (m, 5H), 2.90-2.72 (m, 1H), 2.70-2.06 (m, 10H), 2.05-1.93 (m, 2H), 1.89-1.53 (m, 5H), 1.47-1.36 (m, 9H).

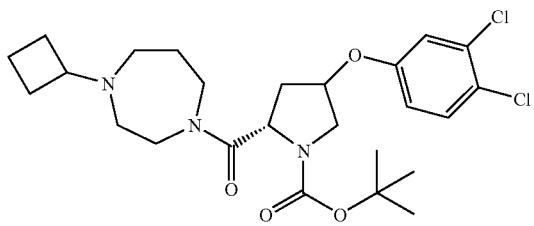

Example 44

(2S)-2-(4-Cyclobutyl-[1,4]diazepane-1-carbonyl)-4-(3,4-dichloro-phenoxy)-pyrrolidine-1-carboxylic acid tert-butyl ester.

MS (ESI): mass calcd. for $C_{25}H_{35}Cl_2N_3O_4$, 511.20; m/z found, 512.2 [M+H]$^+$. $^1$H NMR (CDCl$_3$): 7.37-7.25 (m, 1H), 6.98-6.94 (m, 1H), 6.77-6.69 (m, 1H), 5.02-4.53 (m, 2H), 4.05-3.44 (m, 6H), 2.92-2.08 (m, 8H), 2.07-1.96 (m, 2H), 1.89-1.56 (m, 5H), 1.48-1.41 (m, 9H).

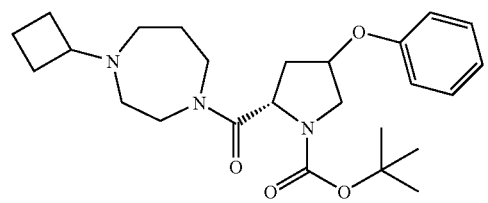

Example 47

(2S)-2-(4-Cyclobutyl-[1,4]diazepane-1-carbonyl)-4-phenoxy-pyrrolidine-1-carboxylic acid tert-butyl ester.

MS (ESI): mass calcd. for $C_{25}H_{37}N_3O_4$, 443.28; m/z found, 444.3 [M+H]$^+$. $^1$H NMR (CDCl$_3$): 7.28 (dd, J=15.9, 8.2 Hz, 2H), 7.01-6.93 (m, 1H), 6.85 (dd, J=7.7, 5.5 Hz, 1H), 5.04-4.91 (m, 1H), 4.88-4.71 (m, 1H), 3.89-3.43 (m, 6H), 2.92-2.79 (m, 1H), 2.70-2.20 (m, 6H), 2.07-1.74 (m, 7H), 1.71-1.52 (m, 2H), 1.43-1.41 (m, 9H).

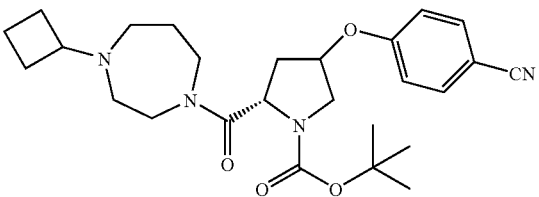

Example 45

(2S)-4-(4-Cyano-phenoxy)-2-(4-cyclobutyl-[1,4]diazepane-1-carbonyl)-pyrrolidine-1-carboxylic acid tert-butyl ester.

MS (ESI): mass calcd. for $C_{26}H_{36}N_4O_4$, 468.27; m/z found, 469.3 [M+H]$^+$. $^1$H NMR (CDCl$_3$): 7.62-7.53 (m, 2H), 6.93-6.86 (m, 2H), 5.14-4.57 (m, 2H), 4.08-3.87 (m, 1H), 3.84-3.41 (m, 5H), 2.93-1.94 (m, 10H), 1.85-1.54 (m, 5H), 1.47-1.37 (m, 9H).

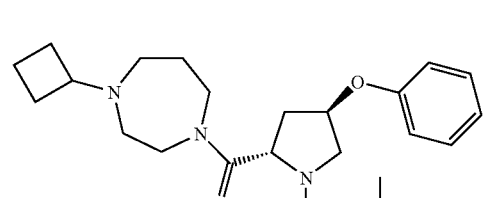

Example 48

(2S,4R)-2-(4-Cyclobutyl-[1,4]diazepane-1-carbonyl)-4-phenoxy-pyrrolidine-1-carboxylic acid tert-butyl ester.

To a stirred suspension of (2S,4R)-2-(4-cyclobutyl-[1,4]diazepane-1-carbonyl)-4-hydroxy-pyrrolidine-1-carboxylic acid tert-butyl ester (116 mg, 0.32 mmol) in toluene (0.65 ml)

was added iodobenzene (129 mg, 0.63 mmol), copper (I) iodide (6 mg, 0.032 mmol), 3,4,7,8-tetramethyl-1,10-phenanthroline (15 mg, 0.063 mmol), and $Cs_2CO_3$ (206 mg, 0.63 mmol). The resulting suspension was heated at 100° C. in a capped scintillation vial with stirring for 2 days. The reaction mixture was filtered through diatomaceous earth, washing with $CH_2Cl_2$. The filtrate was dried and concentrated. Purification of the residue by FCC provided the desired product (97.7 mg, 70%). MS (ESI): mass calcd. for $C_{25}H_{37}N_3O_4$, 443.3; m/z found, 444.3 [M+H]$^+$. $^1$H NMR ($CDCl_3$): 7.30-7.25 (m, 2H), 6.96 (dd, J=14.5, 7.2 Hz, 1H), 6.85 (dd, J=7.7, 5.5 Hz, 1H), 5.04-4.91 (m, 1H), 4.88-4.71 (m, 1H), 3.89-3.43 (m, 6H), 2.92-2.79 (m, 1H), 2.70-2.20 (m, 6H), 2.07-1.74 (m, 7H), 1.71-1.52 (m, 2H), 1.43-1.41 (m, 9H).

The compounds in Examples 49-58 were prepared from the appropriate hydroxy-prolines and heteroaryl iodides, using methods analogous to those described for Example 48.

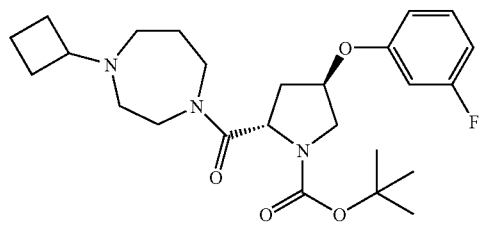

Example 49

(2S,4R)-2-(4-Cyclobutyl-[1,4]diazepane-1-carbonyl)-4-(3-fluoro-phenoxy)-pyrrolidine-1-carboxylic acid tert-butyl ester.

MS (ESI): mass calcd. for $C_{25}H_{36}FN_3O_4$, 461.27; m/z found 462.3 [M+H]$^+$. $^1$H NMR ($CDCl_3$): 7.26-7.16 (m, 1H), 6.72-6.62 (m, 2H), 6.61-6.54 (m, 1H), 5.04-4.70 (m, 2H), 3.92-3.42 (m, 6H), 2.98-2.78 (m, 1H), 2.72-2.19 (m, 6H), 2.12-1.54 (m, 8H), 1.49-1.36 (m, 9H).

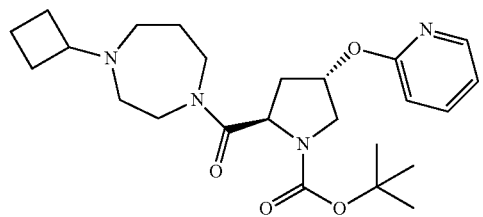

Example 50

(2S,4R)-2-(4-Cyclobutyl-[1,4]diazepane-1-carbonyl)-4-(pyridin-2-yloxy)-pyrrolidine-1-carboxylic acid tert-butyl ester.

MS (ESI): mass calcd. for $C_{24}H_{36}N_4O_4$, 444.27; m/z found, 445.3 [M+H]$^+$. $^1$H NMR ($CDCl_3$): 8.13 (ddd, J=9.0, 5.0, 1.7 Hz, 1H), 7.61-7.52 (m, 1H), 6.87 (dd, J=12.0, 6.5 Hz, 1H), 6.70 (d, J=8.4 Hz, 1H), 5.66-5.56 (m, 1H), 4.88-4.72 (m, 1H), 3.91-3.49 (m, 6H), 2.92-2.81 (m, 1H), 2.70-2.26 (m, 6H), 2.08-1.98 (m, 2H), 1.90-1.75 (m, 4H), 1.72-1.55 (m, 2H), 1.48-1.39 (m, 9H).

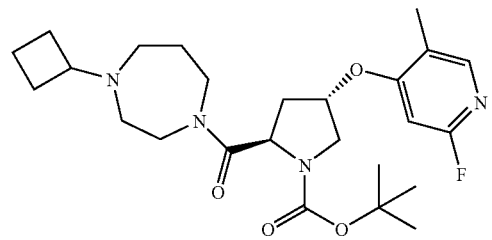

Example 51

(2S,4R)-2-(4-Cyclobutyl-[1,4]diazepane-1-carbonyl)-4-(2-fluoro-5-methyl-pyridin-4-yloxy)-pyrrolidine-1-carboxylic acid tert-butyl ester.

MS (ESI): mass calcd. for $C_{25}H_{37}FN_4O_4$, 476.28; m/z found, 477.3[M+H]$^+$. $^1$H NMR ($CDCl_3$): 7.90-7.87 (m, 1H), 6.32 (d, J=9.7 Hz, 1H), 5.18-5.02 (m, 1H), 4.98-4.76 (m, 1H), 4.05-3.96 (m, 1H), 3.89-3.46 (m, 5H), 2.98-2.86 (m, 1H), 2.62-2.36 (m, 6H), 2.14 (s, 3H), 2.11-2.03 (m, 2H), 1.94-1.79 (m, 4H), 1.72-1.58 (m, 2H), 1.52-1.45 (m, 9H).

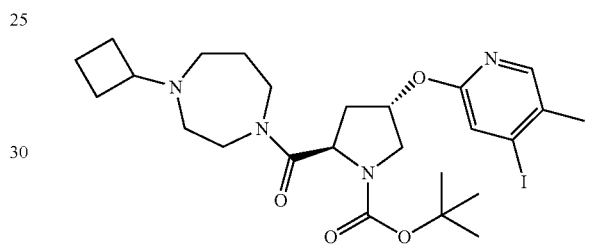

Example 52

(2R,4S)-2-(4-Cyclobutyl-[1,4]diazepane-1-carbonyl)-4-(4-iodo-5-methyl-pyridin-2-yloxy)-pyrrolidine-1-carboxylic acid tert-butyl ester.

The title compound was obtained as a minor product from the reaction used to prepare Example 51. MS (ESI): mass calcd. for $C_{25}H_{37}IN_4O_4$, 584.19; m/z found, 585.2[M+H]$^+$. $^1$H NMR ($CDCl_3$): 7.87 (d, J=6.6 Hz, 1H), 7.23 (s, 1H), 5.55-5.43 (m, 1H), 4.84-4.67 (m, 1H), 3.88-3.43 (m, 6H), 2.93-2.78 (m, 1H), 2.71-2.18 (m, 9H), 2.08-1.94 (m, 3H), 1.90-1.72 (m, 3H), 1.71-1.53 (m, 2H), 1.41 (d, J=4.4 Hz, 9H).

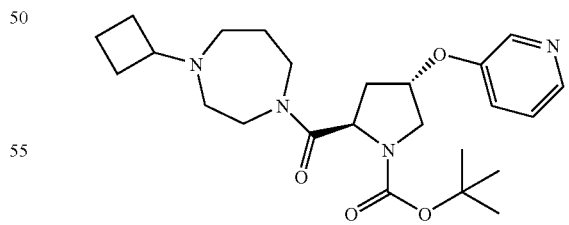

Example 53

(2R,4S)-2-(4-Cyclobutyl-[1,4]diazepane-1-carbonyl)-4-(pyridin-3-yloxy)-pyrrolidine-1-carboxylic acid tert-butyl ester.

MS (ESI): mass calcd. For $C_{24}H_{36}N_4O_4$, 444.27; m/z found, 445.3 [M+H]$^+$. $^1$H NMR ($CDCl_3$): 8.29-8.25 (m, 1H), 8.25-8.20 (m, 1H), 7.24-7.18 (m, 1H), 7.18-7.14 (m, 1H), 5.09-4.93 (m, 1H), 4.90-4.73 (m, 1H), 3.92-3.86 (m, 1H), 3.81-3.45 (m, 5H), 2.92-2.81 (m, 1H), 2.68-2.24 (m, 6H), 2.03-1.72 (m, 6H), 1.71-1.52 (m, 2H), 1.42 (d, J=2.2 Hz, 9H).

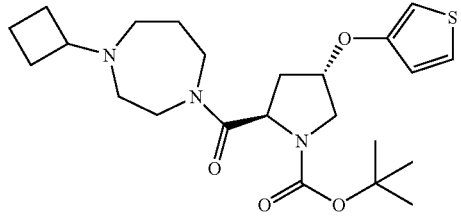

Example 54

(2R,4S)-2-(4-Cyclobutyl-[1,4]diazepane-1-carbonyl)-4-(thiophen-3-yloxy)-pyrrolidine-1-carboxylic acid tert-butyl ester.

MS (ESI): mass calcd. for $C_{23}H_{35}N_3O_4S$, 449.23; m/z found, 450.3 [M+H]$^+$. $^1$H NMR (CDCl$_3$): 7.19-7.16 (m, 1H), 6.71 (d, J=5.2 Hz, 1H), 6.25-6.21 (m, 1H), 4.91-4.69 (m, 2H), 3.88-3.44 (m, 6H), 2.94-2.78 (m, 1H), 2.70-2.19 (m, 6H), 2.07-1.97 (m, 2H), 1.86-1.71 (m, 4H), 1.71-1.54 (m, 2H), 1.47-1.37 (m, 9H).

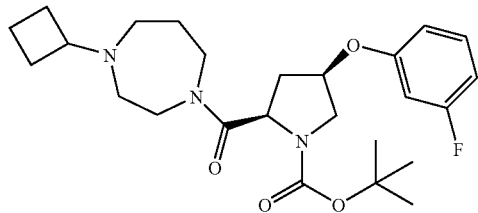

Example 55

(2R,4R)-2-(4-Cyclobutyl-[1,4]diazepane-1-carbonyl)-4-(3-fluoro-phenoxy)-pyrrolidine-1-carboxylic acid tert-butyl ester.

MS (ESI): mass calcd. for $C_{25}H_{36}FN_3O_4$, 461.27; m/z found, 462.3 [M+H]$^+$. $^1$H NMR (CDCl$_3$): 7.20-7.12 (m, 1H), 6.65-6.57 (m, 2H), 6.56-6.50 (m, 1H), 4.85-4.75 (m, 1H), 4.70-4.52 (m, 1H), 4.04-3.91 (m, 1H), 3.75-3.39 (m, 5H), 2.85-2.70 (m, 1H), 2.70-2.25 (m, 5H), 2.23-2.05 (m, 1H), 2.02-1.50 (m, 8H), 1.46-1.35 (m, 9H).

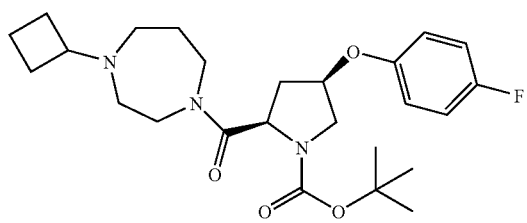

Example 56

(2R,4R)-2-(4-Cyclobutyl-[1,4]diazepane-1-carbonyl)-4-(4-fluoro-phenoxy)-pyrrolidine-1-carboxylic acid tert-butyl ester.

MS (ESI): mass calcd. for $C_{25}H_{36}FN_3O_4$, 461.27; m/z found, 462.3 [M+H]$^+$. $^1$H NMR (CDCl$_3$): 6.97-6.89 (m, 2H), 6.81-6.76 (m, 2H), 4.82-4.72 (m, 1H), 4.70-4.52 (m, 1H), 4.01-3.90 (m, 1H), 3.76-3.40 (m, 5H), 2.86-2.73 (m, 1H), 2.65-2.28 (m, 5H), 2.17-2.05 (m, 1H), 2.04-1.69 (m, 6H), 1.68-1.52 (m, 2H), 1.46-1.38 (m, 9H).

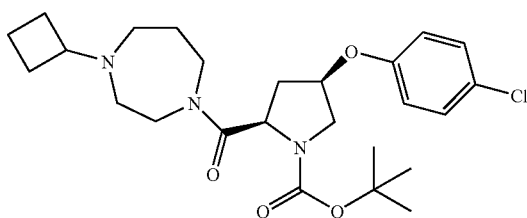

Example 57

(2R,4R)-4-(4-Chloro-phenoxy)-2-(4-cyclobutyl-[1,4]diazepane-1-carbonyl)-pyrrolidine-1-carboxylic acid tert-butyl ester.

MS (ESI): mass calcd. for $C_{25}H_{36}ClN_3O_4$, 477.24; m/z found, 479.3 [M+H]$^+$. $^1$H NMR (CDCl$_3$): 7.16-7.09 (m, 2H), 6.71 (dd, J=8.4, 4.4 Hz, 2H), 4.80-4.69 (m, 1H), 4.65-4.47 (m, 1H), 3.97-3.85 (m, 1H), 3.71-3.33 (m, 5H), 2.79-2.65 (m, 1H), 2.62-2.19 (m, 5H), 2.16-2.00 (m, 1H), 1.98-1.63 (m, 6H), 1.62-1.45 (m, 2H), 1.40-1.32 (m, 9H).

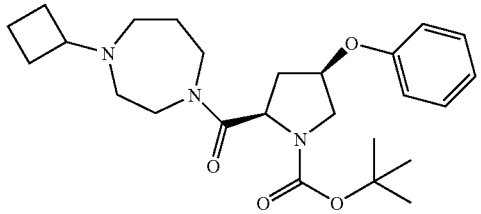

Example 58

(2R,4R)-2-(4-Cyclobutyl-[1,4]diazepane-1-carbonyl)-4-phenoxy-pyrrolidine-1-carboxylic acid tert-butyl ester.

MS (ESI): mass calcd. for $C_{25}H_{37}N_3O_4$, 443.28; m/z found, 444.3 [M+H]$^+$. $^1$H NMR (CDCl$_3$): 7.26-7.18 (m, 2H), 6.94-6.88 (m, 1H), 6.82 (d, J=7.3 Hz, 2H), 4.87-4.76 (m, 1H), 4.68-4.50 (m, 1H), 4.05-3.92 (m, 1H), 3.76-3.38 (m, 5H), 2.83-2.69 (m, 1H), 2.68-2.26 (m, 5H), 2.16-2.04 (m, 1H), 2.02-1.67 (m, 6H), 1.66-1.48 (m, 2H), 1.45-1.36 (m, 9H).

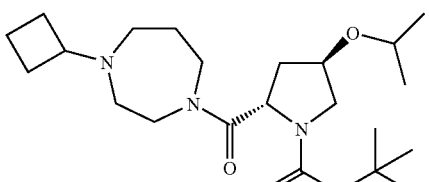

Example 59

(2S,4R)-2-(4-Cyclobutyl-[1,4]diazepane-1-carbonyl)-4-isopropoxy-pyrrolidine-1-carboxylic acid tert-butyl ester.

To a solution of (2S,4R)-2-(4-cyclobutyl-[1,4]diazepane-1-carbonyl)-4-hydroxy-pyrrolidine-1-carboxylic acid tert-butyl ester (287 mg, 0.78 mmol) in DMF (7.8 mL) was added NaH (90%; 31 mg). After 30 min, 2-bromopropane (109 μL, 1.17 mmol) was added and the mixture was allowed to warm to rt and was stirred for 18 h. The mixture was diluted with satd. aq. NaHCO$_3$ and extracted with CH$_2$Cl$_2$. The combined organic layers were dried and concentrated. The crude product was purified by FCC to provide the desired product (26 mg, 8%). MS (ESI): mass calcd. for C$_{22}$H$_{39}$N$_3$O$_4$, 409.29; m/z found, 410.4 [M+H]$^+$. $^1$H NMR (CDCl$_3$): 4.74-4.58 (m, 1H), 4.33-4.16 (m, 1H), 3.74-3.33 (m, 7H), 2.90-2.78 (m, 1H), 2.59-2.30 (m, 4H), 2.19-2.11 (m, 1H), 2.10-1.96 (m, 4H), 1.87-1.72 (m, 3H), 1.69-1.53 (m, 2H), 1.40 (d, J=17.6 Hz, 9H), 1.12 (dd, J=6.0, 2.2 Hz, 6H).

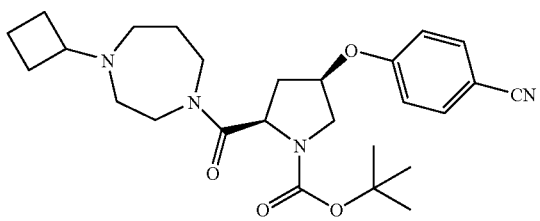

Example 60

(2R,4R)-4-(4-Cyano-phenoxy)-2-(4-cyclobutyl-[1,4]diazepane-1-carbonyl)-pyrrolidine-1-carboxylic acid tert-butyl ester.

The title compound was prepared from 4-bromobenzonitrile and (2R,4R)-2-(4-cyclobutyl-[1,4]diazepane-1-carbonyl)-4-hydroxy-pyrrolidine-1-carboxylic acid tert-butyl ester as described for Example 59. MS (ESI): mass calcd. for C$_{26}$H$_{36}$N$_4$O$_4$, 468.27; m/z found, 469.4 [M+H]$^+$. $^1$H NMR (CDCl$_3$): 7.66-7.51 (m, 2H), 6.99-6.86 (m, 2H), 5.05-4.85 (m, 1H), 4.79-4.54 (m, 1H), 4.12-3.96 (m, 1H), 3.84-3.41 (m, 4H), 2.93-2.77 (m, 1H), 2.75-2.13 (m, 5H), 2.10-1.54 (m, 10H), 1.50-1.40 (m, 9H).

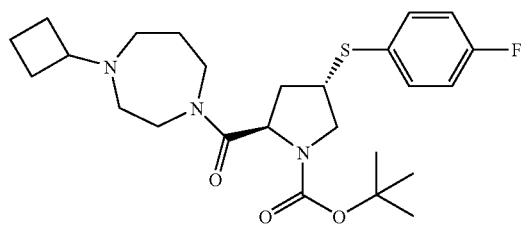

Example 61

(2R,4S)-2-(4-Cyclobutyl-[1,4]diazepane-1-carbonyl)-4-(4-fluoro-phenylsulfanyl)-pyrrolidine-1-carboxylic acid tert-butyl ester.

The title compound was prepared using methods analogous to those described for Example 11, substituting 4-fluorothiophenol for 4-fluorophenol. MS (ESI): mass calcd. for C$_{25}$H$_{36}$FN$_3$O$_3$S, 477.25; m/z found, 478.3 [M+H]$^+$. $^1$H NMR (CDCl$_3$): 7.46-7.40 (m, 2H), 7.07-6.99 (m, 2H), 4.81-4.61 (m, 1H), δ 4.00-3.80 (m, 2H), 3.74-3.38 (m, 5H), 2.94-2.82 (m, 1H), 2.58-2.35 (m, 4H), 2.30-1.99 (m, 4H), 1.89-1.75 (m, 4H), 1.74-1.62 (m, 2H), 1.60 (s, 9H).

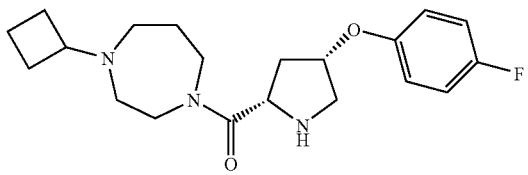

Example 62

(2S,4S)-2-(4-Cyclobutyl-[1,4]diazepane-1-carbonyl)-4-(4-fluoro-phenoxy)-pyrrolidine.

To a solution of (2S,4S)-2-(4-cyclobutyl-[1,4]diazepane-1-carbonyl)-4-(4-fluoro-phenoxy)-pyrrolidine-1-carboxylic acid tert-butyl ester (969 mg, 2.09 mmol) in CH$_2$Cl$_2$ (5 mL) was added trifluoroacetic acid (2 mL). After 1 h, the mixture was concentrated and the residue purified by FCC to give the desired product (665 mg, 88%). MS (ESI): mass calcd. for C$_{20}$H$_{28}$FN$_3$O$_2$, 361.22; m/z found, 362.5 [M+H]$^+$. $^1$H NMR (CDCl$_3$): 6.95-6.90 (m, 2H), 6.78 (dd, J=9.0, 4.3 Hz, 2H), 4.79-4.74 (m, 1H), 3.88 (ddd, J=9.1, 6.3, 6.3 Hz, 1H), 3.81-3.69 (m, 1H), 3.58-3.47 (m, 2H), 3.47-3.37 (m, 2H), 3.08-2.76 (m, 3H), 2.59-2.28 (m, 5H), 2.00 (dd, J=16.1, 7.7 Hz, 2H), 1.95-1.72 (m, 5H), 1.69-1.53 (m, 2H).

The compounds in Examples 63-105 were prepared using methods analogous to those described for Example 62, with exceptions where noted.

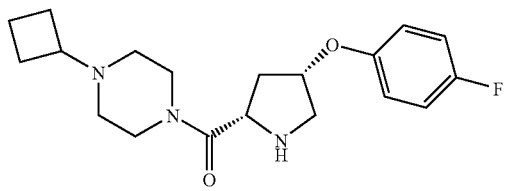

Example 63

(2S,4S)-2-(4-Cyclobutyl-piperazine-1-carbonyl)-4-(4-fluoro-phenoxy)-pyrrolidine.

MS (ESI): mass calcd. for $C_{19}H_{26}FN_3O_2$, 347.20; m/z found, 348.3 $[M+H]^+$. $^1H$ NMR ($CDCl_3$): 6.97-6.92 (m, 2H), 6.78 (dd, J=9.1, 4.3 Hz, 2H), 4.78-4.74 (m, 1H), 3.90 (dd, J=9.3, 6.1 Hz, 1H), 3.71-3.58 (m, 2H), 3.50-3.44 (m, 1H), 3.43-3.36 (m, 2H), 3.32-2.97 (br s, 1H), 2.91 (dd, J=12.8, 3.9 Hz, 1H), 2.72-2.66 (m, 1H), 2.40 (ddd, J=14.9, 9.4, 5.7 Hz, 1H), 2.33-2.22 (m, 4H), 2.06-1.99 (m, 2H), 1.91 (dd, J=13.9, 6.1 Hz, 1H), 1.88-1.81 (m, 2H), 1.76-1.63 (m, 2H).

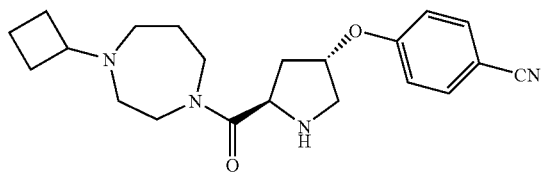

Example 64

(3S,5R)-4-[5-(4-Cyclobutyl-[1,4]diazepane-1-carbonyl)-pyrrolidin-3-yloxy]-benzonitrile.

MS (ESI): mass calcd. for $C_{21}H_{28}N_4O_2$, 368.22; m/z found, 369.3 $[M+H]^+$. $^1H$ NMR ($CDCl_3$): 7.63-7.56 (m, 2H), 6.97-6.89 (m, 2H), 5.00-4.94 (m, 1H), 4.22-4.13 (m, 1H), 3.88-3.41 (m, 5H), 3.16-3.06 (m, 1H), 2.97-2.82 (m, 1H), 2.79-1.56 (m, 15H).

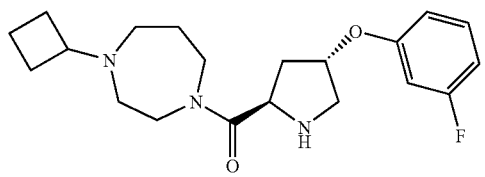

Example 65

(2R,4S)-4-(3-Fluoro-phenoxy)-2-(4-cyclobutyl-[1,4]diazepane-1-carbonyl)-pyrrolidine.

MS (ESI): mass calcd. for $C_{20}H_{28}FN_3O_2$, 361.22; m/z found, 362.3 $[M+H]^+$. $^1H$ NMR ($CDCl_3$): 7.26-7.16 (m, 1H), 6.71-6.64 (m, 1H), 6.63-6.58 (m, 1H), 6.58-6.51 (m, 1H), 5.02-4.92 (m, 1H), 4.63-4.53 (m, 1H), 4.19-4.05 (m, 1H), 3.99-2.61 (m, 11H), 2.47-1.98 (m, 8H), 1.88-1.51 (m, 2H).

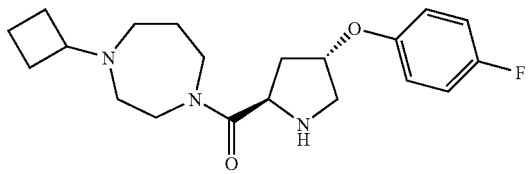

Example 66

(2R,4S)-4-(4-Fluoro-phenoxy)-2-(4-cyclobutyl-[1,4]diazepane-1-carbonyl)-pyrrolidine.

MS (ESI): mass calcd. for $C_{20}H_{28}FN_3O_2$, 361.22; m/z found, 362.3 $[M+H]^+$. $^1H$ NMR ($CDCl_3$): 7.01-6.94 (m, 2H), 6.85-6.79 (m, 2H), 4.88-4.82 (m, 1H), 4.22-4.08 (m, 1H), 3.83-3.48 (m, 5H), 3.14-3.05 (m, 1H), 2.92-2.79 (m, 1H), 2.65-2.21 (m, 5H), 2.13-1.55 (m, 10H).

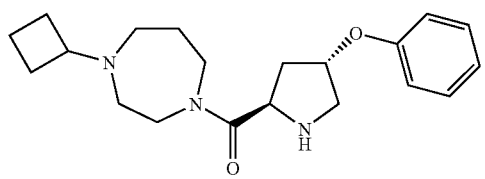

Example 67

(2R,4S)-4-Phenoxy-2-(4-cyclobutyl-[1,4]diazepane-1-carbonyl)-pyrrolidine.

MS (ESI): mass calcd. for $C_{20}H_{29}N_3O_2$, 343.23; m/z found, 344.4 $[M+H]^+$. $^1H$ NMR ($CDCl_3$): 7.32-7.28 (m, 2H), 7.00-6.94 (m, 1H), 6.91-6.86 (m, 2H), 4.95-4.89 (m, 1H), 4.20-4.14 (m, 1H), 3.83-3.70 (m, 1H), 3.68-3.49 (m, 4H), 3.14-3.09 (m, 1H), 2.93-2.82 (m, 1H), 2.62-2.21 (m, 5H), 2.16-1.51 (m, 10H).

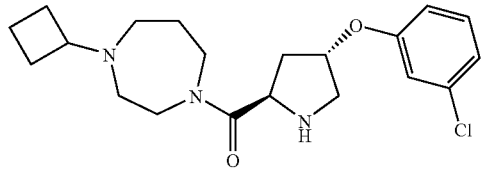

Example 68

(2R,4S)-4-(3-chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 $[M+H]^+$. $^1H$ NMR ($CDCl_3$): 7.21 (t, J=8.2 Hz, 1H), 6.97-6.92 (m, 1H), 6.90-6.87 (m, 1H), 6.79-6.74 (m, 1H), 4.94-4.85 (m, 1H), 4.24-4.11 (m, 1H), 3.90-3.45 (m, 5H), 3.15-3.05 (m, 1H), 2.98-2.86 (m, 1H), 2.71-2.33 (m, 5H), 2.29-1.53 (m, 10H).

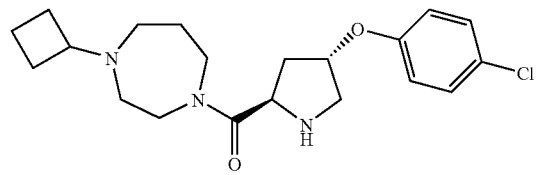

Example 69

(2R,4S)-4-(4-Chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 [M+H]$^+$. $^1$H NMR (CDCl$_3$): 7.27-7.22 (m, 2H), 6.85-6.77 (m, 2H), 4.90-4.84 (m, 1H), 4.19-4.12 (m, 1H), 3.82-3.70 (m, 1H), 3.68-3.49 (m, 4H), 3.12-3.06 (m, 1H), 2.92-2.82 (m, 1H), 2.63-2.34 (m, 4H), 2.30-2.22 (m, 1H), 2.14-1.56 (m, 10H).

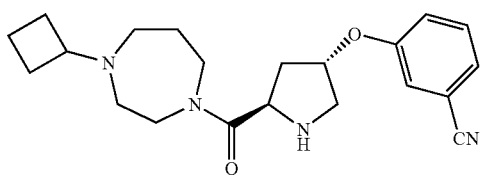

Example 70

(2R,4S)-4-(3-Cyano-phenoxy)-2-(4-cyclobutyl-[1,4]diazepane-1-carbonyl)-pyrrolidine.

MS (ESI): mass calcd. for $C_{21}H_{28}4_3O_2$, 368.22; m/z found, 369.3 [M+H]$^+$. $^1$H NMR (CDCl$_3$): 7.40-7.33 (m, 1H), 7.27-7.22 (m, 1H), 7.13-7.06 (m, 2H), 4.93-4.86 (m, 1H), 4.20-4.06 (m, 1H), 3.83-3.45 (m, 5H), 3.14-3.03 (m, 1H), 2.93-2.77 (m, 1H), 2.63-2.33 (m, 4H), 2.30-2.19 (m, 1H), 2.17-1.53 (m, 10H).

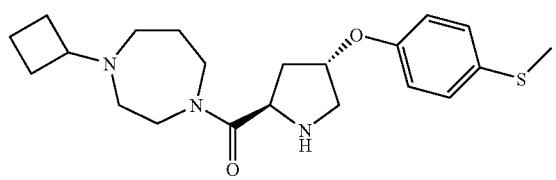

Example 71

(2R,4S)-4-(4-Methylsulfanyl-Phenoxy)-2-(4-cyclobutyl-[1,4]diazepane-1-carbonyl)-pyrrolidine.

MS (ESI): mass calcd. for $C_{21}H_{31}N_3O_2S$, 389.21; m/z found, 390.3 [M+H]$^+$. $^1$H NMR (CDCl$_3$): 7.26-7.23 (m, 2H), 6.82-6.79 (m, 2H), 4.88-4.84 (m, 1H), 4.17-4.09 (m, 1H), 3.80-3.68 (m, 1H), 3.66-3.47 (m, 4H), 3.07 (dd, J=12.4, 2.9 Hz, 1H), 2.90-2.82 (m, 1H), 2.59-2.34 (m, 8H), 2.27-2.21 (m, 1H), 2.11-1.99 (m, 3H), 1.94-1.75 (m, 4H), 1.71-1.57 (m, 2H).

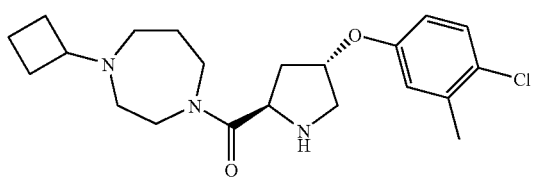

Example 72

(2R,4S)-4-(4-Chloro-3-methyl-phenoxy)-2-(4-cyclobutyl-[1,4]diazepane-1-carbonyl)-pyrrolidine.

MS (ESI): mass calcd. for $C_{21}H_{30}ClN_3O_2$, 391.20; m/z found, 392.3 [M+H]$^+$. $^1$H NMR (CDCl$_3$): 7.20 (d, J=8.7 Hz, 1H), 6.74 (d, J=2.9 Hz, 1H), 6.63 (dd, J=8.7, 3.0 Hz, 1H), 4.86-4.82 (m, 1H), 4.16-4.09 (m, 1H), 3.79-3.68 (m, 1H), 3.65-3.48 (m, 4H), 3.05 (dd, J=12.4, 2.9 Hz, 1H), 2.90-2.82 (m, 1H), δ 2.59-2.30 (m, 8H), 2.26-2.19 (m, 1H), 2.11-1.99 (m, 3H), 1.96-1.75 (m, 4H), 1.71-1.56 (m, 2H).

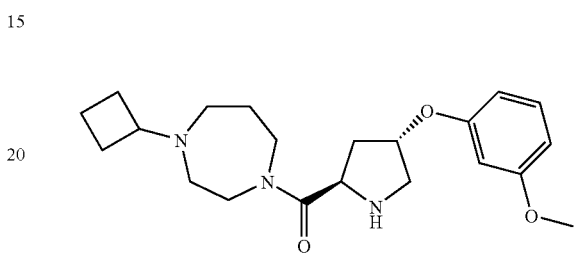

Example 73

(2R,4S)-4-(3-Methoxy-phenoxy)-2-(4-cyclobutyl-[1,4]diazepane-1-carbonyl)-pyrrolidine.

MS (ESI): mass calcd. for $C_{21}H_{31}N_3O_3$, 373.24; m/z found, 374.3 [M+H]$^+$. $^1$H NMR (CDCl$_3$): 7.16 (dd, J=8.2, 8.2 Hz, 1H), 6.50 (dd, J=8.2, 2.3 Hz, 1H), 6.46 (dd, J=8.2, 1.8 Hz, 1H), 6.43 (dd, J=2.3, 2.3 Hz, 1H), 4.89-4.85 (m, 1H), 4.16-4.10 (m, 1H), 3.78 (s, 3H), 3.76-3.69 (m, 1H), 3.64-3.47 (m, 4H), 3.08 (dd, J=12.4, 2.9 Hz, 1H), 2.90-2.81 (m, 1H), 2.58-2.33 (m, 4H), 2.29-2.21 (m, 1H), 2.10-1.99 (m, 5H), 1.92-1.74 (m, 3H), 1.71-1.56 (m, 2H).

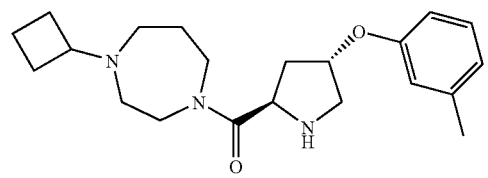

Example 74

(2R,4S)-4-(4-m-Tolyloxy)-2-(4-cyclobutyl-[1,4]diazepane-1-carbonyl)-pyrrolidine.

MS (ESI): mass calcd. for $C_{21}H_{31}N_3O_2$, 357.24; m/z found, 358.3 [M+H]$^+$. $^1$H NMR (CDCl$_3$): 7.15 (dd, J=7.8, 7.8 Hz, 1H), 6.76 (d, J=7.5 Hz, 1H), 6.70-6.64 (m, 2H), 4.90-4.84 (m, 1H), 4.14 (dd, J=14.6, 7.4 Hz, 1H), 3.80-3.68 (m, 1H), 3.65-3.46 (m, 4H), 3.08 (dd, J=12.4, 3.0 Hz, 1H), 2.90-2.81 (m, 1H), 2.59-2.34 (m, 4H), 2.32 (s, 3H), 2.29-2.21 (m, 1H), 2.11-1.97 (m, 4H), 1.88-1.74 (m, 4H), 1.72-1.56 (m, 2H).

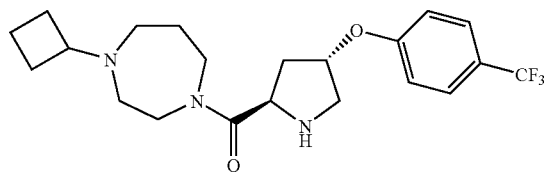

Example 75

(2R,4S)-4-(4-Trifluoromethyl-phenoxy)-2-(4-cyclobutyl-[1,4]diazepane-1-carbonyl)-pyrrolidine.

MS (ESI): mass calcd. for $C_{21}H_{28}F_3N_3O_2$, 411.21; m/z found, 412.3 [M+H]$^+$. $^1$H NMR (CDCl$_3$): 7.53 (d, J=8.7 Hz, 2H), 6.92 (d, J=8.7 Hz, 2H), 4.97-4.91 (m, 1H), 4.15 (dd, J=14.1, 7.2 Hz, 1H), 3.80-3.69 (m, 1H), 3.66-3.48 (m, 4H), 3.10 (dd, J=12.5, 2.5 Hz, 1H), 2.91-2.82 (m, 1H), 2.60-2.35 (m, 4H), 2.29-2.21 (m, 1H), 2.18-2.08 (m, 1H), 2.06-1.99 (m, 3H), 1.89-1.74 (m, 4H), 1.71-1.57 (m, 2H).

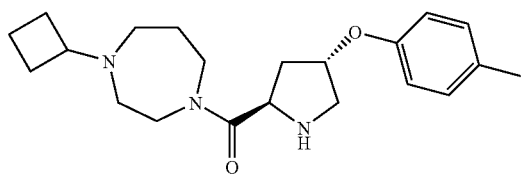

Example 76

(2R,4S)-4-(4-p-Tolyloxy)-2-(4-cyclobutyl-[1,4]diazepane-1-carbonyl)-pyrrolidine.

MS (ESI): mass calcd. for $C_{21}H_{31}N_3O_2$, 357.24; m/z found, 358.4 [M+H]$^+$. $^1$H NMR (CDCl$_3$): 7.06 (d, J=8.4 Hz, 2H), 6.76 (d, J=8.5 Hz, 2H), 4.88-4.82 (m, 2H), 4.14 (dd, J=14.9, 7.2 Hz, 1H), 3.80-3.68 (m, 1H), 3.65-3.46 (m, 4H), 3.07 (dd, J=12.4, 2.6 Hz, 1H), 2.90-2.82 (m, 1H), 2.59-2.29 (m, 5H), 2.27 (s, 3H), 2.07-1.98 (m, 3H), 1.98-1.74 (m, 4H), 1.71-1.56 (m, 2H).

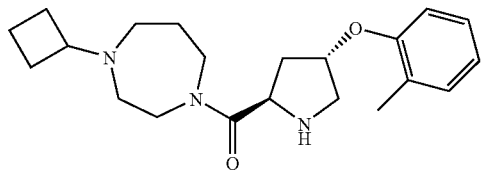

Example 77

(2R,4S)-4-(4-p-Tolyloxy)-2-(4-cyclobutyl-[1,4]diazepane-1-carbonyl)-pyrrolidine.

MS (ESI): mass calcd. for $C_{21}H_{31}N_3O_2$, 357.24; m/z found, 358.4 [M+H]$^+$. $^1$H NMR (CDCl$_3$): 7.17-7.11 (m, 2H), 6.87 (dd, J=7.4, 7.4 Hz, 1H), 6.78 (d, J=7.9 Hz, 1H), 4.93-4.88 (m, 1H), 4.16 (dd, J=15.1, 6.8 Hz, 1H), 3.81-3.71 (m, 1H), 3.66-3.49 (m, 4H), 3.11 (dd, J=12.5, 3.2 Hz, 1H), 2.92-2.83 (m, 1H), 2.61-2.34 (m, 5H), 2.31-2.24 (m, 1H), 2.22 (s, 3H), 2.13-2.01 (m, 3H), 1.96-1.76 (m, 4H), 1.73-1.57 (m, 2H).

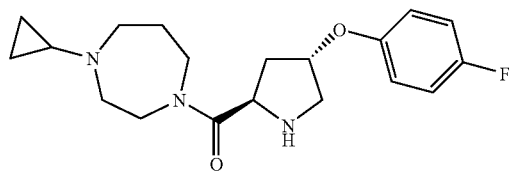

Example 78

(2R,4S)-2-(4-Cyclopropyl-[1,4]diazepane-1-carbonyl)-4-(4-fluoro-phenoxy)-pyrrolidine.

MS (ESI): mass calcd. for $C_{19}H_{26}FN_3O_2$, 347.20; m/z found, 348.3 [M+H]$^+$. $^1$H NMR (CDCl$_3$): 7.05-6.92 (m, 2H), 6.87-6.79 (m, 2H), 4.95-4.79 (m, 1H), 4.40-4.26 (m, 1H), 3.82-3.43 (m, 5H), 3.37-3.04 (m, 2H), 2.95-2.68 (m, 4H), 2.38-2.26 (m, 1H), 2.13-2.01 (m, 1H), 1.99-1.71 (m, 3H), 0.61-0.24 (m, 4H).

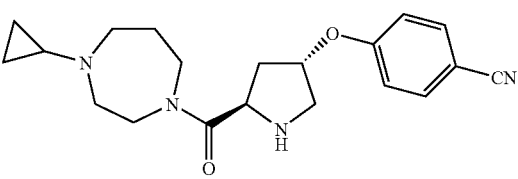

Example 79

(2R,4S)-4-(4-Cyano-phenoxy)-2-(4-cyclopropyl-[1,4]diazepane-1-carbonyl)-pyrrolidine.

MS (ESI): mass calcd. for $C_{20}H_{26}N_4O_2$, 354.21; m/z found, 355.2 [M+H]$^+$. $^1$H NMR (CDCl$_3$): 7.65-7.50 (m, 2H), 6.98-6.87 (m, 2H), 5.01-4.90 (m, 1H), 4.23-4.11 (m, 1H), 3.79-3.44 (m, 5H), 3.15-3.06 (m, 1H), 2.95-2.70 (m, 4H), 2.37-2.01 (m, 4H), 1.98-1.70 (m, 2H), 0.55-0.30 (m, 4H).

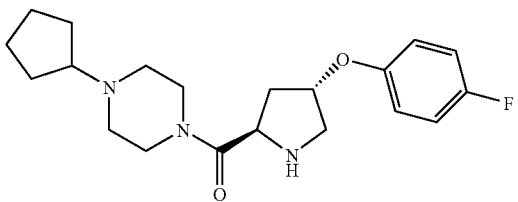

Example 80

(2R,4S)-2-(4-Cyclopentyl-piperazine-1-carbonyl)-4-(4-fluoro-phenoxy)-pyrrolidine.

MS (ESI): mass calcd. for $C_{20}H_{28}FN_3O_2$, 361.22; m/z found, 362.3 [M+H]$^+$. $^1$H NMR (CDCl$_3$): 7.04-6.94 (m, 2H), 6.91-6.80 (m, 2H), 6.78-6.13 (m, 1H), 5.03-4.93 (m, 1H), 4.88-4.77 (m, 1H), 4.08-3.89 (m, 1H), 3.77-3.37 (m, 5H), 2.97-2.80 (m, 4H), 2.77-2.63 (m, 1H), 2.57-2.41 (m, 1H), 2.25-2.11 (m, 1H), 1.99-1.83 (m, 2H), 1.81-1.47 (m, 6H).

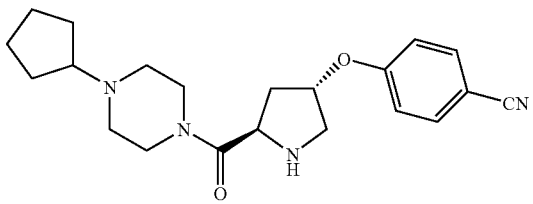

Example 81

(2R,4S)-4-(4-Cyano-phenoxy)-2-(4-cyclopentyl-piperazine-1-carbonyl)-pyrrolidine.

MS (ESI): mass calcd. for $C_{21}H_{28}N_4O_2$, 368.22; m/z found, 369.3 [M+H]$^+$. $^1$H NMR (CDCl$_3$): 7.64-7.56 (m, 2H), 6.97-6.90 (m, 2H), 6.19-5.48 (m, 1H), 5.15-5.04 (m, 1H), 4.72-4.62 (m, 1H), 4.08-3.92 (m, 1H), 3.78-3.53 (m, 4H), 3.46-3.38 (m, 1H), 2.99-2.80 (m, 4H), 2.80-2.67 (m, 1H), 2.49-2.39 (m, 1H), 2.32-2.22 (m, 1H), 2.01-1.85 (m, 2H), 1.84-1.51 (m, 6H).

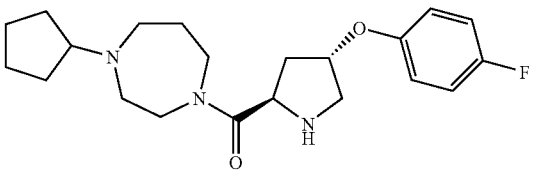

Example 82

(2R,4S)-2-(4-Cyclopentyl-[1,4]diazepane-1-carbonyl)-4-(4-fluoro-phenoxy)-pyrrolidine.

MS (ESI): mass calcd. for $C_{21}H_{30}FN_3O_2$, 375.23; m/z found, 376.3 [M+H]$^+$. $^1$H NMR (CDCl$_3$): 7.22-6.78 (m, 4H), 5.25-5.19 (m, 1H), 5.06-4.95 (m, 1H), 4.23-3.91 (m, 1H), 3.88-3.35 (m, 8H), 3.35-3.29 (m, 3H), 2.87-2.74 (m, 1H), 2.40-2.08 (m, 5H), 1.90-1.61 (m, 6H).

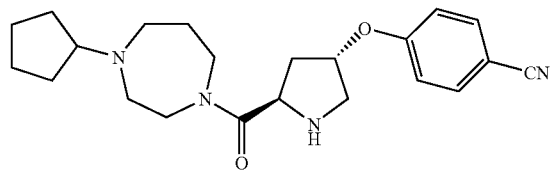

Example 83

(2R,4S)-4-(4-Cyano-phenoxy)-2-(4-cyclopentyl-[1,4]diazepane-1-carbonyl)-pyrrolidine.

MS (ESI): mass calcd. for $C_{22}H_{30}N_4O_2$, 382.24; m/z found, 383.3 [M+H]$^+$. $^1$H NMR (CDCl$_3$): 7.72-7.51 (m, 2H), 6.99-6.87 (m, 2H), 5.14-4.86 (m, 1H), 4.43-4.29 (m, 1H), 4.27-4.02 (m, 1H), 3.95-3.63 (m, 3H), 3.61-3.47 (m, 2H), 3.41-2.83 (m, 7H), 2.48-1.89 (m, 5H), 1.85-1.53 (m, 6H).

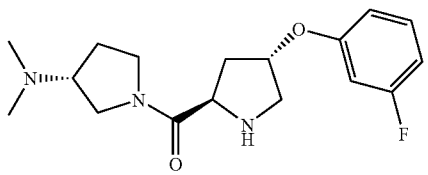

Example 84

(2R,4S)-2-((3R)-3-Dimethylamino-pyrrolidine-1-carbonyl)-4-(3-fluoro-phenoxy)-pyrrolidine.

MS (ESI): mass calcd. for $C_{24}H_{27}FN_3O_2$, 321.19; m/z found, 322.3 [M+H]$^+$. $^1$H NMR (CDCl$_3$): 7.29-7.17 (m, 1H), 6.74-6.56 (m, 3H), 5.04-4.95 (m, 1H), 4.55-4.40 (m, 1H), 4.00-3.86 (m, 1H), 3.85-3.72 (m, 1H), 3.68-3.13 (m, 9H), 3.08-2.93 (m, 1H), 2.57-1.84 (m, 9H).

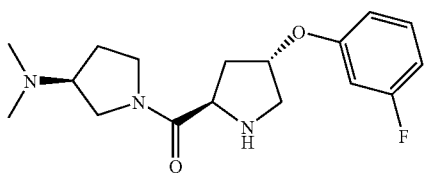

Example 85

(2R,4S)-2-((3S-3-Dimethylamino-pyrrolidine-1-carbonyl)-4-(3-fluoro-phenoxy)-pyrrolidine.

MS (ESI): mass calcd. for $C_{24}H_{27}FN_3O_2$, 321.19; m/z found, 322.3 [M+H]$^+$. $^1$H NMR (CDCl$_3$): 7.28-7.21 (m, 1H), 6.75-6.57 (m, 3H), 5.09-4.95 (m, 1H), 4.84-4.16 (m, 4H), 4.03-3.54 (m, 5H), 3.53-3.35 (m, 2H), 3.25-3.04 (m, 1H), 2.79-1.91 (m, 10H).

The compounds in Examples 86-97 were prepared using methods analogous to those described for Example 62, followed by separation of the resulting diastereomers using reversed phase HPLC. Relative stereochemistry of isolated diastereomers was determined by $^1$H NMR.

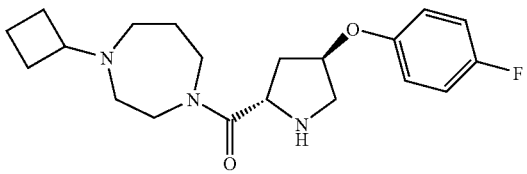

Example 86

(2S,4R)-2-(4-Cyclobutyl-[1,4]diazepane-1-carbonyl)-4-(4-fluoro-phenoxy)-pyrrolidine.

MS (ESI): mass calcd. for $C_{20}H_{28}FN_3O_2$, 361.22; m/z found, 362.3 [M+H]$^+$. $^1$H NMR (CDCl$_3$): 7.00-6.93 (m, 2H), 6.85-6.77 (m, 2H), 4.89-4.80 (m, 1H), 4.27-4.11 (m, 1H), 3.86-3.46 (m, 6H), 3.10 (d, J=12.3 Hz, 1H), 2.94-2.84 (m, 1H), 2.67-2.35 (m, 4H), 2.33-2.18 (m, 1H), 2.14-2.00 (m, 3H), 1.99-1.75 (m, 4H), 1.75-1.55 (m, 2H).

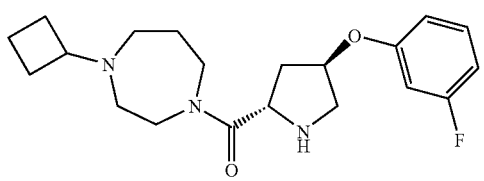

Example 87

(2S,4R)-2-(4-Cyclobutyl-[1,4]diazepane-1-carbonyl)-4-(3-fluoro-phenoxy)-pyrrolidine.

MS (ESI): mass calcd. for $C_{20}H_{28}FN_3O_2$, 361.22; m/z found, 362.3 [M+H]+. 1H NMR (CDCl3): 7.22 (ddd, J=8.3, 8.3, 7.0 Hz, 2H), 6.71-6.62 (m, 2H), 6.58 (ddd, J=10.9, 2.3, 2.3 Hz, 1H), 4.90-4.84 (m, 1H), 4.18-4.11 (m, 1H), 3.84-3.68 (m, 1H), 3.66-3.48 (m, 4H), 3.09 (dd, J=12.5, 2.8 Hz, 1H), 2.92-2.81 (m, 1H), 2.60-2.34 (m, 4H), 2.31-2.22 (m, 1H), 2.15-1.99 (m, 4H), 1.97-1.90 (m, 1H), 1.88-1.76 (m, 3H), 1.74-1.56 (m, 2H).

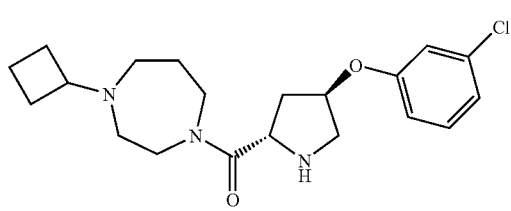

Example 88

(2S,4R)-4-(3-Chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 [M+H]+. 1H NMR (CDCl3): 7.18 (dd, J=8.1, 8.1 Hz, 1H), 6.94-6.91 (m, 1H), 6.87-6.80 (m, 1H), 6.74 (dd, J=8.4, 2.4 Hz, 1H), 4.97-4.84 (m, 1H), 4.13 (dd, J=15.8, 8.5 Hz, 1H), 3.84-3.70 (m, 1H), 3.68-3.48 (m, 4H), 3.08 (dd, J=12.5, 2.7 Hz, 1H), 2.94-2.84 (m, 1H), 2.62-2.55 (m, 1H), 2.54-2.41 (m, 3H), 2.40-2.32 (m, 1H), 2.27-2.21 (m, 1H), 2.13-1.77 (m, 7H), 1.74-1.57 (m, 2H).

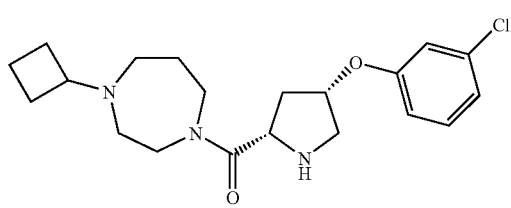

Example 89

(2S,4S)-4-(3-Chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 [M+H]+. 1H NMR (CDCl3): 7.15 (ddd, J=8.2, 8.2, 1.1 Hz, 1H), 6.92-6.88 (m, 1H), 6.85-6.77 (m, 1H), 6.74-6.66 (m, 1H), 4.82-4.73 (m, 1H), 3.90 (ddd, J=9.2, 6.1, 6.1 Hz, 1H), 3.81-3.69 (m, 1H), 3.58-3.38 (m, 4H), 2.92 (dd, J=13.0, 4.1 Hz, 1H), 2.89-2.78 (m, 2H), 2.59-2.29 (m, 5H), 2.06-1.96 (m, 2H), 1.96-1.72 (m, 5H), 1.70-1.54 (m, 2H).

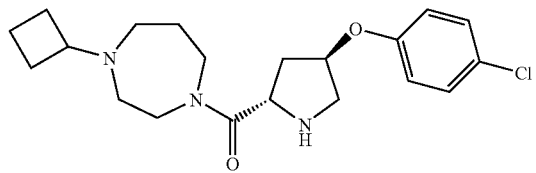

Example 90

(2S,4R)-4-(4-Chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 [M+H]+. 1H NMR (CDCl3): 7.23-7.17 (m, 2H), 6.79-6.69 (m, 2H), 4.93-4.81 (m, 1H), 4.13 (dd, J=15.9, 8.6 Hz, 1H), 3.81-3.68 (m, 1H), 3.64-3.46 (m, 4H), 3.06 (dd, J=12.5, 2.7 Hz, 1H), 3.02-2.81 (m, 2H), 2.60-2.53 (m, 1H), 2.53-2.33 (m, 3H), 2.26-2.18 (m, 1H), 2.11-1.76 (m, 7H), 1.71-1.54 (m, 2H).

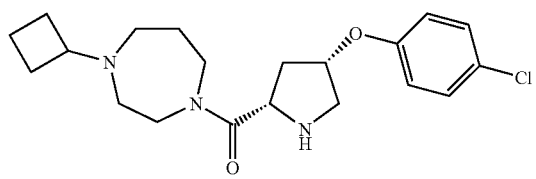

Example 91

(2S,4S)-4-(4-Chloro-phenoxy)-2-(4-cyclobutyl-[1,4]diazepane-1-carbonyl)-pyrrolidine.

MS (ESI): mass calcd. for $C_{20}H_{28}ClN_3O_2$, 377.19; m/z found, 378.3 [M+H]+. 1H NMR (CDCl3): 7.22-7.15 (m, 2H), 6.80-6.69 (m, 2H), 4.82-4.76 (m, 1H), 3.90 (ddd, J=9.1, 6.2, 6.2 Hz, 1H), 3.79-3.69 (m, 1H), 3.58-3.47 (m, 2H), 3.47-3.37 (m, 2H), 2.91 (dd, J=13.0, 4.0 Hz, 1H), 2.88-2.72 (m, 2H), 2.59-2.29 (m, 5H), 2.06-1.97 (m, 2H), 1.96-1.73 (m, 5H), 1.71-1.54 (m, 2H).

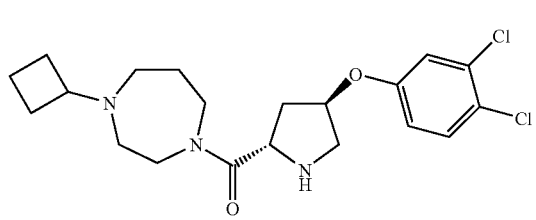

Example 92

(2S,4R)-2-(4-Cyclobutyl-[1,4]diazepane-1-carbonyl)-4-(3,4-dichloro-phenoxy)-pyrrolidine.

MS (ESI): mass calcd. for $C_{20}H_{27}Cl_2N_3O_2$, 411.15; m/z found, 412.2 [M+H]+. 1H NMR (CDCl3): 7.31 (d, J=8.9 Hz, 1H), 6.95 (d, J=2.8 Hz, 1H), 6.72 (dd, J=8.8, 2.9 Hz, 1H), 4.89-4.79 (m, 1H), 4.16-4.09 (m, 1H), 3.82-3.68 (m, 1H), 3.67-3.46 (m, 4H), 3.06 (dd, J=12.5, 2.7 Hz, 1H), 2.92-2.81 (m, 1H), 2.65-2.31 (m, 4H), 2.28-2.18 (m, 1H), 2.11-1.99 (m, 4H), 1.97-1.90 (m, 1H), 1.90-1.76 (m, 3H), 1.72-1.56 (m, 2H).

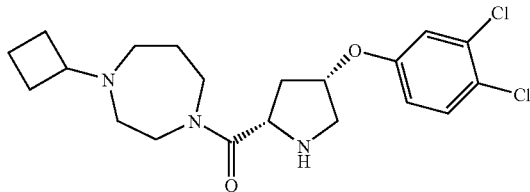

Example 93

(2S,4S)-2-(4-Cyclobutyl-[1,4]diazepane-1-carbonyl)-4-(3,4-dichloro-phenoxy)-pyrrolidine.

MS (ESI): mass calcd. for $C_{20}H_{27}Cl_2N_3O_2$, 411.15; m/z found, 412.2 [M+H]$^+$. $^1$H NMR (CDCl$_3$): 7.29 (dd, J=8.9, 1.3 Hz, 1H), 6.93 (dd, J=2.8, 0.9 Hz, 1H), 6.70 (ddd, J=8.9, 2.8, 1.4 Hz, 1H), 4.79-4.75 (m, 1H), 3.94-3.87 (m, 1H), 3.80-3.68 (m, 1H), 3.59-3.38 (m, 4H), 2.91 (dd, J=13.1, 4.0 Hz, 1H), 2.88-2.74 (m, 1H), 2.59-2.52 (m, 2H), 2.48-2.28 (m, 5H), 2.07-1.96 (m, 2H), 1.95-1.78 (m, 4H), 1.70-1.54 (m, 2H).

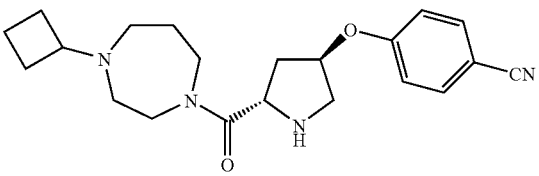

Example 94

(2S,4R)-4-(4-Cyano-phenoxy)-2-(4-cyclobutyl-[1,4]diazepane-1-carbonyl)-pyrrolidine.

MS (ESI): mass calcd. for $C_{21}H_{28}N_4O_2$, 368.22; m/z found, 369.3 [M+H]$^+$. $^1$H NMR (CDCl$_3$): 7.59-7.55 (m, 2H), 6.91 (d, J=8.6 Hz, 2H), 4.98-4.92 (m, 1H), 4.16 (dd, J=15.3, 7.4 Hz, 1H), 3.82-3.69 (m, 1H), 3.67-3.59 (m, 1H), 3.59-3.46 (m, 3H), 3.09 (dd, J=12.6, 2.7 Hz, 1H), 2.92-2.83 (m, 1H), 2.63-2.55 (m, 1H), 2.55-2.45 (m, 2H), 2.45-2.35 (m, 1H), 2.28-2.10 (m, 3H), 2.09-2.00 (m, 2H), 1.97-1.91 (m, 1H), 1.88-1.77 (m, 3H), 1.73-1.56 (m, 2H).

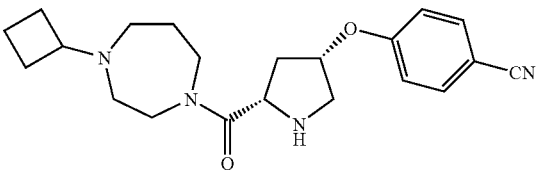

Example 95

(2S,4S)-4-(4-Cyano-phenoxy)-2-(4-cyclobutyl-[1,4]diazepane-1-carbonyl)-pyrrolidine.

MS (ESI): mass calcd. for $C_{21}H_{28}N_4O_2$, 368.22; m/z found, 369.3 [M+H]$^+$. $^1$H NMR (CDCl$_3$): 7.57-7.42 (m, 2H), 6.86-6.80 (m, 2H), 4.86-4.82 (m, 1H), 3.97-3.91 (m, 1H), 3.81-3.62 (m, 1H), 3.55-3.37 (m, 4H), 3.00-2.92 (m, 1H), 2.85-2.78 (m, 1H), 2.67-2.52 (m, 2H), 2.49-2.25 (m, 4H), 2.04-1.71 (m, 7H), 1.68-1.50 (m, 2H).

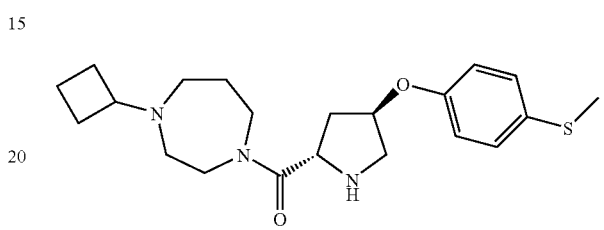

Example 96

(2S,4R)-2-(4-Cyclobutyl-[1,4]diazepane-1-carbonyl)-4-(4-methylsulfanyl-phenoxy)-pyrrolidine.

MS (ESI): mass calcd. for $C_{21}H_{31}N_3O_2S$, 389.21; m/z found, 390.3 [M+H]$^+$. $^1$H NMR (CDCl$_3$): 7.30-7.27 (m, 2H), 6.89-6.82 (m, 2H), 4.94-4.87 (m, 1H), 4.19 (dd, J=14.9, 6.8 Hz, 1H), 3.88-3.73 (m, 1H), 3.71-3.52 (m, 4H), 3.12 (dd, J=12.4, 2.9 Hz, 1H), 2.98-2.85 (m, 1H), 2.65-2.50 (m, 3H), 2.48 (s, 3H), 2.47-2.37 (m, 2H), 2.33-2.24 (m, 1H), 2.15-2.05 (m, 3H), 2.01-1.94 (m, 1H), 1.92-1.83 (m, 3H), 1.78-1.59 (m, 2H).

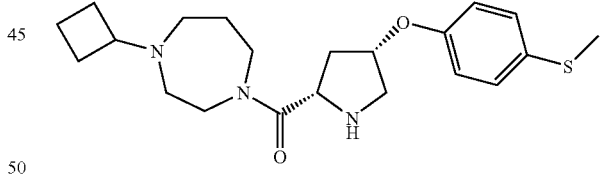

Example 97

(2S,4S)-2-(4-Cyclobutyl-[1,4]diazepane-1-carbonyl)-4-(4-methylsulfanyl-phenoxy)-pyrrolidine.

MS (ESI): mass calcd. for $C_{21}H_{31}N_3O_2S$, 389.21; m/z found, 390.3 [M+H]$^+$. $^1$H NMR (CDCl$_3$): 7.24-7.19 (m, 2H), 6.79 (d, J=8.8 Hz, 2H), 4.84-4.78 (m, 1H), 3.96-3.90 (m, 1H), 3.82-3.69 (m, 1H), 3.58-3.48 (m, 2H), 3.47-3.39 (m, 2H), 2.93 (dd, J=12.9, 4.0 Hz, 1H), 2.90-2.76 (m, 2H), 2.62-2.44 (m, 3H), 2.43 (d, J=1.1 Hz, 3H), 2.41-2.30 (m, 2H), 2.04-1.97 (m, 2H), 1.96-1.87 (m, 2H), 1.87-1.73 (m, 3H), 1.70-1.54 (m, 2H).

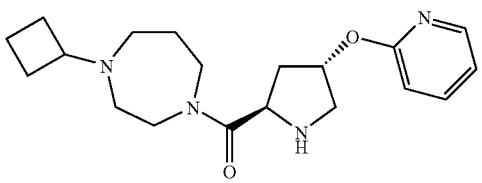

Example 98

(2R,4S)-2-(4-Cyclobutyl-[1,4]diazepane-1-carbonyl)-4-(pyridin-2-yloxy)-pyrrolidine.

MS (ESI): mass calcd. for $C_{19}H_{28}N_4O_2$, 344.22; m/z found, 345.4 [M+H]+. 1H NMR (CDCl3): 8.11 (dd, J=5.0, 1.5 Hz, 1H), 7.54 (ddd, J=8.5, 7.1, 2.0 Hz, 1H), 6.83 (ddd, J=7.0, 5.1, 0.8 Hz, 1H), 6.70 (d, J=8.4 Hz, 1H), 5.54-5.48 (m, 1H), 4.12 (ddd, J=8.9, 7.1, 4.6 Hz, 1H), 3.79-3.69 (m, 1H), 3.64-3.44 (m, 4H), 3.03 (dd, J=12.4, 2.9 Hz, 1H), 2.89-2.78 (m, 1H), 2.58-2.33 (m, 5H), 2.32-2.22 (m, 1H), 2.13-1.96 (m, 3H), 1.94-1.73 (m, 4H), 1.71-1.53 (m, 2H).

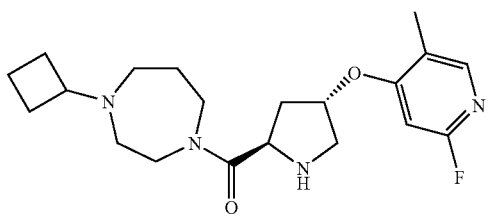

Example 99

(2R,4S)-2-(4-Cyclobutyl-[1,4]diazepane-1-carbonyl)-4-(2-fluoro-5-methyl-pyridin-4-yloxy)-pyrrolidine.

MS (ESI): mass calcd. for $C_{20}H_{29}FN_4O_2$, 376.23; m/z found, 377.3 [M+H]+. 1H NMR (CDCl3): 7.83 (s, 1H), 6.26 (s, 1H), 4.95-4.89 (m, 1H), 4.15 (ddd, J=7.8, 7.6, 3.8 Hz, 1H), 3.81-3.69 (m, 1H), 3.66-3.47 (m, 4H), 3.12 (dd, J=12.7, 2.9 Hz, 1H), 2.91-2.80 (m, 1H), 2.61-2.34 (m, 4H), 2.29-2.13 (m, 2H), 2.11 (s, 3H), 2.08-1.98 (m, 2H), 1.96-1.73 (m, 5H), 1.72-1.56 (m, 2H).

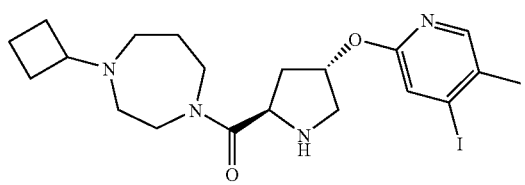

Example 100

(2R,4S)-2-(4-Cyclobutyl-[1,4]diazepane-1-carbonyl)-4-(4-iodo-5-methyl-pyridin-2-yloxy)-pyrrolidine.

MS (ESI): mass calcd. for $C_{20}H_{29}IN_4O_2$, 484.13; m/z found, 485.2 [M+H]+. 1H NMR (CDCl3): 7.87 (s, 1H), 7.24 (s, 1H), 5.48-5.41 (m, 1H), 4.14-4.07 (m, 1H), 3.80-3.69 (m, 1H), 3.64-3.44 (m, 4H), 3.00 (dd, J=12.5, 2.7 Hz, 1H), 2.91-2.79 (m, 1H), 2.60-2.32 (m, 4H), 2.29 (s, 3H), 2.27-2.12 (m, 2H), 2.08-1.96 (m, 3H), 1.94-1.73 (m, 4H), 1.72-1.54 (m, 2H).

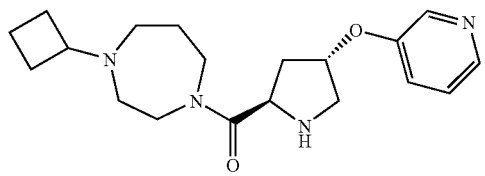

Example 101

(2R,4S)-2-(4-Cyclobutyl-[1,4]diazepane-1-carbonyl)-4-(Pyridin-3-yloxy)-pyrrolidine.

MS (ESI): mass calcd. for $C_{19}H_{28}N_4O_2$, 344.22; m/z found, 345.3 [M+H]+. 1H NMR (CDCl3): 8.27 (d, J=2.8 Hz, 1H), 8.20 (dd, J=4.5, 1.4 Hz, 1H), 7.21 (dd, J=8.0, 4.5 Hz, 1H), 7.15 (ddd, J=8.4, 2.8, 1.4 Hz, 1H), 4.95-4.89 (m, 1H), 4.19-4.10 (m, 1H), 3.80-3.67 (m, 1H), 3.66-3.46 (m, 4H), 3.09 (dd, J=12.5, 2.6 Hz, 1H), 2.90-2.79 (m, 1H), 2.60-2.33 (m, 4H), 2.30-2.22 (m, 1H), 2.17-2.07 (m, 1H), 2.07-1.98 (m, 3H), 1.96-1.72 (m, 4H), 1.71-1.54 (m, 2H).

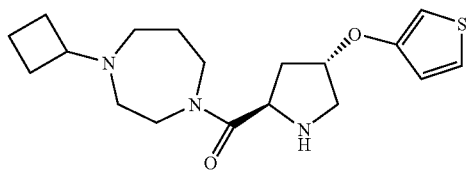

Example 102

(2R,4S)-2-(4-Cyclobutyl-[1,4]diazepane-1-carbonyl)-4-(thiophen-3-yloxy)-pyrrolidine.

MS (ESI): mass calcd. for $C_{18}H_{27}N_3O_2S$, 349.18; m/z found, 351.3 [M+H]+. 1H NMR (CDCl3): 7.17 (dd, J=5.2, 3.1 Hz, 1H), 6.72 (dd, J=5.2, 1.5 Hz, 1H), 6.19 (dd, J=3.1, 1.6 Hz, 1H), 4.82-4.76 (m, 1H), 4.12 (ddd, J=8.4, 7.1, 5.0 Hz, 1H), 3.81-3.68 (m, 1H), 3.66-3.45 (m, 4H), 3.10 (dd, J=12.5, 2.6 Hz, 1H), 2.93-2.78 (m, 1H), 2.61-2.26 (m, 5H), 2.09-1.97 (m, 4H), 1.96-1.75 (m, 4H), 1.72-1.55 (m, 2H).

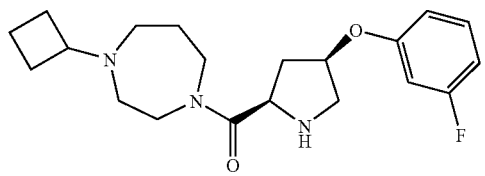

Example 103

(2R,4R)-4-(3-fluoro-phenoxy)-2-(4-cyclobutyl-[1,4]diazepane-1-carbonyl)-pyrrolidine.

MS (ESI): mass calcd. for $C_{20}H_{28}FN_3O_2$, 361.22; m/z found, 362.3 [M+H]+. 1H NMR (CDCl3): 7.18-7.11 (m, 1H), 6.63-6.56 (m, 2H), 6.52 (ddd, J=10.9, 2.3, 2.3 Hz, 1H), 4.80-4.74 (m, 1H), 3.93-3.84 (m, 1H), 3.78-3.63 (m, 1H), 3.57-3.35 (m, 4H), 3.31-3.19 (m, 1H), 2.95-2.87 (m, J=12.9, 4.2 Hz, 1H), 2.86-2.73 (m, 1H), 2.56-2.25 (m, 5H), 2.03-1.69 (m, 7H), 1.67-1.50 (m, 2H).

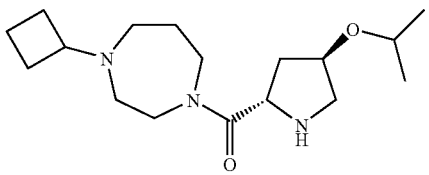

Example 104

(2S,4R)-2-(4-Cyclobutyl-[1,4]diazepane-1-carbonyl)-4-isopropoxy-pyrrolidine.

MS (ESI): mass calcd. for $C_{17}H_{31}N_3O_2$, 309.24; m/z found, 310.3 [M+H]$^+$. $^1$H NMR (CDCl$_3$): 4.16-4.11 (m, 1H), 4.06 (dd, J=14.8, 7.68 Hz, 1H), 3.80-3.70 (m, 1H), 3.65-3.58 (m, 2H), 3.58-3.48 (m, 2H), 3.37-3.32 (m, 1H), 2.91-2.79 (m, 2H), 2.63-2.35 (m, 4H), 2.08-2.02 (m, 4H), 1.93-1.77 (m, 5H), 1.73-1.58 (m, 2H), 1.16 (d, J=6.1 Hz, 6H).

Example 105

(2R,4S)-4-(4-Cyano-phenoxy)-2-(4-cyclobutyl-[1,4]diazepane-1-carbonyl)-pyrrolidine.

MS (ESI): mass calcd. for $C_{21}H_{28}N_4O_2$, 368.22; m/z found, 369.4 [M+H]$^+$. $^1$H NMR (CDCl$_3$): 7.69-7.45 (m, 2H), 6.99-6.85 (m, 2H), 4.96-4.82 (m, 1H), 4.04-3.90 (m, 1H), 3.87-3.68 (m, 1H), 3.64-3.38 (m, 4H), 3.05-2.94 (m, 1H), 2.92-2.75 (m, 1H), 2.67-2.24 (m, 5H), 2.14-1.50 (m, 10H).

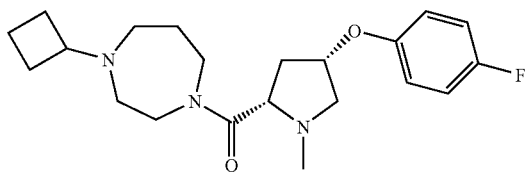

Example 106

(2S,4S)-1-Methyl-2-(4-cyclobutyl-[1,4]diazepane-1-carbonyl)-4-(4-fluoro-phenoxy)-pyrrolidine.

To a solution of (2S,4S)-2-(4-cyclobutyl-[1,4]diazepane-1-carbonyl)-4-(4-fluoro-phenoxy)-pyrrolidine (26 mg, 0.072 mmol) in ethanol (EtOH; 1 mL) was added formaldehyde (37% in H$_2$O; 150 μL) and sodium triacetoxyborohyrdide (46 mg, 0.216 mmol). After 18 h, the mixture was diluted with 1 M NaOH and, stirred for 1 h, and extracted with CH$_2$Cl$_2$ (3×). The combined organic layers were dried and concentrated. Purification by FCC provided the desired product (17 mg, 63%). MS (ESI): mass calcd. for $C_{21}H_{30}FN_3O_2$, 375.23; m/z found, 376.6 [M+H]$^+$. $^1$H NMR (CDCl$_3$): 6.97-6.91 (m, 2H), 6.80-6.73 (m, 2H), 4.77-4.70 (m, 1H), 3.85-3.53 (m, 4H), 3.37 (dd, J=10.7, 3.8 Hz, 1H), 3.15 (ddd, J=8.9, 8.8, 2.7 Hz, 1H), 2.88-2.78 (m, 1H), 2.66-2.57 (m, 1H), 2.51-2.44 (m, 3H), 2.40 (dd, J=10.9, 5.2 Hz, 2H), 2.35 (s, 3H), 2.16-2.07 (m, 1H), 2.06-1.98 (m, 2H), 1.91-1.78 (m, 4H), 1.71-1.56 (m, 2H).

The compounds in Examples 107-113 were prepared using methods analogous to those described for Example 106.

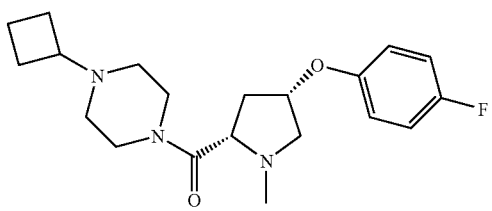

Example 107

(2S,4S)-1-Methyl-2-(4-cyclobutyl-piperazine-1-carbonyl)-4-(4-fluoro-phenoxy)-pyrrolidine.

MS (ESI): mass calcd. for $C_{20}H_{28}FN_3O_2$, 361.22; m/z found, 362.3 [M+H]$^+$. $^1$H NMR (CDCl$_3$): 6.95-6.89 (m, 2H), 6.75-6.69 (m, 2H), 4.73-4.69 (m, 1H), 3.99-3.92 (m, 1H), 3.75-3.65 (m, 2H), 3.30 (d, J=10.7 Hz, 1H), 3.10 (dd, J=9.0, 9.0 Hz, 1H), 2.71-2.56 (m, 2H), 2.40 (dd, J=10.8, 5.4 Hz, 1H), 2.32 (s, 3H), 2.32-2.26 (m, 2H), 2.24-2.15 (m, 2H), 2.07-1.95 (m, 3H), 1.89-1.79 (m, 2H), 1.73-1.62 (m, 2H).

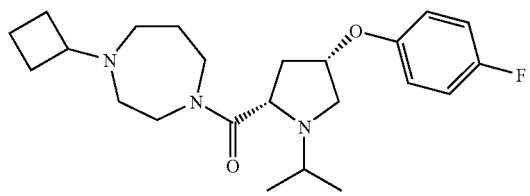

Example 108

(2S,4S)-(4-Cyclobutyl-[1,4]diazepan-1-yl)-[4-(4-fluoro-phenoxy)-1-isopropyl-pyrrolidin-2-yl]-methanone.

MS (ESI): mass calcd. for $C_{23}H_{34}FN_3O_2$, 403.26; m/z found, 404.3 [M+H]$^+$. $^1$H NMR (CDCl$_3$): 6.97-6.93 (dd, J=8.6, 8.6 Hz, 2H), 6.77-6.71 (m, 2H), 4.75-4.67 (m, 1H), 4.13-3.72 (m, 2H), 3.69-3.58 (m, 2H), 3.55-3.43 (m, 1H), 3.27 (d, J=10.4 Hz, 1H), 2.97-2.85 (m, 1H), 2.86-2.71 (m, 2H), 2.67-2.56 (m, 1H), 2.55-2.41 (m, 2H), 2.40-2.28 (m, 2H), 2.07-1.93 (m, 3H), 1.89-1.71 (m, 4H), 1.69-1.52 (m, 2H), 1.09 (d, J=6.5 Hz, 3H), 0.99 (dd, J=6.3, 1.4 Hz, 3H).

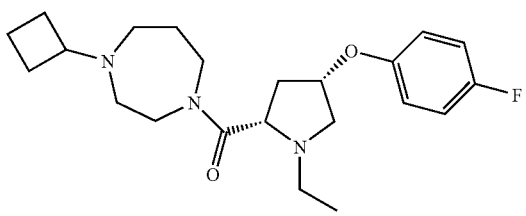

Example 109

(2S,4S)-(4-Cyclobutyl-[1,4]diazepan-1-yl)-[1-ethyl-4-(4-fluoro-phenoxy)-pyrrolidin-2-yl]-methanone.

MS (ESI): mass calcd. for $C_{22}H_{32}FN_3O_2$, 389.25; m/z found, 390.3 [M+H]+. 1H NMR (CDCl3): 6.97-6.89 (m, 2H), 6.77-6.73 (m, 2H), 4.77-4.71 (m, 1H), 3.95-3.72 (m, 2H), 3.67-3.50 (m, 2H), 3.42 (dd, J=10.6, 3.5 Hz, 1H), 3.32-3.25 (m, 1H), 2.88-2.74 (m, 2H), 2.65-2.57 (m, 1H), 2.49-2.35 (m, 5H), 2.31-2.22 (m, 1H), 2.12-2.05 (m, 1H), 2.04-1.95 (m, 2H), 1.88-1.73 (m, 4H), 1.69-1.55 (m, 2H), 1.09 (t, J=7.2 Hz, 3H).

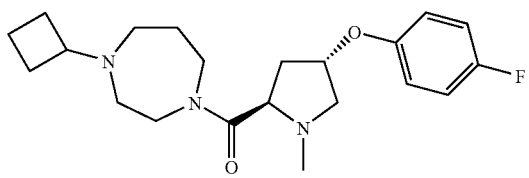

Example 110

(2R,4S)-1-Methyl-2-(4-cyclobutyl-[1,4]diazepane-1-carbonyl)-4-(4-fluoro-phenoxy)-pyrrolidine.

MS (ESI): mass calcd. for $C_{21}H_{30}FN_3O_2$, 375.23; m/z found, 376.3 [M+H]+. 1H NMR (CDCl3): 7.02-6.92 (m, 2H), 6.83-6.74 (m, 2H), 4.93-4.84 (m, 1H), 3.80-3.71 (m, 1H), 3.71-3.52 (m, 5H), 2.93-2.83 (m, 1H), 2.61-2.48 (m, 3H), 2.48-2.31 (m, 6H), 2.25-2.13 (m, 1H), 2.11-1.98 (m, 2H), 1.97-1.74 (m, 4H), 1.75-1.54 (m, 2H).

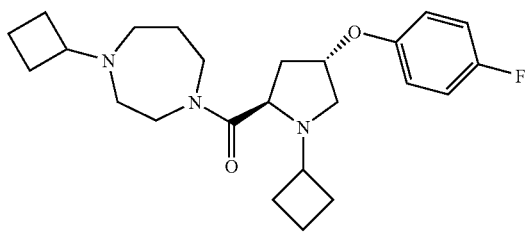

Example 111

(2R,4S)-1-Cyclobutyl-2-(4-cyclobutyl-[1,4]diazepane-1-carbonyl)-4-(4-fluoro-phenoxy)-pyrrolidine.

MS (ESI): mass calcd. for $C_{24}H_{34}FN_3O_2$, 415.26; m/z found, 416.3 [M+H]+. 1H NMR (CDCl3): 7.02-6.90 (m, 2H), 6.84-6.74 (m, 2H), 4.96-4.87 (m, 1H), 3.86-3.74 (m, 1H), 3.70-3.54 (m, 5H), 3.35-3.20 (m, 1H), 2.95-2.81 (m, 1H), 2.74-2.64 (m, 1H), 2.60-2.29 (m, 5H), 2.24-2.11 (m, 1H), 2.10-1.75 (m, 10H), 1.74-1.54 (m, 4H).

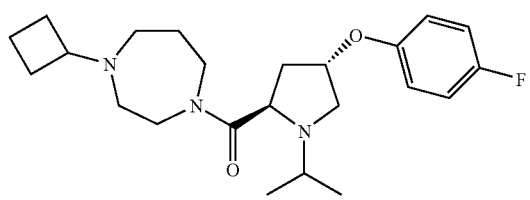

Example 112

(2R,4S)-1-Isopropyl-1-cyclobutyl-2-(4-cyclobutyl-[1,4]diazepane-1-carbonyl)-4-(4-fluoro-phenoxy)-pyrrolidine.

MS (ESI): mass calcd. for $C_{23}H_{34}FN_3O_2$, 403.26; m/z found, 404.3 [M+H]+. 1H NMR (CDCl3): 7.02-6.91 (m, 2H), 6.85-6.75 (m, 2H), 4.95-4.87 (m, 1H), 4.08-3.97 (m, 1H), 3.74-3.54 (m, 5H), 3.06-2.95 (m, 1H), 2.93-2.81 (m, 2H), 2.59-2.36 (m, 4H), 2.35-2.20 (m, 2H), 2.10-2.00 (m, 2H), 1.97-1.75 (m, 4H), 1.73-1.55 (m, 2H), 1.17-0.97 (m, 6H).

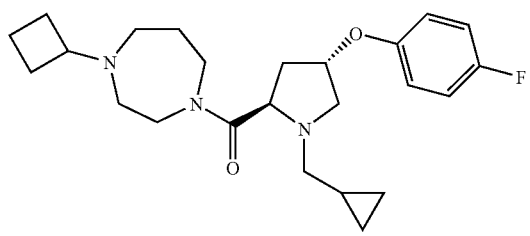

Example 113

(2R,4S)-1-Cyclopropylmethyl-2-(4-cyclobutyl-[1,4]diazepane-1-carbonyl)-4-(4-fluoro-phenoxy)-pyrrolidine.

MS (ESI): mass calcd. for $C_{24}H_{34}FN_3O_2$, 415.26; m/z found, 416.3 [M+H]+. 1H NMR (CDCl3): 7.20-7.13 (m, 1H), 6.64-6.56 (m, 2H), 6.55-6.49 (m, 1H), 4.95-4.87 (m, 1H), 3.82-3.71 (m, 2H), 3.69-3.49 (m, 4H), 2.88-2.77 (m, 1H), 2.71-2.60 (m, 2H), 2.51-2.42 (m, 2H), 2.41-2.28 (m, 3H), 2.24-2.10 (m, 2H), 2.04-1.94 (m, 2H), 1.89-1.70 (m, 4H), 1.69-1.50 (m, 2H), 0.95-0.84 (m, 1H), 0.51-0.39 (m, 2H), 0.13-0.01 (m, 2H).

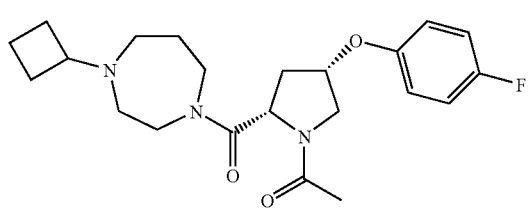

Example 114

(2S,4S)-1-[2-(4-Cyclobutyl-[1,4]diazepane-1-carbonyl)-4-(4-fluoro-phenoxy)-pyrrolidin-1-yl]-ethanone.

To a solution of (2S,4S)-2-(4-cyclobutyl-[1,4]diazepane-1-carbonyl)-4-(4-fluoro-phenoxy)-pyrrolidine (102 mg, 0.85 mmol) and Et₃N (0.197 mL) in THF (2.82 mL) was added acetyl chloride (60 µL, 0.85 mmol). After 48 h, the mixture was diluted with saturated (satd.) aq. NaHCO₃ and extracted with CH₂Cl₂ (3×). The combined organic layers were dried and evaporated. The residue was purified by FCC, followed by reverse phase HPLC (5-99% CH₃CN/20 mM NH₄OH) to give the desired product (69 mg, 61%). MS (ESI): mass calcd. for $C_{22}H_{30}FN_3O_3$, 403.23; m/z found, 404.3 [M+H]⁺. ¹H NMR (CDCl₃): 7.02-6.92 (m, 2H), 6.87-6.77 (m, 2H), 4.92-4.79 (m, 2H), 4.12-3.96 (m, 1H), 3.84-3.47 (m, 5H), 2.92-2.77 (m, 1H), 2.66-2.51 (m, 2H), 2.50-2.41 (m, 2H), 2.39-2.30 (m, 1H), 2.22-2.12 (m, 1H), 2.10 (d, J=2.1 Hz, 3H), 2.07-1.98 (m, 2H), 1.92-1.72 (m, 4H), 1.71-1.54 (m, 2H).

The compounds in Examples 115-130 were prepared by reaction with the appropriate acid chlorides or chloroformates, using methods analogous to those described for Example 114.

Example 115

(2S,4S)-1-[2-(4-Cyclobutyl-[1,4]diazepane-1-carbonyl)-4-(3-fluoro-phenoxy)-pyrrolidin-1-yl]-ethanone.

MS (ESI): mass calcd. for $C_{22}H_{30}FN_3O_3$, 403.23; m/z found, 404.3 [M+H]⁺. ¹H NMR (CDCl₃): 7.29-7.18 (m, 1H), 6.75-6.51 (m, 3H), 4.99-4.83 (m, 2H), 4.12-3.98 (m, 1H), 3.88-3.41 (m, 5H), 2.94-2.29 (m, 6H), 2.25-2.08 (m, 4H), 2.06-1.55 (m, 8H).

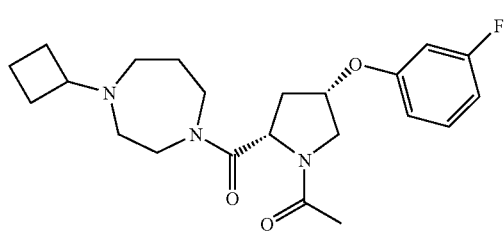

Example 116

(2S,4S)-1-[2-(4-Cyclobutyl-[1,4]diazepane-1-carbonyl)-4-(4-fluoro-phenoxy)-pyrrolidin-1-yl]-propan-1-one.

MS (ESI): mass calcd. for $C_{23}H_{32}FN_3O_3$, 417.24; m/z found, 418.3 [M+H]⁺. ¹H NMR (CDCl₃): 6.92-6.85 (m, 2H), 6.79-6.70 (m, 2H), 4.83-4.71 (m, 2H), 3.93 (dd, J=10.5, 6.6 Hz, 1H), 3.73-3.67 (m, 1H), 3.65-3.56 (m, 1H), 3.55-3.46 (m, 2H), 2.83-2.69 (m, 1H), 2.59-2.19 (m, 7H), 2.11-2.00 (m, 1H), 2.00-1.87 (m, 3H), 1.87-1.64 (m, 4H), 1.63-1.46 (m, 2H), 1.07 (ddd, J=7.5, 7.5, 1.3 Hz, 3H).

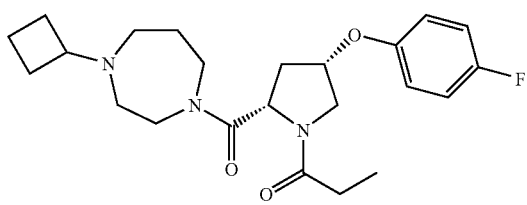

Example 117

(2S,4S)-1-[2-(4-Cyclobutyl-[1,4]diazepane-1-carbonyl)-4-(4-fluoro-phenoxy) pyrrolidin-1-yl]-2-methyl-propan-1-one.

MS (ESI): mass calcd. for $C_{24}H_{34}FN_3O_3$, 431.26; m/z found, 432.3 [M+H]⁺. ¹H NMR (CDCl₃): 6.94-6.85 (m, 2H), 6.79-6.70 (m, 2H), 4.83-4.75 (m, 2H), 4.05-3.98 (m, 1H), 3.77-3.71 (m, 1H), 3.67-3.41 (m, 4H), 2.81-2.69 (m, 1H), 2.64-2.51 (m, 2H), 2.50-2.20 (m, 4H), 2.12-1.99 (m, 1H), 1.98-1.65 (m, 6H), 1.62-1.46 (m, 2H), 1.09 (dd, J=6.8, 2.4 Hz, 3H), 1.05 (dd, J=6.7, 1.0 Hz, 3H).

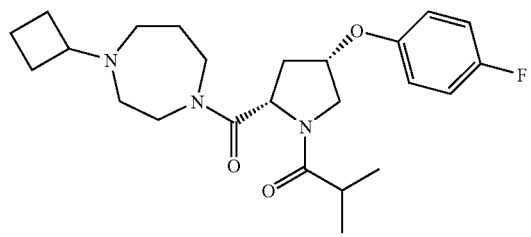

Example 118

(2S,4S)-1-[2-(4-Cyclobutyl-[1,4]diazepane-1-carbonyl)-4-(4-fluoro-phenoxy)-pyrrolidin-1-yl]-3,3-dimethyl-butan-1-one.

MS (ESI): mass calcd. for $C_{26}H_{38}FN_3O_3$, 459.29; m/z found, 460.3 [M+H]⁺. ¹H NMR (CDCl₃): 6.93-6.87 (m, 2H), 6.80-6.70 (m, 2H), 4.82 (dd, J=8.7, 6.4 Hz, 1H), 4.78-4.71 (m, 1H), 3.99 (dd, J=10.5, 6.6 Hz, 1H), 3.74-3.68 (m, 1H), 3.68-3.61 (m, 1H), 3.60-3.40 (m, 2H), 2.86-2.71 (m, 1H), 2.61-2.49 (m, 1H), 2.50-2.25 (m, 5H), 2.22 (dd, J=13.5, 3.1 Hz, 1H), 2.14-1.99 (m, 2H), 1.99-1.88 (m, 3H), 1.83-1.63 (m, 3H), 1.64-1.46 (m, 2H), 1.00 (s, 9H).

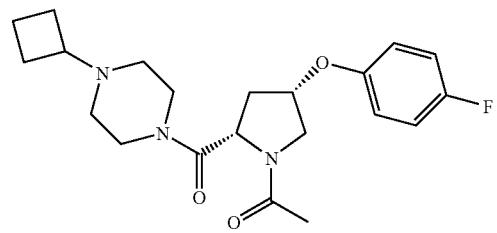

Example 119

(2S,4S)-1-[2-(4-Cyclobutyl-piperazine-1-carbonyl)-4-(4-fluoro-phenoxy)-pyrrolidin-1-yl]-ethanone.

MS (ESI): mass calcd. for $C_{21}H_{28}FN_3O_3$, 389.21; m/z found, 390.3 [M+H]$^+$. $^1$H NMR (CD$_3$OD): 7.02-6.95 (m, 2H), 6.90-6.80 (m, 2H), 5.05-4.88 (m, 2H), 4.06-3.83 (m, 1H), 3.79-3.70 (m, 1H), 3.65-3.53 (m, 1H), 3.52-3.39 (m, 4H), 2.71-2.52 (m, 2H), 2.46-2.26 (m, 2H), 2.15-1.94 (m, 7H), 1.88-1.76 (m, 2H), 1.75-1.63 (m, 2H).

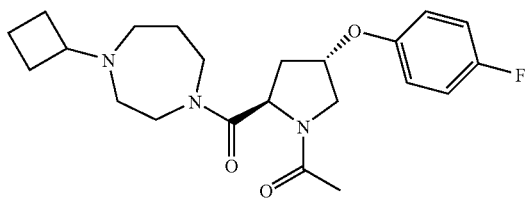

Example 120

(2R,4S)-1-[2-(4-Cyclobutyl-[1,4]diazepane-1-carbonyl)-4-(4-fluoro-phenoxy)-pyrrolidin-1-yl]-ethanone.

MS (ESI): mass calcd. for $C_{22}H_{30}FN_3O_3$ 403.23; m/z found, 404.3 [M+H]$^+$. $^1$H NMR (CDCl$_3$): 7.06-6.94 (m, 2H), 6.86-6.78 (m, 2H), 5.07-4.94 (m, 2H), 4.10-3.98 (m, 1H), 3.87-3.76 (m, 1H), 3.74-3.57 (m, 3H), 3.54-3.44 (m, 1H), 2.96-2.84 (m, 1H), 2.70-2.47 (m, 3H), 2.46-2.35 (m, 2H), 2.34-2.24 (m, 1H), 2.19-1.97 (m, 6H), 1.94-1.52 (m, 5H).

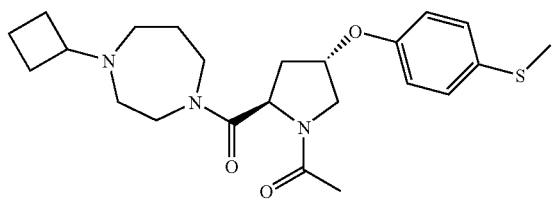

Example 121

(2R,4S)-1-[2-(4-Cyclobutyl-[1,4]diazepane-1-carbonyl)-4-(4-methylsulfanyl-phenoxy)-pyrrolidin-1-yl]-ethanone.

MS (ESI): mass calcd. for $C_{23}H_{33}N_3O_3S$, 431.22; m/z found, 432.3 [M+H]$^+$. $^1$H NMR (CDCl$_3$): 7.28-7.22 (m, 2H), 6.84-6.77 (m, 2H), 5.10-5.05 (m, 1H), 5.01-4.94 (m, 1H), 4.02 (dd, J=11.0, 4.6 Hz, 1H), 3.86-3.59 (m, 4H), 2.96-2.83 (m, 1H), 2.69-2.47 (m, 3H), 2.45 (s, 3H), 2.43-2.34 (m, 2H), 2.34-2.25 (m, 1H), 2.07-1.99 (m, 5H), 1.93-1.74 (m, 5H), 1.71-1.55 (m, 2H).

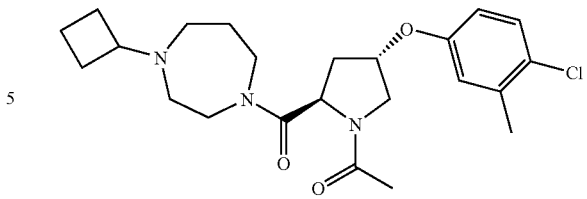

Example 122

(2R,4S)-1-[4-(4-Chloro-3-methyl-phenoxy)-2-(4-cyclobutyl-[1,4]diazepane-1-carbonyl)-pyrrolidin-1-yl]-ethanone.

MS (ESI): mass calcd. for $C_{23}H_{32}ClN_3O_3$, 433.21; m/z found, 434.3 [M+H]$^+$. $^1$H NMR (CDCl$_3$): 7.28-7.21 (m, 1H), 6.76-6.71 (m, 1H), 6.66-6.59 (m, 1H), 5.10-5.03 (m, 1H), 5.01-4.94 (m, 1H), 4.03 (dd, J=11.1, 4.6 Hz, 1H), 3.87-3.44 (m, 5H), 2.96-2.83 (m, 1H), 2.69-2.47 (m, 3H), 2.46-2.24 (m, 6H), 2.08-1.98 (m, 5H), 1.91-1.75 (m, 4H), 1.72-1.54 (m, 2H).

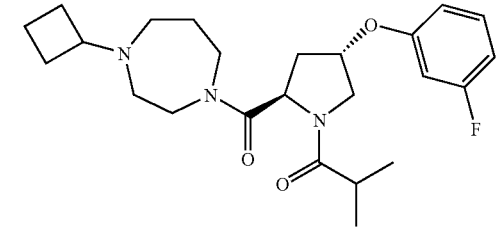

Example 123

(2R,4S)-1-[2-(4-Cyclobutyl-[1,4]diazepane-1-carbonyl)-4-(3-fluoro-phenoxy)-pyrrolidin-1-yl]-2-methyl-propan-1-one.

MS (ESI): mass calcd. for $C_{24}H_{34}FN_3O_3$, 431.26; m/z found, 434.3 [M+H]$^+$. $^1$H NMR (CDCl$_3$): 7.21 (m, 1H), 6.66 (ddd, J=8.3, 8.3, 2.2 Hz, 1H), 6.61 (dd, J=8.3, 2.1 Hz, 1H), 6.55 (ddd, J=10.7, 2.3, 2.3 Hz, 1H), 5.09-5.03 (m, 1H), 5.03-4.94 (m, 1H), 4.02 (dd, J=11.1, 4.7 Hz, 1H), 3.81-3.40 (m, 5H), 2.89-2.79 (m, 1H), 2.66-2.22 (m, 8H), 2.05-1.93 (m, 2H), 1.86-1.72 (m, 3H), 1.68-1.51 (m, 2H), 1.11 (d, J=6.8 Hz, 3H), 1.06 (d, J=6.7 Hz, 3H).

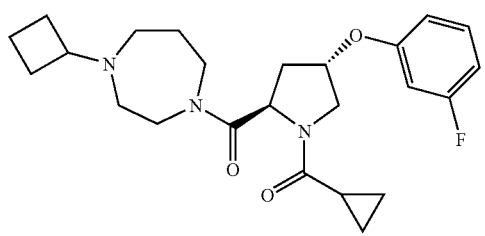

Example 124

(2R,4S)-1-Cyclopropanecarbonyl-2-(4-cyclobutyl-[1,4]diazepane-1-carbonyl)-4-(4-fluoro-phenoxy)-pyrrolidine.

MS (ESI): mass calcd. for $C_{24}H_{32}FN_3O_3$, 429.24; m/z found, 430.3 [M+H]$^+$. $^1$H NMR (CDCl$_3$): 7.24-7.17 (m, 1H), 6.69-6.62 (m, 2H), 6.58 (ddd, J=10.7, 2.3, 2.3 Hz, 1H), 5.14-5.09 (m, 1H), 5.02-4.96 (m, 1H), 4.18 (ddd, J=10.9, 5.1, 2.0 Hz, 1H), 3.93 (dd, J=10.9, 1.8 Hz, 1H), 3.85-3.41 (m, 4H), 2.88-2.78 (m, 1H), 2.53-2.25 (m, 7H), 2.05-1.90 (m2), 1.85-1.69 (m, 3H), 1.68-1.50 (m, 3H), 1.06-0.98 (m, 1H), 0.92-0.85 (m, 1H), 0.78-0.66 (m, 2H).

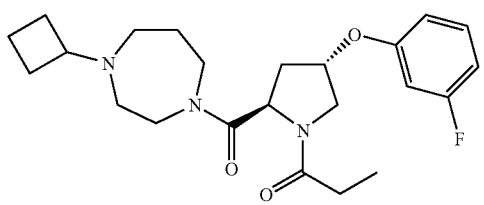

Example 125

(2R,4S)-1-[2-(4-Cyclobutyl-[1,4]diazepane-1-carbonyl)-4-(3-fluoro-phenoxy)-pyrrolidin-1-yl]-propan-1-one.

MS (ESI): mass calcd. for $C_{23}H_{32}FN_3O_3$, 417.24; m/z found, 418.3 [M+H]$^+$. $^1$H NMR (CDCl$_3$): 7.21 (ddd, J=8.3, 8.3, 6.9 Hz, 1H), 6.67 (ddd, J=8.3, 8.3, 2.3 Hz, 1H), 6.62 (dd, J=8.3, 2.1 Hz, 1H), 6.56 (ddd, J=10.7, 2.4, 2.4 Hz, 1H), 5.10-5.04 (m, 1H), 5.02-4.95 (m, 1H), 3.99 (dd, J=11.2, 4.9 Hz, 1H), 3.81-3.44 (m, 4H), 2.93-2.80 (m, 1H), 2.54-2.23 (m, 8H), 2.05-1.94 (m, 3H), 1.87-1.71 (m, 4H), 1.69-1.52 (m, 2H), 1.10 (t, J=7.4 Hz, 3H).

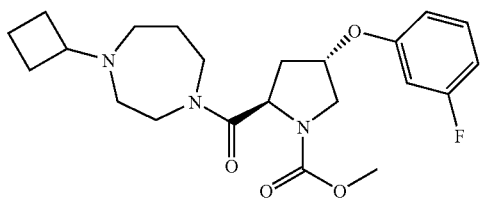

Example 126

(2R,4S)-2-(4-Cyclobutyl-[1,4]diazepane-1-carbonyl)-4-(3-fluoro-phenoxy)-pyrrolidine-1-carboxylic acid methyl ester.

MS (ESI): mass calcd. for $C_{22}H_{30}FN_3O_4$, 419.22; m/z found, 420.3 [M+H]$^+$. $^1$H NMR (CDCl$_3$): 7.24-7.16 (m, 1H), 6.66 (dt, J=7.8, 7.8, 2.4 Hz, 1H), 6.61 (dd, J=8.2, 2.3 Hz, 1H), 6.55 (ddd, J=10.7, 2.1, 2.1 Hz, 1H), 4.99-4.89 (m, 1H), 4.87-4.74 (m, 1H), 3.89-3.84 (m, 1H), 3.77-3.70 (m, 1H), 3.68-3.63 (m, 4H), 3.59-3.45 (m, 1H), 2.92-2.81 (m, 1H), 2.65-2.22 (m, 7H), 2.07-1.93 (m, 3H), 1.91-1.73 (m, 4H), 1.71-1.52 (m, 2H).

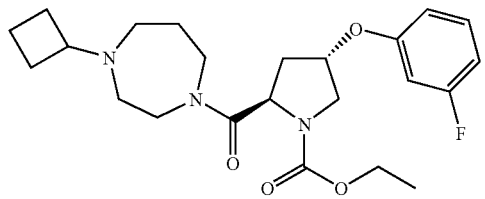

Example 127

(2R,4S)-2-(4-Cyclobutyl-[1,4]diazepane-1-carbonyl)-4-(3-fluoro-phenoxy) pyrrolidine-1-carboxylic acid ethyl ester.

MS (ESI): mass calcd. for $C_{23}H_{32}FN_3O_3$, 433.24; m/z found, 434.2 [M+H]$^+$. $^1$H NMR (CDCl$_3$): 7.23 (dd, J=15.0, 8.2 Hz, 1H), 6.70-6.60 (m, 2H), 6.60-6.55 (m, 1H), 5.03-4.91 (m, 1H), 4.91-4.76 (m, 1H), 4.12 (dd, J=14.2, 7.1 Hz, 1H), 3.93-3.46 (m, 6H), 2.94-2.84 (m, 1H), 2.66-2.25 (m, 6H), 2.08-1.96 (m, 2H), 1.91-1.72 (m, 4H), 1.72-1.54 (m, 2H), 1.25-1.20 (m, 3H).

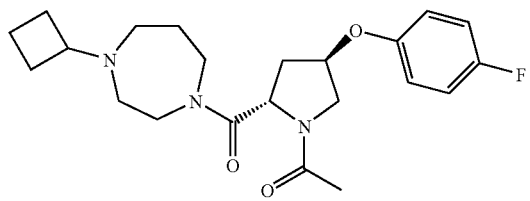

Example 128

(2S,4R)-1-[2-(4-Cyclobutyl-[1,4]diazepane-1-carbonyl)-4-(4-fluoro-phenoxy)-pyrrolidin-1-yl]-ethanone.

MS (ESI): mass calcd. for $C_{22}H_{30}FN_3O_3$, 403.23; m/z found, 404.3 [M+H]$^+$. $^1$H NMR (CDCl$_3$): 7.01-6.94 (m, 2H), 6.82-6.77 (m, 2H), 5.05-4.99 (m, 1H), 4.99-4.93 (m, 1H), 3.99 (dd, J=11.1, 4.8 Hz, 1H), 3.84-3.74 (m, 1H), 3.71-3.43 (m, 4H), 2.92-2.82 (m, 1H), 2.68-2.45 (m, 3H), 2.43-2.32 (m, 2H), 2.31-2.22 (m, 1H), 2.06-1.97 (m, 6H), 1.87-1.73 (m, 3H), 1.69-1.53 (m, 2H).

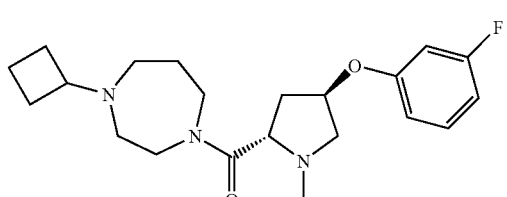

Example 129

(2S,4R)-1-[2-(4-Cyclobutyl-[1,4]diazepane-1-carbonyl)-4-(3-fluoro-phenoxy)-pyrrolidin-1-yl]-ethanone.

MS (ESI): mass calcd. for $C_{22}H_{30}FN_3O_3$, 403.23; m/z found, 404.3 [M+H]$^+$. $^1$H NMR (CDCl$_3$): 7.31-7.18 (m, 1H), 6.75-6.55 (m, 3H), 5.14-4.82 (m, 2H), 4.14-4.02 (m, 1H), 3.90-3.47 (m, 5H), 2.98-2.79 (m, 1H), 2.71-2.26 (m, 6H), 2.14-2.00 (m, 5H), 2.00-1.52 (m, 6H).

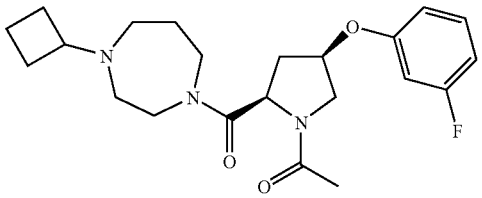

Example 130

(2R,4R)-4-(3-Fluoro-phenoxy)-2-(4-cyclobutyl-[1,4] diazepane-1-carbonyl)-pyrrolidine.

MS (ESI): mass calcd. for $C_{22}H_{30}FN_3O_3$, 403.23; m/z found, 405.3 [M+H]$^+$. $^1$H NMR (CDCl$_3$): 7.25-7.16 (m, 1H), 6.71-6.52 (m, 3H), 4.95-4.89 (m, 1H), 4.89-4.83 (m, 1H), 4.16-4.00 (m, 1H), 3.86-3.40 (m, 5H), 2.90-2.61 (m, 2H), 2.60-2.21 (m, 5H), 2.21-2.11 (m, 1H), 2.10 (d, J=2.4 Hz, 2H), 2.05-1.93 (m, 3H), 1.93-1.70 (m, 3H), 1.69-1.52 (m, 2H).

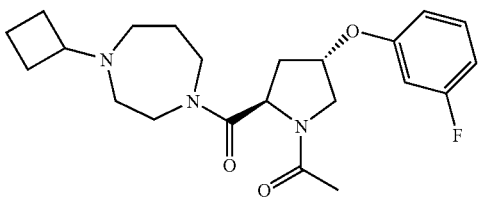

Example 131

(2R,4S)-1-[2-(4-Cyclobutyl-[1,4]diazepane-1-carbonyl)-4-(3-fluoro-phenoxy)-pyrrolidin-1-yl]-ethanone.

The title compound was prepared by Preparation 1: acylation as described for Example 114; or Preparation 2: reaction of 3-fluoro-iodobenzene and (2R,4S)-1-[2-(4-cyclobutyl-[1,4]diazepane-1-carbonyl)-4-hydroxy-pyrrolidin-1-yl]-ethanone as described for Example 48. MS (ESI): mass calcd. for $C_{22}H_{30}FN_3O_3$, 403.23; m/z found, 404.3 [M+H]$^+$. $^1$H NMR (CDCl$_3$): 7.28-7.23 (m, 1H), 6.75-6.69 (m, 1H), 6.69-6.64 (m, 1H), 6.65-6.55 (m, 1H), 5.15-4.90 (m, 1H), 4.07 (dd, J=11.2, 4.9 Hz, 1H), 3.89-3.47 (m, 5H), 3.01-2.83 (m, 1H), 2.74-2.27 (m, 6H), 2.13-2.00 (m, 6H), 1.95-1.65 (m, 6H).
Preparation 3:

Step A: (1R,4R)-5-Acetyl-2-oxa-5-aza-bicyclo[2.2.1]heptan-3-one. A mixture of N-acetyl-trans-L-hydroxyproline (400 g, 2.31 mol) in acetic anhydride (2 L) was warmed to 90° C. for 7 h and then cooled to rt. The resulting solution was concentrated and then taken up in IPA (500 mL). The mixture was stirred for 1 h at rt, and a precipitate formed. The slurry was then cooled to 0° C. and stirred for 4 h. The precipitate was collected by filtration, washing with IPA (300 mL), and dried to obtain the title compound (161 g, 45%). MS (ESI): mass calcd. for $C_7H_9NO_3$, 155.1; m/z found, 156.0 [M+H]$^+$. $^1$H NMR (CDCl$_3$): 5.16 (br s, 1H), 5.09 (s, 0.35H), 4.45 (s, 0.65H), 3.7-3.5 (m, 2H), 2.36-2.24 (m, 1H), 2.19 (s, 2H), 2.15-2.10 (m, 0.65H), 2.06 (s, 1H), 2.0-1.95 (m, 0.35H).

Step B: (2R,4R)-1-[2-([1,4]Diazepane-1-carbonyl)-4-hydroxy-pyrrolidin-1-yl]-ethanone. A mixture of (1R,4R)-5-acetyl-2-oxa-5-aza-bicyclo[2.2.1]heptan-3-one (310.3 g, 2.0 mol) and [1,4]diazepane (500.85 g, 5 mol) in t-amyl alcohol (3.0 L) was held at 90° C. for 17 h. The mixture was then concentrated to remove t-amyl alcohol (2.4 L). The resulting slurry was filtered and washed with EtOAc (1 L) to provide the title compound as a solid (367 g, 72%). MS (ESI): mass calcd. for $C_{12}H_{21}N_3O_3$, 255.2; m/z found, 256.2 [M+H]$^+$. $^1$H NMR (CDCl$_3$): 5.95 (br s, 1H), 4.93-4.68 (m, 1H), 4.48-4.32 (m, 1H), 3.90-3.65 (m, 5H), 3.54-3.41 (m, 1H), 3.12-2.74 (m, 4H), 2.32-2.22 (m, 1H), 2.16-1.68 (m, 6H).

Step C: (2R,4R)-1-[2-(4-Cyclobutyl-[1,4]diazepane-1-carbonyl)-4-hydroxy-pyrrolidin-1-yl]-ethanone. A solution of cyclobutanone (137 mL, 1.83 mol) and (2R,4R)1-[2-([1,4]diazepane-1-carbonyl)-4-hydroxy-pyrrolidin-1-yl]-ethanone (358 g, 1.4 mol) in dichloroethane (3.7 L) was stirred for 1 h at rt. Sodium triacetoxyborohydride (422.4 g, 1.99 mol) was then added in 4 portions over 2 h. The mixture was stirred for 14 h and then NaOH$_{(aq)}$ (50 wt %, 210 mL) was added. The mixture was stirred for 2 h and then MgSO$_4$ (264 g) was added. After an additional 1.5 h of stirring, the mixture was filtered and then concentrated. Purification by FCC (5% 2 M NH$_3$ in MeOH/95% CH$_2$Cl$_2$) provided the title compound as an oil (277 g, 64%). MS (ESI): mass calcd. for $C_{16}H_{27}N_3O_3$, 309.2; m/z found, 310.2 [M+H]$^+$. $^1$H NMR (CDCl$_3$): 6.11-6.04 (m, 1H), 4.93-4.70 (m, 1H), 4.46-4.34 (m, 1H), 3.96-3.44 (m, 6H), 2.96-2.83 (m, 1H), 2.76-2.37 (m, 4H), 2.30-2.20 (m 1H), 2.10-1.55 (m, 12H).

Step D: (2R,4S)-1-[2-(4-Cyclobutyl-[1,4]diazepane-1-carbonyl)-4-hydroxy-pyrrolidin-1-yl]-ethanone. To a heterogeneous mixture of (2R,4R)-1-[2-(4-cyclobutyl-[1,4]diazepane-1-carbonyl)-4-hydroxy-pyrrolidin-1-yl]-ethanone (139 g, 448.5 mmol), 3-fluoro-phenol (52 mL, 462 mmol), and triphenylphosphine resin (1.52 mmol/g loading, 339 g, 516 mmol) in CH$_2$Cl$_2$ (4.3 L) was slowly added DIAD (91 mL, 462 mmol) over 15 min. The mixture was stirred at rt for 15 h. The resin was filtered off and washed with CH$_2$Cl$_2$ (4 L). The filtrate was concentrated and partitioned between methyl tert-butyl ether (MTBE; 2 L) and water (2 L). The aqueous layer was extracted with additional MTBE (2×1.8 L). The combined organic layers were concentrated to a volume of 2 L and extracted with 1 N HCl$_{(aq)}$ (2 L). The acidic aqueous layer was washed with MTBE (1 L) and then basified to pH>12 with 50% NaOH$_{(aq)}$ (118 mL). The basic aqueous layer was extracted with CH$_2$Cl$_2$ (2×1.5 L) and the combined organics were dried with MgSO$_4$, filtered, and concentrated to an oil. The oil was optionally purified by FCC (0 to 5% 2 M NH$_3$ in MeOH/95% CH$_2$Cl$_2$) to provide the title compound (89 g, 49%). MS (ESI): mass calcd. for $C_{22}H_{30}FN_3O_3$, 403.2; m/z found, 404.3 [M+H]$^+$. $^1$H NMR (CDCl$_3$): 7.28-7.19 (m, 1H), 6.74-6.54 (m, 3H), 5.12-5.05 (m, 0.91H), 5.02-4.95 (m, 0.91H), 4.93-4.79 (m, 0.18H), 4.13-4.02 (m, 1H), 3.88-3.60 (m, 5H), 2.96-2.82 (m, 1H), 2.70-2.27 (m, 6H), 2.1-1.55 (m, 11H).

The compounds in Examples 132-136 were prepared using methods analogous to those described for Example 131, Preparation 2.

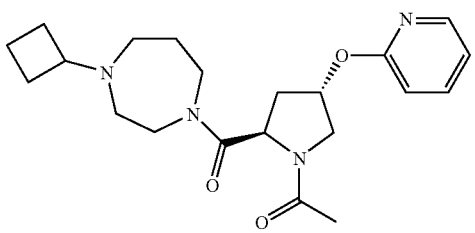

Example 132

(2R,4S)-1-[2-(4-Cyclobutyl-[1,4]diazepane-1-carbonyl)-4-(Pyridin-2-yloxy)-pyrrolidin-1-yl]-ethanone.

MS (ESI): mass calcd. for $C_{21}H_{30}N_4O_3$, 386.23; m/z found, 387.2 [M+H]$^+$. $^1$H NMR (CDCl$_3$): 8.10 (ddd, J=5.2, 2.1, 0.8 Hz, 1H), 7.55 (ddd, J=8.4, 7.1, 2.0 Hz, 1H), 6.86 (ddd, J=7.1, 5.0, 0.7 Hz, 1H), 6.67 (ddd, J=8.3, 0.8, 0.8 Hz, 1H), 5.66-5.61 (m, 1H), 4.93 (ddd, J=7.8, 7.8, 5.0 Hz, 1H), 4.04 (dd, J=11.5, 4.6 Hz, 1H), 3.83-3.75 (m, 1H), 3.72 (d, J=11.4 Hz, 1H), 3.71-3.42 (m, 3H), 2.90-2.80 (m, 1H), 2.66-2.44 (m, 4H), 2.43-2.26 (m, 3H), 2.03 (s, 3H), 2.01-1.95 (m, 2H), 1.90-1.71 (m, 3H), 1.69-1.52 (m, 2H).

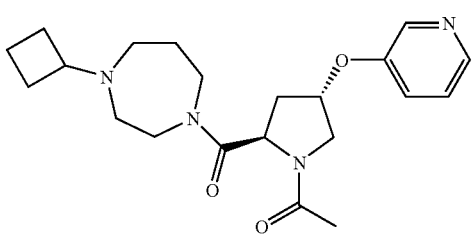

Example 133

(2R,4S)-1-[2-(4-Cyclobutyl-[1,4]diazepane-1-carbonyl)-4-(Pyridin-3-yloxy)-pyrrolidin-1-yl]-ethanone.

MS (ESI): mass calcd. for $C_{21}H_{30}N_4O_3$, 386.23; m/z found, 387.2 [M+H]$^+$. $^1$H NMR (CDCl$_3$): 8.26 (d, J=2.9 Hz, 1H), 8.25 (dd, J=4.6, 1.1 Hz, 1H), 7.23 (dd, J=8.4, 4.6 Hz, 1H), 7.16 (ddd, J=8.4, 2.9, 1.3 Hz, 1H), 5.16-5.12 (m, 1H), 5.00-4.92 (m, 1H), 4.06 (dd, J=11.2, 4.8 Hz, 1H), 3.86-3.75 (m, 1H), 3.75-3.71 (m, 1H), 3.70-3.43 (m, 3H), 2.92-2.81 (m, 1H), 2.69-2.43 (m, 3H), 2.42-2.25 (m, 4H), 2.05 (s, 3H), 2.04-1.97 (m, 2H), 1.91-1.73 (m, 3H), 1.69-1.53 (m, 2H).

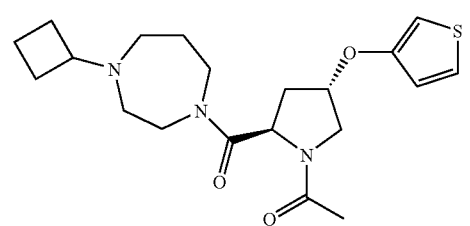

Example 134

(2R,4S)-1-[2-(4-Cyclobutyl-[1,4]diazepane-1-carbonyl)-4-(thiophen-3-yloxy)-pyrrolidin-1-yl]-ethanone.

MS (ESI): mass calcd. for $C_{20}H_{29}N_3O_3S$, 391.19; m/z found, 392.2 [M+H]$^+$. $^1$H NMR (CDCl$_3$): 7.21 (ddd, J=5.2, 3.1, 1.0 Hz, 1H), 6.73-6.70 (m, 1H), 6.27-6.21 (m, 1H), 4.98-4.92 (m, 2H), 4.01 (dd, J=11.3, 4.6 Hz, 1H), 3.86-3.75 (m, 2H), 3.74-3.43 (m, 3H), 2.92-2.83 (m, 1H), 2.67-2.46 (m, 3H), 2.46-2.35 (m, 2H), 2.31-2.24 (m, 1H), 2.06 (s, 3H), 2.05-1.98 (m, 3H), 1.86-1.74 (m, 3H), 1.70-1.55 (m, 2H).

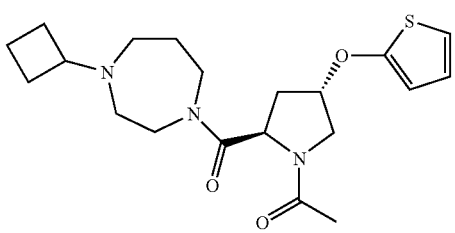

Example 135

(2R,4S)-1-[2-(4-Cyclobutyl-[1,4]diazepane-1-carbonyl)-4-(thiophen-2-yloxy)-pyrrolidin-1-yl]-ethanone.

MS (ESI): mass calcd. for $C_{20}H_{29}N_3O_3S$, 391.19; m/z found, 392.2 [M+H]$^+$. $^1$H NMR (CDCl$_3$): 6.73 (dd, J=5.8, 3.8 Hz, 1H), 6.63 (dd, J=5.8, 1.3 Hz, 1H), 6.25 (dd, J=3.8, 1.4 Hz, 1H), 4.98-4.91 (m, 2H), 3.95 (dd, J=11.5, 4.4 Hz, 1H), 3.86-3.77 (m, 2H), 3.75-3.45 (m, 3H), 2.93-2.83 (m, 1H), 2.68-2.46 (m, 4H), 2.43-2.36 (m, 1H), 2.29-2.22 (m, 1H), 2.07 (s, 3H), 2.06-2.00 (m, 2H), 1.87-1.76 (m, 4H), 1.70-1.56 (m, 2H).

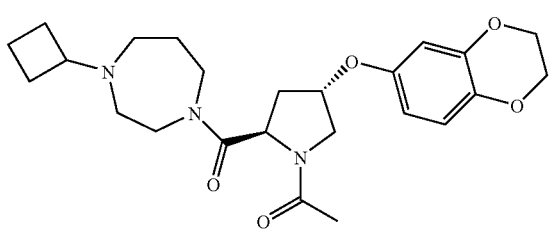

Example 136

(2R,4S)-1-[2-(4-Cyclobutyl-[1,4]diazepane-1-carbonyl)-4-(2,3-dihydro-benzo[1,4]dioxin-6-yloxy)-pyrrolidin-1-yl]-ethanone.

MS (ESI): mass calcd. for $C_{24}H_{33}N_3O_5$, 443.24; m/z found, 444.2 [M+H]$^+$. $^1$H NMR (CDCl$_3$): 6.78 (dd, J=8.8, 0.6 Hz, 1H), 6.41 (d, J=2.8 Hz, 1H), 6.38 (ddd, J=8.8, 2.9, 0.7 Hz, 1H), 4.98-4.93 (m, 2H), 4.27-4.20 (m, 4H), 3.97 (dd, J=11.2, 4.6 Hz, 1H), 3.87-3.78 (m, 1H), 3.76-3.44 (m, 4H), 2.95-2.84 (m, 1H), 2.68-2.47 (m, 3H), 2.44-2.35 (m, 2H), 2.28-2.21 (m, 1H), 2.06 (s, 3H), 2.05-2.00 (m, 2H), 1.88-1.76 (m, 4H), 1.71-1.56 (m, 2H).

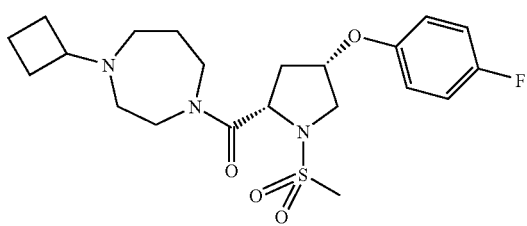

Example 137

(2S,4S)-1-Methanesulfonyl-2-(4-cyclobutyl-[1,4]
diazepane-1-carbonyl)-4-(4-fluoro-phenoxy)-pyrrolidine.

To an ice-cooled solution of (2S,4S)-2-(4-cyclobutyl-[1,4]
diazepane-1-carbonyl)-4-(4-fluoro-phenoxy)-pyrrolidine
(29 mg, 0.08 mmol) in THF (0.8 mL) with Et$_3$N (60 μL, 0.4
mmol) was added methanesulfonyl chloride (19 μL, 0.24
mmol). The reaction mixture was allowed to warm to rt and
was stirred for 18 h. The mixture was diluted with satd. aq.
NaHCO$_3$ and extracted with CH$_2$Cl$_2$ (3×). The combined
organic layers were dried and concentrated. Purification by
FCC provided the desired product (31 mg, 87%). MS (ESI):
mass calcd. for C$_{21}$H$_{30}$FN$_3$O$_4$S, 439.19; m/z found, 440.5
[M+H]$^+$. $^1$H NMR (CDCl$_3$): 7.00-6.94 (m, 2H), 6.83-6.78 (m,
2H), 4.94-4.89 (m, 1H), 4.86 (ddd, J=8.8, 4.4, 4.4 Hz, 1H),
4.10-4.03 (m, 1H), 3.78-3.40 (m, 5H), 3.08 (d, J=4.0 Hz, 3H),
2.84 (dd, J=16.2, 7.8 Hz, 1H), 2.75-2.66 (m, 1H), 2.57-2.26
(m, 4H), 2.25-2.14 (m, 1H), 2.07-1.97 (m, 2H), 1.97-1.71 (m,
4H), 1.69-1.55 (m, 2H).

The compounds in Examples 138-140 were prepared using
methods analogous to those described for Example 137.

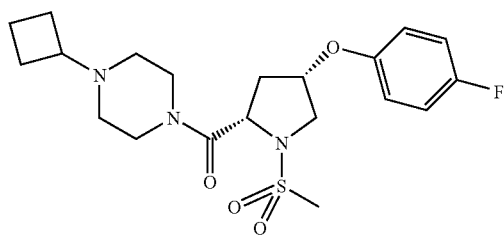

Example 138

(2S,4S)-2-(4-Cyclobutyl-piperazin-1-yl)-[4-(4-fluoro-phenoxy)-1-methanesulfonyl-pyrrolidin-2-yl]-methanone.

MS (ESI): mass calcd. for C$_{20}$H$_{28}$FN$_3$O$_4$S, 425.18; m/z
found, 426.2 [M+H]$^+$. $^1$H NMR (CDCl$_3$): 6.90-6.84 (m, 2H),
6.72-6.68 (m, 2H), 4.86-4.81 (m, 1H), 4.79 (dd, J=9.1, 3.8 Hz,
1H), 3.95 (dd, J=10.0, 6.2 Hz, 1H), 3.57-3.50 (m, 2H), 3.48
(dd, J=10.0, 4.3 Hz, 1H), 3.38-3.24 (m, 2H), 3.02 (s, 3H),
2.63-2.52 (m, 2H), 2.29-2.18 (m, 2H), 2.14-2.04 (m, 3H),
1.97-1.87 (m, 2H), 1.86-1.77 (m, 2H), 1.67-1.55 (m, 2H).

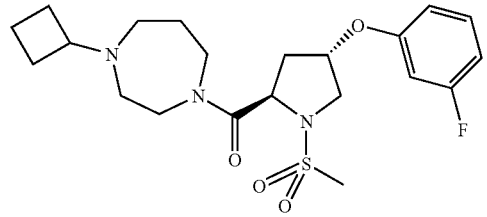

Example 139

(2R,4S)-1-Methanesulfonyl-2-(4-cyclobutyl-[1,4]
diazepane-1-carbonyl)-4-(4-fluoro-phenoxy)-pyrrolidine.

MS (ESI): mass calcd. for C$_{21}$H$_{30}$FN$_3$O$_4$S, 439.55; m/z
found, 440.3 [M+H]$^+$. $^1$H NMR (CDCl$_3$): 7.25-7.19 (m, 1H),
6.69 (ddd, J=8.3, 8.3, 2.3 Hz, 1H), 6.64 (dd, J=8.3, 1.2 Hz,
1H), 6.60-6.55 (m, 1H), 5.02-4.98 (m, 1H), 4.98-4.92 (m,
1H), 3.82 (d, J=2.7 Hz, 2H), 3.74-3.47 (m, 4H), 2.96 (d, J=1.8
Hz, 3H), 2.94-2.85 (m, 1H), 2.66-2.40 (m, 5H), 2.40-2.29 (m,
1H), 2.09-1.75 (m, 6H), 1.72-1.55 (m, 2H).

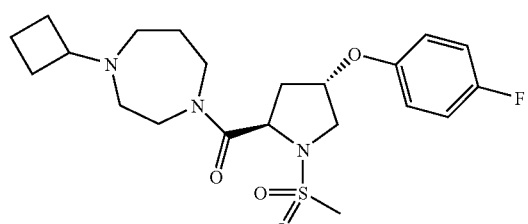

Example 140

(2R,4S)-(4-Cyclobutyl-[1,4]diazepan-1-yl)-[4-(4-fluoro-phenoxy)-1-methanesulfonyl-pyrrolidin-2-yl]-methanone.

MS (ESI): mass calcd. for C$_{21}$H$_{30}$FN$_3$O$_4$S, 439.19; m/z
found, 440.2 [M+H]$^+$. $^1$H NMR (CDCl$_3$): 7.02-6.96 (m, 2H),
6.86-6.81 (m, 2H), 5.02-4.93 (m, 2H), 3.86-3.47 (m, 6H),
3.01-2.96 (m, 3H), 2.93-2.84 (m, 1H), 2.61-2.27 (m, 6H),
2.09-2.00 (m, 2H), 1.93-1.75 (m, 4H), 1.73-1.57 (m, 2H).

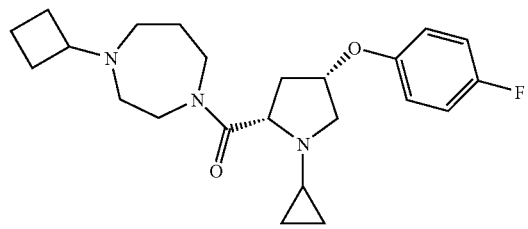

Example 141

(2S,4S)-2-(4-Cyclobutyl-[1,4]diazepan-1-yl)-[1-cyclopropyl-4-(4-fluoro-phenoxy)-pyrrolidin-2-yl]-methanone.

To a stirred solution of (2S,4S)-4-(4-fluoro-phenoxy)-2-
(4-cyclobutyl-[1,4]diazepane-1-carbonyl)-pyrrolidine (83 mg, 0.219 mmol) in THF (10 mL) was added acetic acid (125 μL, 2.22 mmol) followed by (1-ethoxy-cyclopropoxy)-trimethyl-silane (219 μL, 1.09 mmol) and sodium cyanoborohydride (42 mg, 0.66 mmol). The resulting reaction mixture was heated at 60° C. for 18 h. The reaction mixture was allowed to cool to rt, and was filtered through a fritted glass funnel, eluting with CH$_2$Cl$_2$. The filtrate was concentrated and purified by FCC to provide the desired product (21 mg, 24%). MS (ESI): mass calcd. for C$_{23}$H$_{32}$FN$_3$O$_2$, 401.25; m/z found, 401.3 [M+H]$^+$. $^1$H NMR (CDCl$_3$): 6.93-6.87 (m, 2H), 6.74-6.69 (m, 2H), 4.86 (t, J=3.9, Hz, 1H), 4.07-3.98 (m, 1H), 3.75-3.52 (m, 3H), 3.47-3.14 (m, 4H), 2.82-2.68 (m, 1H), 2.63-2.48 (m, 2H), 2.43-2.31 (m, 2H), 2.29 (t, J=5.5 Hz, 1H), 2.21-2.05 (m, 2H), 1.99-1.46 (m, 11H).

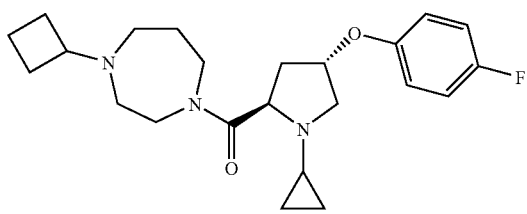

Example 142

(2R,4S)-1-Cyclopropyl-2-(4-cyclobutyl-[1,4]diazepane-1-carbonyl)-4-(4-fluoro-phenoxy)-pyrrolidine.

The title compound was prepared from (2R,4S)-4-(4-fluoro-phenoxy)-2-(4-cyclobutyl-[1,4]diazepane-1-carbonyl)-pyrrolidine using methods analogous to those described for Example 141. MS (ESI): mass calcd. for C$_{23}$H$_{32}$FN$_3$O$_2$, 401.25; m/z found, 402.3 [M+H]$^+$. $^1$H NMR (CDCl$_3$): 7.03-6.90 (m, 2H), 6.85-6.75 (m, 2H), 4.97-4.88 (m, 1H), 4.13-3.99 (m, 1H), 3.78-3.55 (m, 5H), 2.99-2.79 (m, 2H), 2.64-2.26 (m, 6H), 2.20-1.76 (m, 7H), 1.73-1.54 (m, 2H), 0.62-0.30 (m, 4H).

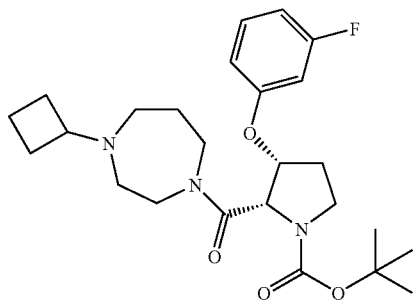

Example 143

(2S,3R)-2-(4-Cyclobutyl-[1,4]diazepane-1-carbonyl)-3-(3-fluoro-phenoxy)-pyrrolidine-1-carboxylic acid tert-butyl ester.

Step A: (2S,3S)-2-(4-Cyclobutyl-[1,4]diazepane-1-carbonyl)-3-methanesulfonyloxy-pyrrolidine-1-carboxylic Acid Tert-Butyl Ester A 0° C. solution of (2S,3S)-2-(4-cyclobutyl-[1,4]diazepane-1-carbonyl)-3-hydroxy-pyrrolidine-1-carboxylic acid tert-butyl ester (466 mg, 1.3 mmol) in CH$_2$Cl$_2$ (13 mL) was treated with methanesulfonylchloride (108 mL, 1.4 mmol) and Et$_3$N (211 mL, 1.5 mmol). The reaction mixture was allowed to warm to rt and was stirred for 1 h. The mixture was diluted with satd. aq. NaHCO$_3$ and extracted with CH$_2$Cl$_2$ (3×). The combined organic layers were dried and concentrated to give the title compound (531 mg, 95%). The material was used in the next reaction without further purification. MS (ESI): mass calcd. for C$_{20}$H$_{35}$N$_3$O$_6$S, 445.22; m/z found, 446.3 [M+H]$^+$.

Step B. A vial containing a mixture of (2S,3S)-2-(4-cyclobutyl-[1,4]diazepane-1-carbonyl)-3-methanesulfonyloxy-pyrrolidine-1-carboxylic acid tert-butyl ester (106.0 mg, 0.24 mmol), 3-fluorophenol (29.3 mg, 0.26 mmol), and K$_2$CO$_3$ (39.5 mg) in DMF (2.5 mL) was capped and heated for 60 h at 90° C. The mixture was cooled to rt and filtered. The filtrate was concentrated and the residue was purified by FCC to afford the title compound (17 mg, 15%). MS (ESI): mass calcd. for C$_{25}$H$_{36}$FN$_3$O$_4$, 461.57; m/z found, 462.3 [M+H]$^+$. $^1$H NMR (CDCl$_3$): 7.25-7.19 (m, 1H), 6.74-6.64 (m, 2H), 6.64-6.57 (m, 1H), 5.09-4.70 (m, 2H), 3.81-3.49 (m, 6H), 2.90-2.76 (m, 1H), 2.59-2.29 (m, 5H), 2.15-1.72 (m, 7H), 1.64-1.53 (m, 2H), 1.49-1.41 (m, 9H).

The compounds in Examples 144-146 were prepared using methods analogous to those described for Example 143.

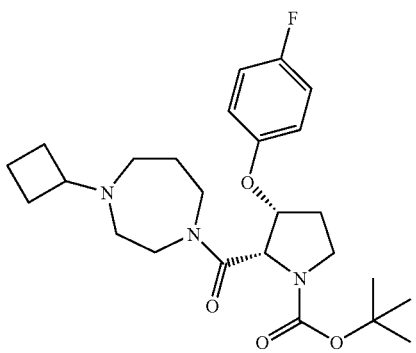

Example 144

(2S,3R)-2-(4-Cyclobutyl-[1,4]diazepane-1-carbonyl)-3-(4-fluoro-phenoxy)-pyrrolidine-1-carboxylic acid tert-butyl ester.

MS (ESI): mass calcd. for C$_{25}$H$_{36}$FN$_3$O$_4$, 461.57; m/z found, 462.3 [M+H]$^+$. $^1$H NMR (CDCl$_3$): 7.05-6.97 (m, 2H), 6.90-6.83 (m, 2H), 4.84-4.69 (m, 2H), 3.82-3.52 (m, 6H), 2.92-2.78 (m, 1H), 2.56-2.29 (m, 5H), 2.17-1.66 (m, 9H), 1.51-1.42 (m, 9H).

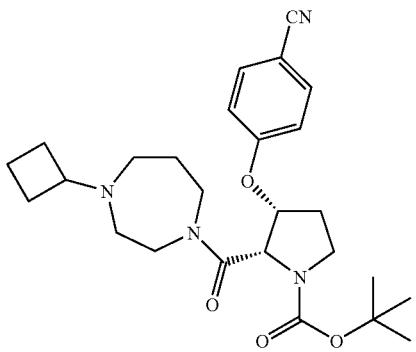

Example 145

(2S,3R)-3-(4-Cyano-phenoxy)-2-(4-cyclobutyl-[1,4]diazepane-1-carbonyl)-pyrrolidine-1-carboxylic acid tert-butyl ester.

MS (ESI): mass calcd. for C$_{26}$H$_{36}$N$_4$O$_4$, 468.27; m/z found, 469.3 [M+H]$^+$. $^1$H NMR (CDCl$_3$): 7.60 (dd, J=8.8, 2.0 Hz, 2H), 7.04-6.89 (m, 2H), 5.16-4.98 (m, 1H), 4.98-4.73 (m, 1H), 3.89-3.36 (m, 6H), 2.88-2.75 (m, 1H), 2.67-2.22 (m, 5H), 2.07-1.91 (m, 2H), 1.88-1.54 (m, 7H), 1.45 (dd, J=12.8, 1.7 Hz, 9H).

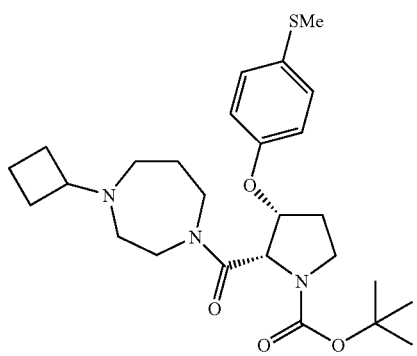

Example 146

(2S,3R)-2-(4-Cyclobutyl-[1,4]diazepane-1-carbonyl)-3-(4-methylsulfanyl-phenoxy)-pyrrolidine-1-carboxylic acid tert-butyl ester.

MS (ESI): mass calcd. for C$_{26}$H$_{39}$N$_3$O$_4$S, 489.27; m/z found, 490.3 [M+H]$^+$. $^1$H NMR (CDCl$_3$): 7.28-7.24 (m, 2H), 6.87-6.81 (m, 2H), 4.83-4.70 (m, 2H), 3.82-3.51 (m, 6H), 2.90-2.74 (m, 1H), 2.56-2.46 (m, 2H), 2.45 (s, 3H), 2.42-2.28 (m, 2H), 2.15-1.95 (m, 3H), 1.86-1.72 (m, 3H), 1.69-1.56 (m, 4H), 1.48-1.42 (m, 9H).

The compounds in Examples 147-151 were prepared using methods analogous to those described for Example 59, substituting the appropriate benzyl bromides for the alkyl bromides.

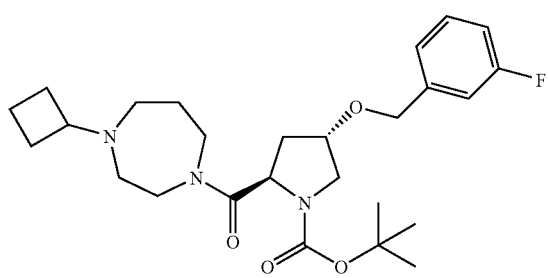

Example 147

(2R,4S)-2-(4-Cyclobutyl-[1,4]diazepane-1-carbonyl)-4-(3-fluoro-benzyloxy)-pyrrolidine-1-carboxylic acid tert-butyl ester.

MS (ESI): mass calcd. for C$_{26}$H$_{38}$FN$_3$O$_4$, 475.28; m/z found, 476.4 [M+H]$^+$. $^1$H NMR (CDCl$_3$): 7.34-7.26 (m, 2H), 7.08-7.00 (m, 2H), 4.82-4.62 (m, 1H), 4.57-4.39 (m, 2H), 4.37-4.18 (m, 1H), 3.92-3.33 (m, 6H), 3.12-2.75 (m, 1H), 2.69-1.96 (m, 8H), 1.96-1.53 (m, 6H), 1.50-1.38 (m, 9H).

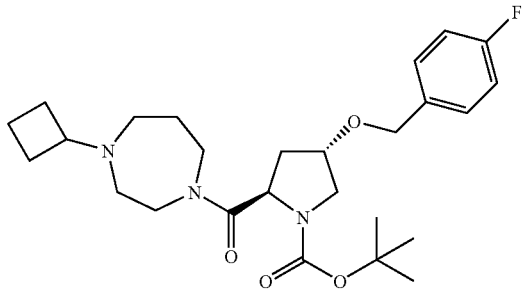

Example 148

(2R,4S)-2-(4-Cyclobutyl-[1,4]diazepane-1-carbonyl)-4-(4-fluoro-benzyloxy)-pyrrolidine-1-carboxylic acid tert-butyl ester.

MS (ESI): mass calcd. for C$_{26}$H$_{38}$FN$_3$O$_4$, 475.28; m/z found, 476.4 [M+H]$^+$. $^1$H NMR (CDCl$_3$): 7.35-7.28 (m, 1H), 7.12-7.03 (m, 2H), 7.02-6.95 (m, 1H), 4.85-4.65 (m, 1H), 4.60-4.42 (m, 2H), 4.38-4.19 (m, 1H), 3.90-3.39 (m, 6H), 3.05-1.55 (m, 15H), 1.49-1.39 (m, 9H).

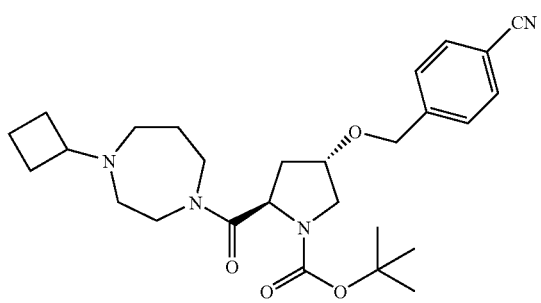

Example 149

(2R,4S)-4-(4-Cyano-benzyloxy)-2-(4-cyclobutyl-[1,4]diazepane-1-carbonyl)-pyrrolidine-1-carboxylic acid tert-butyl ester.

MS (ESI): mass calcd. for C$_{27}$H$_{38}$N$_4$O$_4$, 482.29; m/z found, 483.4 [M+H]$^+$. $^1$H NMR (CDCl$_3$): 7.71-7.60 (m, 2H), 7.47-7.41 (m, 2H), 4.84-4.66 (m, 1H), 4.65-4.48 (m, 2H), 4.40-4.22 (m, 1H), 3.90-3.28 (m, 6H), 3.05-2.81 (m, 1H), 2.71-1.54 (m, 14H), 1.49-1.35 (m, 9H).

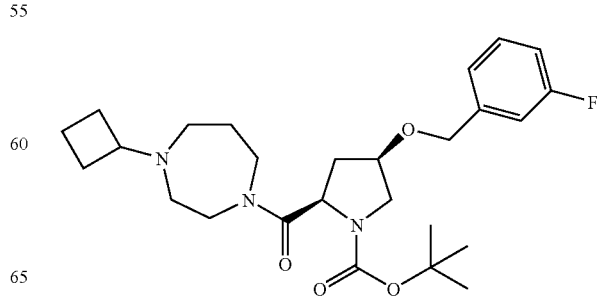

Example 150

(2R,4R)-2-(4-Cyclobutyl-[1,4]diazepane-1-carbonyl)-4-(3-fluoro-benzyloxy)-pyrrolidine-1-carboxylic acid tert-butyl ester.

MS (ESI): mass calcd. for $C_{26}H_{38}FN_3O_4$, 475.28; m/z found, 476.3 [M+H]$^+$. $^1$H NMR (CDCl$_3$): 7.36-7.24 (m, 1H), 7.12-7.02 (m, 2H), 7.01-6.94 (m, 1H), 4.65-4.39 (m, 3H), 4.18-4.05 (m, 1H), 3.95-3.40 (m, 6H), 2.97-2.73 (m, 1H), 2.71-2.28 (m, 5H), 2.11-1.53 (m, 9H), 1.49-1.36 (m, 9H).

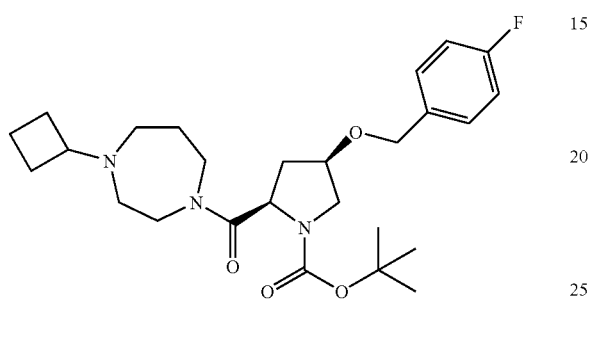

Example 151

(2R,4R)-2-(4-Cyclobutyl-[1,4]diazepane-1-carbonyl)-4-(4-fluoro-benzyloxy)-pyrrolidine-1-carboxylic acid tert-butyl ester.

MS (ESI): mass calcd. for $C_{26}H_{38}FN_3O_4$, 475.28; m/z found, 476.3 [M+H]$^+$. $^1$H NMR (CDCl$_3$): 7.33-7.26 (m, 2H), 7.06-6.99 (m, 2H), 4.65-4.55 (m, 1H), 4.55-4.40 (m, 2H), 4.17-4.04 (m, 1H), 3.96-3.40 (m, 6H), 2.96-2.75 (m, 1H), 2.71-2.29 (m, 5H), 2.10-1.53 (m, 9H), 1.49-1.37 (m, 9H).

The compounds in Examples 152-155 were prepared using methods analogous to those described for Example 62.

Example 152

(2R,4S)-2-(4-Cyclobutyl-[1,4]diazepane-1-carbonyl)-4-(3-fluoro-benzyloxy)-pyrrolidine.

MS (ESI): mass calcd. for $C_{21}H_{30}FN_3O_4$, 375.23; m/z found, 376.4 [M+H]$^+$. $^1$H NMR (CDCl$_3$): 7.36-7.29 (m, 2H), 7.08-7.01 (m, 2H), 4.55-4.41 (m, 2H), 4.28-4.16 (m, 2H), 3.89-3.42 (m, 4H), 3.39-3.29 (m, 1H), 3.16-3.09 (m, 1H), 3.02-2.86 (m, 1H), 2.79-2.36 (m, 4H), 2.30-1.43 (m, 11H).

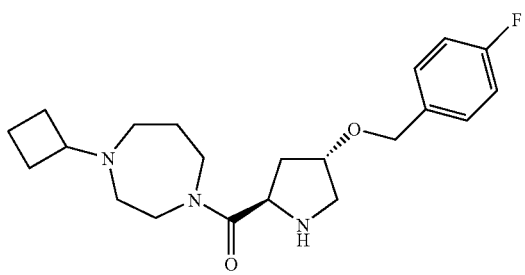

Example 153

(2R,4S)-2-(4-Cyclobutyl-[1,4]diazepane-1-carbonyl)-4-(4-fluoro-benzyloxy)-pyrrolidine.

MS (ESI): mass calcd. for $C_{21}H_{30}FN_3O_2$, 375.23; m/z found, 376.4 [M+H]$^+$. $^1$H NMR (CDCl$_3$): 7.36-7.25 (m, 1H), 7.13-7.04 (m, 2H), 7.02-6.95 (m, 1H), 4.60-4.42 (m, 2H), 4.24-4.14 (m, 2H), 3.86-3.69 (m, 1H), 3.66-3.46 (m, 3H), 3.40-3.31 (m, 1H), 3.13-3.04 (m, 1H), 2.97-2.86 (m, 1H), 2.69-2.14 (m, 7H), 2.11-1.80 (m, 6H), 1.76-1.57 (m, 2H).

Example 154

(2R,4R)-2-(4-Cyclobutyl-[1,4]diazepane-1-carbonyl)-4-(3-fluoro-benzyloxy)-pyrrolidine.

MS (ESI): mass calcd. for $C_{20}H_{30}FN_3O_2$, 375.23; m/z found, 376.3 [M+H]$^+$. $^1$H NMR (CDCl$_3$): 7.34-7.28 (m, 1H), 7.12-7.02 (m, 2H), 6.99-6.93 (m, 1H), 4.55-4.39 (m, 2H), 4.14-4.09 (m, 1H), 3.89-3.74 (m, 2H), 3.67-3.42 (m, 3H), 3.34-3.29 (m, 2H), 2.91-2.74 (m, 2H), 2.66-2.44 (m, 3H), 2.43-2.26 (m, 3H), 2.09-1.53 (m, 8H).

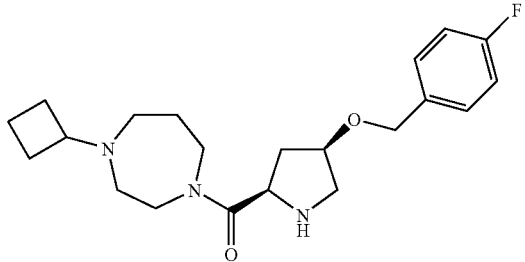

Example 155

(2R,4R)-2-(4-Cyclobutyl-[1,4]diazepane-1-carbonyl)-4-(4-fluoro-benzyloxy)-pyrrolidine.

MS (ESI): mass calcd. for $C_{20}H_{30}FN_3O_2$, 375.23; m/z found, 376.3[M+H]$^+$. $^1$H NMR (CDCl$_3$): 7.33-7.25 (m, 2H), 7.06-6.98 (m, 2H), 4.50-4.39 (m, 2H), 4.14-4.07 (m, 1H), 3.89-3.73 (m, 2H), 3.62-3.43 (m, 3H), 3.33-3.27 (m, 1H), 2.92-2.75 (m, 2H), 2.64-2.43 (m, 3H), 2.42-2.11 (m, 4H), 2.10-1.55 (m, 8H).

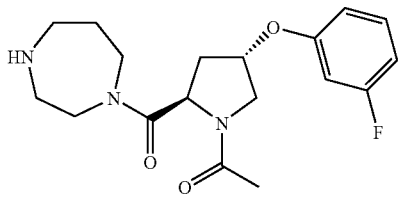

Example 156

(2R,4S)-4-[1-Acetyl-4-(3-fluoro-Phenoxy)-pyrrolidine-2-carbonyl]-[1,4]diazepane.

Step A: (2R,4S)-4-[1-Acetyl-4-(3-fluoro-phenoxy)-pyrrolidine-2-carbonyl]-[1,4]diazepane-1-carboxylic Acid Tert-Butyl Ester This compound was prepared using methods analogous to those described for Example 48. MS (ESI): mass calcd. for $C_{23}H_{32}FN_3O_5$, 449.52; m/z found, 450.3 [M+H]$^+$. $^1$H NMR (CDCl$_3$): 7.16-7.08 (m, 1H), 6.60-6.51 (m, 2H), 6.50-6.44 (m, 1H), 5.00-4.91 (m, 1H), 4.85-4.76 (m, 1H), 3.96-3.83 (m, 1H), 3.76-2.94 (m, 9H), 2.38-2.25 (m, 1H), 2.20-2.10 (m, 1H), 1.97-1.90 (m, 3H), 1.86-1.67 (m, 2H), 1.37-1.30 (m, 9H).

Step B. The title compound was prepared from (2R,4S)-4-[1-acetyl-4-(3-fluoro-phenoxy)-pyrrolidine-2-carbonyl]-[1,4]diazepane-1-carboxylic acid tert-butyl ester using a method analogous to that described for Example 62. MS (ESI): mass calcd. for $C_{18}H_{24}FN_3O_3$, 349.18; m/z found, 350.3 [M+H]$^+$. $^1$H NMR (CDCl$_3$): 7.34-7.21 (m, 1H), 6.77-6.70 (m, 1H), 6.69-6.64 (m, 1H), 6.63-6.58 (m, 1H), 5.10-5.04 (m, 1H), 4.83-4.74 (m, 1H), 4.44-4.33 (m, 1H), 4.23-4.05 (m, 1H), 4.04-3.98 (m, 1H), 3.82-2.96 (m, 7H), 2.56-1.71 (m, 8H).

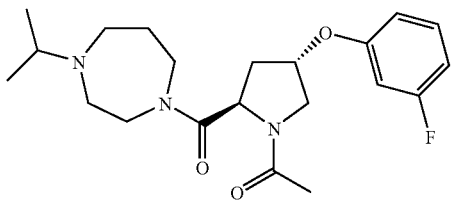

Example 157

(2R,4S)-1-[4-(3-Fluoro-phenoxy)-2-(4-isopropyl-[1,4]diazepane-1-carbonyl)-pyrrolidin-1-yl]-ethanone.

To a solution of (2R,4S)-1-[2-([1,4]diazepane-1-carbonyl)-4-(3-fluoro-phenoxy)-pyrrolidin-1-yl]-ethanone (220 mg, 0.63 mmol) in dichloroethane (3 mL) was added acetone (324 µL, 4.41 mmol) and sodium triacetoxyborohydride (199 mg, 0.945 mmol). After 2 days, the reaction mixture was diluted with satd. aq. NaHCO$_3$ and extracted with CH$_2$Cl$_2$ (4×). The combined organic layers were dried and concentrated. Purification of the residue by FCC provided the desired product (205 mg, 83%). MS (ESI): mass calcd. for $C_{21}H_{30}FN_3O_3$, 391.23; m/z found, 392.3 [M+H]$^+$. $^1$H NMR (CDCl$_3$): 7.22 (ddd, J=8.3, 8.3, 6.9 Hz, 1H), 6.69-6.64 (m, 1H), 6.63 (dd, J=8.3, 2.3 Hz, 1H), 6.57 (ddd, J=10.6, 2.2, 2.2 Hz, 1H), 5.09-5.03 (m, 1H), 5.00-4.95 (m, 1H), 4.03 (dd, J=11.1, 4.9 Hz, 1H), 3.74-3.59 (m, 4H), 3.55-3.45 (m, 1H), 2.92-2.78 (m, 1H), 2.75-2.51 (m, 4H), 2.40-2.23 (m, 2H), 2.04 (s, 3H), 2.01-1.92 (m, 1H), 1.85-1.67 (m, 1H), 1.00-0.94 (m, 6H).

The compounds in Examples 158-163 were prepared using methods analogous to those described for Example 157.

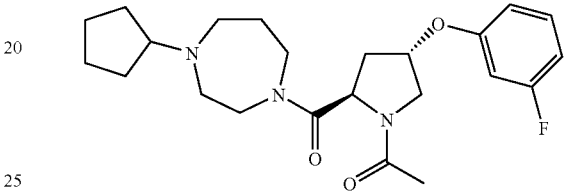

Example 158

(2R,4S)-1-[2-(4-Cyclopentyl-[1,4]diazepane-1-carbonyl)-4-(3-fluoro-phenoxy)-pyrrolidin-1-yl]-ethanone.

MS (ESI): mass calcd. for $C_{23}H_{32}FN_3O_3$, 417.24; m/z found, 418.3 [M+H]$^+$. $^1$H NMR (CDCl$_3$): 7.21 (ddd, J=8.3, 8.3, 6.9 Hz, 1H), 6.66 (ddd, J=8.3, 8.3, 2.3 Hz, 1H), 6.62 (dd, J=8.2, 2.2 Hz, 1H), 6.56 (ddd, J=10.6, 2.3, 2.3 Hz, 1H), 5.08-5.02 (m, 1H), 4.97-4.91 (m, 1H), 4.05-3.97 (m, 1H), 3.84-3.42 (m, 5H), 2.94-2.54 (m, 5H), 2.40-2.24 (m, 2H), 2.03 (s, 3H), 1.93-1.73 (m, 4H), 1.68-1.56 (m, 2H), 1.54-1.29 (m, 4H).

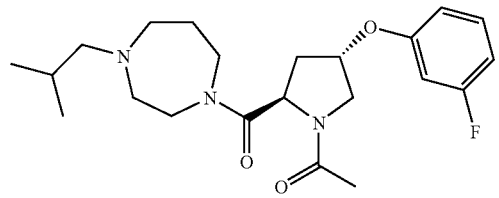

Example 159

(2R,4S)-1-[4-(3-Fluoro-phenoxy)-2-(4-isobutyl-[1,4]diazepane-1-carbonyl)-pyrrolidin-1-yl]-ethanone.

MS (ESI): mass calcd. for $C_{22}H_{32}FN_3O_3$, 405.24; m/z found, 407.3 [M+H]$^+$. $^1$H NMR (CDCl$_3$): 7.21 (ddd, J=8.3, 8.3, 6.9 Hz, 1H), 6.66 (ddd, J=8.3, 8.3, 2.1 Hz, 1H), 6.62 (dd, J=8.3, 2.2 Hz, 1H), 6.56 (ddd, J=10.6, 2.3, 2.3 Hz, 1H), 5.09-5.03 (m, 1H), 5.00-4.93 (m, 1H), 4.02 (dd, J=11.2, 4.9 Hz, 1H), 3.75-3.46 (m, 5H), 2.85-2.54 (m, 4H), 2.39-2.25 (m, 2H), 2.21-2.14 (m, 2H), 2.03 (s, 3H), 2.01-1.90 (m, 1H), 1.83-1.73 (m, 1H), 1.71-1.59 (m, 1H), 0.84 (dd, J=6.6, 1.2 Hz, 6H).

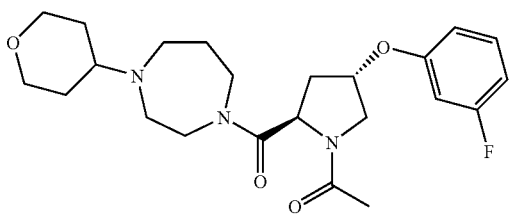

Example 160

(2R,4S)-1-{4-(3-Fluoro-phenoxy)-2-[4-(tetrahydro-pyran-4-yl)-[1,4]diazepane-1-carbonyl]-pyrrolidin-1-yl}-ethanone.

MS (ESI): mass calcd. for $C_{23}H_{32}FN_3O_4$, 433.24; m/z found, 434.3 [M+H]$^+$. $^1$H NMR (CDCl$_3$): 7.20 (ddd, J=8.3, 8.3, 6.8 Hz, 1H), 6.65 (ddd, J=9.0, 8.6, 2.4 Hz, 1H), 6.61 (dd, J=8.3, 2.3 Hz, 1H), 6.55 (ddd, J=4.6, 2.0, 2.0 Hz, 1H), 5.06-5.01 (m, 1H), 4.94 (t, J=7.3 Hz, 1H), 4.01 (dd, J=11.2, 4.9 Hz, 1H), 3.97-3.91 (m, 2H), 3.78-3.53 (m, 4H), 3.43-3.36 (m, 1H), 3.34-3.25 (m, 2H), 2.94-2.58 (m, 5H), 2.39-2.22 (m, 2H), 2.02 (d, J=1.1 Hz, 3H), 1.92-1.46 (m, 6H).

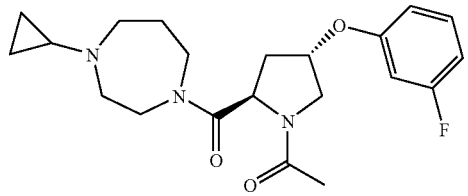

Example 161

(2R,4S)-1-[2-(4-Cyclopropyl-[1,4]diazepane-1-carbonyl)-4-(3-fluoro-phenoxy)-pyrrolidin-1-yl]-ethanone.

MS (ESI): mass calcd. for $C_{21}H_{28}FN_3O_3$, 389.21; m/z found, 390.3 [M+H]$^+$. $^1$H NMR (CDCl$_3$): 7.25 (ddd, J=8.3, 8.3, 6.9 Hz, 1H), 6.73-6.67 (m, 1H), 6.65 (dd, J=8.3, 2.2 Hz, 1H), 6.59 (ddd, J=10.7, 2.4, 2.4 Hz, 1H), 5.11-5.05 (m, 1H), 5.02-4.97 (m, 1H), 4.06 (dd, J=11.2, 4.8 Hz, 1H), 3.84-3.45 (m, 5H), 2.93-2.75 (m, 3H), 2.43-2.27 (m, 2H), 2.16-1.98 (m, 4H), 1.96-1.75 (m, 3H), 0.51-0.43 (m, 2H), 0.42-0.34 (m, 2H).

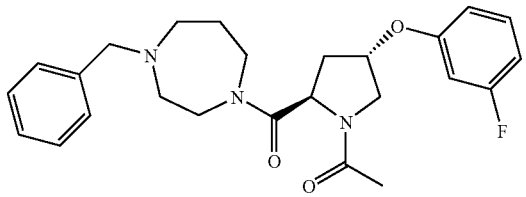

Example 162

(2R,4S)-1-[2-(4-Benzyl-[1,4]diazepane-1-carbonyl)-4-(3-fluoro-phenoxy)-pyrrolidin-1-yl]-ethanone.

MS (ESI): mass calcd. for $C_{25}H_{30}FN_3O_3$, 439.23; m/z found, 440.3 [M+H]$^+$. $^1$H NMR (CDCl$_3$): 7.35-7.19 (m, 6H), 6.70 (ddd, J=8.3, 8.3, 2.4 Hz, 1H), 6.65 (ddd, J=8.4, 2.0, 2.0 Hz, 1H), 6.59 (ddd, J=10.7, 4.5, 2.2 Hz, 1H), 5.13-5.05 (m, 1H), 5.03-4.94 (m, 1H), 4.06 (dd, J=11.1, 4.9 Hz, 1H), 3.88-3.48 (m, 7H), 2.91-2.57 (m, 4H), 2.45-2.25 (m, 2H), 2.07 (d, J=1.2 Hz, 3H), 2.04-1.92 (m, 1H), 1.90-1.77 (m, 1H).

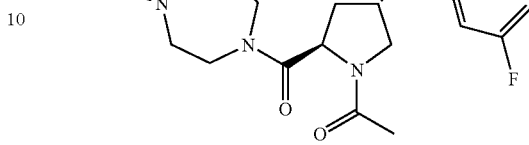

Example 163

(2R,4S)-1-[4-(3-Fluoro-phenoxy)-2-(4-methyl-[1,4]diazepane-1-carbonyl)-pyrrolidin-1-yl]-ethanone.

MS (ESI): mass calcd. for $C_{19}H_{26}FN_3O_3$, 363.20; m/z found, 365.2 [M+H]$^+$. $^1$H NMR (CDCl$_3$): 7.24 (ddd, J=8.3, 8.3, 6.9 Hz, 1H), 6.70 (ddd, J=8.3, 8.3, 2.3 Hz, 1H), 6.65 (dd, J=8.3, 2.0 Hz, 1H), 6.59 (ddd, J=10.6, 2.4, 2.4 Hz, 1H), 5.13-5.05 (m, 1H), 5.03-4.95 (m, 1H), 4.05 (dd, J=11.2, 4.8 Hz, 1H), 3.92-3.48 (m, 5H), 2.90-2.54 (m, 4H), 2.43-2.27 (m, 5H), 2.07 (s, 3H), 1.99-1.83 (m, 2H).

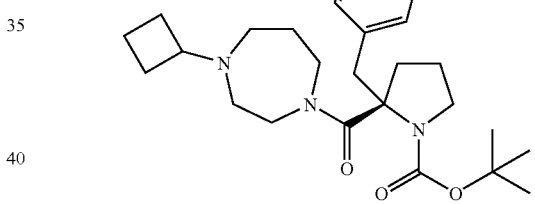

Example 164

(2S)-2-(4-Cyclobutyl-[1,4]diazepane-1-carbonyl)-2-(3-fluoro-benzyl)-pyrrolidine-1-carboxylic acid tert-butyl ester.

A mixture of (2S)-2-(3-fluoro-benzyl)-pyrrolidine-1,2-dicarboxylic acid 1-tert-butyl ester (97.0 mg, 0.3 mmol), 1-cyclobutyl-[1,4]diazepane hydrochloride (75.0 mg, 0.3 mmol), HOBt (49.0 mg, 0.36 mmol), EDC (69.2 mg, 0.36 mmol) and N-methylmorpholine (98.0 mg, 0.96 mmol) in CH$_2$Cl$_2$ (10 mL) was stirred at rt for 18 h. The reaction mixture was diluted with CH$_2$Cl$_2$, washed successively with 1 N NaOH and water, dried, and concentrated. The residue (210 mg) was purified by FCC to provide the title compound (47.0 mg, 34%). MS (ESI): mass calcd. for $C_{26}H_{38}FN_3O_3$, 459.60; m/z found, 460.2 [M+H]$^+$. $^1$H NMR (CDCl$_3$): 7.25-7.18 (m, 1H), 6.99-6.83 (m, 3H), 3.61-3.48 (m, 2H), 3.37-3.10 (m, 4H), 2.92-2.52 (m, 3H), 2.49-2.25 (m, 2H), 2.23-1.80 (m, 9H), 1.76-1.55 (m, 5H), 1.51-1.48 (m, 9H).

The compounds in Examples 165-167 were prepared using methods analogous to those described for Example 164.

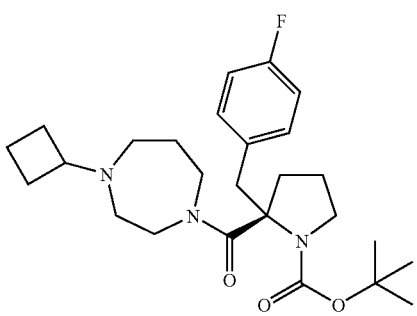

Example 165

(2S)-2-(4-Cyclobutyl-[1,4]diazepane-1-carbonyl)-2-(4-fluoro-benzyl)-pyrrolidine-1-carboxylic acid tert-butyl ester.

MS (ESI): mass calcd. for $C_{26}H_{38}FN_3O_3$, 459.29; m/z found, 460.3 [M+H]+. $^1$H NMR (CDCl$_3$): 7.03-6.92 (m, 2H), 6.92-6.76 (m, 2H), 3.93-1.42 (m, 24H), 1.36 (s, 9H), 0.85-0.48 (m, 1H).

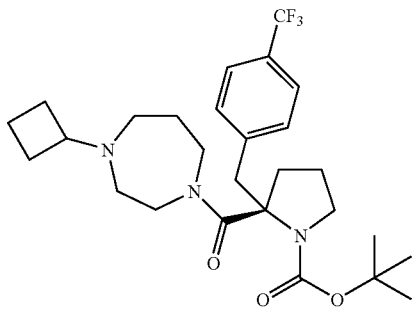

Example 166

(2S)-2-(4-Cyclobutyl-[1,4]diazepane-1-carbonyl)-2-(4-trifluoromethyl-benzyl)-pyrrolidine-1-carboxylic acid tert-butyl ester.

MS (ESI): mass calcd. for $C_{27}H_{38}F_3N_3O_3$, 509.29; m/z found, 510.3 [M+H]+. $^1$H NMR (CDCl$_3$): 7.62-7.47 (m, 2H), 7.34-7.24 (m, 2H), 4.10-0.69 (m, 34H).

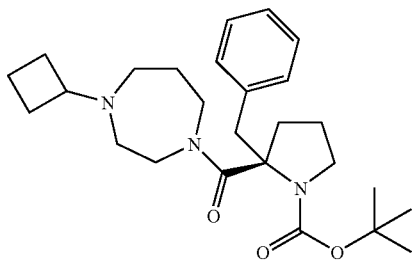

Example 167

(2S)-2-Benzyl-2-(4-cyclobutyl-[1,4]diazepane-1-carbonyl)-pyrrolidine-1-carboxylic acid tert-butyl ester.

MS (ESI): mass calcd. for $C_{26}H_{39}N_3O_3$, 441.30; m/z found, 442.4 [M+H]+. $^1$H NMR (CDCl$_3$): 7.32-7.22 (m, 3H), 7.21-7.12 (m, 2H), 4.10-0.57 (m, 34H).

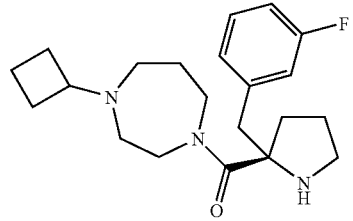

Example 168

(2S)-2-(4-Cyclobutyl-[1,4]diazepane-1-carbonyl)-2-(3-fluoro-benzyl)-pyrrolidine.

A solution of 2-(4-cyclobutyl-[1,4]diazepane-1-carbonyl)-2-(3-fluoro-benzyl)-pyrrolidine-1-carboxylic acid tert-butyl ester (40.0 mg) in EtOH (5.0 mL) and 4 M HCl in dioxane (2.0 mL) was stirred for 10 h. The mixture was concentrated and the residue diluted with CH$_2$Cl$_2$ and treated with Et$_3$N. The mixture was washed with water and concentrated to yield title compound (17 mg, 54%). MS (ESI): mass calcd. for $C_{26}H_{38}FN_3O_3$, 359.60; m/z found, 360.3 [M+H]+. $^1$H NMR (CDCl$_3$): 7.23-6.84 (m, 4H), 3.87-3.40 (m, 4H), 3.15-3.0 (m, 1H), 2.97-2.71 (m, 4H), 2.68-2.40 (m, 4H), 2.10-1.98 (m, 3H), 1.93-1.54 (m, 9H).

The compounds in Examples 169-171 were prepared using methods analogous to those described for Example 168.

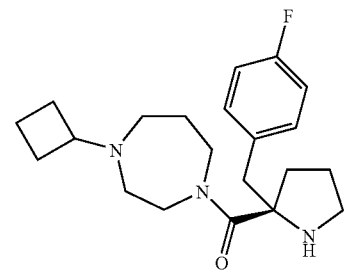

Example 169

(2S)-(4-Cyclobutyl-[1,4]diazepan-1-yl)-[2-(4-fluoro-benzyl)-pyrrolidin-2-yl]-methanone.

MS (ESI): mass calcd. for $C_{21}H_{30}FN_3O$, 359.24; m/z found, 360.3 [M+H]+. $^1$H NMR (CDCl$_3$): 7.44-7.14 (m, 2H), 7.06-6.90 (m, 2H), 3.90-1.52 (m, 26H).

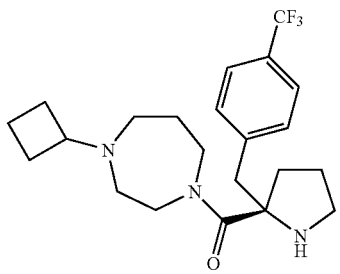

Example 170

(2S)-(4-Cyclobutyl-[1,4]diazepan-1-yl)-[2-(4-trifluoromethyl-benzyl)-pyrrolidin-2-yl]-methanone.

MS (ESI): mass calcd. for $C_{22}H_{30}F_3N_3O$, 409.25; m/z found, 410.3 [M+H]+. $^1$H NMR (CDCl$_3$): 7.56-7.28 (m, 4H), 3.96-1.54 (m, 25H).

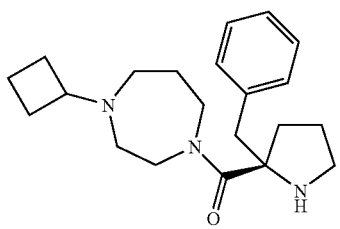

Example 171

(2S)-(2-Benzyl-pyrrolidin-2-yl)-(4-cyclobutyl-[4]diazepan-1-yl)-methanone.

MS (ESI): mass calcd. for $C_{21}H_{31}N_3O$, 341.25; m/z found, 342.3 [M+H]+. $^1$H NMR (CDCl$_3$): 7.49-7.05 (m, 5H), 3.92-3.52 (m, 4H), 3.32-1.56 (m, 21H).

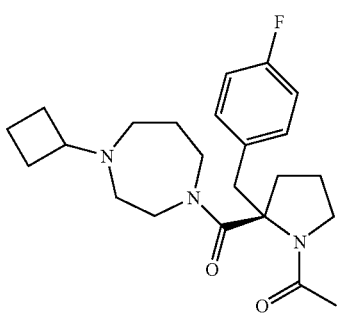

Example 172

(2S)-(1-[2-(4-Cyclobutyl-[1,4]diazepane-1-carbonyl)-2-(4-fluoro-benzyl)-pyrrolidin-1-yl]-ethanone.

The title compound was prepared from (2S)-(4-cyclobutyl-[1,4]diazepan-1-yl)-[2-(4-fluoro-benzyl)-pyrrolidin-2-yl]-methanone using a method analogous to that described for Example 4. MS (ESI): mass calcd. for $C_{23}H_{32}FN_3O_2$, 401.25; m/z found, 402.3 [M+H]+. $^1$H NMR (CDCl$_3$): 7.17-7.09 (m, 2H), 7.05-6.91 (m, 2H), 3.96-3.21 (m, 7H), 3.07-1.53 (m, 21H).

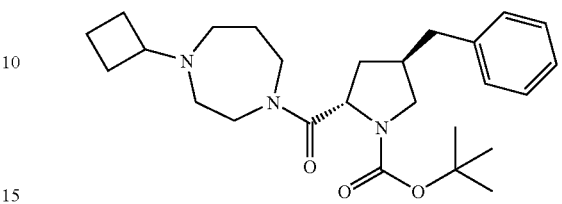

Example 173

(2S,4R)-4-Benzyl-2-(4-cyclobutyl-r[1,4]diazepane-1-carbonyl)-pyrrolidine-1-carboxylic acid tert-butyl ester.

A solution of (2S,4R)-4-benzyl-pyrrolidine-2-carboxylic acid (254.1 mg, 0.832 mmol) in DMF:THF (10 mL/5 mL) and was treated with 1-cyclobutyl-[1,4]diazepane bishydrochloride (326.6 mg), EDC (273.8 mg), HOBt (171.4 mg), 4-(dimethylamino)pyridine (~5 mg), and Et$_3$N (0.5 mL). After 16 h, the reaction mixture was diluted with 1 N NaOH and extracted with EtOAc. The organic layer was dried and concentrated. Purification by FCC(CH$_2$Cl$_2$ to 10% MeOH/0.1% NH$_4$OH in CH$_2$Cl$_2$) gave the title compound (350.8 mg, 95%). MS (ESI): mass calcd. for $C_{26}H_{39}N_3O_3$, 441.30; m/z found, 442.3 [M+H]+. $^1$H NMR (CDCl$_3$): 7.33-7.25 (m, 2H), 7.25-7.14 (m, 3H), 4.73-4.51 (m, 0.5H), 3.86-3.39 (m, 4.5H), 3.26-2.24 (m, 8H), 2.14-1.38 (m, 21H).

The compounds in Examples 174-176 were prepared using methods analogous to those described for Example 173.

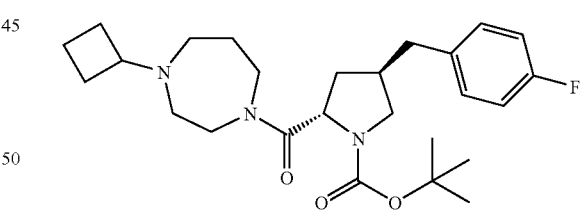

Example 174

(2S,4R)-2-(4-Cyclobutyl-[1,4]diazepane-1-carbonyl)-4-(4-fluoro-benzyl)pyrrolidine-1-carboxylic acid tert-butyl ester.

MS (ESI): mass calcd. for $C_{26}H_{38}FN_3O_3$, 459.29; m/z found, 460.3 [M+H]+. $^1$H NMR (CDCl$_3$): 7.18-7.06 (m, 2H), 7.02-6.94 (m, 2H), 4.75-4.51 (m, 0.5H), 3.86-3.41 (m, 4.5H), 3.23-3.02 (m, 1H), 2.96-2.27 (m, 7H), 2.12-1.53 (m, 12H), 1.53-1.36 (m, 9H).

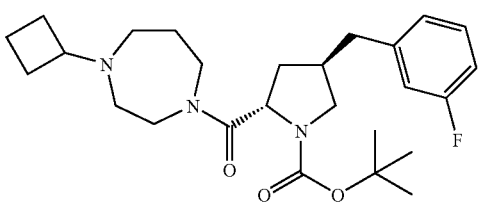

Example 175

(2S,4R)-2-(4-Cyclobutyl-[1,4]diazepane-1-carbonyl)-4-(3-fluoro-benzyl)-pyrrolidine-1-carboxylic acid tert-butyl ester.

MS (ESI): mass calcd. for $C_{26}H_{38}FN_3O_3$, 459.29; m/z found, 460.3 [M+H]$^+$. $^1$H NMR (CDCl$_3$): 7.29-7.19 (m, 1H), 6.98-6.82 (m, 3H), 4.74-4.51 (m, 0.7H), 3.84-3.39 (m, 5.3H), 3.21-3.04 (m, 0.8H), 2.96-2.27 (m, 8.2H), 2.14-1.53 (m, 10H), 1.51-1.38 (m, 9H).

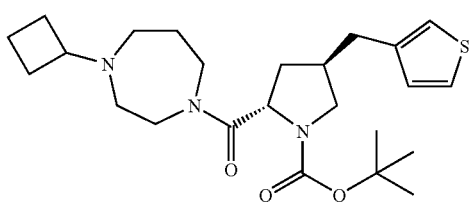

Example 176

(2S,4R)-2-(4-Cyclobutyl-[1,4]diazepane-1-carbonyl)-4-thiophen-3-ylmethyl-pyrrolidine-1-carboxylic acid tert-butyl ester.

MS (ESI): mass calcd. for $C_{24}H_{37}N_3O_3S$, 447.26; m/z found, 448.3 [M+H—C$_5$H$_9$O$_2$]$^+$. $^1$H NMR (CDCl$_3$): 7.31-7.23 (m, 1H), 7.00-6.88 (m, 2H), 4.77-4.47 (m, 0.5H), 3.88-3.38 (m, 5.5H), 3.23-2.27 (m, 9H), 2.13-1.56 (m, 10H), 1.52-1.39 (m, 9H).

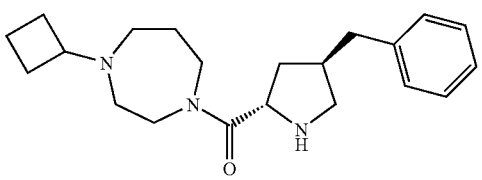

Example 177

(2S,4R)-(4-Benzyl-pyrrolidin-2-yl)-(4-cyclobutyl-[1,4]diazepan-1-yl)-methanone.

A solution of (2S,4R)-4-benzyl-2-(4-cyclobutyl-[1,4]diazepane-1-carbonyl)-pyrrolidine-1-carboxylic acid tert-butyl ester (350.8 mg, 0.794 mmol) in CH$_2$Cl$_2$ (2 mL) was treated with TFA (0.5 mL). After 16 h, the mixture was concentrated and the residue was purified by FCC(CH$_2$Cl$_2$ to 10% MeOH/ 0.1% NH$_4$OH in CH$_2$Cl$_2$) to give the title compound (266.3 mg, 98%). MS (ESI): mass calcd. for $C_{21}H_{31}N_3O$, 341.25; m/z found, 342.3 [M+H]$^+$. $^1$H NMR (CDCl$_3$): 7.35-7.29 (m, 2H), 7.28-7.22 (m, 1H), 7.16 (d, J=7.9 Hz, 2H), 4.91-4.80 (m, 1H), 4.03-3.38 (m, 4H), 3.20-2.90 (m, 2H), 2.85-2.33 (m, 7H), 2.25-1.56 (m, 11H).

The compounds in Examples 178-180 were prepared using methods analogous to those described for Example 177.

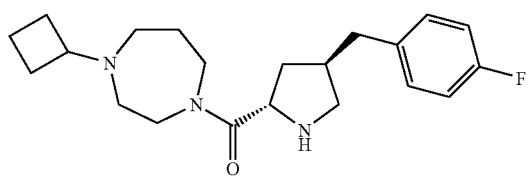

Example 178

(2S,4R)-(4-Cyclobutyl-[1,4]diazepan-1-yl)-[4-(4-fluoro-benzyl)-pyrrolidin-2-yl]-methanone.

MS (ESI): mass calcd. for $C_{21}H_{30}FN_3O$ 359.24; m/z found, 360.3 [M+H]$^+$. $^1$H NMR (CDCl$_3$): 7.17-7.10 (m, 2H), 7.05-6.98 (m, 2H), 4.93-4.84 (m, 1H), 4.01-3.68 (m, 1H), 3.68-3.36 (m, 4H), 3.19-2.33 (m, 9H), 2.24-1.56 (m, 10H).

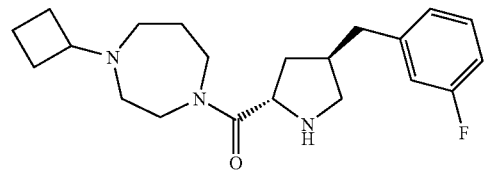

Example 179

(2S,4R)-(4-Cyclobutyl-[1,4]diazepan-1-yl)-[4-(3-fluoro-benzyl)-pyrrolidin-2-yl]-methanone.

MS (ESI): mass calcd. for $C_{21}H_{30}FN_3O$ 359.24; m/z found, 360.3 [M+H]$^+$. $^1$H NMR (CDCl$_3$): 7.32-7.24 (m, 1H), 6.99-6.91 (m, 2H), 6.90-6.85 (m, 1H), 4.88-4.77 (m, 1H), 4.01-3.40 (m, 5H), 3.15-2.34 (m, 9H), 2.24-1.57 (m, 10H).

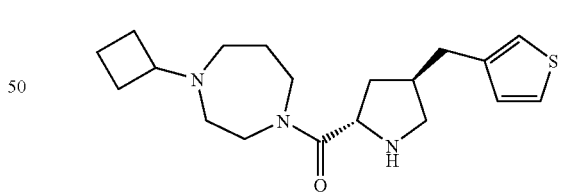

Example 180

(2S,4R)-(4-Cyclobutyl-[1,4]diazepan-1-yl)-(4-thiophen-3-ylmethyl-pyrrolidin-2-yl)-methanone.

MS (ESI): mass calcd. for $C_{19}H_{29}N_3OS$, 347.20; m/z found, 348.3 [M+H]$^+$. $^1$H NMR (CDCl$_3$): 7.29-7.22 (m, 1H), 6.96-6.90 (m, 2H), 4.07-3.94 (m, 1H), 3.88-3.72 (m, 1H), 3.64-3.53 (m, 1H), 3.54-3.39 (m, 2H), 3.38-3.27 (m, 1H), 2.95-2.82 (m, 1H), 2.80-2.67 (m, 2H), 2.68-2.23 (m, 9H), 2.11-1.99 (m, 2H), 1.98-1.76 (m, 5H), 1.75-1.53 (m, 2H).

The compounds in Examples 181-183 were prepared using a method analogous to that described for Example 4.

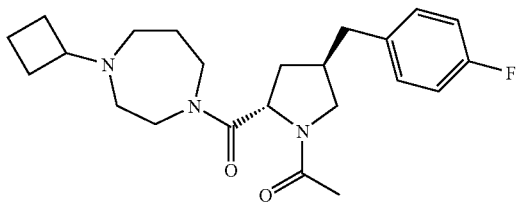

Example 181

(2S,4R)-(1-[2-(4-Cyclobutyl-[1,4]diazepane-1-carbonyl)-4-(4-fluoro-benzyl)-pyrrolidin-1-yl]-ethanone.

MS (ESI): mass calcd. for $C_{23}H_{32}FN_3O_2$, 401.25; m/z found, 402.3 [M+H]$^+$. $^1$H NMR (CDCl$_3$): 7.17-7.08 (m, 2H), 7.05-6.93 (m, 2H), 4.90-4.82 (m, 1H), 3.93-3.36 (m, 4H), 3.28-2.82 (m, 2H), 2.76-2.24 (m, 6H), 2.13-1.55 (m, 15H).

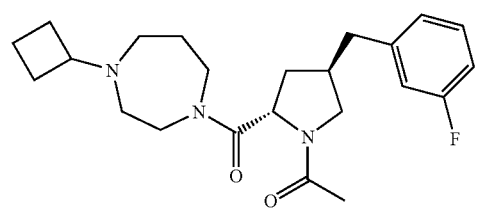

Example 182

(2S,4R)-(1-[2-(4-Cyclobutyl-[1,4]diazepane-1-carbonyl)-4-(3-fluoro-benzyl)-pyrrolidin-1-yl]-ethanone.

MS (ESI): mass calcd. for $C_{23}H_{32}FN_3O_2$ 401.25; m/z found, 402.3 [M+H]$^+$. $^1$H NMR (CDCl$_3$): 7.32-7.22 (m, 1H), 7.00-6.82 (m, 3H), 4.95-4.81 (m, 0.5H), 3.95-3.34 (m, 4.5H), 3.31-3.11 (m, 1.5H), 3.08-2.80 (m, 1.5H), 2.78-2.25 (m, 5H), 2.15-1.46 (m, 15H).

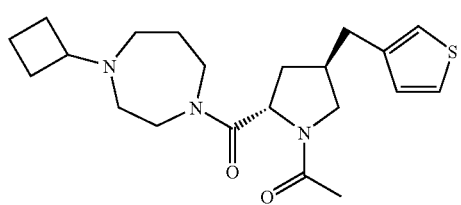

Example 183

(2S,4R)-(1-[2-(4-Cyclobutyl-[1,4]diazepane-1-carbonyl)-4-thiophen-3-ylmethyl-pyrrolidin-1-yl]-ethanone.

MS (ESI): mass calcd. for $C_{21}H_{31}N_3O_2S$ 389.21; m/z found, 390.3 [M+H]$^+$. $^1$H NMR (CDCl$_3$): 7.31-7.27 (m, 1H), 6.97 (d, J=2.7 Hz, 1H), 6.94 (d, J=5.0 Hz, 1H), 4.92-4.79 (m, 1H), 3.98-3.36 (m, 7H), 3.31-3.11 (m, 1H), 3.07-1.54 (m, 19H).

The compounds in Examples 184-200 may be prepared using the methods described in the preceding examples.

Example 184

(2R,4S)-(4-Cyclobutyl-[1,4]diazepan-1-yl)-[4-(3-fluoro-phenoxy)-1-(2-hydroxy-ethyl)-pyrrolidin-2-yl]-methanone.

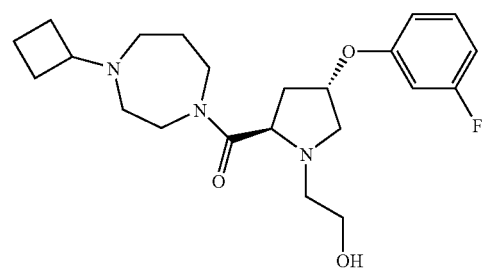

Example 185

(2R,4S)-(4-Cyclobutyl-[1,4]diazepan-1-yl)-[1-(2-fluoro-ethyl)-4-(3-fluoro-phenoxy)-pyrrolidin-2-yl]-methanone.

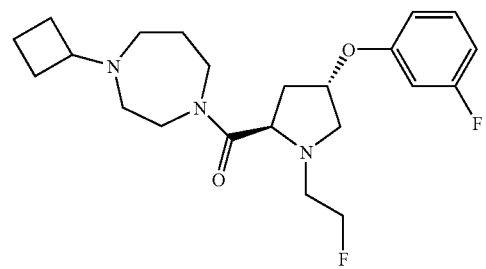

Example 186

(2R,4S)-(4-Cyclobutyl-[1,4]diazepan-1-yl)-[4-(3-fluoro-phenoxy)-1-(tetrahydro-pyran-4-yl)-pyrrolidin-2-yl]-methanone.

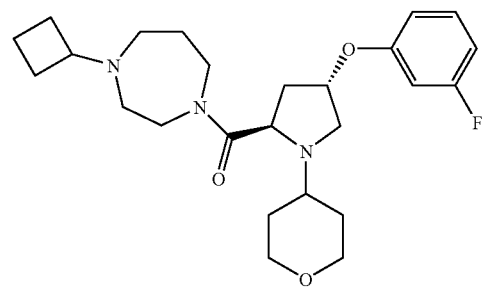

Example 187

(2R,4S)-[2-(4-Cyclobutyl-[1,4]diazepane-1-carbonyl)-4-(3-fluoro-phenoxy)-pyrrolidin-1-yl]-phenyl-methanone.

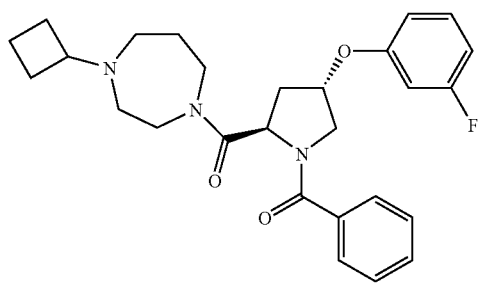

Example 188

(2R,4S)-1-[4-Cyclobutoxy-2-(4-cyclobutyl-[1,4]diazepane-1-carbonyl)-pyrrolidin-1-yl]-ethanone.

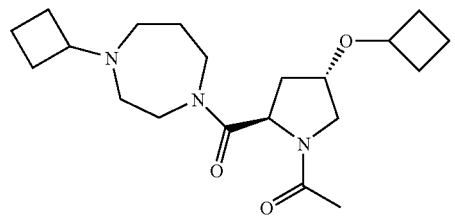

Example 189

(2R,4S)-1-[2-(4-Cyclobutyl-[1,4]diazepane-1-carbonyl)-4-(tetrahydro-furan-3-yloxy)-pyrrolidin-1-yl]-ethanone.

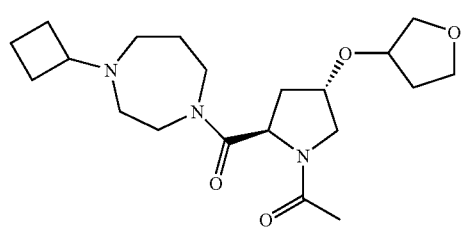

Example 190

(2R,4S)-1-[2-(4-Cyclobutyl-[1,4]diazepane-1-carbonyl)-4-(tetrahydro-pyran-4-yloxy)-pyrrolidin-1-yl]-ethanone.

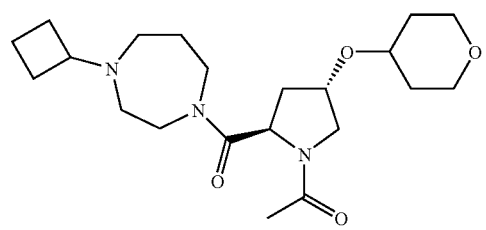

Example 191

(2R,4S)-1-[2-(4-Cyclobutyl-[1,4]diazepane-1-carbonyl)-4-(Pyridin-4-yloxy)-pyrrolidin-1-yl]-ethanone.

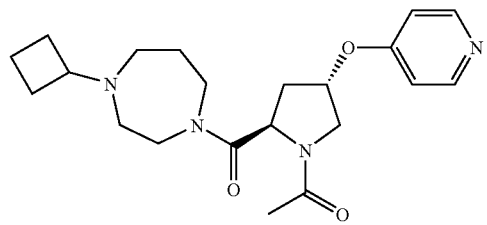

Example 192

(2R,4S)-1-[2-(4-Cyclobutyl-[1,4]diazepane-1-carbonyl)-4-(Pyrimidin-5-yloxy)-pyrrolidin-1-yl]-ethanone.

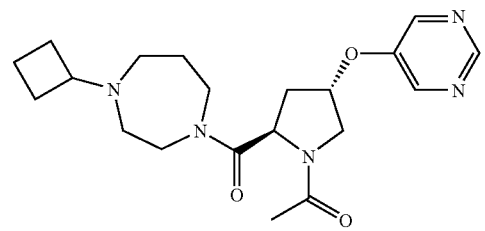

Example 193

(2R,4S)-1-[2-(4-Cyclobutyl-[1,4]diazepane-1-carbonyl)-4-(Pyrazin-2-yloxy)-pyrrolidin-1-yl]-ethanone.

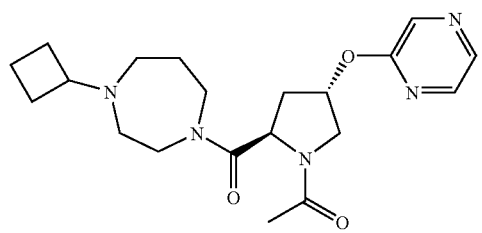

Example 194

(2R,4S)-1-[2-(4-Cyclobutyl-[1,4]diazepane-1-carbonyl)-4-(thiazol-4-yloxy)-pyrrolidin-1-yl]-ethanone.

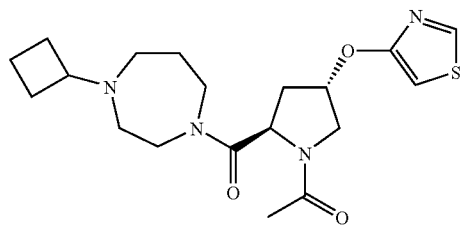

Example 195

(2R,4S)-1-[2-(4-Cyclobutyl-[1,4]diazepane-1-carbonyl)-4-(thiazol-5-yloxy)-pyrrolidin-1-yl]-ethanone.

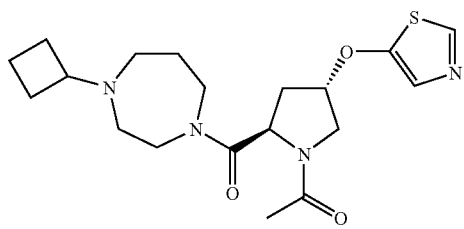

Example 196

(2R,4S)-1-[2-(4-Cyclobutyl-[1,4]diazepane-1-carbonyl)-4-(5-methyl-isoxazol-4-yloxy)-pyrrolidin-1-yl]-ethanone.

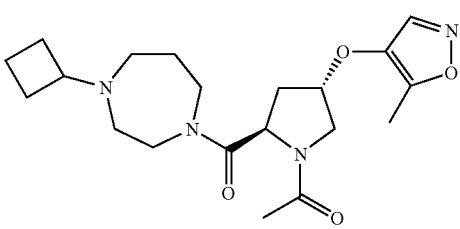

Example 197

(2R,4S)-1-[2-(4-Cyclobutyl-[1,4]diazepane-1-carbonyl)-4-(3,5-dimethyl-isoxazol-4-yloxy)-pyrrolidin-1-yl]-ethanone.

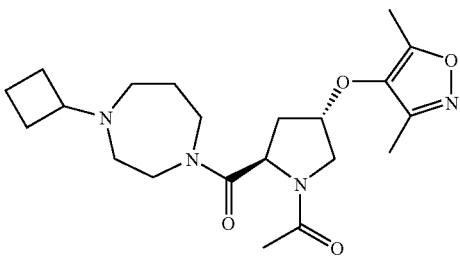

Example 198

(2R,4S)-(4-Cyclobutyl-[1,4]diazepan-1-yl)-[4-(3-fluoro-phenoxy)-1-(tetrahydro-furan-3-yl)-pyrrolidin-2-yl]-methanone.

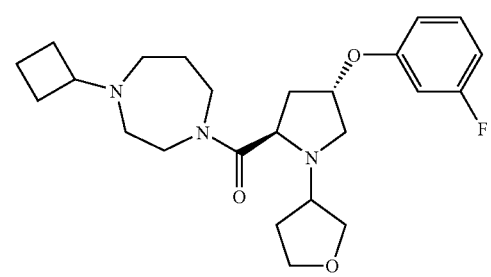

Example 199

(2R,4S)-(4-Cyclobutyl-[1,4]diazepan-1-yl)-[4-(3-fluoro-Phenoxy)-1-(tetrahydro-pyran-3-yl)-pyrrolidin-2-yl]-methanone.

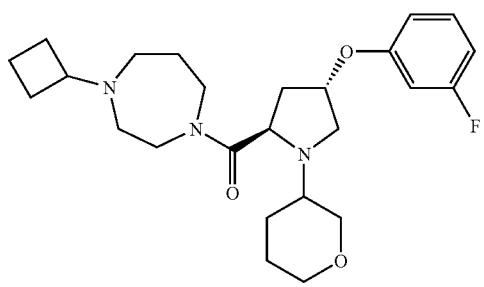

The compounds in Examples 200-210 may be prepared from substituted proline esters using methods analogous to those described in the preceding examples. Substituted proline esters are commercially available or may be prepared using the methods described by Kawabata et al. (*J. Am. Chem. Soc.* 1993, 125(43), 13012-13013; *J. Am. Chem. Soc.* 1996, 128(48), 15394-15395).

Example 200

1-[2-Benzyl-2-(4-cyclobutyl-[1,4]diazepane-1-carbonyl)-pyrrolidin-1-yl]-ethanone.

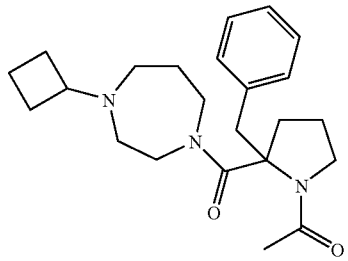

Example 201

1-[2-(4-Cyclobutyl-[1,4]diazepane-1-carbonyl)-2-(3-fluoro-benzyl)-pyrrolidin-1-yl]-ethanone.

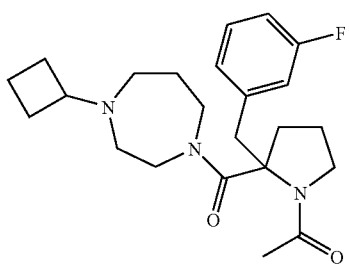

Example 202

1-[2-(4-Cyclobutyl-[1,4]diazepane-1-carbonyl)-2-(4-trifluoromethyl-benzyl)-pyrrolidin-1-yl]-ethanone.

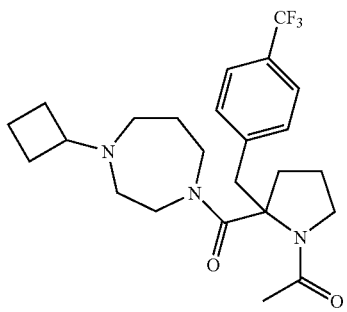

Example 203

3-[1-Acetyl-2-(4-cyclobutyl-[1,4]diazepane-1-carbonyl)-pyrrolidin-2-ylmethyl]-benzonitrile.

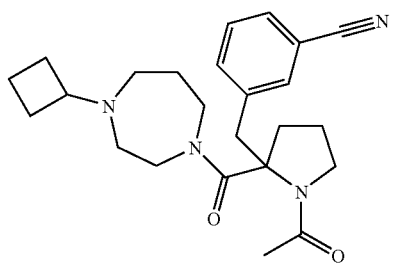

Example 204

3-[2-(4-Cyclobutyl-[1,4]diazepane-1-carbonyl)-pyrrolidin-2-ylmethyl]-benzonitrile.

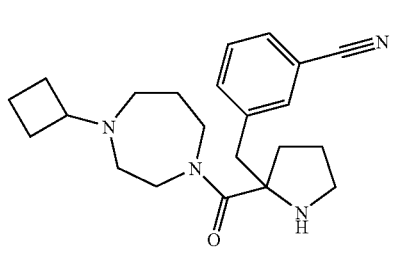

Example 205

4-[2-(4-Cyclobutyl-[1,4]diazepane-1-carbonyl)-pyrrolidin-2-ylmethyl]-benzonitrile.

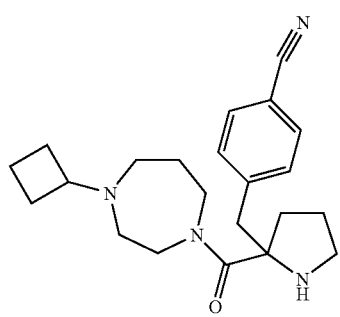

Example 206

4-[1-Acetyl-2-(4-cyclobutyl-[1,4]diazepane-1-carbonyl)-pyrrolidin-2-ylmethyl]-benzonitrile.

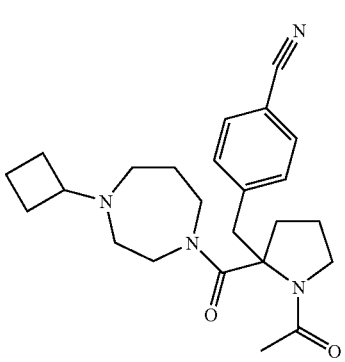

Example 207

1-[2-(4-Cyclobutyl-[1,4]diazepane-1-carbonyl)-2-(2-fluoro-benzyl)-pyrrolidin-1-yl]-ethanone.

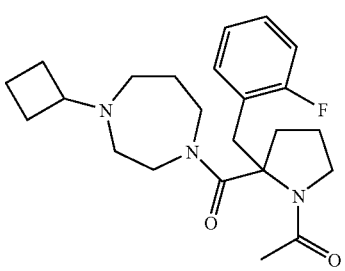

Example 208

(4-Cyclobutyl-[1,4]diazepan-1-yl)-[2-(2-fluoro-benzyl)-pyrrolidin-2-yl]-methanone.

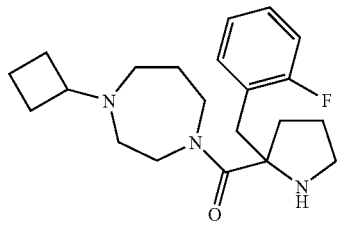

Example 209

[2-(2-Chloro-benzyl)-pyrrolidin-2-yl]-(4-cyclobutyl-[1,4]diazepan-1-yl)-methanone.

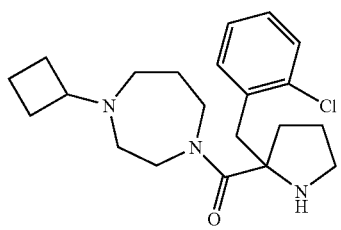

Example 210

1-[2-(2-Chloro-benzyl)-2-(4-cyclobutyl-[1,4]diazepane-1-carbonyl)-pyrrolidin-1-yl]-ethanone.

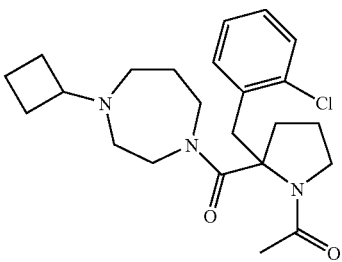

Biological Methods:

$H_3$ Receptor Binding (Human)

Method 1

Binding of compounds to the cloned human $H_3$ receptors, stably expressed in SK-N-MC cells, was performed as described by Barbier, A. J. et al. (Br. J. Pharmacol. 2004, 143(5), 649-661) and Lovenberg, T. W. et al. (J. Pharmacol Exp. Ther. 2000, 293, 771-778). Compounds were tested in their free base forms. Data for compounds tested in this assay are presented in Table 1, as an average of results obtained.

TABLE 1

| Ex. | Human $H_3$ $K_i$ (nM) |
|---|---|
| 1 | 70 |
| 2 | >10000 |
| 11 | 37 |
| 12 | >1500 |
| 15 | 25 |
| 16 | 3 |
| 17 | 3 |
| 18 | 5 |
| 19 | 5 |
| 20 | 12 |
| 21 | 12 |
| 22 | 3 |
| 41 | 18 |
| 42 | 24 |
| 43 | 33 |
| 44 | 52 |
| 45 | 8 |
| 46 | 35 |
| 47 | 50 |
| 59 | 16 |
| 62 | 46 |
| 63 | 284 |
| 65 | 2 |
| 66 | 2 |
| 70 | 1 |
| 86 | 18 |
| 87 | 20 |
| 88 | 11 |
| 89 | 44 |
| 90 | 13 |
| 91 | 130 |
| 92 | 51 |
| 93 | 88 |
| 94 | 8 |
| 95 | 67 |
| 96 | 11 |
| 97 | 89 |
| 104 | 58 |
| 106 | 71 |
| 107 | 523 |
| 114 | 34 |
| 116 | 152 |
| 117 | 796 |
| 118 | 816 |
| 119 | 300 |
| 128 | 573 |
| 137 | 206 |
| 138 | >10000 |
| 150 | 77 |
| 151 | 34 |
| 154 | 149 |
| 155 | 160 |

Method 2

The affinity of test compounds for the human recombinant $H_3$ receptor stably expressed in SK-N-MC cells was determined by competitive radioligand binding using $[^{125}I]$-iodoproxyfan as the radioligand.

SK-N-MC cells expressing the human $H_3$ receptor were grown to confluence and tissue culture plates, washed with phosphate-buffered saline, and scraped into 50 mL tubes. After centrifugation, the supernatant was aspirated, and the pellets frozen and stored at −80° C. Thawed pellets were homogenized with a polytron tissue grinder for 15 s in 50 mM Tris-HCl, 5 mM EDTA. The homogenate was centrifuged at 25000×g for 25 min. The resulting pellet was resuspended in binding buffer (50 mM Tris-HCl, 5 mM EDTA). Membranes were incubated with $[^{125}I]$-iodoproxyfan (1 nM) in the presence or absence of test compound for 1 h at rt. Reactions were stopped by filtration through GF/B filter plates pre-soaked in 0.3% polyethylenimine and subsequently washed with Tris 50 mM, 5 mM EDTA buffer. Plates were dried for 1 h in a 55° C. oven. Scintillation fluid was added and the radioactivity was counted in a Packard TopCount. Non-specific binding to the $H_3$ receptor was defined by radioactivity that was bound in the presence of 100 μM histamine. $IC_{50}$ values (i.e. concentration of tested compound required to compete for 50% of specific binding to the radioligand) were calculated using the GraphPad Prism software (GraphPad Software Inc., San Diego Calif.) with a fit to a sigmoidal dose response curve. Apparent $K_i$ values were calculated as $K_i=IC_{50}/(1+C/K_D)$, where C is concentration of the radioligand and $K_D=1$ nM.

Compounds were tested in their free base or hydrochloride salt forms. Data for compounds tested in these assays are presented in Table 2, as an average of results obtained.

TABLE 2

| Ex. | Human $H_3$ $K_i$ (nM) |
|---|---|
| 3 | 1272 |
| 4 | 53 |
| 5 | 1250 |
| 6 | 1109 |
| 7 | 432 |
| 8 | 534 |
| 9 | 50 |
| 10 | 115 |
| 14 | 126 |
| 16 | 2 |
| 17 | 3 |
| 19 | 9 |
| 20 | 4 |
| 21 | 3 |
| 23 | 7 |
| 24 | 4 |
| 25 | 5 |
| 26 | 12 |
| 27 | 5 |
| 28 | 7 |
| 29 | 8 |
| 30 | 8 |
| 31 | 15 |
| 32 | 10 |
| 33 | 24 |
| 34 | 14 |
| 35 | 2 |
| 36 | 3 |
| 37 | >10000 |
| 38 | 8999 |
| 39 | 43 |
| 40 | 1236 |
| 48 | 14 |
| 49 | 6 |
| 50 | 5 |
| 51 | 2 |
| 52 | 8 |
| 53 | 2 |
| 54 | 11 |
| 55 | 57 |
| 56 | 49 |
| 57 | 93 |
| 58 | 211 |
| 60 | 160 |
| 61 | 17 |
| 64 | 2 |
| 65 | 3 |
| 67 | 5 |
| 68 | 3 |
| 69 | 2 |
| 71 | 3 |
| 72 | 3 |
| 73 | 1143 |
| 74 | 5 |
| 75 | 4 |
| 76 | 5 |
| 77 | 3 |
| 78 | 20 |
| 79 | 12 |

TABLE 2-continued

| Ex. | Human $H_3$ $K_i$ (nM) |
|---|---|
| 80 | 40 |
| 81 | 23 |
| 82 | 4 |
| 83 | 3 |
| 84 | 8999 |
| 85 | 1296 |
| 98 | 5 |
| 99 | 2 |
| 100 | 2 |
| 101 | 3 |
| 102 | 5 |
| 103 | 29 |
| 105 | 50 |
| 108 | 594 |
| 109 | 55 |
| 110 | 2 |
| 111 | 17 |
| 112 | 12 |
| 113 | 7 |
| 115 | 21 |
| 120 | 1 |
| 121 | 2 |
| 122 | 1 |
| 123 | 18 |
| 124 | 7 |
| 125 | 3 |
| 126 | 11 |
| 127 | 16 |
| 129 | 379 |
| 130 | 569 |
| 131 | 2 |
| 132 | 3 |
| 133 | 3 |
| 134 | 3 |
| 135 | 3 |
| 136 | 2 |
| 139 | 3 |
| 140 | 1 |
| 141 | 55 |
| 142 | 13 |
| 143 | 845 |
| 144 | 957 |
| 145 | 1102 |
| 146 | 1468 |
| 147 | 8 |
| 148 | 6 |
| 149 | 13 |
| 152 | 4 |
| 153 | 3 |
| 156 | 1161 |
| 164 | 53 |
| 165 | 257 |
| 166 | 60 |
| 167 | 51 |
| 168 | 44 |
| 169 | 27 |
| 170 | 201 |
| 171 | 11 |
| 172 | 8999 |
| 173 | 39 |
| 174 | 53 |
| 175 | 72 |
| 176 | 20 |
| 177 | 263 |
| 178 | 299 |
| 179 | 348 |
| 180 | 50 |
| 181 | 2110 |
| 182 | 1165 |
| 183 | 203 |

$H_3$ Receptor Binding (Rat)

Compounds were tested for binding to cloned rat $H_3$ receptors, stably expressed in SK-N-MC cells. Data for this assay were obtained as described by Barbier, A. J. et al. (Br. J. Pharmacol. 2004, 143(5), 649-661) and Lovenberg, T. W. et al. (J. Pharmacol Exp. Ther. 2000, 293, 771-778).

Compounds were tested in their free base or hydrochloride salt forms. Data for compounds tested in this assay are presented in Table 3, as an average of results obtained.

TABLE 3

| Ex. | Rat $H_3$ $K_i$ (nM) |
|---|---|
| 27 | 232 |
| 64 | 466 |
| 65 | 12 |
| 66 | 9 |
| 67 | 502 |
| 69 | 18 |
| 71 | 54 |
| 72 | 36 |
| 82 | 18 |
| 83 | 16 |
| 88 | 130 |
| 94 | 150 |
| 96 | 84 |
| 110 | 477 |
| 120 | 30 |
| 121 | 15 |
| 122 | 12 |
| 131 | 17 |
| 152 | 8 |
| 153 | 13 |

Cyclic AMP Accumulation

Sublines of SK-N-MC cells were created that expressed a reporter construct and either the human or rat $H_3$ receptor. The $pA_2$ values were obtained as described by Barbier et al. (2004). Compounds were tested in their free base or trifluoroacetate salt forms. Data for compounds tested in this assay are presented in Table 4, as an average of results obtained.

TABLE 4

| Ex. | Human $pA_2$ | Rat $pA_2$ |
|---|---|---|
| 64 | 8.68 | 7.89 |
| 65 | 8.60 | 8.13 |
| 66 | 8.90 | 7.92 |
| 67 | 8.09 | 7.24 |
| 68 | 9.28 | 8.59 |
| 69 | 9.02 | 8.30 |
| 70 | 9.16 | 8.16 |
| 71 | 8.69 | 7.97 |
| 72 | 8.99 | 8.31 |
| 82 | 8.80 | 8.21 |
| 83 | 9.15 | 8.51 |
| 94 | 7.92 | 6.96 |
| 96 | 7.68 | 6.95 |
| 102 | 8.65 | 7.66 |
| 110 | 9.13 | 7.78 |
| 120 | 9.83 | 8.79 |
| 131 | 9.50 | 8.22 |
| 134 | 9.28 | 8.06 |
| 139 | 9.15 | 8.19 |

What is claimed is:

1. A compound of Formula (I):

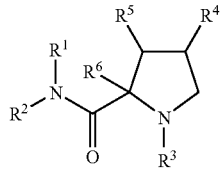

wherein

R$^1$ and R$^2$ taken together with the nitrogen to which they are attached form

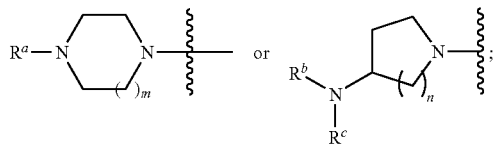

where m is 1 or 2;

n is 1 or 2;

R$^a$ is H, C$_{1-6}$alkyl, cycloalkyl, heterocycloalkyl, or benzyl; and

R$^b$ and R$^c$ are each independently H or C$_{1-4}$alkyl; or

R$^b$ and R$^c$ taken together with the nitrogen to which they are attached form a heterocycloalkyl ring;

R$^3$ is H; C$_{1-6}$alkyl; C$_{2-6}$alkyl substituted with OH, —OC$_{1-4}$alkyl, fluoro, or cycloalkyl; cycloalkyl; heterocycloalkyl; —COC$_{1-6}$alkyl; —CO-(cycloalkyl); benzoyl; —CO$_2$-benzyl; —SO$_2$C$_{1-4}$alkyl; —SO$_2$-(cycloalkyl); or —SO$_2$-phenyl;

R$^4$, R$^5$, and R$^6$ are defined as one of a), b) or c);

a) R$^4$ is —X—R$^d$ and R$^5$ and R$^6$ are each H;

b) R$^5$ is —X—R$^d$ and R$^4$ and R$^6$ are each H;

c) R$^6$ is —CH$_2$—R$^e$ and R$^4$ and R$^5$ are each H;

X is O;

R$^d$ is H or C$_{1-6}$alkyl, or a phenyl, benzyl, cycloalkyl, heterocycloalkyl, or monocyclic heteroaryl group, each group unsubstituted or substituted with one or two R$^f$ substituents;

where each R$^f$ substituent is independently selected from the group consisting of: halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^g$R$^h$; and —NO$_2$; or two R$^f$ substituents together form —O(CH$_2$)$_{1-2}$—O—;

where R$^g$ and R$^h$ are each independently —H or —C$_{1-4}$ alkyl;

and

R$^e$ is phenyl or monocyclic heteroaryl, each unsubstituted or substituted with one or two R$^f$ substituents;

or a pharmaceutically acceptable salt thereof.

2. A compound as defined in claim 1, wherein R$^1$ and R$^2$ are taken together with the nitrogen to which they are attached to form:

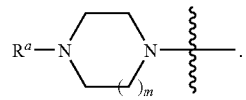

3. A compound as defined in claim 1, wherein m is 1.

4. A compound as defined in claim 1, wherein m is 2.

5. A compound as defined in claim 1, wherein n is 1.

6. A compound as defined in claim 1, wherein R$^a$ is H, methyl, isopropyl, isobutyl, cyclopropyl, cyclobutyl, cyclopentyl, tetrahydropyranyl, or benzyl.

7. A compound as defined in claim 1, wherein R$^a$ is cyclopropyl or cyclobutyl.

8. A compound as defined in claim 1, wherein R$^a$ is cyclobutyl.

9. A compound as defined in claim 1, wherein R$^b$ is H.

10. A compound as defined in claim 1, wherein R$^c$ is dimethylamino.

11. A compound as defined in claim 1, wherein R$^b$ and R$^c$ are taken together with the nitrogen to which they are attached to form pyrrolidinyl.

12. A compound as defined in claim 1, wherein R$^3$ is H, methyl, ethyl, isopropyl, hydroxyethyl, fluoroethyl, cyclopropylmethyl, cyclopropyl, cyclobutyl, tetrahydrofuranyl, tetrahydropyranyl, acetyl, propionyl, isobutyryl, 3,3-dimethylbutyryl, cyclopropanecarbonyl, benzoyl, methoxycarbonyl, ethoxycarbonyl, tert-butoxycarbonyl, benzyloxycarbonyl, or methylsulfonyl.

13. A compound as defined in claim 1, wherein R$^3$ is —COC$_{1-6}$alkyl, —CO-(cycloalkyl), or —SO$_2$C$_{1-4}$alkyl.

14. A compound as defined in claim 1, wherein R$^3$ is acetyl or methanesulfonyl.

15. A compound as defined in claim 1, wherein R$^4$ is —X—R$^d$ and R$^5$ and R$^6$ are each H.

16. A compound as defined in claim 1, wherein R$^5$ is —X—R$^d$ and R$^4$ and R$^6$ are each H.

17. A compound as defined in claim 1, wherein R$^6$ is —CH$_2$—R$^e$ and R$^4$ and R$^5$ are each H.

18. A compound as defined in claim 1, wherein R$^d$ is H.

19. A compound as defined in claim 1, wherein R$^d$ is isopropyl.

20. A compound as defined in claim 1, wherein R$^d$ is cyclopropyl, cyclobutyl, tetrahydrofuranyl, or tetrahydropyranyl.

21. A compound as defined in claim 1, wherein R$^d$ is phenyl, unsubstituted or substituted with one or two R$^f$ substituents.

22. A compound as defined in claim 1, wherein R$^d$ is benzyl, 3-fluorobenzyl, 4-fluorobenzyl, or 4-cyanobenzyl.

23. A compound as defined in claim 1, wherein R$^d$ is phenyl, unsubstituted or substituted with one or two R$^f$ substituents.

24. A compound as defined in claim 1, wherein R$^d$ is phenyl, 4-fluorophenyl, 3-fluorophenyl, 3-chlorophenyl, 4-chlorophenyl, 3-cyanophenyl, 4-methanesulfanyl-phenyl, 4-chloro-3-methylphenyl, 4-methanesulfonylphenyl, 3-methoxyphenyl, 3-methylphenyl, 3-trifluoromethylphenyl, 4-methylphenyl, 2-methylphenyl, 4-cyanophenyl, 3,4-dichlorophenyl, or 2,3-dihydro-benzo[1,4]dioxin-6-yl.

25. A compound as defined in claim 1, wherein R$^d$ is pyridin-2-yl, pyridin-4-yl, 2-fluoro-5-methyl-pyridin-4-yl, 4-iodo-5-methyl-pyridin-2-yl, pyridin-3-yl, pyrimidin-2-yl, pyrazin-2-yl, thiophen-3-yl, thiophen-2-yl, thiazol-4-yl, thiazol-5-yl, 5-methyl-isoxazol-4-yl, or 3,5-dimethyl-isoxazol-4-yl.

26. A compound as defined in claim 1, wherein each $R^f$ substituent is independently selected from the group consisting of: fluoro, chloro, bromo, iodo, methyl, ethyl, isopropyl, trifluoromethyl, hydroxy, methoxy, ethoxy, isopropoxy, methanesulfanyl, methanesulfonyl, cyano, dimethylcarbamoyl, and nitro; or two $R^f$ substituents together form —O(CH$_2$)$_2$—O—.

27. A compound as defined in claim 1, wherein $R^e$ is phenyl unsubstituted or substituted with one or two $R^f$ substituents.

28. A compound as defined in claim 1, wherein $R^e$ is phenyl, 3-fluorophenyl, 4-fluorophenyl, 4-trifluoromethylphenyl, 3-cyanophenyl, 4-cyanophenyl, 2-fluorophenyl, or 2-chlorophenyl.

29. A compound as defined in claim 1, wherein the —X—$R^d$ substituent is in the S configuration.

30. A compound as defined in claim 1, wherein the —CO$_2$N($R^1$)$R^2$ substituent is in the R configuration.

31. A compound as defined in claim 1, wherein compounds of Formula (I) are compounds of Formula (II):

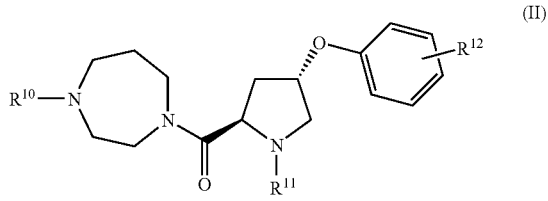

(II)

wherein
$R^{10}$ is isopropyl, cyclopropyl, or cyclobutyl;
$R^{11}$ is —C(O)C$_{1-4}$alkyl or —SO$_2$C$_{1-4}$alkyl; and
$R^{12}$ is halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^s$R$^t$; and —NO$_2$; or two $R^{12}$ substituents together form —O(CH$_2$)$_{1-2}$—O—;
where $R^s$ and $R^t$ are each independently —H or —C$_{1-4}$alkyl;
or a pharmaceutically acceptable salt thereof.

32. A compound selected from the group consisting of:
(2S,4R)-2-(4-Cyclobutyl-[1,4]diazepane-1-carbonyl)-4-hydroxy-pyrrolidine-1-carboxylic acid tert-butyl ester;
(2S,4R)-2-(4-Cyclobutyl-piperazine-1-carbonyl)-4-hydroxy-pyrrolidine-1-carboxylic acid tert-butyl ester;
(2S,3S)-2-(4-Cyclobutyl-[1,4]diazepane-1-carbonyl)-3-hydroxy-pyrrolidine-1-carboxylic acid tert-butyl ester;
(2R,4S)-2-(4-Cyclobutyl-[1,4]diazepane-1-carbonyl)-4-hydroxy-pyrrolidine-1-carboxylic acid tert-butyl ester;
(2R,4R)-2-(4-Cyclopropyl-[1,4]diazepane-1-carbonyl)-4-hydroxy-pyrrolidine-1-carboxylic acid tert-butyl ester;
(2R,4R)-2-(4-Cyclopentyl-piperazine-1-carbonyl)-4-hydroxy-pyrrolidine-1-carboxylic acid tert-butyl ester;
(2R,4R)-2-(4-Cyclopentyl-[1,4]diazepane-1-carbonyl)-4-hydroxy-pyrrolidine-1-carboxylic acid tert-butyl ester;
(2R,4R)-2-(4-Cyclobutyl-[1,4]diazepane-1-carbonyl)-4-hydroxy-pyrrolidine-1-carboxylic acid tert-butyl ester;
(2R,4R)-2-(4-Cyclobutyl-[1,4]diazepane-1-carbonyl)-4-hydroxy-pyrrolidine-1-carboxylic acid benzyl ester;
(2R,4S)-1-[2-(4-Cyclobutyl-[1,4]diazepane-1-carbonyl)-4-hydroxy-pyrrolidin-1-yl]-ethanone;
(2S,4S)-2-(4-Cyclobutyl-[1,4]diazepane-1-carbonyl)-4-(4-fluoro-phenoxy)-pyrrolidine-1-carboxylic acid tert-butyl ester;
(2S,4S)-2-(4-Cyclobutyl-piperazine-1-carbonyl)-4-(4-fluoro-phenoxy)-pyrrolidine-1-carboxylic acid tert-butyl ester;
(2S,4S)-2-(4-Cyclobutyl-[1,4]diazepane-1-carbonyl)-4-(3-fluoro-phenoxy)-pyrrolidine-1-carboxylic acid tert-butyl ester;
(2S,4S)-2-(4-Cyclobutyl-[1,4]diazepane-1-carbonyl)-4-phenoxy-pyrrolidine-1-carboxylic acid tert-butyl ester;
(2S,4R)-2-(4-Cyclobutyl-[1,4]diazepane-1-carbonyl)-4-(4-fluoro-phenoxy)-pyrrolidine-1-carboxylic acid tert-butyl ester;
(2R,4S)-4-(4-Cyano-phenoxy)-2-(4-cyclobutyl-[1,4]diazepane-1-carbonyl)-pyrrolidine-1-carboxylic acid tert-butyl ester;
(2R,4S)-2-(4-Cyclobutyl-[1,4]diazepane-1-carbonyl)-4-(3-fluoro-phenoxy)-pyrrolidine-1-carboxylic acid tert-butyl ester;
(2R,4S)-2-(4-Cyclobutyl-[1,4]diazepane-1-carbonyl)-4-(4-fluoro-phenoxy)-pyrrolidine-1-carboxylic acid tert-butyl ester;
(2R,4S)-2-(4-Cyclobutyl-[1,4]diazepane-1-carbonyl)-4-phenoxy-pyrrolidine-1-carboxylic acid tert-butyl ester;
(2R,4S)-4-(3-Chloro-phenoxy)-2-(4-cyclobutyl-[1,4]diazepane-1-carbonyl)-pyrrolidine-1-carboxylic acid tert-butyl ester;
(2R,4S)-4-(4-Chloro-phenoxy)-2-(4-cyclobutyl-[1,4]diazepane-1-carbonyl)-pyrrolidine-1-carboxylic acid tert-butyl ester;
(2R,4S)-4-(3-Cyano-phenoxy)-2-(4-cyclobutyl-[1,4]diazepane-1-carbonyl)-pyrrolidine-1-carboxylic acid tert-butyl ester;
(2R,4S)-2-(4-Cyclobutyl-[1,4]diazepane-1-carbonyl)-4-(4-methylsulfanyl-phenoxy)-pyrrolidine-1-carboxylic acid tert-butyl ester;
(2R,4S)-4-(4-Chloro-3-methyl-phenoxy)-2-(4-cyclobutyl-[1,4]diazepane-1-carbonyl)-pyrrolidine-1-carboxylic acid tert-butyl ester;
(2R,4S)-2-(4-Cyclobutyl-[1,4]diazepane-1-carbonyl)-4-(4-methanesulfonyl-phenoxy)-pyrrolidine-1-carboxylic acid tert-butyl ester;
(2R,4S)-2-(4-Cyclobutyl-[1,4]diazepane-1-carbonyl)-4-(3-methoxy-phenoxy)-pyrrolidine-1-carboxylic acid tert-butyl ester;
(2R,4S)-2-(4-Cyclobutyl-[1,4]diazepane-1-carbonyl)-4-m-tolyloxy-pyrrolidine-1-carboxylic acid tert-butyl ester;
(2R,4S)-2-(4-Cyclobutyl-[1,4]diazepane-1-carbonyl)-4-(4-trifluoromethyl-phenoxy)-pyrrolidine-1-carboxylic acid tert-butyl ester;
(2R,4S)-2-(4-Cyclobutyl-[1,4]diazepane-1-carbonyl)-4-p-tolyloxy-pyrrolidine-1-carboxylic acid tert-butyl ester;
(2R,4S)-2-(4-Cyclobutyl-[1,4]diazepane-1-carbonyl)-4-o-tolyloxy-pyrrolidine-1-carboxylic acid tert-butyl ester;
(2R,4S)-2-(4-Cyclopropyl-[1,4]diazepane-1-carbonyl)-4-(4-fluoro-phenoxy)-pyrrolidine-1-carboxylic acid tert-butyl ester;
(2R,4S)-4-(4-Cyano-phenoxy)-2-(4-cyclopropyl-[1,4]diazepane-1-carbonyl)-pyrrolidine-1-carboxylic acid tert-butyl ester;
(2R,4S)-2-(4-Cyclopentyl-piperazine-1-carbonyl)-4-(4-fluoro-phenoxy)-pyrrolidine-1-carboxylic acid tert-butyl ester;
(2R,4S)-4-(4-Cyano-phenoxy)-2-(4-cyclopentyl-piperazine-1-carbonyl)-pyrrolidine-1-carboxylic acid tert-butyl ester;

(2R,4S)-2-(4-Cyclopentyl-[1,4]diazepane-1-carbonyl)-4-(4-fluoro-phenoxy)-pyrrolidine-1-carboxylic acid tert-butyl ester;
(2R,4S)-4-(4-Cyano-phenoxy)-2-(4-cyclopentyl-[1,4]diazepane-1-carbonyl)-pyrrolidine-1-carboxylic acid tert-butyl ester;
(2R,4S)-2-((3R)-3-Dimethylamino-pyrrolidine-1-carbonyl)-4-(3-fluoro-phenoxy)-pyrrolidine-1-carboxylic acid tert-butyl ester;
(2R,4S)-2-((3S)-3-Dimethylamino-pyrrolidine-1-carbonyl)-4-(3-fluoro-phenoxy)-pyrrolidine-1-carboxylic acid tert-butyl ester;
(2R,4S)-2-([1,3']Bipyrrolidinyl-1'-carbonyl)-4-(3-fluoro-phenoxy)-pyrrolidine-1-carboxylic acid tert-butyl ester;
(2R,4S)-2-(4-Dimethylamino-piperidine-1-carbonyl)-4-(4-fluoro-phenoxy)-pyrrolidine-1-carboxylic acid tert-butyl ester;
(2S)-2-(4-Cyclobutyl-[1,4]diazepane-1-carbonyl)-4-(3-fluoro-phenoxy)-pyrrolidine-1-carboxylic acid tert-butyl ester;
(2S)-4-(3-Chloro-phenoxy)-2-(4-cyclobutyl-[1,4]diazepane-1-carbonyl)-pyrrolidine-1-carboxylic acid tert-butyl ester;
(2S)-4-(4-Chloro-phenoxy)-2-(4-cyclobutyl-[1,4]diazepane-1-carbonyl)-pyrrolidine-1-carboxylic acid tert-butyl ester;
(2S)-2-(4-Cyclobutyl-[1,4]diazepane-1-carbonyl)-4-(3,4-dichloro-phenoxy)-pyrrolidine-1-carboxylic acid tert-butyl ester;
(2S)-4-(4-Cyano-phenoxy)-2-(4-cyclobutyl-[1,4]diazepane-1-carbonyl)-pyrrolidine-1-carboxylic acid tert-butyl ester;
(2S)-2-(4-Cyclobutyl-[1,4]diazepane-1-carbonyl)-4-(4-methylsulfanyl-phenoxy)-pyrrolidine-1-carboxylic acid tert-butyl ester;
(2S)-2-(4-Cyclobutyl-[1,4]diazepane-1-carbonyl)-4-phenoxy-pyrrolidine-1-carboxylic acid tert-butyl ester;
(2S,4R)-2-(4-Cyclobutyl-[1,4]diazepane-1-carbonyl)-4-phenoxy-pyrrolidine-1-carboxylic acid tert-butyl ester;
(2S,4R)-2-(4-Cyclobutyl-[1,4]diazepane-1-carbonyl)-4-(3-fluoro-phenoxy)-pyrrolidine-1-carboxylic acid tert-butyl ester;
(2S,4R)-2-(4-Cyclobutyl-[1,4]diazepane-1-carbonyl)-4-(pyridin-2-yloxy)-pyrrolidine-1-carboxylic acid tert-butyl ester;
(2S,4R)-2-(4-Cyclobutyl-[1,4]diazepane-1-carbonyl)-4-(2-fluoro-5-methyl-pyridin-4-yloxy)-pyrrolidine-1-carboxylic acid tert-butyl ester;
(2R,4S)-2-(4-Cyclobutyl-[1,4]diazepane-1-carbonyl)-4-(4-iodo-5-methyl-pyridin-2-yloxy)-pyrrolidine-1-carboxylic acid tert-butyl ester;
(2R,4S)-2-(4-Cyclobutyl-[1,4]diazepane-1-carbonyl)-4-(pyridin-3-yloxy)-pyrrolidine-1-carboxylic acid tert-butyl ester;
(2R,4S)-2-(4-Cyclobutyl-[1,4]diazepane-1-carbonyl)-4-(thiophen-3-yloxy)-pyrrolidine-1-carboxylic acid tert-butyl ester;
(2R,4R)-2-(4-Cyclobutyl-[1,4]diazepane-1-carbonyl)-4-(3-fluoro-phenoxy)-pyrrolidine-1-carboxylic acid tert-butyl ester;
(2R,4R)-2-(4-Cyclobutyl-[1,4]diazepane-1-carbonyl)-4-(4-fluoro-phenoxy)-pyrrolidine-1-carboxylic acid tert-butyl ester;
(2R,4R)-4-(4-Chloro-phenoxy)-2-(4-cyclobutyl-[1,4]diazepane-1-carbonyl)-pyrrolidine-1-carboxylic acid tert-butyl ester;
(2R,4R)-2-(4-Cyclobutyl-[1,4]diazepane-1-carbonyl)-4-phenoxy-pyrrolidine-1-carboxylic acid tert-butyl ester;
(2S,4R)-2-(4-Cyclobutyl-[1,4]diazepane-1-carbonyl)-4-isopropoxy-pyrrolidine-1-carboxylic acid tert-butyl ester;
(2R,4R)-4-(4-Cyano-phenoxy)-2-(4-cyclobutyl-[1,4]diazepane-1-carbonyl)-pyrrolidine-1-carboxylic acid tert-butyl ester;
(2R,4S)-2-(4-Cyclobutyl-[1,4]diazepane-1-carbonyl)-4-(4-fluoro-phenylsulfanyl)-pyrrolidine-1-carboxylic acid tert-butyl ester;
(2S,4S)-2-(4-Cyclobutyl-[1,4]diazepane-1-carbonyl)-4-(4-fluoro-phenoxy)-pyrrolidine;
(2S,4S)-2-(4-Cyclobutyl-piperazine-1-carbonyl)-4-(4-fluoro-phenoxy)-pyrrolidine;
(3S,5R)-4-[5-(4-Cyclobutyl-[1,4]diazepane-1-carbonyl)-pyrrolidin-3-yloxy]-benzonitrile;
(2R,4S)-4-(3-Fluoro-phenoxy)-2-(4-cyclobutyl-[1,4]diazepane-1-carbonyl)-pyrrolidine;
(2R,4S)-4-(4-Fluoro-phenoxy)-2-(4-cyclobutyl-[1,4]diazepane-1-carbonyl)-pyrrolidine;
(2R,4S)-4-Phenoxy-2-(4-cyclobutyl-[1,4]diazepane-1-carbonyl)-pyrrolidine;
(2R,4S)-4-(3-chloro-phenoxy)-2-(4-cyclobutyl-[1,4]diazepane-1-carbonyl)-pyrrolidine;
(2R,4S)-4-(4-Chloro-phenoxy)-2-(4-cyclobutyl-[1,4]diazepane-1-carbonyl)-pyrrolidine;
(2R,4S)-4-(3-Cyano-phenoxy)-2-(4-cyclobutyl-[1,4]diazepane-1-carbonyl)-pyrrolidine;
(2R,4S)-4-(4-Methylsulfanyl-phenoxy)-2-(4-cyclobutyl-[1,4]diazepane-1-carbonyl)-pyrrolidine;
(2R,4S)-4-(4-Chloro-3-methyl-phenoxy)-2-(4-cyclobutyl-[1,4]diazepane-1-carbonyl)-pyrrolidine;
(2R,4S)-4-(3-Methoxy-phenoxy)-2-(4-cyclobutyl-[1,4]diazepane-1-carbonyl)-pyrrolidine;
(2R,4S)-4-(4-m-Tolyloxy)-2-(4-cyclobutyl-[1,4]diazepane-1-carbonyl)-pyrrolidine;
(2R,4S)-4-(4-Trifluoromethyl-phenoxy)-2-(4-cyclobutyl-[1,4]diazepane-1-carbonyl)-pyrrolidine;
(2R,4S)-4-(4-p-Tolyloxy)-2-(4-cyclobutyl-[1,4]diazepane-1-carbonyl)-pyrrolidine;
(2R,4S)-4-(4-o-Tolyloxy)-2-(4-cyclobutyl-[1,4]diazepane-1-carbonyl)-pyrrolidine;
(2R,4S)-2-(4-Cyclopropyl-[1,4]diazepane-1-carbonyl)-4-(4-fluoro-phenoxy)-pyrrolidine;
(2R,4S)-4-(4-Cyano-phenoxy)-2-(4-cyclopropyl-[1,4]diazepane-1-carbonyl)-pyrrolidine;
(2R,4S)-2-(4-Cyclopentyl-piperazine-1-carbonyl)-4-(4-fluoro-phenoxy)-pyrrolidine;
(2R,4S)-4-(4-Cyano-phenoxy)-2-(4-cyclopentyl-piperazine-1-carbonyl)-pyrrolidine;
(2R,4S)-2-(4-Cyclopentyl-[1,4]diazepane-1-carbonyl)-4-(4-fluoro-phenoxy)-pyrrolidine;
(2R,4S)-4-(4-Cyano-phenoxy)-2-(4-cyclopentyl-[1,4]diazepane-1-carbonyl)-pyrrolidine;
(2R,4S)-2-((3R)-3-Dimethylamino-pyrrolidine-1-carbonyl)-4-(3-fluoro-phenoxy)-pyrrolidine;
(2R,4S)-2-((3S-3-Dimethylamino-pyrrolidine-1-carbonyl)-4-(3-fluoro-phenoxy)-pyrrolidine;
(2S,4R)-2-(4-Cyclobutyl-[1,4]diazepane-1-carbonyl)-4-(4-fluoro-phenoxy)-pyrrolidine;
(2S,4R)-2-(4-Cyclobutyl-[1,4]diazepane-1-carbonyl)-4-(3-fluoro-phenoxy)-pyrrolidine;
(2S,4R)-4-(3-Chloro-phenoxy)-2-(4-cyclobutyl-[1,4]diazepane-1-carbonyl)-pyrrolidine;
(2S,4S)-4-(3-Chloro-phenoxy)-2-(4-cyclobutyl-[1,4]diazepane-1-carbonyl)-pyrrolidine;

(2S,4R)-4-(4-Chloro-phenoxy)-2-(4-cyclobutyl-[1,4]diazepane-1-carbonyl)-pyrrolidine;
(2S,4S)-4-(4-Chloro-phenoxy)-2-(4-cyclobutyl-[1,4]diazepane-1-carbonyl)-pyrrolidine;
(2S,4R)-2-(4-Cyclobutyl-[1,4]diazepane-1-carbonyl)-4-(3,4-dichloro-phenoxy)-pyrrolidine;
(2S,4S)-2-(4-Cyclobutyl-[1,4]diazepane-1-carbonyl)-4-(3,4-dichloro-phenoxy)-pyrrolidine;
(2S,4R)-4-(4-Cyano-phenoxy)-2-(4-cyclobutyl-[1,4]diazepane-1-carbonyl)-pyrrolidine;
(2S,4S)-4-(4-Cyano-phenoxy)-2-(4-cyclobutyl-[1,4]diazepane-1-carbonyl)-pyrrolidine;
(2S,4R)-2-(4-Cyclobutyl-[1,4]diazepane-1-carbonyl)-4-(4-methylsulfanyl-phenoxy)-pyrrolidine;
(2S,4S)-2-(4-Cyclobutyl-[1,4]diazepane-1-carbonyl)-4-(4-methylsulfanyl-phenoxy)-pyrrolidine;
(2R,4S)-2-(4-Cyclobutyl-[1,4]diazepane-1-carbonyl)-4-(pyridin-2-yloxy)-pyrrolidine;
(2R,4S)-2-(4-Cyclobutyl-[1,4]diazepane-1-carbonyl)-4-(2-fluoro-5-methyl-pyridin-4-yloxy)-pyrrolidine;
(2R,4S)-2-(4-Cyclobutyl-[1,4]diazepane-1-carbonyl)-4-(4-iodo-5-methyl-pyridin-2-yloxy)-pyrrolidine;
(2R,4S)-2-(4-Cyclobutyl-[1,4]diazepane-1-carbonyl)-4-(pyridin-3-yloxy)-pyrrolidine;
(2R,4S)-2-(4-Cyclobutyl-[1,4]diazepane-1-carbonyl)-4-(thiophen-3-yloxy)-pyrrolidine;
(2R,4R)-4-(3-fluoro-phenoxy)-2-(4-cyclobutyl-[1,4]diazepane-1-carbonyl)-pyrrolidine;
(2S,4R)-2-(4-Cyclobutyl-[1,4]diazepane-1-carbonyl)-4-isopropoxy-pyrrolidine;
(2R,4S)-4-(4-Cyano-phenoxy)-2-(4-cyclobutyl-[1,4]diazepane-1-carbonyl)-pyrrolidine;
(2S,4S)-1-Methyl-2-(4-cyclobutyl-[1,4]diazepane-1-carbonyl)-4-(4-fluoro-phenoxy)-pyrrolidine;
(2S,4S)-1-Methyl-2-(4-cyclobutyl-piperazine-1-carbonyl)-4-(4-fluoro-phenoxy)-pyrrolidine;
(2S,4S)-(4-Cyclobutyl-[1,4]diazepan-1-yl)-[4-(4-fluoro-phenoxy)-1-isopropyl-pyrrolidin-2-yl]-methanone;
(2S,4S)-(4-Cyclobutyl-[1,4]diazepan-1-yl)-[1-ethyl-4-(4-fluoro-phenoxy)-pyrrolidin-2-yl]-methanone;
(2R,4S)-1-Methyl-2-(4-cyclobutyl-[1,4]diazepane-1-carbonyl)-4-(4-fluoro-phenoxy)-pyrrolidine;
(2R,4S)-1-Cyclobutyl-2-(4-cyclobutyl-[1,4]diazepane-1-carbonyl)-4-(4-fluoro-phenoxy)-pyrrolidine;
(2R,4S)-1-Isopropyl-1-cyclobutyl-2-(4-cyclobutyl-[1,4]diazepane-1-carbonyl)-4-(4-fluoro-phenoxy)-pyrrolidine;
(2R,4S)-1-Cyclopropylmethyl-2-(4-cyclobutyl-[1,4]diazepane-1-carbonyl)-4-(4-fluoro-phenoxy)-pyrrolidine;
(2S,4S)-1-[2-(4-Cyclobutyl-[1,4]diazepane-1-carbonyl)-4-(4-fluoro-phenoxy)-pyrrolidin-1-yl]-ethanone;
(2S,4S)-1-[2-(4-Cyclobutyl-[1,4]diazepane-1-carbonyl)-4-(3-fluoro-phenoxy)-pyrrolidin-1-yl]-ethanone;
(2S,4S)-1-[2-(4-Cyclobutyl-[1,4]diazepane-1-carbonyl)-4-(4-fluoro-phenoxy)-pyrrolidin-1-yl]-propan-1-one;
(2S,4S)-1-[2-(4-Cyclobutyl-[1,4]diazepane-1-carbonyl)-4-(4-fluoro-phenoxy)pyrrolidin-1-yl]-2-methyl-propan-1-one;
(2S,4S)-1-[2-(4-Cyclobutyl-[1,4]diazepane-1-carbonyl)-4-(4-fluoro-phenoxy)-pyrrolidin-1-yl]-3,3-dimethyl-butan-1-one;
(2S,4S)-1-[2-(4-Cyclobutyl-piperazine-1-carbonyl)-4-(4-fluoro-phenoxy)-pyrrolidin-1-yl]-ethanone;
(2R,4S)-1-[2-(4-Cyclobutyl-[1,4]diazepane-1-carbonyl)-4-(4-fluoro-phenoxy)-pyrrolidin-1-yl]-ethanone;
(2R,4S)-1-[2-(4-Cyclobutyl-[1,4]diazepane-1-carbonyl)-4-(4-methylsulfanyl-phenoxy)-pyrrolidin-1-yl]-ethanone;
(2R,4S)-1-[4-(4-Chloro-3-methyl-phenoxy)-2-(4-cyclobutyl-[1,4]diazepane-1-carbonyl)-pyrrolidin-1-yl]-ethanone;
(2R,4S)-1-[2-(4-Cyclobutyl-[1,4]diazepane-1-carbonyl)-4-(3-fluoro-phenoxy)-pyrrolidin-1-yl]-2-methyl-propan-1-one;
(2R,4S)-1-Cyclopropanecarbonyl-2-(4-cyclobutyl-[1,4]diazepane-1-carbonyl)-4-(4-fluoro-phenoxy)-pyrrolidine;
(2R,4S)-1-[2-(4-Cyclobutyl-[1,4]diazepane-1-carbonyl)-4-(3-fluoro-phenoxy)-pyrrolidin-1-yl]-propan-1-one;
(2R,4S)-2-(4-Cyclobutyl-[1,4]diazepane-1-carbonyl)-4-(3-fluoro-phenoxy)-pyrrolidine-1-carboxylic acid methyl ester;
(2R,4S)-2-(4-Cyclobutyl-[1,4]diazepane-1-carbonyl)-4-(3-fluoro-phenoxy)pyrrolidine-1-carboxylic acid ethyl ester;
(2S,4R)-1-[2-(4-Cyclobutyl-[1,4]diazepane-1-carbonyl)-4-(4-fluoro-phenoxy)-pyrrolidin-1-yl]-ethanone;
(2S,4R)-1-[2-(4-Cyclobutyl-[1,4]diazepane-1-carbonyl)-4-(3-fluoro-phenoxy)-pyrrolidin-1-yl]-ethanone;
(2R,4R)-4-(3-Fluoro-phenoxy)-2-(4-cyclobutyl-[1,4]diazepane-1-carbonyl)-pyrrolidine;
(2R,4S)-1-[2-(4-Cyclobutyl-[1,4]diazepane-1-carbonyl)-4-(3-fluoro-phenoxy)-pyrrolidin-1-yl]-ethanone;
(2R,4S)-1-[2-(4-Cyclobutyl-[1,4]diazepane-1-carbonyl)-4-(pyridin-2-yloxy)-pyrrolidin-1-yl]-ethanone;
(2R,4S)-1-[2-(4-Cyclobutyl-[1,4]diazepane-1-carbonyl)-4-(pyridin-3-yloxy)-pyrrolidin-1-yl]-ethanone;
(2R,4S)-1-[2-(4-Cyclobutyl-[1,4]diazepane-1-carbonyl)-4-(thiophen-3-yloxy)-pyrrolidin-1-yl]-ethanone;
(2R,4S)-1-[2-(4-Cyclobutyl-[1,4]diazepane-1-carbonyl)-4-(thiophen-2-yloxy)-pyrrolidin-1-yl]-ethanone;
(2R,4S)-1-[2-(4-Cyclobutyl-[1,4]diazepane-1-carbonyl)-4-(2,3-dihydro-benzo[1,4]dioxin-6-yloxy)-pyrrolidin-1-yl]-ethanone;
(2S,4S)-1-Methanesulfonyl-2-(4-cyclobutyl-[1,4]diazepane-1-carbonyl)-4-(4-fluoro-phenoxy)-pyrrolidine;
(2S,4S)-2-(4-Cyclobutyl-piperazin-1-yl)-[4-(4-fluoro-phenoxy)-1-methanesulfonyl-pyrrolidin-2-yl]-methanone;
(2R,4S)-1-Methanesulfonyl-2-(4-cyclobutyl-[1,4]diazepane-1-carbonyl)-4-(4-fluoro-phenoxy)-pyrrolidine;
(2R,4S)-(4-Cyclobutyl-[1,4]diazepan-1-yl)-[4-(4-fluoro-phenoxy)-1-methanesulfonyl-pyrrolidin-2-yl]-methanone;
(2S,4S)-2-(4-Cyclobutyl-[1,4]diazepan-1-yl)-[1-cyclopropyl-4-(4-fluoro-phenoxy)-pyrrolidin-2-yl]-methanone;
(2R,4S)-1-Cyclopropyl-2-(4-cyclobutyl-[1,4]diazepane-1-carbonyl)-4-(4-fluoro-phenoxy)-pyrrolidine;
(2S,3R)-2-(4-Cyclobutyl-[1,4]diazepane-1-carbonyl)-3-(3-fluoro-phenoxy)-pyrrolidine-1-carboxylic acid tert-butyl ester;
(2S,3R)-2-(4-Cyclobutyl-[1,4]diazepane-1-carbonyl)-3-(4-fluoro-phenoxy)-pyrrolidine-1-carboxylic acid tert-butyl ester;
(2S,3R)-3-(4-Cyano-phenoxy)-2-(4-cyclobutyl-[1,4]diazepane-1-carbonyl)-pyrrolidine-1-carboxylic acid tert-butyl ester;
(2S,3R)-2-(4-Cyclobutyl-[1,4]diazepane-1-carbonyl)-3-(4-methylsulfanyl-phenoxy)-pyrrolidine-1-carboxylic acid tert-butyl ester;

(2R,4S)-2-(4-Cyclobutyl-[1,4]diazepane-1-carbonyl)-4-(3-fluoro-benzyloxy)-pyrrolidine-1-carboxylic acid tert-butyl ester;
(2R,4S)-2-(4-Cyclobutyl-[1,4]diazepane-1-carbonyl)-4-(4-fluoro-benzyloxy)-pyrrolidine-1-carboxylic acid tert-butyl ester;
(2R,4S)-4-(4-Cyano-benzyloxy)-2-(4-cyclobutyl-[1,4]diazepane-1-carbonyl)-pyrrolidine-1-carboxylic acid tert-butyl ester;
(2R,4R)-2-(4-Cyclobutyl-[1,4]diazepane-1-carbonyl)-4-(3-fluoro-benzyloxy)-pyrrolidine-1-carboxylic acid tert-butyl ester;
(2R,4R)-2-(4-Cyclobutyl-[1,4]diazepane-1-carbonyl)-4-(4-fluoro-benzyloxy)-pyrrolidine-1-carboxylic acid tert-butyl ester;
(2R,4S)-2-(4-Cyclobutyl-[1,4]diazepane-1-carbonyl)-4-(3-fluoro-benzyloxy)-pyrrolidine;
(2R,4S)-2-(4-Cyclobutyl-[1,4]diazepane-1-carbonyl)-4-(4-fluoro-benzyloxy)-pyrrolidine;
(2R,4R)-2-(4-Cyclobutyl-[1,4]diazepane-1-carbonyl)-4-(3-fluoro-benzyloxy)-pyrrolidine;
(2R,4R)-2-(4-Cyclobutyl-[1,4]diazepane-1-carbonyl)-4-(4-fluoro-benzyloxy)-pyrrolidine;
(2R,4S)-4-[1-Acetyl-4-(3-fluoro-phenoxy)-pyrrolidine-2-carbonyl]-[1,4]diazepane;
(2R,4S)-1-[4-(3-Fluoro-phenoxy)-2-(4-isopropyl-[1,4]diazepane-1-carbonyl)-pyrrolidin-1-yl]-ethanone;
(2R,4S)-1-[2-(4-Cyclopentyl-[1,4]diazepane-1-carbonyl)-4-(3-fluoro-phenoxy)-pyrrolidin-1-yl]-ethanone;
(2R,4S)-1-[4-(3-Fluoro-phenoxy)-2-(4-isobutyl-[1,4]diazepane-1-carbonyl)-pyrrolidin-1-yl]-ethanone;
(2R,4S)-1-{4-(3-Fluoro-phenoxy)-2-[4-(tetrahydro-pyran-4-yl)-[1,4]diazepane-1-carbonyl]-pyrrolidin-1-yl}-ethanone;
(2R,4S)-1-[2-(4-Cyclopropyl-[1,4]diazepane-1-carbonyl)-4-(3-fluoro-phenoxy)-pyrrolidin-1-yl]-ethanone;
(2R,4S)-1-[2-(4-Benzyl-[1,4]diazepane-1-carbonyl)-4-(3-fluoro-phenoxy)-pyrrolidin-1-yl]-ethanone;
(2R,4S)-1-[4-(3-Fluoro-phenoxy)-2-(4-methyl-[1,4]diazepane-1-carbonyl)-pyrrolidin-1-yl]-ethanone;
(2S)-2-(4-Cyclobutyl-[1,4]diazepane-1-carbonyl)-2-(3-fluoro-benzyl)-pyrrolidine-1-carboxylic acid tert-butyl ester;
(2S)-2-(4-Cyclobutyl-[1,4]diazepane-1-carbonyl)-2-(4-fluoro-benzyl)-pyrrolidine-1-carboxylic acid tert-butyl ester;
(2S)-2-(4-Cyclobutyl-[1,4]diazepane-1-carbonyl)-2-(4-trifluoromethyl-benzyl)-pyrrolidine-1-carboxylic acid tert-butyl ester;
(2S)-2-Benzyl-2-(4-cyclobutyl-[1,4]diazepane-1-carbonyl)-pyrrolidine-1-carboxylic acid tert-butyl ester;
(2S)-2-(4-Cyclobutyl-[1,4]diazepane-1-carbonyl)-2-(3-fluoro-benzyl)-pyrrolidine;
(2S)-(4-Cyclobutyl-[1,4]diazepan-1-yl)-[2-(4-fluoro-benzyl)-pyrrolidin-2-yl]-methanone;
(2S)-(4-Cyclobutyl-[1,4]diazepan-1-yl)-[2-(4-trifluoromethyl-benzyl)-pyrrolidin-2-yl]-methanone;
(2S)-(2-Benzyl-pyrrolidin-2-yl)-(4-cyclobutyl-[1,4]diazepan-1-yl)-methanone;
(2S)-(1-[2-(4-Cyclobutyl-[1,4]diazepane-1-carbonyl)-2-(4-fluoro-benzyl)-pyrrolidin-1-yl]-ethanone;
(2S,4R)-4-Benzyl-2-(4-cyclobutyl-[1,4]diazepane-1-carbonyl)-pyrrolidine-1-carboxylic acid tert-butyl ester;
(2S,4R)-2-(4-Cyclobutyl-[1,4]diazepane-1-carbonyl)-4-(4-fluoro-benzyl)pyrrolidine-1-carboxylic acid tert-butyl ester;
(2S,4R)-2-(4-Cyclobutyl-[1,4]diazepane-1-carbonyl)-4-(3-fluoro-benzyl)-pyrrolidine-1-carboxylic acid tert-butyl ester;
(2S,4R)-2-(4-Cyclobutyl-[1,4]diazepane-1-carbonyl)-4-thiophen-3-ylmethyl-pyrrolidine-1-carboxylic acid tert-butyl ester;
(2S,4R)-(4-Benzyl-pyrrolidin-2-yl)-(4-cyclobutyl-[1,4]diazepan-1-yl)-methanone;
(2S,4R)-(4-Cyclobutyl-[1,4]diazepan-1-yl)-[4-(4-fluoro-benzyl)-pyrrolidin-2-yl]-methanone;
(2S,4R)-(4-Cyclobutyl-[1,4]diazepan-1-yl)-[4-(3-fluoro-benzyl)-pyrrolidin-2-yl]-methanone;
(2S,4R)-(4-Cyclobutyl-[1,4]diazepan-1-yl)-(4-thiophen-3-ylmethyl-pyrrolidin-2-yl)-methanone;
(2S,4R)-(1-[2-(4-Cyclobutyl-[1,4]diazepane-1-carbonyl)-4-(4-fluoro-benzyl)-pyrrolidin-1-yl]-ethanone;
(2S,4R)-(1-[2-(4-Cyclobutyl-[1,4]diazepane-1-carbonyl)-4-(3-fluoro-benzyl)-pyrrolidin-1-yl]-ethanone;
(2S,4R)-(1-[2-(4-Cyclobutyl-[1,4]diazepane-1-carbonyl)-4-thiophen-3-ylmethyl-pyrrolidin-1-yl]-ethanone;
(2R,4S)-(4-Cyclobutyl-[1,4]diazepan-1-yl)-[4-(3-fluoro-phenoxy)-1-(2-hydroxy-ethyl)-pyrrolidin-2-yl]-methanone;
(2R,4S)-(4-Cyclobutyl-[1,4]diazepan-1-yl)-[1-(2-fluoro-ethyl)-4-(3-fluoro-phenoxy)-pyrrolidin-2-yl]-methanone;
(2R,4S)-(4-Cyclobutyl-[1,4]diazepan-1-yl)-[4-(3-fluoro-phenoxy)-1-(tetrahydro-pyran-4-yl)-pyrrolidin-2-yl]-methanone;
(2R,4S)-[2-(4-Cyclobutyl-[1,4]diazepane-1-carbonyl)-4-(3-fluoro-phenoxy)-pyrrolidin-1-yl]-phenyl-methanone;
(2R,4S)-1-[4-Cyclobutoxy-2-(4-cyclobutyl-[1,4]diazepane-1-carbonyl)-pyrrolidin-1-yl]-ethanone;
(2R,4S)-1-[2-(4-Cyclobutyl-[1,4]diazepane-1-carbonyl)-4-(tetrahydro-furan-3-yloxy)-pyrrolidin-1-yl]-ethanone;
(2R,4S)-1-[2-(4-Cyclobutyl-[1,4]diazepane-1-carbonyl)-4-(tetrahydro-pyran-4-yloxy)-pyrrolidin-1-yl]-ethanone;
(2R,4S)-1-[2-(4-Cyclobutyl-[1,4]diazepane-1-carbonyl)-4-(pyridin-4-yloxy)-pyrrolidin-1-yl]-ethanone;
(2R,4S)-1-[2-(4-Cyclobutyl-[1,4]diazepane-1-carbonyl)-4-(pyrimidin-5-yloxy)-pyrrolidin-1-yl]-ethanone;
(2R,4S)-1-[2-(4-Cyclobutyl-[1,4]diazepane-1-carbonyl)-4-(pyrazin-2-yloxy)-pyrrolidin-1-yl]-ethanone;
(2R,4S)-1-[2-(4-Cyclobutyl-[1,4]diazepane-1-carbonyl)-4-(thiazol-4-yloxy)-pyrrolidin-1-yl]-ethanone;
(2R,4S)-1-[2-(4-Cyclobutyl-[1,4]diazepane-1-carbonyl)-4-(thiazol-5-yloxy)-pyrrolidin-1-yl]-ethanone;
(2R,4S)-1-[2-(4-Cyclobutyl-[1,4]diazepane-1-carbonyl)-4-(5-methyl-isoxazol-4-yloxy)-pyrrolidin-1-yl]-ethanone;
(2R,4S)-1-[2-(4-Cyclobutyl-[1,4]diazepane-1-carbonyl)-4-(3,5-dimethyl-isoxazol-4-yloxy)-pyrrolidin-1-yl]-ethanone;
(2R,4S)-(4-Cyclobutyl-[1,4]diazepan-1-yl)-[4-(3-fluoro-phenoxy)-1-(tetrahydro-furan-3-yl)-pyrrolidin-2-yl]-methanone;
(2R,4S)-(4-Cyclobutyl-[1,4]diazepan-1-yl)-[4-(3-fluoro-phenoxy)-1-(tetrahydro-pyran-3-yl)-pyrrolidin-2-yl]-methanone;
1-[2-Benzyl-2-(4-cyclobutyl-[1,4]diazepane-1-carbonyl)-pyrrolidin-1-yl]-ethanone;
1-[2-(4-Cyclobutyl-[1,4]diazepane-1-carbonyl)-2-(3-fluoro-benzyl)-pyrrolidin-1-yl]-ethanone;

1-[2-(4-Cyclobutyl-[1,4]diazepane-1-carbonyl)-2-(4-trifluoromethyl-benzyl)-pyrrolidin-1-yl]-ethanone;
3-[1-Acetyl-2-(4-cyclobutyl-[1,4]diazepane-1-carbonyl)-pyrrolidin-2-ylmethyl]-benzonitrile;
3-[2-(4-Cyclobutyl-[1,4]diazepane-1-carbonyl)-pyrrolidin-2-ylmethyl]-benzonitrile;
4-[2-(4-Cyclobutyl-[1,4]diazepane-1-carbonyl)-pyrrolidin-2-ylmethyl]-benzonitrile;
4-[1-Acetyl-2-(4-cyclobutyl-[1,4]diazepane-1-carbonyl)-pyrrolidin-2-ylmethyl]-benzonitrile;
1-[2-(4-Cyclobutyl-[1,4]diazepane-1-carbonyl)-2-(2-fluoro-benzyl)-pyrrolidin-1-yl]-ethanone;
(4-Cyclobutyl-[1,4]diazepan-1-yl)-[2-(2-fluoro-benzyl)-pyrrolidin-2-yl]-methanone;
[2-(2-Chloro-benzyl)-pyrrolidin-2-yl]-(4-cyclobutyl-[1,4]diazepan-1-yl)-methanone; and
1-[2-(2-Chloro-benzyl)-2-(4-cyclobutyl-[1,4]diazepane-1-carbonyl)-pyrrolidin-1-yl]-ethanone;
and pharmaceutically acceptable salts thereof.

33. A pharmaceutical composition comprising:
(a) an effective amount of a compound of Formula (I):

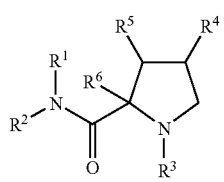
(I)

wherein
$R^1$ and $R^2$ taken together with the nitrogen to which they are attached form

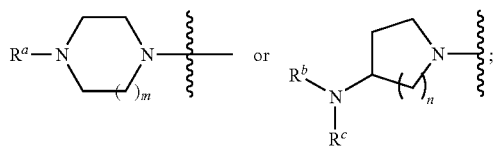

where m is 1 or 2;
n is 1 or 2;
$R^a$ is H, $C_{1-6}$alkyl, cycloalkyl, heterocycloalkyl, or benzyl; and
$R^b$ and $R^c$ are each independently H or $C_{1-4}$alkyl; or
$R^b$ and $R^c$ taken together with the nitrogen to which they are attached form a heterocycloalkyl ring;
$R^3$ is H; $C_{1-6}$alkyl; $C_{2-6}$alkyl substituted with OH, —$OC_{1-4}$alkyl, fluoro, or cycloalkyl; cycloalkyl; heterocycloalkyl; —$COC_{1-6}$alkyl; —CO-(cycloalkyl); benzoyl; —$CO_2C_{1-4}$alkyl; —$CO_2$-benzyl; —$SO_2C_{1-4}$alkyl; —$SO_2$-(cycloalkyl); or —$SO_2$-phenyl;
$R^4$, $R^5$, and $R^6$ are defined as one of a), b) or c);
  a) $R^4$ is —X—$R^d$ and $R^5$ and $R^6$ are each H;
  b) $R^5$ is —X—$R^d$ and $R^4$ and $R^6$ are each H;
  c) $R^6$ is —$CH_2$—$R^e$ and $R^4$ and $R^5$ are each H;
X is O;
$R^d$ is H or $C_{1-6}$alkyl, or a phenyl, benzyl, cycloalkyl, heterocycloalkyl, or monocyclic heteroaryl group, each group unsubstituted or substituted with one or two $R^f$ substituents;
  where each $R^f$ substituent is independently selected from the group consisting of: halo; —$C_{1-4}$alkyl; —$C_{2-4}$alkyl substituted with OH, F, or —$OC_{1-4}$alkyl; —$CHF_2$; —$CF_3$; —OH; —$OC_{1-4}$alkyl; —$SC_{1-4}$alkyl; —$SO_2C_{1-4}$alkyl; —CN; —$CONR^gR^h$; and —$NO_2$; or two $R^f$ substituents together form —$O(CH_2)_{1-2}$—O—;
  where $R^g$ and $R^h$ are each independently —H or —$C_{1-4}$ alkyl;
and
$R^e$ is phenyl or monocyclic heteroaryl, each unsubstituted or substituted with one or two $R^f$ substituents;
or a pharmaceutically acceptable salt thereof; and
(b) a pharmaceutically acceptable excipient.

34. A method of making a compound of Formula (II) or a pharmaceutically acceptable salt thereof:

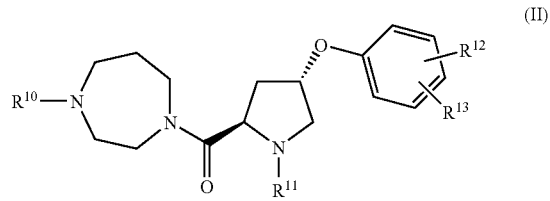
(II)

comprising
a) activating a compound of formula 10:

(10)

wherein said activating comprises:
1) reacting the compound of formula (10) under Mitsunobu conditions; or
2) reacting the compound of formula (10) with an activating agent selected from the group consisting of methanesulfonyl chloride, p-toluenesulfonyl chloride, and p-nitrophenylsulfonyl chloride;
to form an activated compound; and
b) reacting the activated compound with a phenol of formula 11:

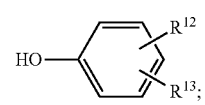
(11)

wherein
$R^{10}$ is isopropyl, cyclopropyl, or cyclobutyl;
$R^{11}$ is —$C(O)C_{1-4}$alkyl or —$SO_2C_{1-4}$alkyl;
$R^{12}$ is —H; halo; —$C_{1-4}$alkyl; —$C_{2-4}$alkyl substituted with OH, F, or —$OC_{1-4}$alkyl; —$CHF_2$; —$CF_3$; —OH; —$OC_{1-4}$alkyl; —$SC_{1-4}$alkyl; —$SO_2C_{1-4}$alkyl; —CN; —$CONR^sR^t$; and —$NO_2$; and
$R^{13}$ is halo; —$C_{1-4}$alkyl; —$C_{2-4}$alkyl substituted with OH, F, or —$OC_{1-4}$alkyl; —$CHF_2$; —$CF_3$; —OH; —$OC_{1-4}$alkyl; —$SC_{1-4}$alkyl; —$SO_2C_{1-4}$alkyl; —CN; —$CONR^sR^t$; and —$NO_2$;

or adjacent $R^{12}$ and $R^{13}$ substituents together form —O(CH$_2$)$_{1-2}$—O—;

where $R^s$ and $R^t$ are each independently —H or —C$_{1-4}$ alkyl.

35. The method according to claim 34, further comprising reacting a compound of formula B2a:

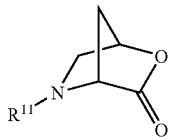

B2a with an amine of formula 12:

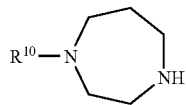

(12)

to form a compound of formula (10).

36. The method according to claim 34, further comprising reacting a compound of formula B2a:

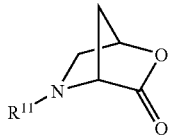

B2a with [1,4]diazepane to form a compound of formula 13:

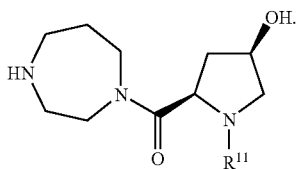

(13)

37. The method according to claim 36, wherein the compound of formula 13 is produced in greater than 70% yield.

38. A compound of Formula (I):

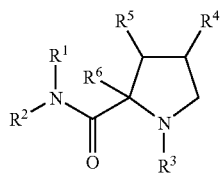

(I)

wherein $R^1$ and $R^2$ taken together with the nitrogen to which they are attached form

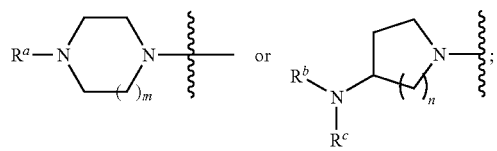

where m is 1 or 2;

n is 1 or 2;

$R^a$ is H, C$_{1-6}$alkyl, cycloalkyl, heterocycloalkyl, or benzyl; and $R^b$ and $R^c$ are each independently H or C$_{1-4}$alkyl; or $R^b$ and $R^c$ taken together with the nitrogen to which they are attached form a heterocycloalkyl ring;

$R^3$ is H; C$_{1-6}$alkyl; C$_{2-6}$alkyl substituted with OH, —OC$_{1-4}$alkyl, fluoro, or cycloalkyl; cycloalkyl; heterocycloalkyl; —COC$_{1-6}$alkyl; —CO-(cycloalkyl); benzoyl; —CO$_2$-benzyl; —SO$_2$C$_{1-4}$alkyl; —SO$_2$-(cycloalkyl); or —SO$_2$-phenyl;

$R^4$, $R^5$, and $R^6$ are defined as one of a), b) or c);

a) $R^4$ is —X—$R^d$ and $R^5$ and $R^6$ are each H;

b) $R^5$ is —X—$R^d$ and $R^4$ and $R^6$ are each H;

c) $R^6$ is —CH$_2$—$R^e$ and $R^4$ and $R^5$ are each H;

X is CH$_2$;

$R^d$ is H or C$_{1-6}$alkyl, or a phenyl, benzyl, cycloalkyl, heterocycloalkyl, or monocyclic heteroaryl group, each group unsubstituted or substituted with one or two $R^f$ substituents;

where each $R^f$ substituent is independently selected from the group consisting of: halo; —C$_{1-4}$alkyl; —C$_{2-4}$alkyl substituted with OH, F, or —OC$_{1-4}$alkyl; —CHF$_2$; —CF$_3$; —OH; —OC$_{1-4}$alkyl; —SC$_{1-4}$alkyl; —SO$_2$C$_{1-4}$alkyl; —CN; —CONR$^g$R$^h$; and —NO$_2$; or two $R^f$ substituents together form —O(CH$_2$)$_{1-2}$—O—;

where $R^g$ and $R^h$ are each independently —H or —C$_{1-4}$ alkyl;

and $R^e$ is phenyl or monocyclic heteroaryl, each unsubstituted or substituted with one or two $R^f$ substituents;

or a pharmaceutically acceptable salt thereof.

39. A compound as defined in claim 38, wherein m is 2.

40. A pharmaceutical composition comprising:

(a) an effective amount of a compound of Formula (I):

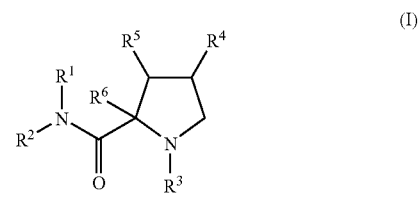

(I)

wherein $R^1$ and $R^2$ taken together with the nitrogen to which they are attached form

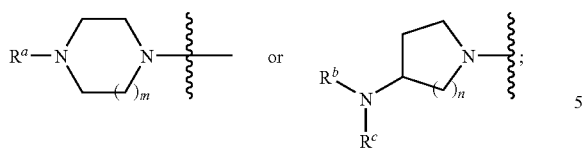

where m is 1 or 2;
n is 1 or 2;
$R^a$ is H, $C_{1-6}$alkyl, cycloalkyl, heterocycloalkyl, or benzyl; and
$R^b$ and $R^c$ are each independently H or $C_{1-4}$alkyl; or
$R^b$ and $R^c$ taken together with the nitrogen to which they are attached form a heterocycloalkyl ring;
$R^3$ is H; $C_{1-6}$alkyl; $C_{2-6}$alkyl substituted with OH, —$OC_{1-4}$alkyl, fluoro, or cycloalkyl; cycloalkyl; heterocycloalkyl; —$COC_{1-6}$alkyl; —CO-(cycloalkyl); benzoyl; —$CO_2C_{1-4}$alkyl; —$CO_2$-benzyl; —$SO_2C_{1-4}$alkyl; —$SO_2$-(cycloalkyl); or —$SO_2$-phenyl;
$R^4$, $R^5$, and $R^6$ are defined as one of a), b) or c);
  a) $R^4$ is —X—$R^d$ and $R^5$ and $R^6$ are each H;
  b) $R^5$ is —X—$R^d$ and $R^4$ and $R^6$ are each H;
  c) $R^6$ is —$CH_2$—$R^e$ and $R^4$ and $R^5$ are each H;
X is $CH_2$;
$R^d$ is H or $C_{1-6}$alkyl, or a phenyl, benzyl, cycloalkyl, heterocycloalkyl, or monocyclic heteroaryl group, each group unsubstituted or substituted with one or two $R^f$ substituents;
  where each $R^f$ substituent is independently selected from the group consisting of: halo; —$C_{1-4}$alkyl; —$C_{2-4}$alkyl substituted with OH, F, or —$OC_{1-4}$alkyl; —$CHF_2$; —$CF_3$; —OH; —$OC_{1-4}$alkyl; —$SC_{1-4}$alkyl; —$SO_2C_{1-4}$alkyl; —CN; —$CONR^gR^h$; and —$NO_2$; or two $R^f$ substituents together form —$O(CH_2)_{1-2}$—O—;
  where $R^g$ and $R^h$ are each independently —H or —$C_{1-4}$ alkyl;
and
$R^e$ is phenyl or monocyclic heteroaryl, each unsubstituted or substituted with one or two $R^f$ substituents;
or a pharmaceutically acceptable salt thereof; and
(b) a pharmaceutically acceptable excipient.

* * * * *